US008753849B2

(12) United States Patent
Kozlov et al.

(10) Patent No.: US 8,753,849 B2
(45) **Date of Patent: *Jun. 17, 2014**

(54) USE OF PHOSPHOKETOLASE FOR PRODUCING USEFUL METABOLITES

(71) Applicant: Ajinomoto Co., Inc., Tokyo (JP)

(72) Inventors: Yury Ivanovich Kozlov, Moscow (RU); Akito Chinen, Kanagawa (JP); Hiroshi Izui, Kanagawa (JP); Yoshihiko Hara, Kanagawa (JP); Hisashi Yasueda, Kanagawa (JP); Konstantin Vyacheslavovich Rybak, Moscow (RU); Ekaterina Aleksandrovna Slivinskaya, Moscow (RU); Joanna Yosifovna Katashkina, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/774,153

(22) Filed: Feb. 22, 2013

(65) Prior Publication Data

US 2013/0157321 A1 Jun. 20, 2013

Related U.S. Application Data

(60) Division of application No. 12/824,826, filed on Jun. 28, 2010, now Pat. No. 8,404,474, which is a continuation of application No. 11/200,296, filed on Aug. 10, 2005, now Pat. No. 7,785,858.

(60) Provisional application No. 60/644,562, filed on Jan. 19, 2005.

(30) Foreign Application Priority Data

Aug. 10, 2004 (RU) ................................ 2004124226

(51) Int. Cl.
*C12P 13/14* (2006.01)

(52) U.S. Cl.
USPC ......... 435/110; 435/41; 435/106; 435/252.32

(58) Field of Classification Search
None
See application file for complete search history.

(56) References Cited

U.S. PATENT DOCUMENTS

| | | | |
|---|---|---|---|
| 5,908,768 | A | 6/1999 | Ono et al. |
| 6,878,533 | B2 | 4/2005 | Tsujimoto et al. |
| 6,911,332 | B2 | 6/2005 | Usuda et al. |
| 6,960,455 | B2 | 11/2005 | Livshits et al. |
| 7,026,149 | B2 | 4/2006 | Usuda et al. |
| 7,029,893 | B2 | 4/2006 | Usuda et al. |
| 7,037,690 | B2 | 5/2006 | Hara et al. |
| 7,060,475 | B2 | 6/2006 | Usuda et al. |
| 7,138,266 | B2 | 11/2006 | Debabov et al. |
| 7,169,587 | B2 | 1/2007 | Gunji et al. |
| 7,179,623 | B2 | 2/2007 | Livshits et al. |
| 7,186,531 | B2 | 3/2007 | Akhverdian et al. |
| 7,192,747 | B2 | 3/2007 | Ono et al. |
| 7,192,748 | B2 | 3/2007 | Usuda et al. |
| 7,211,416 | B2 | 5/2007 | Asahara et al. |
| 7,211,421 | B2 | 5/2007 | Tsujimoto |
| 7,217,543 | B2 | 5/2007 | Gunji et al. |
| 7,220,570 | B2 | 5/2007 | Usuda et al. |
| 7,223,572 | B1 | 5/2007 | Gunji et al. |
| 7,300,786 | B2 | 11/2007 | Klyachko et al. |
| 7,335,506 | B2 | 2/2008 | Gunji et al. |
| 7,344,874 | B2 | 3/2008 | Hara et al. |
| 7,381,548 | B2 | 6/2008 | Sheremet'eva et al. |
| 7,399,618 | B2 | 7/2008 | Klyachko et al. |
| 7,422,880 | B2 | 9/2008 | Rybak et al. |
| 7,439,038 | B2 | 10/2008 | Gunji et al. |
| 7,470,524 | B2 | 12/2008 | Rybak et al. |
| 7,476,531 | B2 | 1/2009 | Tabolina et al. |
| 7,501,282 | B2 | 3/2009 | Hara et al. |
| 7,604,979 | B2 | 10/2009 | Katashkina et al. |
| 7,618,803 | B2 | 11/2009 | Tabolina et al. |
| 7,618,804 | B2 | 11/2009 | Tabolina et al. |
| 2001/0049126 | A1 | 12/2001 | Livshits et al. |
| 2003/0013174 | A1 | 1/2003 | Tsujimoto et al. |
| 2003/0124687 | A1 | 7/2003 | Gunji et al. |
| 2003/0166174 | A1 | 9/2003 | Ono et al. |
| 2003/0232338 | A1 | 12/2003 | Usuda et al. |
| 2004/0038380 | A1 | 2/2004 | Debabov et al. |
| 2004/0132165 | A1 | 7/2004 | Akhverdian et al. |
| 2004/0142435 | A1 | 7/2004 | Gunji et al. |
| 2004/0146974 | A1 | 7/2004 | Gunji et al. |

(Continued)

FOREIGN PATENT DOCUMENTS

| | | |
|---|---|---|
| JP | 11-113588 | 4/1999 |
| WO | WO01/07626 | 2/2001 |

(Continued)

OTHER PUBLICATIONS

NPL search results, Aug. 8, 2013.*
Score search results, Aug. 7, 2013.*
Chinen, A., et al., "Innovative Metabolic Pathway Design for Efficient L-Glutamate Production by Suppressing $CO_2$ Emission," J. Biosci. Bioeng. 2007;103(3):262-269.
Office Communication for EP Patent App. No. 05772660.6 (Nov. 19, 2007).
Written Opinion for PCT Patent App. No. PCT/JP2005/014966 (Dec. 13, 2005).
International Search Report for PCT Patent App. No. PCT/JP2005/014966 (Dec. 13, 2005).
International Preliminary Report on Patentability for PCT Patent App. No. PCT/JP2005/014966 (Feb. 22, 2007).

(Continued)

*Primary Examiner* — Kade Arian
(74) *Attorney, Agent, or Firm* — Shelly Guest Cermak; Cermak Nakajima LLP

(57) ABSTRACT

The present invention provides a bacterium which has an ability to produce a useful metabolite derived from acetyl-coenzyme A, such as L-glutamic acid, L-glutamine, L-proline, L-arginine, L-leucine, L-cysteine, succinate, and polyhydroxybutyrate, wherein said bacterium is modified so that activities of D-xylulose-5-phosphate phosphoketolase and/or fructose-6-phosphate phosphoketolase are enhanced. The present invention also provides a method for producing the useful metabolite using the bacterium.

6 Claims, 12 Drawing Sheets

(56) References Cited

U.S. PATENT DOCUMENTS

| | | | |
|---|---|---|---|
| 2004/0166570 | A1 | 8/2004 | Asahara et al. |
| 2004/0170985 | A1 | 9/2004 | Usuda et al. |
| 2004/0170986 | A1 | 9/2004 | Usuda et al. |
| 2004/0170987 | A1 | 9/2004 | Usuda et al. |
| 2004/0171134 | A1 | 9/2004 | Asahara et al. |
| 2004/0191875 | A1 | 9/2004 | Takeshita et al. |
| 2004/0214296 | A1 | 10/2004 | Asahara et al. |
| 2004/0229311 | A1 | 11/2004 | Hirano et al. |
| 2004/0229320 | A1 | 11/2004 | Stoynova et al. |
| 2004/0229321 | A1 | 11/2004 | Savrasova et al. |
| 2005/0003495 | A1 | 1/2005 | Gunji et al. |
| 2005/0048631 | A1 | 3/2005 | Klyachko et al. |
| 2005/0054061 | A1 | 3/2005 | Klyachko et al. |
| 2005/0124048 | A1 | 6/2005 | Akhverdian et al. |
| 2005/0176033 | A1 | 8/2005 | Klyachko et al. |
| 2005/0176121 | A1 | 8/2005 | Takeshita et al. |
| 2005/0191684 | A1 | 9/2005 | Zimenkov et al. |
| 2005/0196846 | A1 | 9/2005 | Hara et al. |
| 2005/0208634 | A1 | 9/2005 | Usuda et al. |
| 2005/0214911 | A1 | 9/2005 | Marchenko et al. |
| 2005/0214913 | A1 | 9/2005 | Marchenko et al. |
| 2006/0014257 | A1 | 1/2006 | Katashkina et al. |
| 2006/0088919 | A1 | 4/2006 | Rybak et al. |
| 2007/0087403 | A1 | 4/2007 | Bestel-Corre et al. |
| 2007/0212764 | A1 | 9/2007 | Ptitsyn et al. |
| 2008/0038825 | A1 | 2/2008 | Gunji et al. |
| 2008/0113416 | A1 | 5/2008 | Filippov et al. |
| 2008/0199919 | A1 | 8/2008 | Gunji et al. |
| 2008/0241888 | A1 | 10/2008 | Zakataeva et al. |
| 2009/0098621 | A1 | 4/2009 | Rybak et al. |
| 2009/0117623 | A1 | 5/2009 | Marchenko et al. |
| 2009/0155861 | A1 | 6/2009 | Rybak et al. |
| 2009/0203090 | A1 | 8/2009 | Ptitsyn et al. |
| 2009/0209011 | A1 | 8/2009 | Rybak et al. |
| 2009/0215129 | A1 | 8/2009 | Rybak et al. |
| 2009/0215131 | A1 | 8/2009 | Hara et al. |
| 2009/0226981 | A1 | 9/2009 | Hara et al. |
| 2009/0239266 | A1 | 9/2009 | Gulevich et al. |
| 2009/0239267 | A1 | 9/2009 | Rybak et al. |
| 2009/0275089 | A1 | 11/2009 | Klyachko et al. |
| 2009/0275092 | A1 | 11/2009 | Kodera et al. |
| 2009/0286290 | A1 | 11/2009 | Hara et al. |
| 2009/0317876 | A1 | 12/2009 | Rybak et al. |
| 2010/0028958 | A1 | 2/2010 | Asakura et al. |
| 2010/0062496 | A1 | 3/2010 | Takikawa et al. |
| 2010/0062497 | A1 | 3/2010 | Shiraga et al. |
| 2010/0099152 | A1 | 4/2010 | Chinen et al. |
| 2010/0190216 | A1 | 7/2010 | Gunji et al. |
| 2010/0267094 | A1 | 10/2010 | Kozlov et al. |
| 2010/0279362 | A1 | 11/2010 | Rybak et al. |

FOREIGN PATENT DOCUMENTS

| | | |
|---|---|---|
| WO | WO03/066816 | 8/2003 |
| WO | WO03/078643 | 9/2003 |
| WO | WO2005/047498 | 5/2005 |

OTHER PUBLICATIONS

Dandekar, A. M., "A Single Base Pair Change in Proline Biosynthesis Genes Causes Osmotic Stress Tolerance," J. Bacteriol. 1988;170(12):5943-5945.

Deuschle, U., et al., "Promoter of *Escherichia coli*: a hierarchy of in vivo strength indicates alternate structures," The EMBO Journal 1986;5(11):2987-2994.

DSMZ, *Pantoea ananatis* synonyms, http://www.dsmz.de/microorganisms/html/bacteria.species/pantoea,ananatis.html8/11/2009 (1 pg).

Fraenkel, D. G., *Escherichia coli* and *Salmonella*: Cellular and Molecular Biology, Section A, Class I Reactions: Generation of Precursor Metabolites and Energy, Section Al—Central Metabolism, Glycolysis, Chapter 14, 1996, ASM Press, Washington, DC, US, pp. 189-198.

GenBank Accession No. AJ309011, 2 pp.

Gottschalk, G., Bacterial Metabolism, Second Edition, Springer-Verlag, New York, US, pp. 214-225.

Herman, T., "Industrial production of amino acids by coryneform bacteria," J. Biotechnol. 2003;104:155-172.

Kegg (Kyoto Encyclopedia of Genes and Genomes) Entry No. 1p_2659, 2 pp.

Kegg (Kyoto Encyclopedia of Genes and Genomes) Entry No. 1p_3551, 2 pp.

Lee, J. M., et al., "Cloning and characterization of the gene encoding phosphoketolase in *Leuconostoc mesenteroides* isolated from kimchi," Biotechnol. Lett. 2005;27:853-858.

Marx, A., et al., "Metabolic phenotype of phosphoglucose isomerase mutants of *Corynebacterium glutamicum*," J. Biotechnol. 2003;104:185-197.

Meile, L., et al., "Characterization of the D-Xylulose 5-Phosphate/D-Fructose 6-Phosphate Phosphoketolase Gene (*xfp*) from *Bifidobacterium lactis*," J. Bacteriol. 2001;183(9):2929-2936.

Moat , A. G., et al., Microbial Physiology, $4^{th}$ edition, John Wiley and Sons, New York, 2002, Chapter 8, pp. 350-367.

Nakamura, Y., et al., "Codon usage tabulated from international DNA sequence databases: status for the year 2000," Nucleic Acids Res. 2000;28(1):292.

Posthuma, C. C., et al., "Expression of the Xylulose 5-Phosphate Phosphoketolase Gene, *xpkA*, from *Lactobacillus pentosus* MD363 Is Induced by Sugars That Are Fermented via the Phosphoketolase Pathway and Is Repressed by Glucose Mediated by CcpA and the Mannose Phosphoenolpyruvate Phosphotransferase System," Appl. Environment. Microbiol. 2002;68(2):831-837.

Print-out from NCBI Web Database, GenPept Accession No. NP_736274, 2 pp.

Print-out from NCBI Web Database, GenPept Accession No. NP_267658, 2 pp.

Print-out from NCBI Web Database, GenPept Accession No. YP_193510, 2 pp.

Print-out from NCBI Web Database, GenPept Accession No. NP_696135, 2 pp.

Print-out from NCBI Web Database, GenPept Accession No. NP_662409, 2 pp.

Print-out from NCBI Web Database, GenPept Accession No. NP_699578, 2 pp.

Print-out from NCBI Web Database, GenPept Accession No. YP_223570, 2 pp.

Schramm, M., et al., "Phosphorolytic Cleavage of Fructose-6-phosphate by Fructose-6-phosphate Phosphoketolase from *Acetobacter xylinum*," J. Biol. Chem. 1958;233(6):1283-1288.

Sonderegger, M., et al., "Metabolic Engineering of a Phosphoketolase Pathway for Pentose Catabolism in *Saccaromyces cerevisiae*," Appl. Environment. Microbiol. 2004;70(5):2892-2897.

Wendisch, V. F., et al., "Quantitative Determination of Metabolic Fluxes during Coutilization of Two Carbon Sources: Comparative Analyses with *Corynebacterium glutamicum* during Growth on Acetate and/or Glucose," J. Bacteriol. 2000;182(11):3088-3096.

Sánchez, B., et al., "Acquired resistance to bile increases fructose-6-phosphate phosphoketolase activity in *Bifidobacterium*," FEMS Microbiol. Lett. 2004;235:35-41.

Notice of Reason for Rejection for Japanese Patent App. No. 2007-525501 (Feb. 15, 2011) with English translation thereof.

dE Vos, W. M., et al., "Engineering metabolic highways in *Lactococci* and other lactic acid bacteria," Trends in Biotechnol. 2004;22(2):72-79.

Babul, J., "Phosphofructokinases from *Escherichia coli*," J. Biol. Chem. 1978;253(12):4350-4355.

* cited by examiner

Figure 1

```
L.pentosus   MSTDYSSPAYLQKVDKYWRAANYLSVGQLYLKDNPLLQRPLKASDVKVHPIGHWGTIAGQ
L.plantarum  MTTDYSSPAYLQKVDKYWRAANYLSVGQLYLKDNPLLQRPLKASDVKVHPIGHWGTIAGQ
             *:**********************************************************

L.pentosus   NFIYAHLNRVINKYGLKMFYVEGPGHGGQVMVSNSYLDGTYTDIYPEITQDVEGMQKLFK
L.plantarum  NFIYAHLNRVINKYGLKMFYVEGPGHGGQVMVSNSYLDGTYTDIYPEITQDVEGMQKLFK
             ************************************************************

L.pentosus   QFSFPGGVASHAAPETPGSIHEGGELGYSISHGVGAILDNPDEIAAVVVGDGESETGPLA
L.plantarum  QFSFPGGVASHAAPETPGSIHEGGELGYSISHGVGAILDNPDEIAAVVVGDGESETGPLA
             ************************************************************

L.pentosus   TSWQSTKFINPINDGAVLPILNLNGFKISNPTIFGRTSDEKIKQYFESMNWEPIFVEGDD
L.plantarum  TSWQSTKFINPINDGAVLPILNLNGFKISNPTIFGRTSDAKIKEYFESMNWEPIFVEGDD
             *************************************** ***.****************

L.pentosus   PEKVHPALAKAMDEAVEKIKAIQKNARENDDATLPVWPMIVFRAPKGWTGPKSWDGDKIE
L.plantarum  PEKVHPALAKAMDEAVEKIKAIQKHARENNDATLPVWPMIVFRAPKGWTGPKSWDGDKIE
             ************************.****.******************************

L.pentosus   GSFRAHQIPIPVDQTDMEHADALVDWLESYQPKELFNEDGSLKDDIKEIIPTGDARMAAN
L.plantarum  GSFRAHQIPIPVDQNDMEHADALVDWLESYQPKELFNEDGSLKDDIKEIIPTGDSRMAAN
             **************.****************************************.****

L.pentosus   PITNGGVDPKALNLPNFRDYAVDTSKHGANVKQDMIVWSDYLRDVIKKNPDNPRLPGPDE
L.plantarum  PITNGGVDPKALNLPNFRDYAVDTSKEGANVKQDMIVWSDYLRDVIKKNPDNPRLPGPDE
             ************************** *********************************

L.pentosus   TMSNRLYGVFETTNRQWMEDIHPDSDQYEAPAGRVLDAQLSEHQAEGWLEGYVLTGRHGL
L.plantarum  TMSNRLYGVFETTNRQWMEDIHPDSDQYEAPAGRVLDAQLSEHQAEGWLEGYVLTGRHGL
             ************************************************************

L.pentosus   FASYEAFLRVVDSMLTQHFKWLRKANELDWRKKYPSLNIIAASTVFQQDHNGYTHQDPGA
L.plantarum  FASYEAFLRVVDSMLTQHFKWLRKANELDWRKKYPSLNIIAASTVFQQDHNGYTHQDPGA
             ************************************************************

L.pentosus   LTHLAEKKPEYIREYLPADANSLLAVGDVIFRSQEKINYVVTSKHPRQQWPSIEEAKQLV
L.plantarum  LTHLAEKKPEYIREYLPADANTLLAVGDVIFRSQEKINYVVTSKHPRQQWPSIEEAKQLV
             *********************.**************************************

L.pentosus   DNGLGIIDWASTDQGSEPDIVFAAAGTEPTLETLAAIQLLHDSFPDMKIRFVNVVDILKL
L.plantarum  DNGLGIIDWASTDQGSEPDIVFAAAGTEPTLETLAAIQLLHDSFPEMKIRFVNVVDILKL
             *********************************************.**************

L.pentosus   RSPEKDPRGLSDAEFDHYFTKDKPVVFAFHGYEDLVRDIFFDRHNHNLHVHGYRENGDIT
L.plantarum  RSPEKDPRGLSDAEFDHYFTKDKPVVFAFHGYEDLVRDIFFDRHNHNLYVHGYRENGDIT
             ************************************************:***********

L.pentosus   TPFDVRVMNQMDRFDLAKSAIAAQPAMENTGAAFVQDMDNMLAKHNAYIRDAGTDLPEVN
L.plantarum  TPFDVRVMNQMDRFDLAKSAIAAQPAMENTGAAFVQSMDNMLAKHNAYIRDAGTDLPEVN
             ************************************ ***********************

L.pentosus   DWQWKGLK   SEQ ID NO: 2
L.plantarum  DWQWKGLK   SEQ ID NO: 4
             ********
```

USE OF PHOSPHOKETOLASE FOR PRODUCING USEFUL METABOLITES

This application is a Divisional of, and claims priority under 35 U.S.C. §120 to, U.S. patent application Ser. No. 12/824,826, filed Jun. 28, 2010, which was a Continuation of, and claimed priority under 35 U.S.C. §120 to, U.S. patent application Ser. No. 11/200,296, filed Aug. 10, 2005, now U.S. Pat. No. 7,785,858, issued Aug. 31, 2010, which claimed priority under 35 U.S.C. §119(e) to Russian Patent Application No. 2004124226, filed Aug. 10, 2004, and U.S. Provisional Application No. 60/644,562, filed Jan. 19, 2005, which are hereby incorporated by reference in their entireties. The Sequence Listing in electronic format filed herewith is also hereby incorporated by reference in its entirety (File Name: 2013-02-XXT_US-176D_Seq_List; File Size: 358 KB; Date Created: Feb. 22, 2013).

BACKGROUND OF THE INVENTION

1. Field of the Invention

The present invention relates to a method for producing useful metabolites, particularly those derived from acetyl-coenzyme A (acetyl-CoA). The present invention also relates to novel bacteria useful in the production method.

2. Brief Description of the Related Art

Conventionally, useful metabolites such as L-amino acids, their intermediates, and other chemicals of bacterial metabolism are produced by methods in which bacterial strains isolated from natural sources, or mutants thereof, have been modified to enhance their productivity.

Sugar is the main source of carbon in a microorganism which is suitable for fermentation. The Embden-Meyerhof and pentose phosphate (pentose-P) pathways are the two preliminary routes of intermediary sugar metabolism in a microorganism. A third route, the Entner-Doudoroff pathway, is also known, as are some of the connections with carboxylic acid pathways. During glycolysis, glucose is metabolized to main intermediate compounds, such as phosphoenolpyruvate, pyruvate, and acetyl-coenzyme A, which are used as constituents in the formation of many cellular compounds, such as L-amino acids, purines and pyrimidines, vitamins etc. Also, generation of energy (ATP and NADH) occurs during glycolysis. Pyruvate formed after glycolysis is often converted back to phosphoenolpyruvate (PEP) by phosphoenolpyruvate synthase encoded by the pps gene, or to acetyl-CoA by pyruvate dehydrogenase encoded by the pdh gene etc. One of the above-mentioned compounds, acetyl-CoA, is formed from pyruvate via pyruvate dehydrogenase, and accompanied by the release of $CO_2$. This loss of one carbon atom results in decreased production yields of useful compounds derived from acetyl-CoA. Two enzymes of the bifidum pathway, D-xylulose-5-phosphate phosphoketolase (also known as "phosphoketolase") and fructose-6-phosphate phosphoketolase, have been reported. D-xylulose-5-phosphate phosphoketolase (EC 4.1.2.9) catalyzes the phosphate-consuming conversion of xylulose-5-phosphate to glyceraldehyde-3-phosphate and acetylphosphate, with the concommitant release of one molecule of water. Fructose-6-phopshate phosphoketolase (EC 4.1.2.22) catalyzes the phosphate-consuming conversion of fructose-6-phosphate to erythrose-4-phosphate and acetylphosphate, with the concommitant release of one molecule of water. Both enzymes form acetylphosphate, the precursor of acetyl-CoA, without losing carbon via $CO_2$. D-xylulose-5-phosphate phosphoketolase (EC 4.1.2.9) has been reported in bacteria belonging to the genera *Acetobacter* (Schramm, M. et al, J. Biol. Chem., 233(6), 1283-8 (1958)), *Bifidobacterium* (Sgorbati, B. et al, Antonie Van Leeuwenhoek. 42(1-2), 49-57 (1976); Grill, J. P. et al Curr Microbiol., 31(1), 49-54 (1995)), *Lactobacillus* (Posthuma, C. C. et al, Appl. Environ. Microbiol., 68(2), 831-7 (2002)), *Thiobacillus* (Greenley, D. E. and Smith, D. W., Arch. Microbiol., 122, 257-261 (1979)), in yeasts belonging to the genera *Candida, Rhodotorula, Rhodosporidium, Pichia, Yarrowia, Hansenula, Hansenula, Kluyveromyces, Saccharomyces, Trichosporon, Wingea* (Evans, C. T. and Ratledge, C., Arch. Microbiol., 139, 48-52 (1984); Ratledge, C. and Holdsworth, J. E., Appl. Microbiol. Biotechnol., 22, 217-221 (1985)). Fructose-6-phopshate phosphoketolase (EC 4.1.2.22) has been reported in bacteria, such as *Acetobacter xylinum* (Schramm, M. et al, J. Biol. Chem., 233(6), 1283-8 (1958)), *Bifidobacterium globosum* and *Bifidobacterium dentium* (Sgorbath, B. et al, Antonie Leeuwenhoek, 42, 49-57 (1976)), *Bifidobacterium bifidum, Gardnerella vaginalis* (Gavini, F. et al, Anaerobe, 2, 191-193 (1996)), and yeasts, such as *Rhodotorula graminis, Rhodotorula glutinis, Candida* sp., *Candida tropicalis, Saccharomyces pastorianus* (Whitworth, D. A. and Ratledge, C., J. Gen. Microbiol., 102, 397-401 (1977)). It has been reported that in some organisms both activities are represented by one enzyme (see, for example, the articles of Schramm, M. et al (J. Biol. Chem., 233(6), 1283-8 (1958)); Sgorbati, B. et al (Antonie Van Leeuwenhoek. 42(1-2), 49-57 (1976)); Meile, L. et al (J. Bacteriol., 183(9), 2929-36 (2001))). Phosphoketolase genes from two species have been cloned and their sequences determined These are the xfp gene which encodes D-xylulose-5-phosphate phosphoketolase/fructose-6-phopshate phosphoketolase from *Bifidobacterium lactis* (Meile, L. et al, J. Bacteriol., 183(9), 2929-36 (2001)), and the xpkA gene which encodes D-xylulose-5-phosphate phosphoketolase from *Lactobacillus pentosus* (Posthuma, C. C. et al, Appl. Environ. Microbiol., 68(2), 831-7 (2002)). A search of the Microbial Genome database provided by the National Center for Biotechnology information (http://www.ncbi.nlm.nih.gov/entrez/query.fcgi?CMD=&DB=genome) revealed several genes encoding for putative phosphoketolases.

Methods for improving the ability of yeast to produce ethanol from xylose by introducing genes for xylose reductase, xylitol dehydrogenase, and additionally phosphoketolase are known (WO2003078643). However, effects of using the phosphoketolase gene for the elimination of carbon dioxide have never been reported.

SUMMARY OF THE INVENTION

An aspect of the present invention is to enhance production of useful metabolites by strains of bacteria which have the ability to produce the metabolites as well as provide a method for producing the metabolites using these strains.

It is an aspect of the present invention to provide a bacterium having an ability to produce an useful metabolite, wherein the bacterium is modified to have an increased activity of D-xylulose-5-phosphate phosphoketolase and/or fructose-6-phosphate phosphoketolase.

It is the further aspect of the present invention to provide the bacterium described above, wherein the useful metabolite is derived from acetyl-coenzyme A.

It is the further aspect of the present invention to provide the bacterium described above, wherein the useful metabolite is selected from the group consisting of L-glutamic acid, L-glutamine, L-proline, L-arginine, L-leucine, L-cysteine, succinate, and polyhydroxybutyrate.

It is an aspect of the present invention to provide a bacterium having an ability to produce a useful metabolite, wherein the bacterium inherently does not have an activity of D-xylulose-5-phosphate phosphoketolase or fructose-6-phosphate phosphoketolase, and wherein said bacterium has been transformed with a DNA fragment coding for D-xylulose-5-phosphate phosphoketolase and/or fructose-6-phosphate phosphoketolase.

It is the further aspect of the present invention to provide the bacterium described above, wherein the useful metabolite is derived from acetyl-coenzyme A.

It is the further aspect of the present invention to provide the bacterium described above, wherein the useful metabolite is selected from the group consisting of L-glutamic acid, L-glutamine, L-proline, L-arginine, L-leucine, L-cysteine, succinate, and polyhydroxybutyrate.

It is the further aspect of the present invention to provide the bacterium described above, wherein the bacterium is selected from the group consisting of Enterobacteriaceae family, *Coryneform* bacterium, and *Bacillus* bacterium.

It is a further aspect of the present invention to provide the bacterium described above, wherein the bacterium belongs to the genus *Escherichia* or *Pantoea*.

It is the further aspect of the present invention to provide a method for producing a useful metabolite, comprising cultivating the bacterium in a culture medium, and collecting the useful metabolite from the culture medium.

It is the further aspect of the present invention to provide the method described above, wherein the useful metabolite is derived from acetyl-coenzyme A.

It is the further aspect of the present invention to provide the method described above, wherein the useful metabolite is selected from group consisting of L-glutamic acid, L-glutamine, L-proline, L-arginine, L-leucine, L-cysteine, succinate, and polyhydroxybutyrate.

These aspects have been achieved by enhancing an activity of D-xylulose-5-phosphate phosphoketolase or fructose-6-phosphate phosphoketolase in a bacterium which has the ability to produce a useful metabolite, particularly one derived from acetyl-CoA, which has made it possible to utilize carbon more efficiently and increase production of the useful metabolite by the bacterium. Thus, the present invention has been completed.

The present invention is described in detail below.

BRIEF DESCRIPTION OF DRAWINGS

FIG. 1 shows the alignment of D-xylulose-5-phosphate phosphoketolases from *L. pentosus* and *L. plantarum* (identity 98.5%).

DESCRIPTION OF THE PREFERRED EMBODIMENTS

Figure 2:
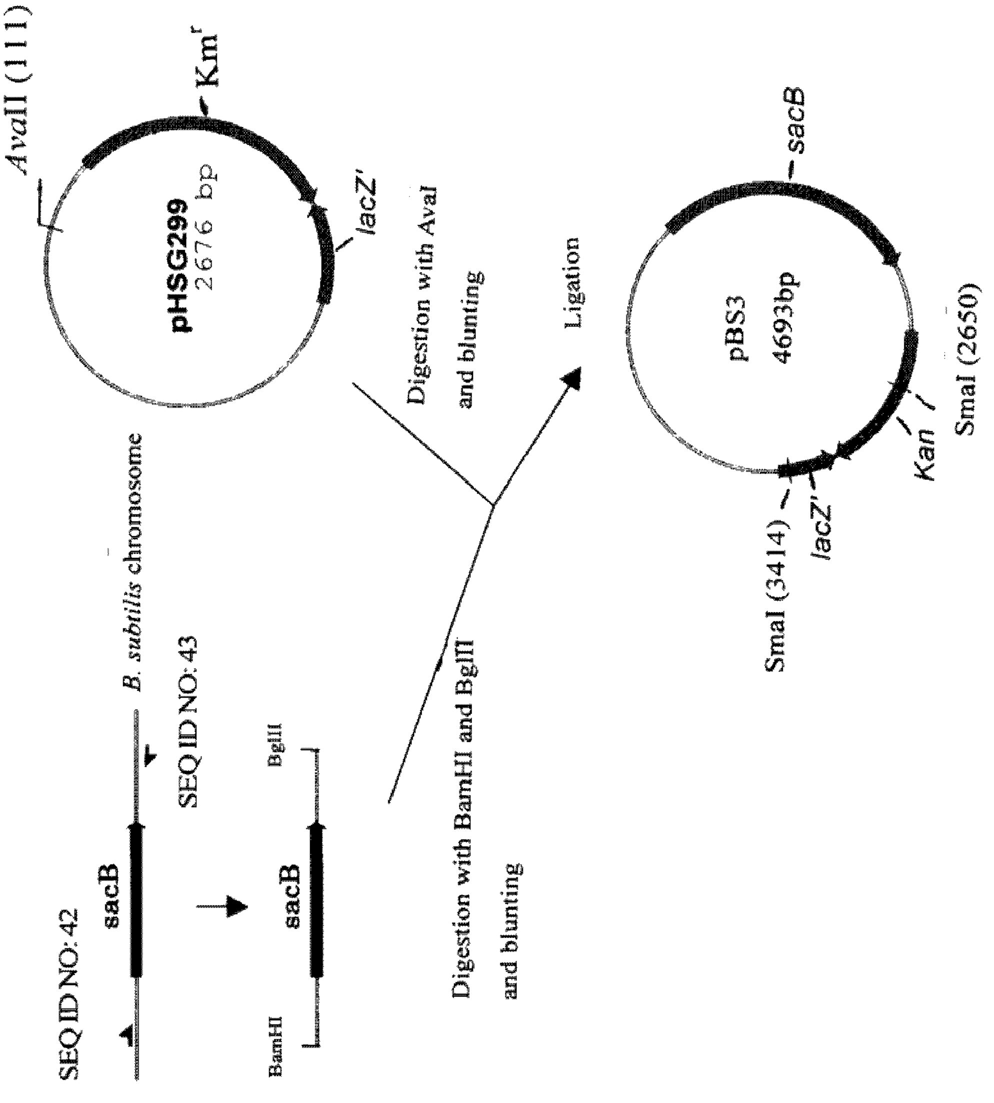
FIG. 2 shows the construction procedure of plasmid pBS3.

The bacterium of present invention encompasses a bacterium which has an ability to produce a useful metabolite, wherein the bacterium has been modified to increase the activity of D-xylulose-5-phosphate phosphoketolase and/or fructose-6-phosphate phosphoketolase.

The bacterium of present invention includes both a bacterium which does not inherently have an activity of D-xylulose-5-phosphate phosphoketolase and fructose-6-phosphate phosphoketolase and a bacterium which inherently has an activity of D-xylulose-5-phosphate phosphoketolase and fructose-6-phosphate phosphoketolase. By introducing a gene encoding D-xylulose-5-phosphate phosphoketolase or fructose-6-phosphate phosphoketolase into such a bacterium, productivity of acetyl-CoA is enhanced in the bacterium, leading to enhanced production of useful metabolites.

In the bacterium of the present invention, either or both of the activities of D-xylulose-5-phosphate phosphoketolase or fructose-6-phosphate phosphoketolase may be enhanced.

In the present invention, the term "phosphoketolase" includes both D-xylulose-5-phosphate phosphoketolase and fructose-6-phosphate phosphoketolase.

In the present invention, the phrase "activity of D-xylulose-5-phosphate phosphoketolase" means an activity which catalyzes the phosphate-consuming conversion reaction of xylulose-5-phosphate to glyceraldehyde-3-phosphate and acetylphosphate with the concommitant release of one molecule of water. This activity can be measured by the method described by Goldberg, M. et al (Methods Enzymol., 9, 515-520 (1966) or L. Meile (J. Bacteriol. (2001) 183; 2929-2936).

In the present invention, the phrase "activity of fructose-6-phopshate phosphoketolase" means an activity which catalyzes the phosphate-consuming conversion reaction of fructose-6-phosphate to erythrose-4-phosphate and acetylphosphate with the concommitant release of one molecule of water. Fructose-6-phopshate phosphoketolase activity can be measured by the method described by Racker, E. (Methods Enzymol., 5, 276-280 (1962) or L. Meile (J. Bacteriol. (2001) 183; 2929-2936).

The activity of phosphoketolase in bacteria which inherently have phosphoketolase activity can be enhanced more than that of a wild-type or non-modified strain, preferably not less than 1.5-fold, more preferably not less than 2-fold, and most preferably not less than 3-fold of a wild-type or non-modified strain. Furthermore, in this invention, a bacterium that inherently does not have activities of D-xylulose-5-phosphate phosphoketolase and fructose-6-phosphate phosphoketolase can be used as a parent strain. The activity of phosphoketolase in the bacterium which inherently does not have phosphoketolase activity can be enhanced by transforming the bacterium with a DNA fragment coding for D-xylulose-5-phosphate phosphoketolase and/or fructose-6-phosphate phosphoketolase. Whether a parent bacterium inherently possesses phosphoketolase activity or not can be measured by the same method as described above.

Whether the phosphoketolase activity has been introduced may be confirmed using a pyruvate dehydrogenase (PDH)-defective strain. PDH-defective strains are auxotrophic for acetate. On the other hand, if phosphoketolase is introduced, a PDH-defective strain will not be auxotrophic for acetate any more. Accordingly, introduction of the gene encoding phosphoketolase can be confirmed based on compensation by the host strain for acetate auxotrophy. As a PDH-defective strain, the ΔaceE strain as described in the Examples can be used.

"D-xylulose-5-phosphate phosphoketolase" may be an enzyme derived from bacteria having an activity of D-xylulose-5-phosphate phosphoketolase, including lactic acid bacterium, methanol-assimilating bacterium, methane-assimilating bacterium, *Streptococcus* bacterium, and especially those bacteria belonging to the genera *Acetobacter, Bifidobacterium, Lactobacillus, Thiobacillus, Streptococcus, Methylococus, Butyrivibrio, Fibrobacter*, and/or yeast belonging to the genera *Candida, Rhodotorula, Rhodosporidium, Pichia, Yarrowia Hansenula, Kluyveromyces Saccharomyces, Trichosporon, Wingea*, or the like.

"Fructose-6-phopshate phosphoketolase" may be an enzyme derived from bacteria having an activity of fructose-6-phopshate phosphoketolase that belong to the genera *Acetobacter, Bifidobacterium, Chlorobium, Brucella, Methylococus, Gardnerella*, and/or yeast belonging to *Rhodotorula, Candida, Saccharomyces*, or the like.

It is also possible that both activities are represented by one enzyme, D-xylulose-5-phosphate/fructose-6-phopshate phosphoketolase.

The nucleotide sequence of the xpkA gene encoding D-xylulose-5-phosphate phosphoketolase of *Lactobacillus pentosus* MD363 has been registered in the EMBL/GenBank database under accession number AJ309011 (Posthuma, C. C. et al, Appl. Environ. Microbiol., 68(2), 831-7 (2002)) and is shown as SEQ ID NO: 1. The nucleotide sequence of the xpk1 gene encoding D-xylulose-5-phosphate phosphoketolase of *Lactobacillus plantarum* has been registered in the EMBL/GenBank database under accession number NC_004567 Region: complement (2362936.2365302) (Kleerebezem, M., et al, Proc. Natl. Acad. Sci. U.S.A. 100 (4), 1990-1995 (2003)) and is shown as SEQ ID NO: 3. The nucleotide sequences of the xpk and xpk homologous genes are shown in Table 1 and the Sequence Listing. The alignment of the amino acid sequences of SEQ ID NOS: 2 and 4 is shown in FIG. 1.

TABLE 1

| Gene | microorganism | description | EC No. | SEQ ID: DNA | SEQ ID: Amino acid | GenBank Accession No |
|---|---|---|---|---|---|---|
| xpkA | *Lactobacillus pentosus* | phosphoketolase | 4.1.2.9 | 1 | 2 | AJ309011 |
| xpk1 | *Lactobacillus plantarum* | phosphoketolase | 4.1.2.9 | 3 | 4 | NC_004567 complement (2362936 . . . 2365302) |
| xpk2 | *Lactobacillus plantarum* | phosphoketolase | 4.1.2.9 | 62 | 63 | NC_004567 Complement (3169067-3171478) |
| xpk | *Streptococcus agalactiae* NEM316 | hypothetical protein gbs1840 | 4.1.2.9 | 64 | 65 | NP_736274. |
| ptk | *Lactococcus lactis* subsp. *lactis* Il1403 | phosphoketolase | 4.1.2.9 | 66 | 67 | NP_267658 |
| xpk | *Lactobacillus johnsonii* NCC 533 | probable xylulose-5-phosphate/fructose-6-phosphate phosphoketolase | 4.1.2.9 | 68 | 69 | NC_005362 |
| xpk | *Lactobacillus acidophilus* NCFM | xylulose-5-phosphate-fructose phosphoketolase | 4.1.2.9 | 70. | 71 | YP_193510 |

The nucleotide sequence of the xfp gene encoding D-xylulose-5-phosphate/fructose-6-phopshate phosphoketolase of *Bifidobacterium lactis* has been registered in the EMBL/GenBank database under accession number AJ293946 (Meile, L. et al, J. Bacteriol., 183(9), 2929-36 (2001)) and is shown as SEQ ID NO: 5, and the amino acid sequence encoded by the xfp gene is shown as SEQ ID NO: 6. The nucleotide sequences of the xfp and xfp homologous genes are shown in Table 2 and the Sequence Listing.

TABLE 2

| Gene | microorganism | description | EC No. | SEQ ID: DNA | SEQ ID: Amino acid | GenBank Accession No |
|---|---|---|---|---|---|---|
| xfp | *Bifidobacterium longum* | xylulose-5-phosphate/fructose-6-phosphate phosphoketolase | EC: 4.1.2.— | 72 | 73 | NP_696135 |
| xfp | *Chlorobium tepidum* | putative phosphoketolase | EC: 4.1.2— | 74 | 75 | NP_662409 |
| xfp | *Brucella suis* | xylulose-5-phosphate/fructose-6-phosphate phosphoketolase | EC: 4.1.2— | 76 | 77 | NP_699578 |

TABLE 2-continued

| Gene | microorganism | description | EC No. | SEQ ID: DNA | SEQ ID: Amino acid | GenBank Accession No |
|---|---|---|---|---|---|---|
| xfp | *Brucella abortus* | xylulose-5-phosphate/fructose-6-phosphate phosphoketolase | EC: 4.1.2— | 78 | 79 | YP_223570 |

XpkA, xpk1, and xfp genes can all be obtained by PCR (polymerase chain reaction; refer to White, T. J. et al., *Trends Genet.,* 5, 185 (1989)) using primers designed based on the nucleotide sequence of the known genes. The genes containing a motif of phosphoketolase can be obtained using pfam and motif (http://pfam.wustl.edu/, http://www.genome.jp/dbget-bin/www_bget?pfam+XFP). The xpk1 gene from *Lactobacillus* can be obtained by using the primers shown in SEQ ID No. 7 and No. 8. The xfp gene from *Bifidobacterium* can be obtained by using the primers shown in SEQ ID No. 13 and No. 14. The xpkA gene from *Lactobacillus* can be obtained by using the primers shown in SEQ ID No. 19 and No. 24.

The activity of phosphoketolase can be enhanced by transforming a parent strain with a DNA encoding phosphoketolase. Transformation of a bacterium with a DNA encoding phosphoketolase can be performed by conventional methods using a DNA encoding phosphoketolase as described above.

A DNA encoding D-xylulose-5-phosphate phosphoketolase may be a DNA which encodes a variant of D-xylulose-5-phosphate phosphoketolase, which can be found in different strains of bacteria, according to natural diversity. The DNA encoding such variants can be obtained by isolating a DNA which hybridizes with xpkA gene (for example, SEQ ID NO: 1 or 3), or part of the gene, under the stringent conditions, and which codes for a protein having the activity of D-xylulose-5-phosphate phosphoketolase. The term "stringent conditions" as used herein include conditions under which a so-called specific hybrid is formed, and a non-specific hybrid is not formed. For example, stringent conditions may include conditions under which DNAs having high homology, for instance, DNAs having homology no less than 70% to each other, preferably 80% or more, more preferably 90% or more, most preferably 95% or more, are hybridized. Alternatively, the stringent conditions are exemplified by conditions which comprise ordinary conditions of washing in Southern hybridization, e.g., 60° C., 1×SSC, 0.1% SDS, preferably, 60° C., 0.1×SSC, 0.1% SDS. Duration of washing depends on the type of membrane used for blotting and, as a rule, is recommended by the manufacturer. For example, recommended duration of washing of the Hybond™ N+ nylon membrane (Amersham) under stringent conditions is 15 minutes. As a probe for screening a variant xpkA gene, a partial sequence of the nucleotide sequence disclosed in Table 1 can be used. Such a probe can be prepared by PCR using oligonucleotides based on the nucleotide sequence disclosed in Table 1 as primers, and a DNA fragment containing the nucleotide sequence disclosed in Table 1 as a template. When a DNA fragment having a length of about 300 bp is used as a probe, washing after the hybridization may be performed under the following conditions: 50° C., 2×SSC, and 0.1% SDS at least twice.

A DNA coding for fructose-6-phosphate phospholetolase can be obtained by similar procedures as described above using the nucleotide sequence disclosed in Table 2 as a probe.

It is known that some distribution bias of synonymous codons exists among the 61 amino acid codons found within the population of mRNA molecules, and the level of cognate tRNA appears directly proportional to the frequency of codon usage (see, for example, Kane, J. F., Curr. Opin. Biotechnol., 6(5), 494-500 (1995)). From this point of view, it is easy to predict translational problems with abundant mRNA species which contain an excess of rare tRNA codons. Such a situation might arise after the initiation of transcription of a cloned heterologous gene in, for example, the *E. coli* host. Recent studies suggest clusters of AGG/AGA, CUA, AUA, CGA, or CCC codons may reduce both the quantity and quality of the synthesized protein. In addition, it is likely that an excess of any of these codons, even without clusters, could create translational problems. So, when a heterologous DNA coding for a protein of interest is transferred to the bacterium, it is desirable to replace rare codons by more frequently-used codons to avoid these translation problems. Frequency of codon usage in more than 11,000 organisms is presented in the "Codon usage database" (http://www.kazusa.or.jp/codon; Nakamura, Y. et al, Nucl. Acids Res., 28, 292 (2000)).

Furthermore, the gene encoding phosphoketolase of the present invention is not limited to a wild-type gene, but may be a mutant or artificially modified gene having modifications in the nucleotide sequences shown in Table 1 and 2. The encoded proteins may include substitutions, deletions, or insertions, of one or several amino acid residues at one or more positions in the amino acid sequences shown in Table 1 and 2, so long as the function of the encoded phosphoketolase protein is maintained. Although the number of "several" amino acid residues referred to herein differs depending on positions in the three-dimensional structure or types of amino acid residues, it may be 2 to 20, preferably 2 to 10, more preferably 2 to 5. Such substitutions of amino acids include functionally neutral sense mutations, and are preferably conservative substitutions. In the case of aromatic amino acids, conservative substitutions include phe, trp, and tyr interchangeably for each other. In the case of hydrophobic amino acids, conservative substitutions include leu, ile, and val interchangeably for each other. In the case of polar amino acids, conservative substitutions include gln and asn interchangeably for each other. In the case of basic amino acids, conservative substitutions include arg, lys, and his interchangeably for each other. In the case of acidic amino acids, conservative substitutions include asp and glu interchangeably for each other. In the case of hydroxyl group-containing amino acids, conservative substitutions include ser and thr interchangeably for each other. The conservative substitutions also include substitution of ser or thr for ala, substitution of gln, his or lys for arg, substitution of glu, gln, lys, his or asp for asn, substitution of asn, glu or gln for asp, substitution of ser or ala for cys, substitution of asn, glu, lys, his, asp or arg for gln, substitution of gly, asn, gln, lys or asp for glu, substitution of pro for gly, substitution of asn, lys, gln, arg or tyr for his, substitution of leu, met, val or phe for ile, substitution of ile, met, val or phe for leu, substitution of asn, glu, gln, his or arg for lys, substitution of ile, leu, val or phe for met, substitution of trp, tyr, met, ile or leu for phe, substitution of thr or ala for ser, substitution of ser or ala for thr, substitution of phe or tyr for trp, substitution of his, phe or trp for tyr and substitution of met, ile or leu for val. Mutations causing such substitution, deletion, or insertion of one or several amino acids as described above also include naturally occurring mutations arising from individual differences, and differences in species of microorganisms that harbor the phosphoketolase gene (mutant or variant). The region to be substituted can be selected by searching for the preserved region (motif) in PKT with MOTIF and Pfam.

Such genes can be obtained by modifying a nucleotide sequence shown in Table 1 or 2, for example, by site-specific mutagenesis, so that one or more substitutions, deletions, or insertions are introduced at a specific site of the protein encoded by the gene.

Furthermore, such genes can also be obtained by conventional mutagenesis treatments such as those mentioned below. Examples of mutagenesis treatments include treating a gene having a nucleotide sequence shown in Table 1 or 2 or a nucleotide sequence of nucleotide numbers 49 to 948 in SEQ ID NO: 1 in vitro with hydroxylamine, and treating a bacterium such as an *Escherichia* bacterium harboring the gene with ultraviolet ray irradiation or a mutagenesis agent used in a typical mutation treatments such as N-methyl-N'-nitro-N-nitrosoguanidine (NTG) or EMS (ethyl methanesulfonate).

Expression of the phosphoketolase gene (hereinafter, referred to as pkt gene, including xpk or xfp gene) may be enhanced by, for example, increasing the copy number of the pkt gene in cells using genetic recombination techniques. For example, a recombinant DNA can be prepared by ligating a gene fragment containing the pkt gene to a vector, preferably a multi-copy vector, which can replicate in the host bacterium, and introducing the resulting vector into the host bacterium.

When the xfp gene of *Bifidobacterium animalis* is used, it may be obtained by, for example, the PCR method (polymerase chain reaction, refer to White, T. J. et al., Trends Genet., 5, 185 (1989)) using primers designed based on the nucleotide sequence of the xfp gene of *Bifidobacterium animalis* (SEQ ID NO: 9 or 11), for example, primers each having a nucleotide sequence of SEQ ID NO: 13 or 14, and using a chromosomal DNA of *Bifidobacterium animalis* as a template. The pkt gene from other microorganisms may also be used, and can be obtained from their chromosomal DNA or chromosomal DNA library by PCR using oligonucleotide primers designed based on a sequence of their pkt gene or a homologous sequence thereof, or by hybridization using an oligonucleotide probe prepared based on such sequence information as shown in Table for 2. A chromosomal DNA to be used as a DNA donor can be prepared from a microorganism, for example, by the method of Saito and Miura (refer to H. Saito and K. Miura, Biochem. Biophys. Acta, 72, 619 (1963), Text for Bioengineering Experiments, Edited by the Society for Bioscience and Bioengineering, Japan, pp. 97-98, Baifukan, 1992).

Then, the pkt gene is ligated to a vector DNA operable in the host bacterium to prepare a recombinant DNA. Preferably, vectors autonomously replicable in the host bacterium are used.

Examples of vectors autonomously replicable in *Escherichia coli* include pUC19, pUC18, pHSG299, pHSG399, pHSG398, pACYC184, (pHSG and pACYC are available from Takara Bio), RSF1010, pBR322, pMW 118, pMW219 (pMW is available from Nippon Gene), and so forth. Phage vectors such as 11059, IBF101, M13 mp 9 may also be used.

Examples of vectors which are autonomously replicable in *Coryneform* bacteria include pAM330 (EP 0077548B), pHM1519 (EP 0078537), pGA1 (EP10977998), and pYM2 (U.S. Pat. No. 6,905,819)

Moreover, a so-called shuttle vector autonomously replicable in both *Escherichia coli* and *Coryneform* bacteria may also be used, for example, pVK9, pVK7 (US2003-0175912), pSFK6 (JP2000-262288A), and pHK4 (JP5-007491A).

The pVK9 is an *E. coli*-coryneform shuttle vector obtained by excising a BamHI-KpnI fragment containing the replicable origin from pHK4 (JP-A-5-007491) and introducing it into the AvaII site of pHSG299 (Product of Takara-Bio).

In order to prepare a recombinant DNA by ligating the pkt gene and any of the vectors mentioned above, the vector and a fragment containing the pkt gene are ligated, usually by using a ligase such as a T4 DNA ligase.

To introduce a recombinant DNA prepared as described above into a bacterium, any known transformation method reported so far can be employed. For example, a method of treating recipient cells with calcium chloride so as to increase the permeability of DNA, which has been reported for *Escherichia coli* (Mandel, M. and Higa, A., J. Mol. Biol., 53, 159 (1970)), and a method of using competent cells prepared from growing cells to introduce a DNA, which has been reported for *Bacillus subtilis* (Duncan, C. H., Wilson, G. A. and Young, F. E., Gene, 1, 153 (1977)) can be employed. In addition to these methods, a method of introducing a recombinant DNA into protoplast- or spheroplast-like recipient cells, which have been reported to be applicable to *Bacillus subtilis*, actinomycetes, and yeasts (Chang, S, and Choen, S. N., Molec. Gen. Genet., 168, 111 (1979); Bibb, M. J., Ward, J. M. and Hopwood, O. A., Nature, 274, 398 (1978); Hinnen, A., Hicks, J. B. and Fink, G. R., Proc. Natl. Sci., USA, 75, 1929 (1978)), can be employed. In addition, transformation of *Coryneform* bacteria can also be performed by the electric pulse method (Sugimoto et al., JP2-207791A).

The pkt gene can be introduced by integrating a single copy or multiple copies of the gene into a chromosomal DNA of a bacterium. Furthermore, the copy number of the pkt gene can also be increased by integrating multiple copies of the gene into a chromosomal DNA of a bacterium. In order to integrate one or more copies of the pkt gene on a chromosomal DNA of a bacterium, homologous recombination can be performed by targeting a sequence which exists in multiple copies on a chromosomal DNA. Repetitive DNA and inverted repeats at an end of a transposon can be used as a sequence which exists on a chromosomal DNA in multiple copies. Alternatively, as disclosed in JP2-109985A, it is also possible to incorporate the pkt gene into a transposon, and allow it to be transferred so that the gene is integrated into the chromosomal DNA. Furthermore, enhancement of gene expression may be performed by transposition such as Mu integration. For example, one round of Mu integration allows for introduction into a bacterial chromosome of up to 3 copies of the gene. Transposons such as Mu, Tn10 and Tn5 may be used. Integration of the pkt gene into the chromosome can be confirmed by Southern hybridization using a probe having a partial sequence of the pkt gene.

Enhancing expression of the pkt gene can also be attained by either replacing an expression regulatory sequence, including a promoter of the pkt gene, on a chromosomal DNA or on a plasmid with a stronger one, as described in WO00/18935, amplifying a regulatory factor that increases expression of the pkt gene, or deleting or attenuating a regulatory factor that reduces expression of the pkt gene. Moreover, it is also possible to introduce several nucleotide substitutions into a promoter region of the pkt gene so that the promoter is more potent. A method for evaluating potency of promoter and examples of potent promoters are disclosed in Goldstein et al. (Prokaryotic promoters in biotechnology. Biotechnol. Annu. Rev., 1995, 1, 105-128). Furthermore, since it is known that a spacer sequence between the ribosome binding site (RBS) and translation initiation codon, especially, several nucleotides just upstream of the initiation codon, has a great influence on translation efficiency, this sequence may be modified. Expression regulatory sequences of pkt gene may be identified using a vector for promoter identification or genetic analysis software such as GENETYX.

Example of such strong promoters include the lac promoter, trp promoter, trc promoter, tac promoter, $P_R$ promoter, $p_L$ promoter of lambda phage, tet promoter, amyE promoter, spac promoter, and so forth. An example of a strong promoter for *corynebacterium* includes the PS2 promoter (Appl Environ Microbiol. 2003 January; 69(1):358-66; Mol. Microbiol. 1993 July; 9(1):97-109; WO93/03158), trc promoter, tac promoter, lacUV5 promoter, araBAD promoter. Promoter strength is defined as the frequency of acts of RNA synthesis initiation. Methods for evaluating the strength of a promoter are described by, for example, Deuschle U., Kammerer W., Gentz R., Bujard H. (Promoters in *Escherichia coli*: a hierarchy of in vivo strength indicates alternate structures. EMBO J., 5, 2987-2994 (1986)).

The expression of the pkt gene is enhanced by such substitution or modification of a promoter. The substitution of an expression regulatory sequence can also be attained by, for example, using a temperature-sensitive plasmid. Examples of a temperature-sensitive plasmid for *Coryneform* bacteria include p48K and pSFKT2 (JP2000-262288A), pHSC4 (refer to France Patent Laid-open Publication No. 2667875, 1992 and JP5-7491A), pBS5T, and so forth. These plasmids can autonomously replicate at least at a temperature of 25° C., but cannot autonomously replicate at a temperature of 37° C. in *Coryneform* bacteria. Modifying the expression regulatory sequence may be combined with increasing the copy number of the pkt gene.

The method of using levansucrase, which is lethal to *corynebacterium*, as a marker of homologous recombination is also suitable. The sacB gene encoding levansucrase can be used to select the strain in which the vector is deleted from chromosome effectively. (Schafer, A. et al. Gene 145 (1994) 69-73). The sacB gene and homologous gene of sacB described below can be used.

*Bacillus subillus*: sacB GenBank Accession Number X02730 (SEQ ID NO: 40)

*Bacillus amyloliqufaciens*: sacB GenBank Accession Number X52988

*Zymomonas mobilis*: sacB GenBank Accession Number L33402

*Bacillus stearothermophilus*: surB GenBank Accession Number U34874

*Lactobacillus sanfranciscensis*: frfA GenBank Accession Number AJ508391

*Acetobacter xylinus*: lsxA GenBank Accession Number AB034152

*Gluconacetobacter diazotrophicus*: lsdA GenBank Accession Number L41732

Preparation of plasmid DNA, digestion and ligation of DNA, transformation, selection of an oligonucleotide as a primer and the like can be performed by ordinary methods well-known by those skilled in the art. Such methods are described, for example, in Sambrook, J., Fritsch, E. F., and Maniatis, T., "Molecular Cloning A Laboratory Manual, Second Edition", Cold Spring Harbor Laboratory Press (1989).

The bacteria of the present invention include not only a bacterium which does not inherently have an activity of D-xylulose-5-phosphate phosphoketolase and fructose-6-phosphate phosphoketolase, but also a bacterium which inherently has an activity of these proteins and has been modified so that the activity is enhanced. The former is preferably used.

Specific examples of the bacterium used in the present invention include bacteria belonging to Enterobacteriaceae family such as the genus *Escherichia, Pantoea, Coryneform* bacterium such as *Corynebacterium glutamicum, Bacillus* bacterium such as *Bacillus subtilis*, and so forth. However, the bacterium of the present invention is not limited to these examples.

The Enterobacteriaceae family includes bacteria belonging to the genera *Enterobacter, Erwinia, Escherichia, Klebsiella, Pantoea, Providencia, Salmonella, Serratia, Shigella, Morganella* etc. Specifically, those classified into the Enterobacteriaceae according to the taxonomy used in the NCBI (National Center for Biotechnology Information) database (http://www.ncbi.nlm.nih.gov/htbin-post/Taxonomy/wgetorg?mode=Tree&id=1236&lvl=3&keep=1&srchmode=1&unlock) can be used. A bacterium belonging to the genus of *Escherichia* or *Pantoea* is preferred.

*Escherichia* bacteria reported in Neidhardt et al. (Neidhardt, F. C. et al., *Escherichia coli* and *Salmonella Typhimurium*, American Society for Microbiology, Washington D.C., 1208, Table 1), such as *Escherichia coli*, can be utilized. Examples of wild-type strains of *Escherichia coli* include, but are not limited to, the K12 strain and derivatives thereof, MG1655 strain (ATCC No. 47076), and W3110 strain (ATCC No. 27325). These strains are available from the American Type Culture Collection (ATCC, Address: P.O. Box 1549, Manassas, Va. 20108, United States of America).

The term "a bacterium belonging to the genus *Pantoea*" means that the bacterium is classified as the genus *Pantoea* according to the classification known to a person skilled in the art of microbiology, and also includes some species of *Enterobacter agglomerans* recently re-classified into *Pantoea agglomerans, Pantoea ananatis, Pantoea stewartii* or the like, based on nucleotide sequence analysis of 16S rRNA etc.

In the present invention, coryneform bacteria include bacteria classified as *Coryneform* bacterium according to the classification known to a person skilled in the art of microbiology, bacteria which were hitherto classified into the genus *Brevibacterium*, but have now been re-classified into the genus *Corynebacterium* (Int. J. Syst. Bacteriol., 41, 255 (1991)), and also bacteria belonging to the genus *Brevibacterium*, which is a close relative of the genus *Corynebacterium*. Examples of such *Coryneform* bacteria are listed below.

*Corynebacterium acetoacidophilum*
*Corynebacterium acetoglutamicum*
*Corynebacterium alkanolyticum*
*Corynebacterium callunae*
*Corynebacterium glutamicum*
*Corynebacterium lilium*
*Corynebacterium melassecola*
*Corynebacterium thermoaminogenes*
*Corynebacterium herculis*
*Brevibacterium divaricatum*
*Brevibacterium flavum*
*Brevibacterium immariophilum*
*Brevibacterium lactofermentum*
*Brevibacterium roseum*
*Brevibacterium saccharolyticum*
*Brevibacterium thiogenitalis*
*Corynebacterium ammoniagenes*
*Brevibacterium album*
*Brevibacterium cerinum*
*Microbacterium ammoniaphilum*

Specifically, the following strains are encompassed:

*Corynebacterium acetoacidophilum* ATCC 13870

*Corynebacterium acetoglutamicum* ATCC 15806
*Corynebacterium alkanolyticum* ATCC 21511
*Corynebacterium callunae* ATCC 15991
*Corynebacterium glutamicum* ATCC 13020, 13032, 13060
*Corynebacterium lilium* ATCC 15990
*Corynebacterium melassecola* ATCC 17965
*Corynebacterium thermoaminogenes* AJ12340 (FERM BP-1539)
*Corynebacterium herculis* ATCC 13868
*Brevibacterium divaricatum* ATCC 14020
*Brevibacterium flavum* ATCC 13826, ATCC 14067, AJ12418 (FERM BP-2205)
*Brevibacterium immariophilum* ATCC 14068
*Brevibacterium lactofermentum* (*Corynebacterium glutamicum*) ATCC 13869
*Brevibacterium roseum* ATCC 13825
*Brevibacterium saccharolyticum* ATCC 14066
*Brevibacterium thiogenitalis* ATCC 19240
*Brevibacterium ammoniagenes* ATCC 6871, ATCC 6872
*Brevibacterium album* ATCC 15111
*Brevibacterium cerium* ATCC 15112
*Microbacterium ammoniaphilum* ATCC 15354

These strains can be obtained from, for example, the American Type Culture Collection (ATCC, Address: P.O. Box 1549, Manassas, Va. 20108, United States of America). Each strain is assigned a registration number, and one can request a provision of each strain by its registration number. The registration number for each strain is indicated in the catalog of the American Type Culture Collection. The AJ12340 strain was deposited on Oct. 27, 1987 at the National Institute of Bioscience and Human-Technology, Agency of Industrial Science and Technology, Ministry of International Trade and Industry (currently, the independent administrative agency, National Institute of Advanced Industrial Science and Technology, International Patent Organism Depositary (Tsukuba Central 6, 1-1, Higashi 1-Chome, Tsukuba-shi, Ibaraki-ken, Japan, postal code: 305-5466)) under the provisions of the Budapest Treaty, and received an accession number of FERM BP-1539. The AJ12418 strain was deposited on Jan. 5, 1989 at the National Institute of Bioscience and Human-Technology, Agency of Industrial Science and Technology, Ministry of International Trade and Industry under the provisions of the Budapest Treaty and received an accession number of FERM BP-2205.

The term "*Bacillus* bacterium" means that the bacterium classified as the genus *Bacillus* according to the classification known to a person skilled in the art of microbiology. In the present invention, the *Bacillus* bacterium include, but are not limited to, the *Bacillus subtilis* 168 Marburg strain (ATCC 6051), *Bacillus subtilis* PY79 strain (Plasmid, 1984, 12, 1-9) and so forth, and examples of *Bacillus amyloliquefaciens* include, but are not limited to, *Bacillus amyloliquefaciens* T strain (ATCC 23842), *Bacillus amyloliquefaciens* N strain (ATCC 23845) and so forth.

The bacterium of the present invention can be obtained by introducing the aforementioned DNA (pkt gene) into a bacterium which already has an ability to produce a useful metabolite. Alternatively, the bacterium of present invention can be obtained by imparting the ability to produce a useful metabolite to the bacterium into which the pkt gene has been introduced. In the latter case, introducing the pkt gene and imparting the ability to produce the useful metabolite may be performed in any order.

The phrase "a bacterium having an ability to produce a useful metabolite" means a bacterium, which has an ability to produce and cause accumulation of the useful metabolite in a medium when the bacterium of the present invention is cultured in the medium. The ability to produce the metabolite may be imparted or enhanced by breeding including mutagenesis treatment and genetic modification. The phrase "bacterium has ability to produce useful metabolite" means that the bacterium is able to produce and cause accumulation of the metabolite in a medium in an amount larger than a wild-type strain or unmutated strain. The phrase "bacterium has ability to produce a useful metabolite" as used herein also means a bacterium that is able to produce and cause accumulation in a medium of an amount not less than 0.5 g/L, more preferably not less than 1.0 g/L of the target metabolite.

The phrase "useful metabolite" means a primary metabolite such as an L-amino acid, organic acid, vitamin, saccharide, and/or intermediate of Embden-Meyerhof, pentose phosphate (pentose-P) pathways, Entner-Doudoroff pathway, citrate cycle, and amino acid biosynthesis. The L-amino acid to be produced in the present invention is not particular limited, and includes L-lysine, L-arginine, L-ornithine, L-histidine, L-citrulline, L-isoleucine, L-alanine, L-valine, L-leucine, and L-glycine, L-threonine, L-serine, L-proline, L-phenylalanine, L-tyrosine, and L-tryptophan, L-cysteine, L-cysteine, L-methionine, L-ornithine, L-glutamic acid, L-aspartic acid, L-glutamine, and L-asparagine. More preferably, the bacterium of present invention is a bacterium having an ability to produce a metabolite derived from acetyl-CoA. Such metabolite is selected from the group consisting of L-glutamic acid, L-glutamine, L-proline, L-arginine, L-leucine, L-cysteine, succinate, and polyhydroxybutyrate.

Hereinafter, examples of strains imparted with an ability to produce useful metabolites and methods of imparting such ability will be explained in detail.

Hereinafter, methods for imparting an ability to produce useful metablites to a parent strain as mentioned above will be explained.

In order to impart an ability to produce useful metabolites, methods conventionally used for breeding an useful metabolite-producing bacterium belonging to the genus *Escherichia* or *Coryneform* bacterium and so forth can be used. For example, methods for obtaining an auxotrophic mutant strain, analogue-resistant strain, or metabolic regulation mutant strain having an ability to produce useful metabolites, and methods for creating a recombinant strain having enhanced activity of an useful metabolites biosynthetic enzyme can be used ("Amino Acid Fermentation", the Japan Scientific Societies Press [Gakkai Shuppan Center], 1st Edition, published on May 30, 1986, pp. 77-100). When breeding useful metabolite-producing bacteria using these methods, one or more properties, including auxotrophy, analogue-resistance, and metabolic regulation mutation, may be imparted.

When a recombinant strain is created, the activity of single or multiple useful metabolites-biosynthetic enzymes may be enhanced. Furthermore, methods imparting properties of auxotrophy, analogue resistance, and metabolic regulation mutation may be combined with methods for enhancing an activity of an useful metabolite-biosynthetic enzyme.

An auxotrophic mutant strain, useful metabolites such as an L-amino acid analogue-resistant strain, or a metabolic regulation-mutated strain having an useful metabolite-producing ability can be obtained by subjecting a parent or wild-type strain to a typical mutagenesis treatment such as X-ray or ultraviolet ray irradiation, treatment with a mutagenesis agent such as N-methyl-N'-nitro-N-nitrosoguanidine (NTG). Then, an auxotrophic strain, analogue-resistant strain, or metabolic regulation mutant strain which has a useful metabolite-producing ability may be selected from the mutated strains.

Methods of imparting L-glutamic acid-producing ability to the bacteria as described above include, for example, modifying the bacteria so that expression of a gene encoding an enzyme involved in L-glutamic acid biosynthesis is enhanced and/or overexpressed. Examples of enzymes involved in the L-glutamic acid biosynthesis include glutamate dehydrogenase (also referred to as "GDH" hereinafter), glutamine synthetase, glutamate synthase, isocitrate dehydrogenase, aconitate hydratase, citrate synthase (also referred to as "CS" hereinafter), phosphoenolpyruvate carboxylase (also referred to as "PEPC" hereinafter), pyruvate carboxylase, pyruvate dehydrogenase, pyruvate kinase, phosphoenolpyruvate synthase, enolase, phosphoglyceromutase, phosphoglycerate kinase, glyceraldehyde-3-phosphate dehydrogenase, triose phosphate isomerase, fructose bisphosphate aldolase, phosphofructokinase, glucose phosphate isomerase, and so forth. Of these enzymes, it is preferable that the activity of one or more of CS, PEPC, and GDH is/are enhanced, and it is more preferable that activities of all three of these enzymes are enhanced.

Examples of bacteria modified by the method as described above so that expression of the CS gene, PEPC gene, and/or GDH gene are enhanced include the bacteria disclosed in U.S. Pat. No. 6,197,559, U.S. Pat. No. 6,331,419, and European Patent Publications No. 0999282 and No. 1078989.

The modification of a bacterium to impart L-glutamic acid-producing ability may be performed by reducing or inactivating the activity of an enzyme that catalyzes a reaction branching from the L-glutamic acid biosynthetic pathway, and producing a compound other than L-glutamic acid. Examples of enzymes which catalyze a reaction branching from the L-glutamic acid biosynthetic pathway and producing a compound other than L-glutamic acid include 2-oxoglutarate dehydrogenase, isocitrate lyase, glutamate decarboxylase, 1-pyrroline dehydrogenase, and so forth. Of these enzymes, it is preferable to reduce or eliminate the activity of 2-oxoglutarate dehydrogenase.

To reduce or inactivate the activities of the aforementioned enzymes, mutations for reducing or inactivating intracellular activities of the enzymes can be introduced by usual mutagenesis treatment or genetic engineering. Examples of mutagenesis treatment include irradiation by X-rays or ultraviolet rays, treatment with a mutagenesis agent such as N-methyl-N'-nitro-N-nitrosoguanidine, and so forth. Examples of methods for reducing or eliminating the intracellular activity of an enzyme include mutating or deleting a gene encoding the enzyme in the cells of a microorganism so that intracellular activity is reduced or eliminated as compared to a non-mutated strain. Examples of methods for mutating or deleting a gene include modification of expression regulatory sequences such as promoters and Shine-Dalgarno (SD) sequences, introduction of mis-sense mutations, non-sense mutations, or frame-shift mutations into an open reading frame, and deletion of a portion of the gene (J Biol Chem. 1997 272(13):8611-7). A mutated gene can be introduced into a microorganism by using a homologous recombination technique in which a wild-type gene on a chromosome is replaced with the mutated gene, or by using a transposon or IS factor. Homologous recombination techniques include methods using linear DNA, a temperature-sensitive plasmid, and non-replicable plasmid. These methods are described in Proc Natl Acad Sci USA. 2000 Jun. 6; 97(12):6640-5., U.S. Pat. No. 6,303,383, JP05-007491A, and the like.

Intracellular activity of the target enzyme and the degree of decrease in the activity can be confirmed by measuring the enzyme activity using a cell extract or a purified fraction thereof obtained from a candidate strain and comparing it with the activity of a wild-type or non-modified strain. For example, the 2-oxoglutarate dehydrogenase activity can be measured by the method of Reed et al. (Reed L. J. and Mukherjee B. B., Methods in Enzymology, 13, pp. 55-61, 1969). Examples of bacteria belonging to the genus *Escherichia* deficient in α-ketoglutarate dehydrogenase activity or having reduced α-ketoglutarate dehydrogenase activity and methods for obtaining them are described in U.S. Pat. Nos. 5,378,616 and 5,573,945. Specifically, these strains include the following:

*E. coli* W3110sucA::Kmr
*E. coli* AJ12624 (FERM BP-3853)
*E. coli* AJ12628 (FERM BP-3854)
*E. coli* AJ12949 (FERM BP-4881)

*E. coli* W3110sucA::Km$^r$ was obtained by disrupting the α-ketoglutarate dehydrogenase gene (hereinafter referred to as "sucA gene") in *E. coli* W3110. This strain is completely deficient in the α-ketoglutarate dehydrogenase.

*Coryneform* bacteria in which sucA gene is disrupted using homologous recombination are explained in detail in WO95/34672 and U.S. Pat. No. 5,977,331.

Other examples of L-glutamic acid-producing bacterium include those which belong to the genus *Escherichia* and have resistance to an aspartic acid antimetabolite. These strains may also be deficient in alpha-ketoglutaric acid dehydrogenase activity and include, for example, strain AF13199 (FERM BP-5807) (U.S. Pat. No. 5,908,768), or strain FFRM P-12379, which is additionally modified to have a lowered L-glutamic acid-decomposing ability (U.S. Pat. No. 5,393,671); *E. coli* strain AJ13138 (FERM BP-5565) (U.S. Pat. No. 6,110,714) and the like.

Examples of L-glutamic acid-producing bacteria belonging to the genus *Pantoea*, include mutant strains deficient in α-ketoglutarate dehydrogenase activity or with decreased α-ketoglutarate dehydrogenase activity, and can be obtained as described above. Such strains include *Pantoea ananatis* AJ13356 or AJ13601 (U.S. Pat. No. 6,331,419). *Pantoea ananatis* AJ13356 was deposited at the National Institute of Bioscience and Human-Technology, Agency of Industrial Science and Technology, Ministry of International Trade and Industry (currently, National Institute of Advanced Industrial Science and Technology, International Patent Organism Depositary, Central 6, 1-1, Higashi 1-Chome, Tsukuba-shi, Ibaraki-ken, 305-8566, Japan) on Feb. 19, 1998 and received an accession number of FERM P-16645. It was then converted to an international deposit under the provisions of Budapest Treaty on Jan. 11, 1999 and received an accession number of FERM BP-6615. *Pantoea ananatis* AJ13601 was deposited at the National Institute of Bioscience and Human-Technology, Agency of Industrial Science and Technology, Ministry of International Trade and Industry (currently, National Institute of Advanced Industrial Science and Technology, International Patent Organism Depositary, Central 6, 1-1, Higashi 1-Chome, Tsukuba-shi, Ibaraki-ken, 305-8566, Japan) on Aug. 18, 1999 and received an accession number of FERM P-17516. It was then converted to an international deposit under the provisions of Budapest Treaty on Jul. 6, 2000 and received an accession number of FERM BP-7207. The *Pantoea ananatis* AJ13356 and AJ13601 are deficient in α-KGDH activity as a result of disruption of the gene encoding the E1 subunit of αKGDH (sucA gene). The above strains were identified as *Enterobacter agglomerans* when they were isolated and deposited as the *Enterobacter agglomerans* AJ13356 strain, and AJ13601 strain, respectively. However, they were recently re-classified as *Pantoea ananatis* on the basis of nucleotide sequencing of 16S rRNA and so forth. Although AJ13356, AJ13601, and their parent strain AJ13355 (FERM BP-6614), were all deposited at the aforementioned depository as *Enterobacter agglomerans*, they are described as *Pantoea ananatis* for the purposes of this specification.

Further examples of *Coryneform* bacteria having L-glutamic acid-producing ability include an organic acid analogue-resistant mutant, and escletin-resistant mutant (JP56-1889A, JP56140895A, JP5702689A, JP88994A).

Examples of analogue-resistant L-glutamic acid-producing *Coryneform* bacterium include the following strains:

*Brevibacterium flavum* AJ11355 (FERM P-5007, JP56-1889A)

*Brevibacterium glutamicum* AJ11368 (FERM P-P-5020, JP56-1889A)

*Brevibacterium flavum* AJ11217 (FERM P-4318, JP57-2689A)

*Brevibacterium flavum* AJ11218 (FERM-P 4319, JP57-2689A)

*Brevibacterium flavum* AJ11564 (FERM P-5472, JP56-140895A)

*Brevibacterium flavum* AJ11439 (FERM P-5316, JP56-35981A)

*Corynebacterium glutamicum* H7684 (FERM BP-3004, JP56-151495A)

Examples of L-glutamine producing bacterium which can be used as a parent strain to be modified to have increased activity of the D-xylulose-5-phosphate phosphoketolase and/or fructose-6-phosphate phosphoketolase include an L-glutamine-producing coryneform bacterium which is modified to have enhanced glutamate dehydrorogenase activity, glutamine synthetase activity (EP 1229121A), or to have decreased glutaminase activity (EP1424397A). Also, a bacterium belonging to the genus *Escherichia* harboring a mutant glutamine synthetase in which the tyrosine amino acid residue corresponding to position 397 in a wild-type glutamine synthetase is replaced with any amino acid residue can be used.

Methods of imparting 6-diazo-5-oxo-norleucine-resistance (JP3-232497A), purine analogue-resistance, methionine sulfoxide-resistance (JP 61-202694A), α-Ketomalinic acid-resistance (JP56-151495) can be used to impart or enhance the L-glutamine producing ability by breeding. Specific examples of *Coryneform* bacteria having L-glutamine-producing ability include, but are not limited to:

*Brevibacterium flavum* AJ11573 (FERM P-5492, JP56-161495A)

*Brevibacterium flavum* AJ11576 (FERMBP-10381, JP56-161495A)

*Brevibacterium flavum* AJ12212 (FERM P-8123, JP61-202694A)

Examples of L-proline-producing bacterium useful as a parent strain to be modified to have increased activity of the D-xylulose-5-phosphate phosphoketolase and/or fructose-6-phosphate phosphoketolase include an L-proline-producing bacterium belonging to the genus *Escherichia* which harbors γ-glutamyl kinase desensitized in feedback inhibition by L-proline, and/or in which the L-proline degradation system is destroyed. A method for breeding the bacterium having γ-glutamyl kinase desensitized in feedback inhibition by L-proline is exemplified by introducing a DNA coding for γ-glutamyl kinase desensitized in feedback inhibition by L-proline into cells (Dandekar, A. M., Uratsu, S. L., J. Bacteriol., 170, 12, 5943-5 (1988)). A method for destroying the L-proline degradation system is exemplified by introducing a mutation into a proline dehydrogenase gene so that the active proline dehydrogenase is not expressed. Also, a bacterium in which the L-proline degradation system is destroyed can be obtained by obtaining a strain deficient in L-proline-assimilating ability and selecting a strain which overproduces L-proline extracellularly by using L-proline auxotrophy as an index. The L-proline-producing bacteria belonging to the genus *Escherichia* include *E. coli* strains NRRL B-12403 and NRRL B-12404 (GB Patent 2075056), VKPM B-8012 (US Patent Laid-open Publication 2002-0058315), and plasmid mutants described in DE Patent 3127361, plasmid mutants described by Bloom F. R. et al (The 15$^{th}$ Miami winter symposium, 1983, p. 34) and the like may be used for obtaining such strains.

Examples of L-arginine-producing bacterium which can be used as a parent strain to be modified to have increased activity of the D-xylulose-5-phosphate phosphoketolase and/or fructose-6-phosphate phosphoketolase include L-arginine-producing bacteria belonging to the genus *Escherichia*, for example, *E. coli* strain 237 (VKPM B-7925) and its derivative strains having mutant N-acetylglutamate synthase (US Patent Laid-open Publication 2002-0034793), an arginine-producing strain into which an argA gene encoding N-acetylglutamate synthetase is introduced (JP57-5693A), and the like.

Another example of an L-arginine-producing bacterium is a strain which has amplified genes coding for L-arginine-biosynthetic enzymes such as N-acetylglutamate synthase (argA), N-acetylglutamyl phosphate reductase (argC), ornithine acetyltransferase (argJ), N-acetylglutamate kinase (argB), acetylornithine transaminase (argD), acetylornithine deacetylase (argE), ornithine carbamoyltransferase (argF), argininosuccinate synthase (argG), argininosuccinate lyase (argH), and carbamoyl-phosphate synthase (carAB). The names of the genes encoding these enzymes are given in parentheses after the names of the enzymes, respectively.

Examples of L-leucine-producing bacterium which can be used as a parent strain to be modified to have increased activity of the D-xylulose-5-phosphate phosphoketolase and/or fructose-6-phosphate phosphoketolase include the L-leucine-producing bacteria belonging to the genus *Escherichia*, such as *E. coli* strains H-9068 (ATCC 21530), H-9070 (FERM BP-4704), and H-9072 (FERM BP-4706) resistant to 4-azaleucine or 5,5,5-trifluoroleucine (U.S. Pat. No. 5,744,331), *E. coli* strains in which feedback inhibition of isopropylmalate synthase by L-leucine is desensitized (EP1067191B), *E. coli* strain AJ11478 resistant to β-2-thienylalanine, and β-hydroxyleucine (U.S. Pat. No. 5,763,231), *E. coli* strain 57 (VKPM B-7386, Russian patent No. 2140450), and the like.

Examples of L-cysteine-producing bacterium which can be used as a parent strain to be modified to have increased activity of the D-xylulose-5-phosphate phosphoketolase and/or fructose-6-phosphate phosphoketolase include the L-cysteine-producing bacterium belonging to the genus *Escherichia*, such as the *E. coli* strain JM15 which is transformed with different cysE alleles coding for feedback-resistant serine acetyltransferases (U.S. Pat. No. 6,218,168); *E. coli* strain W3110 over-expressing a gene encoding a protein suitable for secreting cytotoxic substances (U.S. Pat. No. 5,972,663); *E. coli* strains having lowered cysteine desulfohydraseii activity (JP11-155571A2); *E. coli* strain W3110 using increased activity of positive transcriptional regulator for cysteine regulon encoded by cysB gene (WO01/27307A1), and the like.

Examples of succinate-producing bacterium which can be used as a parent strain to be modified to have increased activity of the D-xylulose-5-phosphate phosphoketolase and/or fructose-6-phosphate phosphoketolase include the succinate-producing bacterium belonging to the genus *Escherichia* and *Coryneform* bacterium such as *Brevibacterium* flavum MJ233Δldh strain (JP11-206385) and *Brevibacterium flavum* MJ233/pPCPYC strain (WO01/27258).

Examples of an L-lysine-producing bacterium which can be used as a parent strain to be modified to have increased activity of the D-xylulose-5-phosphate phosphoketolase and/or fructose-6-phosphate phosphoketolase include S-(2-aminoethyl)cysteine (hereinafter "AEC")-resistant mutant strains of *Brevibacterium lactofermentum* AJ11082 (NRRL B-11470) (described in JP56-1914B, JP56-1915B, JP57-14157B, JP57-14158B, JP57-30474B, JP58-10075B, JP59-4993B, JP61-35840B, JP62-24074B, JP62-36673B, JP5-11958B, JP7-112437B, and JP7-112438B), mutant strains auxotrophic for an amino acid such as L-homoserine (JP48-28078B and JP56-6499B), mutant strains resistant to AEC and auxtrophic for an amino acid such as L-leucine, L-homoserine, L-proline, L-serine, L-arginine, L-alanine, and L-valine (U.S. Pat. Nos. 3,708,395 and 3,825,472), L-lysine-producing mutant strains resistant to DL-α-amino-ε-caprolactam, α-amino-lauryllactam, aspartic acid analogues, sulfa drugs, quinoid, and N-lauroylleucine, L-lysine-producing mutant strains resistant to oxaloacetate decarboxylase inhibitor or a respiratory tract enzyme inhibitor (JP50-53588A, JP50-31093A, JP52-102498A, JP53-9394A, JP53-86089A, JP55-9783A, JP55-9759A, JP56-32995A, JP56-39778A, JP53-43591B and JP53-1833B), L-lysine-producing mutant strains auxotrophic for inositol or acetic acid (JP55-9784A and JP56-8692A), L-lysine-producing mutant strains that are susceptible to fluoropyruvic acid at a temperature of 34° C. or higher (JP55-9783A and JP53-86090A), L-lysine-producing mutant strains of *Brevibacterium* or *Corynebacterium* bacteria resistant to ethylene glycol (U.S. Pat. No. 4,411,997), and so forth.

Further examples of L-lysine-producing bacteria which can be used as a parent strain to be modified to have increased activity of the D-xylulose-5-phosphate phosphoketolase and/or fructose-6-phosphate phosphoketolase include S-(2-aminoethyl)cysteine (hereinafter "AEC")-resistant mutant strains of *Escherichia coli* WC196 (WO96/17930). The WC196 strain was designated as *Escherichia coli* AJ13069, and deposited at the independent administrative agency, National Institute of Advanced Industrial Science and Technology, International Patent Organism Depositary (Tsukuba Central 6, 1-1, Higashi 1-Chome, Tsukuba-shi, Ibaraki-ken, Japan, postal code: 305-8566) on Dec. 6, 1994 and received an accession number of FERM P-14690. Then, the deposit was converted to an international deposit under the provisions of the Budapest Treaty on Sep. 29, 1995, and received an accession number of FERM BP-5252.

Examples of microorganisms having an L-threonine-producing ability include a 6-dimethylaminopurine-resistant mutant (JP5-304969A), a strain in which a gene for a threonine biosynthetic enzyme having a mutation which enhances the enzymatic activity is amplified with a plasmid (JP1-29559B, JP05-227977A), a strain in which the threonine operon is amplified with a plasmid (JP2-109985A), a strain in which a gene encoding pyruvate carboxylase and a gene encoding nicotinamide nucleotide transhydrogenase are amplified (JP2002-51787A), and so forth.

The *Escherichia coli* VKPM B-3996 strain (U.S. Pat. No. 5,175,107) may also be used as an L-threonine-producing strain. VKPM B-3996 was deposited at the Russian National Collection of Industrial Microorganisms (VKPM), GNII Genetika with a registration number of VKPM B-3996 on Nov. 19, 1987. The VKPM B-3996 strain harbors plasmid pVIC40 (International Patent Publication WO90/04636), which is obtained by inserting a threonine operon (thrABC) into plasmid pAYC32 which has a streptomycin-resistance marker gene (Chistorerdov, A. Y., Tsygankov, Y. D., Plasmid, 1986, 16, 161-167). Aspartokinase I-homoserine dehydrogenase I encoded by a mutant thrA gene contained in pVIC40 is released from feedback inhibition by L-threonine.

The *Escherichia coli* VKPM B-5318 strain (EP 0593792B) may also be used as an L-threonine-producing strain. VKPM B-5318 was deposited at the Russian National Collection of Industrial Microorganisms (VKPM), GNII Genetika with a registration number of VKPM B-5318 on Nov. 19, 1987. The VKPM B-5318 strain is auxotrophic to L-isoleucine, and the threonine operon encoding the threonine biosynthesis enzyme is located downstream of the C1 temperature-sensitive represser, the PR-promoter, and the N-terminus end of the Cro protein derived from λphage. Moreover, this strain contains plasmid DNA which was constructed so that expression of the threonine biosynthesis gene is regulated by the promoter and represser from λphage.

Furthermore, the *Escherichia coli* MG442 strain (U.S. Pat. No. 4,278,765) may also be used as an L-threonine-producing strain. The MG442 strain was deposited at the Russian National Collection of Industrial Microorganisms (VKPM) as CMIMB-1628.

Examples of *Escherichia* bacteria having an ability to produce L-phenylalanine include *Escherichia coli* AJ12739 (tyrA::Tn10, TyrR; VKPM B-8197) in which the tyrA and tyrR genes are disrupted, *Escherichia coli* HW1089 in which a mutated pheA has been introduced, (U.S. Pat. No. 5,354,672), and an *Escherichia coli* strain in which the yddG and yedA genes have been amplified (WO 03/044192). Examples of *Coryneform* bacteria having an ability to produce L-phenylalanine include a strain which is auxotrophic for tyrosine and resistant to L-phenylalanyl-L-tyrosine (JP5-49489A).

Bacteria having an ability to produce L-tryptophan can be obtained by enhancing the activities of the L-tryptophan-biosynthetic enzymes including phosphoglycerate dehydrogenase and anthranilate synthase. These enzymes may be resistant to feedback inhibition by L-tryptophan or L-serine. For example, a bacterium having these feedback-resistant enzymes can be obtained by introducing plasmid pGH5, which contains a mutant serA gene encoding L-tryptophan-resistant phosphoglycerate dehydrogenase, into *Escherichia coli* SV164 strain which harbors a gene encoding L-serine-resistant anthranilate synthase (WO94/08031).

Bacteria having an ability to produce L-tryptophan can also be obtained by enhancing the activities of L-tryptophan-biosynthetic enzymes encoded by the tryptophan operon. Such enzymes in the L-tryptophan operon include tryptophan synthase and anthranilate synthase. Examples of these bacteria include an *Escherichia coli* strain in which the tryptophan operon containing a gene encoding L-serine-resistant anthranilate synthase is introduced (JP57-71397A, JP62-244382A, and U.S. Pat. No. 4,371,614).

In addition, examples of bacteria having an ability to produce L-tryptophan include *Escherichia coli* AGX17(pGX44) [NRRL B-12263] which is auxotrophic for L-phenylalanine and L-tyrosine, and AGX6(pGX50)aroP [NRRL B-12264] which harbors plasmid pGX50 containing the tryptophan operon (U.S. Pat. No. 4,371,614).

Examples of *Escherichia* bacteria having an ability to produce L-isoleucine include a mutant strain resistant to 6-dimethylaminopurine (JP5-304969A), a mutant strain resistant to L-isoleucinehydroxamate, thiaisoleucine, DL-ethionine, or argininehydroxamate (JP5-130882A), and a recombinant strain in which a gene encoding threonine deaminase and acetohydroxylic acid synthase have been amplified with a plasmid (JP2-458A, JP2-42988A and JP8-47397A).

Bacteria having an ability to produce L-valine can be obtained by enhancing the activities of L-valine biosynthetic enzymes including those encoded by the ilvGMEDA operon, especially acetohydroxylate synthase encoded by the ilvG gene (JP02-748418B). These enzymes may be resistant to feedback inhibition by L-valine.

Bacteria having an ability to produce L-valine include those which have decreased expression of the acetolactate synthase III gene (ilvIH gene).

Bacteria having an ability to produce L-valine may be resistant to amino acid analogues. Examples of such bacteria include a mutant strain which is auxotrophic for L-isoleucine and L-methionine, and is resistant to D-ribose, purine nucleoside, or pyrimidine ribonucleoside (FERM P-1841, P-5556; JP53-025034A), and a mutant strain resistant to polyketonoid (FERM P-9325; JP04-045314B).

Examples of bacteria having an ability to produce L-alanine include a *Coryneform* bacterium strain which is deficient in $H^+$-ATPase activity (Appl Microbiol Biotechnol. 2001 November; 57(4):534-40) or a *Coryneform* bacterium strain in which aspartic acid β-decarboxylase gene is amplified (JP07-163383A).

Furthermore, it preferable that the bacterium of the present invention is further modified to have reduced activity of 6-phosphofructokinase. 6-phosphofructokinase activity can be measured by the method described by, for example, Denise Kotlars and Henri Buc (Methods in Enzymology (1982) 90: 60-70). The activity of 6-phosphofructokinase in the bacterium of the present invention is reduced less than that of a wild-type or non-modified strain, preferably less than 90%, more preferably less than 70%, and most preferably not less than 50% of a wild-type or non-modified strain. The activity of 6-phosphofructokinase can be reduced by mutating or disrupting a gene encoding this enzyme, wherein said method can be similar to the method used to reduce α-ketoglutarate dehydrogenase activity.

In the present invention, useful metabolites can be produced by cultivating the above-mentioned bacteria in a culture medium, allowing accumulation of the useful metabolite into the culture medium and/or bacterial cells, and collecting said useful metabolite from the culture medium and/or bacterial cells.

Cultivation, collection, and purification of useful metabolites from the medium, may be performed by conventional fermentation methods wherein a useful metabolite is produced using a bacterium. The culture medium may either be synthetic or natural, so long as the medium contains a carbon source and a nitrogen source and minerals and, if necessary, appropriate amounts of nutrients which the bacterium requires for growth. The carbon source includes various carbohydrates such as glucose and sucrose, and various organic acids. Depending on the mode of assimilation of the chosen bacterium, alcohol, including ethanol and glycerol, may be used. As the nitrogen source, ammonia, ammonium sulfate, other nitrogen compounds such as amines, a natural nitrogen source such as peptone, soybean-hydrolysate, and digested fermentative microorganism may be used. As minerals, potassium monophosphate, magnesium sulfate, sodium chloride, ferrous sulfate, manganese sulfate, calcium chloride, and the like may be used. In this invention, it is more desirable to add thiamine hydrochloride (vitamin B1) into the culture medium. The concentration of thiamine hydrochloride is more than 10 μg/L, preferably more than 10 mg/L, more preferably less than 100 mg/L.

The cultivation is performed preferably under aerobic conditions such as a shaking culture, and stirring culture with aeration, at a temperature of 20 to 42° C., preferably 37 to 40° C. The pH of the culture medium is usually between 5 and 9, preferably between 6.5 and 7.2. The pH of the culture medium can be adjusted with ammonia, calcium carbonate, various acids, various bases, and buffers. Usually, 1 to 5-day cultivation is sufficient for the accumulation of the target useful metabolite in the liquid medium.

After cultivation, solids such as cells can be removed from the liquid medium by centrifugation or membrane filtration, and then the target useful metabolite can be collected and purified by ion-exchange, concentration, and crystallization methods etc.

EXAMPLES

The present invention will be explained more specifically below with reference to the following non-limiting Examples. Abbreviations: Pyr—pyruvate, PEP—phosphoenolpyruvate, GA-3P—glyceraldehydes-3-phosphate, Ace-CoA—acetyl-CoA. Theoretical weight yield (Y) is calculated as $$Y=(\text{molecular weight of product}\times\text{moles})/(\text{molecular weight of substrate}\times\text{moles}).$$

Equations are simplified and show only carbon compounds and energy molecules.

Example 1

Calculation of Acetyl-CoA Formation by Bacterium with or without Phosphoketolases Activities 1. Reactions of Acetyl-CoA Biosynthetic Pathway which does not Involve Phosphoketolases Activities.

PTS system followed by glycolysis gives the following equation:

Glucose=PEP+Pyr+ATP+2 NADH

Phosphoenolpyruvate carboxylase encoded by ppc gene catalyzes the following reaction:

$PEP+CO_2$=oxaloacetate

Pyruvate dehydrogenase encoded by pdh gene catalyzes the following reaction:

Pyr=acetyl-CoA+$CO_2$+NADH

And final equation is:

Glucose=acetyl-CoA+oxaloacetate+ATP+3 NADH (A)

2. Reactions of Acetyl-CoA Biosynthetic Pathway which Involves Phosphoketolases Activities.

PTS system followed by glycolysis gives the following equation:

Glucose+PEP=fructose-6-phosphate+Pyr

Phosphoenolpyruvate synthase catalyzes the following reaction:

Pyr+ATP=PEP

Phosphoenolpyruvate carboxylase coded by ppc gene catalyzes the following reaction:

$PEP+CO_2$=oxaloacetate

Fructose-6-phosphate phosphoketolase:

Phosphate+fructose-6-phosphate=$H_2O$+erythrose-4-phosphate+acetyl phosphate

Transaldolase and transketolase:

fructose-6-phosphate+erythrose-4-phosphate=2 xylulose-5-phosphate

D-xylulose-5-phosphate phosphoketolase:

Phosphate+xylulose-5-phosphate=glyceraldehyde-3-phosphate+acetyl phosphate

Glycolysis:

Glyceraldehyde-3-phosphate=PEP+2 ATP+2 NADH

Phosphate acetyltransferase encoded by pta gene

Acetylphosphate=acetyl-CoA

And final equation is:

2 glucose+2$CO_2$=3 acetyl-CoA+2 oxaloacetate+NADH (B)

Comparison of equations (A) and (B) shows that using the activities of phosphoketolases allows generation of 1.5 molecules of acetyl-CoA from 1 molecule of glucose and saves 1 molecule of $CO_2$ in the contrast to the 1 molecule of acetyl-CoA obtained from 1 molecule of glucose in the glucose metabolism without the activities of phosphoketolases.

Example 2

Calculation of Theoretical Yield of L-Glutamic Acid Production Using Bacterium with or without Phosphoketolases Activities 1. Reactions of L-Glutamic Acid Biosynthetic Pathway which Involves PTS, Glycolysis, and the TCA Cycle.

PTS+glycolysis:

glucose=acetyl-CoA+oxaloacetate+ATP+3 NADH (A)

TCA cycle:

acetyl-CoA+oxaloacetate=2-oxoglutarate+NADPH+$CO_2$

Glutamate dehydrogenase:

2-oxoglutarate+$NH_3$+NADPH=glutamic acid

Final equation:

glucose=glutamic acid+ATP+3 NADH+$CO_2$ (C)

Theoretical weight yield of L-glutamic acid is 81.7%

2. Reactions of L-Glutamic Acid Biosynthetic Pathway which Involves Glycolysis, Non-Oxidative PPC, and D-xylulose-5-phosphate Phosphoketolase Only Glycolysis and non oxidative PPC:

5 glucose+5 PEP=5 fructose-6-phosphate+5 Pyr, where fructose-6-phosphate+ATP=2 GA-3P 2 fructose-6-phosphate+2 GA-3P=2 xylulose-5-phosphate+2 erythrose-4-phosphate 2 fructose-6-phosphate+2 erythrose-4-phosphate=4 xylulose-5-phosphate Summary equation:

5 glucose+5 PEP+ATP=6 xylulose-5-phosphate+5 Pyr

Then, D-xylulose-5-phosphate phosphoketolase:

Xylulose-5-phosphate+phosphate=GA-3P+acetylphosphate

Glycolysis and phosphate acetyltransferase:

GA-3P=PEP+ATP+NADH

Acetylphosphate=acetyl-CoA

Summary equation:

5 glucose=6 acetyl-CoA+PEP+5 ATP+6 NADH+5 PYR (1)

Phosphoenolpyruvate synthase

PYR+2 ATP=PEP+phosphate

Presuming that NADH=2 ATP

Summary equation:

5 glucose=6 acetyl-CoA+6 PEP+7 ATP

Phosphoenolpyruvate carboxylase (ppc):

PEP+$CO_2$=oxaloacetate

Summary equation:

5 glucose+6$CO_2$=6 acetyl-CoA+6 oxaloacetate+7 ATP (2)

TCA cycle:

Oxaloacetate+acetyl-CoA=oxoglutarate+$CO_2$+NADPH

Summary equation:

5 glucose=6 oxoglutarate+6 NADPH+7 ATP

Glutamate dehydrogenase:

Oxoglutarate+NADPH=glutamic acid

Final equation:

5 glucose=6 glutamic acid+7 ATP (D)

Theoretical weight yield of L-glutamic acid is 98%

3. Reactions of L-Glutamic Acid Biosynthetic Pathway which Involve Glycolysis, Non-Oxidative PPC, Both Phosphoketolases and Glyoxalate Bypass PTS+glycolysis:

2 glucose+2 PEP=2 fructose-6-phosphate+2 PYR fructose-6-phosphate phosphoketolase2:

fructose-6-phosphate+phosphate=erythrose-4-phosphate+acetylphosphate

Transaldolase and transketolase:

fructose-6-phosphate+erythrose-4-phosphate=2 xylulose-5-phosphate

Xylulose-5-phosphate phosphoketolase:

2 xylulose-5-phosphate+2 phosphate=2 GA-3P+2 acetylphosphate

Summary equation:

2 glucose+2 PEP=2 GA-3P+3 acetylphosphate+2 PYR

Glycolysis:

GA-3P=PEP+ATP+NADH

Summary equation:

2 glucose=3 acetylphosphate+2 PYR+2 ATP+2 NADH (3)

Phosphoenolpyruvate synthase:

PYR+2 ATP=PEP

Phosphate acetyltransferase:

Acetylphospate=acetyl-CoA

Summary equation:

2 glucose=3 acetyl-CoA+2 PEP+NADH

Phosphoenolpyruvate carboxylase:

PEP+$CO_2$=oxaloacetate

Summary equation:

$$2\ glucose+2CO_2=3\ acetyl\text{-}CoA+2\ oxaloacetate+NADH\ or$$

$$6\ glucose+6CO_2=9\ acetyl\text{-}CoA+6\ oxaloacetate+3\ NADH \quad (4)$$

Glyoxalate bypass:

2 Acetyl-CoA=succinate+NADH

TCA cycle:

Succinate=oxaloacetate+ATP+NADH

Summary equation:

$$6\ glucose+6CO_2=7\ acetyl\text{-}CoA+7\ oxaloacetate+ATP+5\ NADH$$

TCA cycle:

$$Acetyl\text{-}CoA+oxaloacetate=2\text{-}oxoglutarate+NADPH+CO_2$$

Glutamate dehydrogenase:

$$2\text{-}oxoglutarate+NH_3+NADPH=glutamic\ acid$$

Final equation:

$$6\ glucose=7\ glutamic\ acid+ATP+5\ NADH+CO_2$$

$$or\ 6\ glucose=7\ glutamic\ acid+11\ ATP+CO_2 \quad (E)$$

Theoretical weight yield of L-glutamic acid is 95.3%

Comparison of equations (C), (D), and (E) shows that using the activities of phosphoketolases significantly increases theoretical yield of L-glutamic acid biosynthesis and allows generation of 1 more molecule of L-glutamic acid than molecules of glucose utilized and prevents $CO_2$ release in contrast to 1 molecule of L-glutamic acid obtained from 1 molecule of glucose in the glucose metabolism without the activities of phosphoketolases.

Example 3

Calculation of Theoretical Yield of Succinate Production Using a Bacterium with or without Phosphoketolases Activities 1. Reactions of Succinate Biosynthetic Pathway which Involves PTS, Glycolysis, and the TCA Cycle.

PTS+glycolysis:

glucose=PEP+PYR+ATP+2 NADH

Phosphoenolpyruvate carboxylase:

$$PEP+CO_2=oxaloacetate$$

Pyruvate dehydrogenase:

$$PYR=acetyl\text{-}CoA+CO_2+NADH$$

Summary equation:

Glucose=oxaloacetate+acetyl-CoA+ATP+3 NADH

TCA cycle:

$$Oxaloacetate+acetyl\text{-}CoA=succinate+NADPH+NADH+ATP+2CO_2$$

Final equation:

$$Glucose=succinate+NADPH+4\ NADH+2\ ATP+2CO_2$$

or presuming that NADH=NADPH=2 ATP $$Glucose=succinate+12\ ATP+2CO_2 \quad (F)$$

Theoretical weight yield of succinate is 65%.

2. Reactions of Succinate Biosynthetic Pathway which Involve Glycolysis, Non-Oxidative PPC, and D-xylulose-5-phosphate Phosphoketolase Only Glycolysis, non oxidative PPC, D-xylulose-5-phosphate phosphoketolase, phosphate acetyltransferase and phosphoenolpyruvate carboxylase gives summary equation (see Example 2, equation 2):

$$5\ glucose+6CO_2=6\ acetyl\text{-}CoA+6\ oxaloacetate+7\ ATP$$

TCA cycle:

$$Oxaloacetate+acetyl\text{-}CoA=succinate+NADPH+NADH+ATP+2CO_2$$

Final equation:

$$5\ glucose=6\ succinate+6CO_2+6\ NADPH+25\ ATP$$

or presuming that NADH=NADPH=2 ATP $$5\ glucose=6\ succinate+6CO_2+37\ ATP \quad (G)$$

Theoretical weight yield of succinate is 79%

3. Reactions of Succinate Biosynthetic Pathway which Involve Glycolysis, Non-Oxidative PPC, Both Phosphoketolases and Glyoxalate Bypass Glycolysis, non-oxidative PPC, fructose-6-phosphate-phosphoketolase, D-xylulose-5-phosphate phosphoketolase, phosphate acetyltransferase, and phosphoenolpyruvate carboxylase gives summary equation (see Example 2, equation 4):

$$2\ glucose+2CO_2=3\ acetyl\text{-}CoA+2\ oxaloacetate+NADH\ or$$

$$4\ glucose+4CO_2=6\ acetyl\text{-}CoA+4\ oxaloacetate+2\ NADH$$

TCA cycle:

$$Oxaloacetate+acetyl\text{-}CoA=succinate+NADPH+NADH+ATP+2CO_2$$

Summary equation:

$$4\ glucose=4\ succinate+2\ acetyl\text{-}CoA+4CO_2+4\ NADPH+6\ NADH$$

Glyoxylate bypass:

2 acetyl-CoA=succinate+NADH

Final equation:

$$4\ glucose=5\ succinate+4CO_2+4\ NADPH+7\ NADH$$

or presuming that NADH=NADPH=2 ATP $$4\ glucose=5\ succinate+4CO_2+22\ ATP \quad (H)$$

Theoretical weight yield of succinate is Y=82%

Comparison of equations (F), (G), and (H) shows that using the activities of phosphoketolases significantly increases theoretical yield of succinate biosynthesis and allows generation of 1 more molecule of succinate than molecules of glucose utilized, and prevents $CO_2$ release in contrast to 1 molecule of succinate obtained from 1 molecule of glucose in the glucose metabolism without the activities of phosphoketolases.

Example 4

Calculation of Theoretical Yield of L-leucine Production Using Bacterium with or without Phosphoketolases Activities 1. Reactions of L-Leucine Biosynthetic Pathway which Involves PTS and Glycolysis.

Glycolysis:

glucose=2 PYR+2 ATP+2 NADH

L-leucine biosynthesis:

2 PYR+NADPH=2-keto-isovalerate+$CO_2$ 2-keto-isovalerate+acetyl-CoA+L-glutamic acid=leucine+NADH+2-oxoglutarate+$CO_2$ or 2-keto-isovalerate+acetyl-CoA=leucine+NADH−NADPH+$CO_2$ where NADPH is used for regeneration of L-glutamic acid Pyruvate dehydrogenase PYR=acetyl-CoA+NADH+$CO_2$ Summary equation:

3 PYR=leucine+2 NADH−2 NADPH+3$CO_2$

Final equation:

3 glucose=2 leucine+4 NADH−4 NADPH+6$CO_2$+6 ATP+6 NADH or presuming that NADH=NADPH=2 ATP 3 glucose=2 leucine+18 ATP+6$CO_2$ (I)

Theoretical weight yield of L-leucine is Y=48%

2. Reactions of L-leucine Biosynthetic Pathway which Involves Glycolysis, Non Oxidative PPC, and D-xylulose-5-phosphate Phosphoketolase Only Glycolysis, non oxidative PPC, D-xylulose-5-phosphate phosphoketolase, and phosphate acetyltransferase gives summary equation (see Example 2, equation 1):

5 glucose=6 acetyl-CoA+PEP+5 ATP+6 NADH+5 PYR

Pyruvate kinase:

PEP=PYR+ATP

Summary equation:

5 glucose=6 acetyl-CoA+6 PYR+6 ATP+6 NADH

L-leucine biosynthesis:

2 PYR+acetyl-CoA=leucine+NADH−2 NADPH+2$CO_2$

Summary equation:

5 glucose=3 leucine+3 acetyl-CoA+6 ATP+9 NADH−6 NADPH+6$CO_2$ (5)

Another act of glycolysis gives:

3 glucose=6 PYR+18 ATP (6)

Adding equations 5 and 6:

3 glucose=6 PYR+18 ATP

+

5 glucose=3 leucine+3 acetyl-CoA+6 ATP+9 NADH−6 NADPH+6$CO_2$

=

8 glucose=3 leucine+(6 PYR+3Ace-CoA)+9 NADH−6 NADPH+24 ATP+6$CO_2$

Final equation:

8 glucose=6 leucine+24 ATP+12 NADH−12 NADPH+12 $CO_2$ or presuming that NADH=NADPH 8 glucose=6 leucine+12 $CO_2$+24 ATP (J)

Theoretical weight yield of L-leucine is Y=55%

3. Reactions of L-leucine Biosynthetic Pathway which Involves Glycolysis, Non-Oxidative PPC, and Both Phosphoketolases.

Glycolysis, non oxidative PPC, fructose-6-phosphatephosphoketolase, D-xylulose-5-phosphate phosphoketolase gives summary equation (see Example 2, equation 3):

2 glucose=3 acetylphosphate+2 PYR+2 ATP+2 NADH

Phosphate acetyltransferase:

Acetylphospate=acetyl-CoA

Summary equation:

2 glucose=3 acetyl-CoA+2 PYR+2 ATP+2 NADH

L-leucine biosynthesis:

2 PYR+acetyl-CoA=leucine+NADH−2 NADPH+2$CO_2$

Summary equation:

2 glucose=leucine+2 acetyl-CoA+2 ATP+3 NADH−2 NADPH+2$CO_2$ (7)

Another act of glycolysis gives:

2 glucose=3 PYR+12 ATP (8)

Adding equations 7 and 8:

2 glucose=leucine+2 acetyl-CoA+2 ATP+3 NADH−2 NADPH+2$CO_2$

+

2 glucose=4 PYR+12 ATP

=

4 glucose=leucine+(4 PYR+2 acetyl-CoA)+14 ATP+3 NADH−2 NADPH+2$CO_2$

L-leucine biosynthesis:

4 PYR+2 acetyl-CoA=2 leucine+2 NADH−4 NADPH+4$CO_2$

Final equation:

4 glucose=3 leucine+14 ATP+5 NADH−6 NADPH+6$CO_2$ or presuming that NADH=NADPH=2 ATP 4 glucose=3 leucine+6$CO_2$+12 ATP (K)

Theoretical weight yield of L-leucine is Y=55%

Comparison of equations (I), (J), and (K) shows that using the activities of phosphoketolases significantly increases theoretical yield of L-leucine biosynthesis.

Example 5

Cloning of Phosphoketolase Gene (Xpk1) from *Lactobacillus plantarum* and Evaluation of the Effect of Xpk1 Gene Amplification on Production of Useful Metabolites by *E. coli*

The xpk1 gene can be cloned from chromosomal DNA of the *Lactobacillus plantarum* strain 8PA3 (VKPM B-7495). Based on the reported nucleotide sequence, the primers depicted in SEQ ID No. 7 (primer 1) and No. 8 (primer 2) for amplification of xpk1 gene can be synthesized. The primer 1 contains a HindIII recognition site introduced at the 5'-end thereof. The primer 2 contains EcoRI recognition site introduced at the 5'-end thereof.

The chromosomal DNA of *Lactobacillus plantarum* strain 8PA3 can be used as a template for PCR and can be prepared by an ordinary method. PCR can be carried out using "Applied Biosystems GeneAmp PCR System 2400" under the following conditions: initial DNA denaturation at 95° C. for 5 min; then 30 cycles of denaturation at 95° C. for 30 sec, annealing at 55° C. for 60 sec and elongation at 72° C. for 120 sec; the final polymerization for 7 min at 72° C. using Fermentas Taq polymerase (Fermentas, Lithuania). The obtained PCR fragment containing xpk1 gene with its own SD sequence and without a promoter sequence can be treated with HindIII and EcoRI and inserted in the vector pMW119 previously treated with the same enzymes. Thus, the plasmid pMW-xpk1 can be obtained.

Transformation of an useful metabolite-producing bacterial strain with the pMW-xpk1 plasmid can be performed by an ordinary method to obtain the strain containing amplified xpk1 gene.

Production of L-Glutamic Acid by *E. coli* Strain VL334thrC$^+$-pMW-xpk1.

Transformation of the *E. coli* L-glutamic acid producing strain VL334thrC$^+$ (European patent publication No. 1172433) with the pMW-xpk1 plasmid can be performed by an ordinary method to obtain the strain VL334thrC$^+$-pMW-xpk1.

Both strains, VL334thrC$^+$ and VL334thrC$^+$-pMW-xpk1, can be grown for 18-24 hours at 37° C. on L-agar plates. Then, one loop of the cells can be transferred into test tubes containing 2 ml of fermentation medium. The fermentation medium should contain 60 g/l glucose, 25 g/l ammonium sulfate, 2 g/l $KH_2PO_4$, 1 g/l $MgSO_4$, 0.1 mg/ml thiamine, 70 μg/ml L-isoleucine and 25 g/l chalk (pH 7.2). Glucose and chalk should be sterilized separately. Cultivation can be carried out at 30° C. for 3 days with shaking. After cultivation, the amount of L-glutamic acid which has accumulated can be determined by paper chromatography (liquid phase composition: butanol-acetic acid-water=4:1:1) with subsequent staining by ninhydrin (1% solution in acetone) and further elution of compounds in 50% ethanol with 0.5% $CdCl_2$.

Production of L-Proline by *E. coli* Strain 702ilvA-pMW-xpk1.

Transformation of the *E. coli* L-proline producing strain 702ilvA (VKPM B-8012, Russian patent application 2000124295, European patent publication NO. 1172433) with the pMW-xpk1 plasmid can be performed by an ordinary method to obtain the strain 702ilvA-pMW-xpk1.

Both *E. coli* strains 702ilvA and 702ilvA-pMW-xpk1 can be grown for 18-24 hours at 37° C. on L-agar plates. Then, these strains can be cultivated in the same conditions as described above.

Production of L-Leucine by *E. coli* Strain 57-pMW-xpk1

Transformation of the *E. coli* L-leucine producing strain 57 (VKPM B-7386, U.S. Pat. No. 6,124,121) with the pMW-xpk1 plasmid can be performed by an ordinary method to obtain the strain 57-pMW-xpk1.

Both *E. coli* strains 57 and 57-pMW-xpk1 can be grown for 18-24 hours at 37° C. on L-agar plates. Then, these strains can be cultivated under the same conditions as described above without addition of isoleucine in the medium.

Production of L-cysteine by *E. coli* strain JM15(ydeD)-pMW-xpk1.

Transformation of the *E. coli* L-cysteine producing strain JM15(ydeD) with the pMW-xpk1 plasmid can be performed by an ordinary method to obtain the strain JM15(ydeD)-pMW-xpk1.

*E. coli* strain JM15(ydeD) is a derivative of *E. coli* strain JM15 (U.S. Pat. No. 6,218,168) which can be transformed with the DNA having ydeD gene coding for a membrane protein, which is not involved in biosynthetic pathway of any L-amino acid (U.S. Pat. No. 5,972,663).

Fermentation conditions for evaluation of L-cysteine production are described in detail in Example 6 of U.S. Pat. No. 6,218,168.

Production of L-Glutamic Acid by *Pantoea ananatis* Strain AJ13356-xpk1.

Transformation of the L-glutamic acid-producing *Enterobacter agglomerans* AJ13356 strain (U.S. Pat. No. 6,331,419) (recently re-classified as *Pantoea ananatis*) with the pMW-xpk1 plasmid can be performed by an ordinary method to obtain the strain AJ13356-pMW-xpk1.

Each of the AJ13356 and AJ13356-xpk1 strains can be inoculated into a 500 ml-volume flask which contains 20 ml of a culture medium comprising 40 g/L glucose, 20 g/L ammonium sulfate, 0.5 g/L magnesium sulfate heptahydrate, 2 g/L potassium dihydrogenphosphate, 0.5 g/L sodium chloride, 0.25 g/L calcium chloride heptahydrate, 0.02 g/L ferrous sulfate heptahydrate, 0.02 g/L manganese sulfate tetrahydrate, 0.72 mg/L zinc sulfate dihydrate, 0.64 mg/L copper sulfate pentahydrate, 0.72 mg/L cobalt chloride hexahydrate, 0.4 mg/L boric acid, 1.2 mg/L sodium molybdate dihydrate, 2 g/L yeast extract, 30 g/L calcium carbonate, 200 mg/L L-lysine monohydrochloride, 200 mg/L L-methionine and 200 mg/L DL-α,ε-diaminopimelic acid (DAP), and can be cultured at 37° C. with shaking until the glucose contained in the culture medium is completely consumed. After the cultivation is completed, L-glutamic acid which has accumulated in the culture medium can be measured as above.

Example 6

Confirmation of Physiological Activity of Phosphoketolase Gene Using *Coryneform* Bacterium (6-1) Cloning of phosphoketolase Gene and Construction of Expression Plasmid (1) Construction of pVK9-xfp The xfp gene was cloned from chromosomal DNA of the strain *Bifidobacterium animalis* JCM1190. Based on the reported nucleotide sequence of the xfp gene of *Bifidobacterium animalis* ATCC 27674 (GenBank Accession No. AY518213, SEQ ID No: 9), the primers depicted in SEQ ID No: 13 and No: 14 can be synthesized and used for amplification of the xfp gene. *Bifidobacterium animalis* JCM1190 can be obtained from the Japan Collection of Microorganisms (JCM).

The DNA sequence of the xfp gene from *B. animalis* JCM1190 is shown in SEQ ID No. 11.

In order to amplify the xfp gene (SEQ ID NO: 11) from *Bifidobacterium animalis* JCM1190 and clone it into a pVK9 *E. coli*-coryneform shuttle vector, chromosomal DNA of *Bifidobacterium animalis* JCM1190 was extracted using the Wizard Genomic Purification Kit (Promega). The pVK9 is an *E. coli*-coryneform shuttle vector, obtained by digesting pHK4 (JP 5-007491A) with BamHI and KpnI to obtain the region including its replicable origin and introducing the region into the AvaII site of pHSG299 (product of Takara Bio Inc.) The xfp gene fragment including a promoter region was amplified by PCR using the chromosomal DNA of *B. anima-*

*lis* as a template and using the primers shown in SEQ ID NO: 13 and NO: 14 as primers. PCR was carried out by a conventional method.

The resulting PCR product was purified in a conventional manner and digested with Xba I. The digested PCR product was ligated by using Ligation Kit (product of Takara Bio Inc) to pVK9 which had been digested with Xba I. The ligation mixture was used to transform competent cells of *Escherichia coli* DH5α (product of Takara Bio Inc.). The cells were plated on LB medium (10 g of bacto-tryptone, 5 g of bacto-yeast extract and 10 g of NaCl in 1 L) containing 100 μM of IPTG, 40 mg/ml of X-Gal and 25 mg/ml of Km and cultured overnight. Then, the white colonies which emerged were selected and separated into single colonies to obtain transformants. The target plasmid pVK9-xfp containing the xfp gene was isolated from the transformants.

(2) Construction of pVK9-PS2_xfp

A DNA fragment, wherein a native promoter region of *B. animalis* xfp gene was replaced with a PS2 promoter (Peyret J L, Mol Microbiol. 1993 Jub9(1):97-109, WO93/03158), was obtained in accordance with the overlap PCR method (R. M. Horton, H. D. Hunts, S. N. Ho, J. K. Pullen, and L. R. Pease, Gene, 77, 61-68 (1989)). The method is specifically described below.

First, PCR was performed by using pPSTG1 containing the PS2 promoter (Y. Kikuchi, M. Date, K. Yokoyama, Y. Umezawa and H. Matsui, Appl. Environ. Microbiol. Appl. Environ. Microbiol 69, 358-366 (2003)) as a template and the synthetic DNAs of SEQ ID NO: 15 and No: 16 as primers to obtain an amplification product of the PS2 promoter. Then, in order to obtain an amplification product of a sequence of the xfp gene (coding region), PCR was performed using the pVK9-xfp as a template and the synthetic DNAs of SEQ ID NO: 17 and NO: 18 as primers. SEQ ID NO: 16 and NO: 18 are complementary to each other.

Then, in order to obtain a fragment containing the PS2 promoter and the *B. animalis* xfp gene, the aforementioned gene fragments of PS2 promoter and the *B. animalis* xfp gene were mixed in substantially equimolar amounts, and PCR was performed using this mixture as a template and the synthetic DNAs of SEQ ID NO: 14 and NO: 19 as primers.

The resulting PCR product was purified in a conventional manner and digested with Xba I. The digested PCR product was ligated by using Ligation Kit (product of Takara Bio Inc) to pVK9 which had been digested with Xba I. The ligation mixture was used to transform competent cells of *Escherichia coli* DH5α (product of Takara Bio Inc.). The cells were plated on LB medium (10 g of bacto-tryptone, 5 g of bacto-yeast extract and 10 g of NaCl in 1 L) containing 100 μM of IPTG, 40 mg/ml of X-Gal and 25 mg/ml of Km and cultured overnight. Then, the white colonies which emerged were selected and separated into single colonies to obtain transformants. The object plasmid pVK9-PS2_xfp containing the PS2 promoter and xfp gene was isolated from the transformants.

(3) Construction of pVK9-tac_xfp

A DNA fragment wherein the native promoter region of the *B. animalis* xfp gene was replaced with a tac promoter was obtained in accordance with the overlap PCR method (R. M. Horton, H. D. Hunt, S. N. Ho, J. K. Pullen and L. R. Pease, Gene, 77, 61-68 (1989)). The method is specifically described below.

First, PCR was performed by using the pKK223-3 (Pharmacia) as a template and the synthetic DNAs of SEQ ID NO: 20 and NO: 21 as primers to obtain an amplification product of the tac promoter. Then, in order to obtain an amplification product of a sequence of the xfp gene (coding region), PCR was performed using the chromosomal DNA of *B. animalis* JCM1190 as a template and synthetic DNAs SEQ ID NO:14 and NO: 22 as primers. The nucleotide sequences of SEQ ID NO: 20 and NO: 22 are complementary to each other.

Then, in order to obtain a fragment containing the tac promoter and the *B. animalis* xfp gene, the aforementioned gene fragments of the tac promoter and the *B. animalis* xfp gene were mixed in substantially equimolar amounts, and PCR was performed using this mixture as a template and synthetic DNAs SEQ ID NO: 14 and NO: 21 as primers.

The resulting PCR product was purified in a conventional manner and digested with Xba I. The digested PCR product was ligated by using Ligation Kit (product of Takara Bio Inc) to pVK9 which had been digested with Xba I. The ligation mixture was used to transform competent cells (product of Takara Bio Inc.) of *Escherichia coli* DH5α. The cells were plated on LB medium (10 g of bacto-tryptone, 5 g of bacto-yeast extract and 10 g of NaCl in 1 L) containing 100 μM of IPTG, 40 mg/ml of X-Gal and 25 mg/ml of Km and cultured overnight. Then, the white colonies which emerged were selected and separated into single colonies to obtain transformants. The object plasmid pVK9-tac_xfp containing the xfp gene and tac promoter was isolated from the transformants.

(4) Construction of pVK9-PS2_xpkA

The xpkA gene was cloned from chromosomal DNA of the strain *Lactobacillus pentosus* JCM1558. *Lactobacillus pentosus* JCM1558 can be obtained from the Japan Collection of Microorganisms (JCM). In order to amplify an xpkA gene encoding phosphoketolase (SEQ ID NO: 1; AJ309011: gi: 16605513) from *Lactobacillus pentosus* JCM1558 and clone it into a pVK9 shuttle vector, the chromosomal DNA of *Lactobacillus pentosus* JCM1558 was extracted using a Wizard Genomic Purification Kit (Promega).

A DNA fragment was obtained by replacing the promoter region of the *L. pentosus* xpkA gene encoding phosphoketolase with a PS2 promoter in accordance with the overlap PCR method. The method is specifically described herein.

First PCR was performed by using pPSTG1 containing the PS2 promoter (Y. Kikuchi, M. Date, K. Yokoyama, Y. Umezawa and H. Matsui, Appl. Environ. Microbiol. Appl. Environ. Microbiol 69, 358-366 (2003)) as a template and the synthetic DNAs of SEQ ID NO: 15 and No: 23 as primers to obtain an amplification product of the PS2 promoter. Then, in order to obtain an amplification product of a sequence of the xpkA gene (coding region), PCR was performed using the chromosomal DNA of *Lactobacillus pentosus* JCM1558 as a template and the synthetic DNAs of SEQ ID NO: 24 and NO: 25 as primers. The nucleotide sequences of SEQ ID NO: 23 and NO: 25 are complementary to each other.

Then, in order to obtain a fragment containing the PS2 promoter and *L. pentosus* xpkA gene, the aforementioned gene fragments of PS2 promoter and the *L. pentosus* xpkA gene were mixed in substantially equimolar amounts, and PCR was performed using this mixture as a template and the synthetic DNAs of SEQ ID NO: 19 and NO: 24 as primers.

The resulting PCR product was purified in a conventional manner and digested with Xba I. The digested PCR product was ligated by using Ligation Kit (product of Takara Bio Inc) to pVK9 which had been digested with Xba I. The ligation mixture was used to transform competent cells (product of Takara Bio Inc.) of *Escherichia coli* DH5α. The cells were plated on LB medium (10 g of bacto-tryptone, 5 g of bacto-yeast extract and 10 g of NaCl in 1 L) containing 100 μM of IPTG, 40 mg/ml of X-Gal and 25 mg/ml of Km and cultured overnight. Then, the white colonies which emerged were selected and separated into single colonies to obtain transformants. The object plasmid pVK9-PS2_xpkA containing the PS2 promoter and xpkA was isolated from the transformants.

(6-2) Confirmation of the In Vivo Physiological Activity of Phosphoketolase (1) Construction of ATCC13869ΔaceE Strain A PDH-defective strain is auxotrophic for acetate. On the other hand, a PDH (pyruvate dehydrogenase)-defective strain into which the phosphoketolase gene is introduced will not be auxotrophic for acetate any more. Accordingly, the effect of the introduction of the xfp or xpkA gene was confirmed.

Construction of a Gene-Disruption Vector (A) Construction of pBS3

With chromosomal DNA of *Bacillus subtilis* as a template for PCR and synthetic DNAs of SEQ ID NO: 42 and NO: 43 as primers, a sacB gene (SEQ ID NO: 40) was obtained by PCR. The PCR reaction was conducted by, after 1 cycle maintaining 94° C. for 5 minutes, repeating 25 times a cycle of 94° C. for 30 seconds, 49° C. for 30 seconds and 72° C. for 2 minutes, using LA taq (TaKaRa Bio). The PCR product was digested with BglII and BamHI and blunt-ended after purification by an ordinary method. The resulting PCR product was ligated with pHSG299 which had been digested with AvaII and blunt-ended. The plasmid was used to transform competent cells of *Escherichia coli* JM109 (Takara Bio Inc.), and then the transformants were suspended in LB medium containing 25 mg/ml of kanamycin and cultivated overnight. The colonies were picked and subjected to single colony isolation, and then transformants were obtained. The target plasmid pBS3 containing the sacB gene was isolated from the transformants.

The construction procedure of pBS3 is illustrated in FIG. 2.

(B) Construction of pBS4S

By overlap PCR, a plasmid was obtained by disrupting the SmaI site in the coding region of the kanamycin-resistant gene in the plasmid pBS3. First, using pBS3 as a template and synthetic DNAs of SEQ ID NO: 44 and NO: 45 as primers, PCR was performed, and the PCR product containing the N-terminal region of the kanamycin resistant gene was obtained. On the other hand, in order to obtain a PCR product containing the C-terminal region of kanamycin-resistance gene, PCR was performed using pBS3 as a template and synthetic DNAs of SEQ ID NO: 46 and NO: 47 as primers. The PCR product can be obtained by, after 1 cycle of heat treatment at 98° C. for 5 minutes, repeating 25 times a cycle of 98° C. for 10 seconds, 57° C. for 30 seconds, and 72° C. for 1 minute, using Pyrobest DNA Polymerase (Takara Bio Inc.). The nucleotide sequences of SEQ ID NO: 45 and NO: 46 are partially complementary to each other.

The SmaI site of this sequence was disrupted by introducing a mutation without causing an amino acid substitution. In order to obtain a mutant kanamycin-resistance gene fragment in which the SmaI site is disrupted, the N-terminal region of the gene product and the C-terminal region of the gene product of the kanamycin-resistance gene were mixed to form a nearly equimolar mixture. Using the resulting mixture as a template for PCR and synthetic DNA of SEQ ID NO: 44 and NO: 47 as primers, PCR was performed. The PCR product having the mutation in kanamycin-resistance gene was obtained. The target PCR product can be obtained by, after 1 cycle of heat treatment at 98° C. for 5 minutes, repeating 25 times a cycle comprising of 98° C. for 10 seconds, 57° C. for 30 seconds a 72° C. for 1.5 minute using Pyrobest DNA Polymerase (Takara Bio Inc.).

Figure 3:
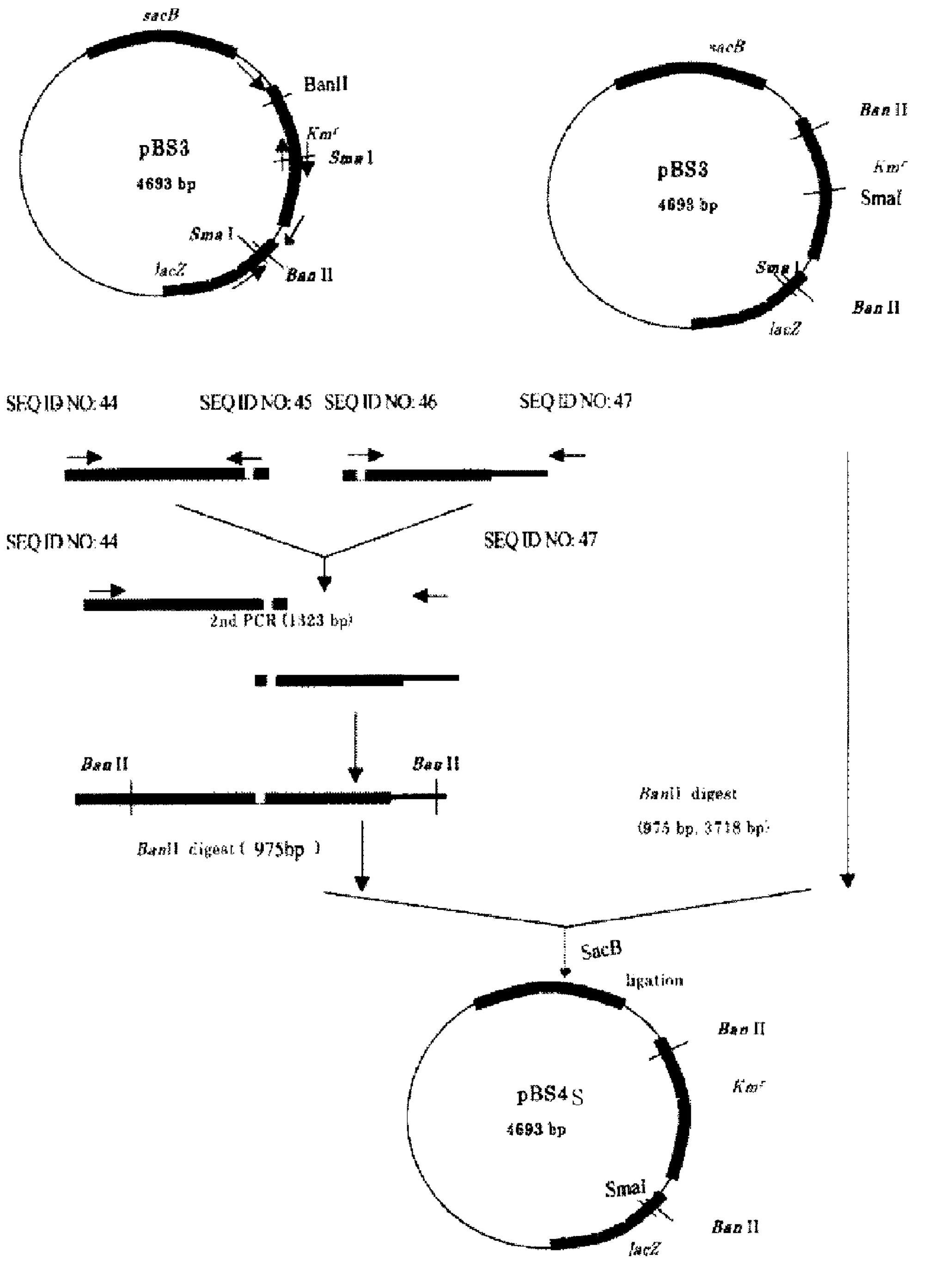
FIG. 3 shows the construction procedure of plasmid pBS4S.

The PCR product was digested with BanII after purification and inserted into the BanII site of the above-described pBS3. The obtained DNA was used to transform competent cells of *Escherichia coli* JM109 (Takara Bio Inc.), suspended to LB medium containing 25 mg/ml of kanamycin and cultivated overnight. The colonies were picked and subjected to single colony isolation, and transformants were obtained. The object plasmid pBS4S was isolated from the transformants. The construction procedure of pBS4S is illustrated in FIG. 3.

(C) Construction of pBS5T

A plasmid pBS5T having a temperature-sensitive replication origin from coryneform bacterium was constructed by the following procedure.

Figure 4:
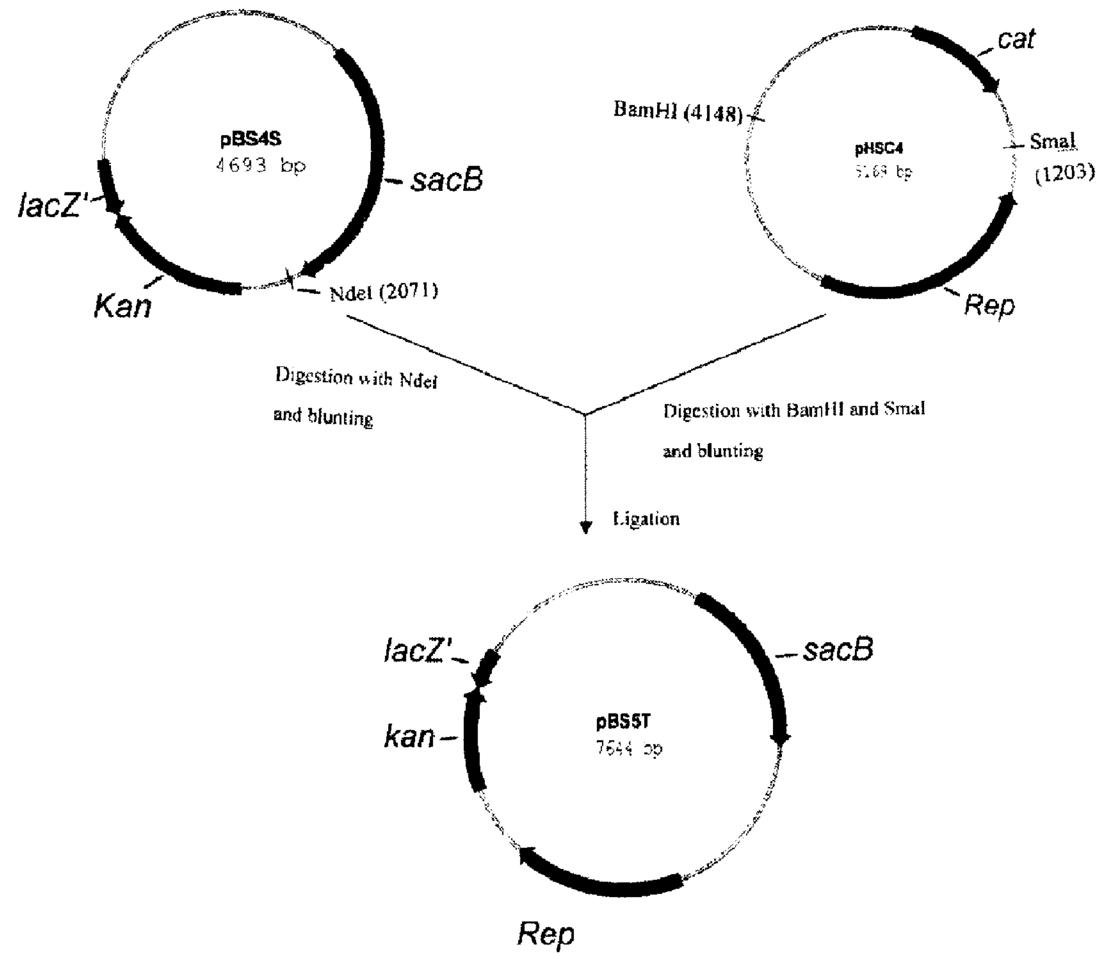
FIG. 4 shows the construction procedure of plasmid pBS5T.

The region of temperature-sensitive replication was obtained by digesting pHSC4 (U.S. Pat. No. 5,616,480A) with BamHI and SmaI and blunt-ending the digested fragment, and then this region was ligated to the blunt-ended NdeI site of pBS4S. The obtained DNA was used to transform competent cells of *Escherichia coli* JM109 (product of Takara Bio Inc.), and transformants were suspended in LB medium containing 25 mg/ml of Km and cultivated overnight. The colonies were picked and subjected to single colony isolation, and then transformants were obtained. The object plasmid pBS5T containing the sacB fragment and temperature-sensitive replication origin was isolated from the transformants. FIG. 4 illustrates the construction scheme of pBS5T.

(2) Cloning of a Fragment for aceE Gene-Disruption

A DNA fragment for aceE encoding pyruvate dehydrogenase (pyruvate dehydrogenase E1 component) gene disruption was obtained from ATCC13869 by the overlap PCR method using as primers synthetic DNAs based on the reported nucleotide sequence of aceE gene of *Corynebacterium glutamicum* ATCC13032 (GenBank Database Accession No. NC 003450; SEQ ID NO: 38).

First, PCR was performed by using a chromosomal DNA of *C. glutamicum* ATCC 13869 as a template and the synthetic DNAs of SEQ ID NO: 26 and No: 27 as primers to obtain an amplification product of the N-terminus side of the aceE gene. Then, in order to obtain an amplification product of the C-terminus side of the aceE gene, PCR was performed using the chromosomal DNA of *C. glutamicum* ATCC13869 as a template and the synthetic DNAs of SEQ ID NO: 28 and NO: 29 as primers. The sequences of SEQ ID NO: 26 and NO: 28 are complementary to each other.

Then, in order to obtain an aceE fragment in which an internal sequence is deleted, the aforementioned gene fragments of the N- and C-terminus were mixed in substantially equimolar amounts, and PCR was performed using this mixture as a template and the synthetic DNAs of SEQ ID NO: 30 and NO: 31 as primers.

The resulting PCR product was purified in a conventional manner and digested with Sma I. The digested PCR product was ligated by using Ligation Kit (product of Takara Bio Inc) to the above-described pBS5T which had been digested with Sma I. The ligation mixture was used to transform competent cells of *Escherichia coli* DH5α (product of Takara Bio Inc.). The cells were plated on LB medium (10 g of bacto-tryptone, 5 g of bacto-yeast extract and 10 g of NaCl in 1 L) containing 100 μM of IPTG, 40 mg/ml of X-Gal and 25 mg/ml of Km and cultured overnight. Then, the white colonies which emerged were selected and separated into single colonies to obtain transformants. The object plasmid pBS5T-ΔaceE was isolated from the transformants.

(3) Construction of aceE-Disrupted Strain aceE gene encodes pyruvate dehydrogenase E1 component.

First, the ATCC13869 strain was transformed with a high concentration of plasmid pBS5T-ΔaceE by the electric pulse method, plated on the CM-Dex medium (5 g/L of glucose, 10 g/L of polypeptone, 10 g/L of yeast extract, 1 g/L of $KH_2PO_4$, 0.4 g/L of $MgSO_4.7H_2O$, 0.01 g/L of $FeSO_4.7H_2O$, 0.01 g/L of $MnSO_4.7H_2O$, 3 g/L of urea, 1.2 g/L of soybean hydrolysate and 10 μg/L of biotin, pH 7.5 (NaOH)) containing 25 mg/ml of kanamycin, and cultured at 25° C. for about 60 hours, and colonies which emerged were isolated as transformants. Next, the transformants were cultured on a CM-Dex liquid medium at 34° C. overnight. After appropriate dilution, the cultured transformant was suspended to a CM-Dex medium containing 25 mg/ml of kanamycin and cultured at 34° C. for about 30 hours. The ΔaceE strain, which can grow in this medium and has both the kanamycin-resistant gene and the sacB gene derived from the plasmid on the chromosome, was obtained as a result of single cross-over homologous recombination between the disrupted-type of aceE gene (ΔaceE) on the plasmid and the native aceE gene on the chromosome.

Next, the ΔaceE strain obtained by single cross-over homologous recombination was cultured overnight on a CM-Dex liquid medium at 31.5° C. After appropriate dilution, the single cross-over homologous recombinant ΔaceE strain was suspended in a kanamycin-free and 10%-sucrose-containing Dex-S10 medium (10 g/L of sucrose, 10 g/L of polypeptone, 10 g/L of yeast extract, 1 g/L of $KH_2PO_4$, 0.4 g/L of $MgSO_4.7H_2O$, 0.01 g/L of $FeSO_4.7H_2O$, 0.01 g/L of $MnSO_4.4H_2O$, 3 g/L of urea, 1.2 g/L of soybean hydrolysate, 10 μg/L of biotin and 2 g/l of sodium acetate, adjusted to pH 7.5 by KOH). Culture was performed at 34° C. for about 30 hours. As a result of second cross-over homologous recombination, a strain which does not have the chromosomal SacB gene and is not sensitive to sucrose was obtained.

The strains obtained in this manner include those having the disrupted-type of aceE gene and those having the wild-type aceE gene. Whether the aceE gene is the disrupted-type or the wild-type was confirmed by a direct PCR reaction using the cells obtained by culturing on a Dex-S10 agar medium. The strain containing the disrupted-type of aceE gene was selected and named "ATCC13869ΔaceE".

(4) Evaluation of Physiological Activity of Phosphoketolase in ΔaceE Strain pVK9 (plasmid for control), pVK9-xfp (plasmid for amplifying xfp gene of *Bifidobacterium animalis*), pVK9-PS2_xfp (plasmid for amplifying xfp gene of *Bifidobacterium animalis*, in which its native promoter is replaced with a PS2 promoter), and pVK9-PS2_xpkA (plasmid for amplifying xpkA gene of *Lactobacillus pentosus*, in which its native promoter is replaced with a PS2 promoter) were each introduced into the ATCC13869ΔaceE strain to obtain phosphoketolase-expressing strains, and pVK9 was introduced into the ATCC13869 strain as the control. Specifically, the ATCC13869ΔaceE strain and the ATCC13869 strain were each transformed by the electric pulse method, plated on a CM-Dex medium (5 g/L of glucose, 10 g/L of polypeptone, 10 g/L of yeast extract, 1 g/L of $KH_2PO_4$, 0.4 g/L of $MgSO_4.7H_2O$, 0.01 g/L of $FeSO_4.7H_2O$, 0.01 g/L of $MnSO_4.7H_2O$, 3 g/L of urea, 1.2 g/L of soybean hydrolysate and 10 μg/L of biotin, adjusted to pH 7.5 by NaOH) containing 25 mg/ml of kanamycin, and cultured at 31.5° C. for about 30 hours. The colonies which emerged were isolated as transformants and designated ATCC13869ΔaceE(pVK9), ATCC13869ΔaceE(pVK9-xfp), ATCC13869ΔaceE(pVK9-PS2_xfp), ATCC13869ΔaceE(pVK9-PS2_xpkA) and ATCC1869(pVK9), respectively.

Figure 5:
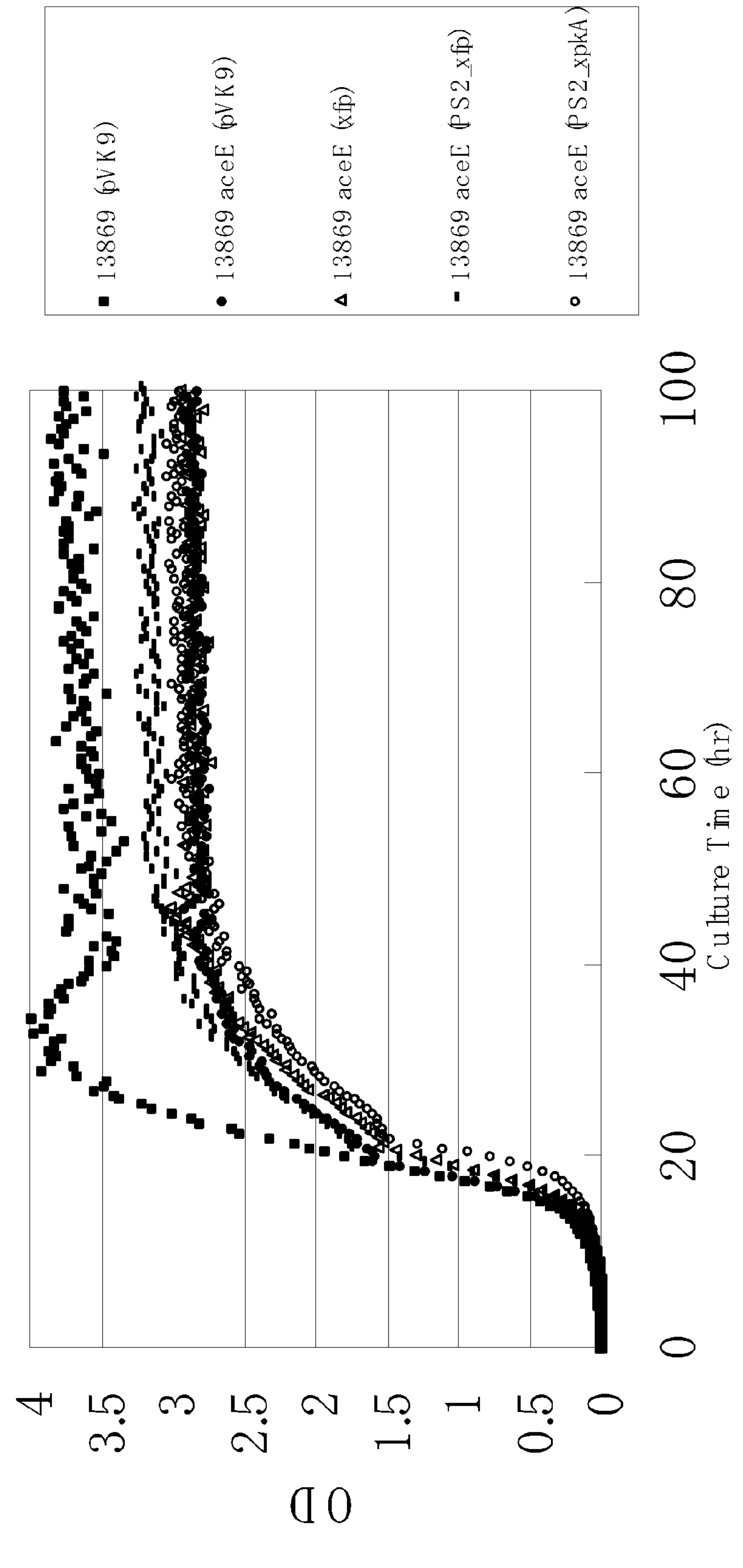
FIG. 5 shows the growth curves of phosphoketolase gene amplified strains and a control strain on a minimum medium containing acetate.
Figure 6:
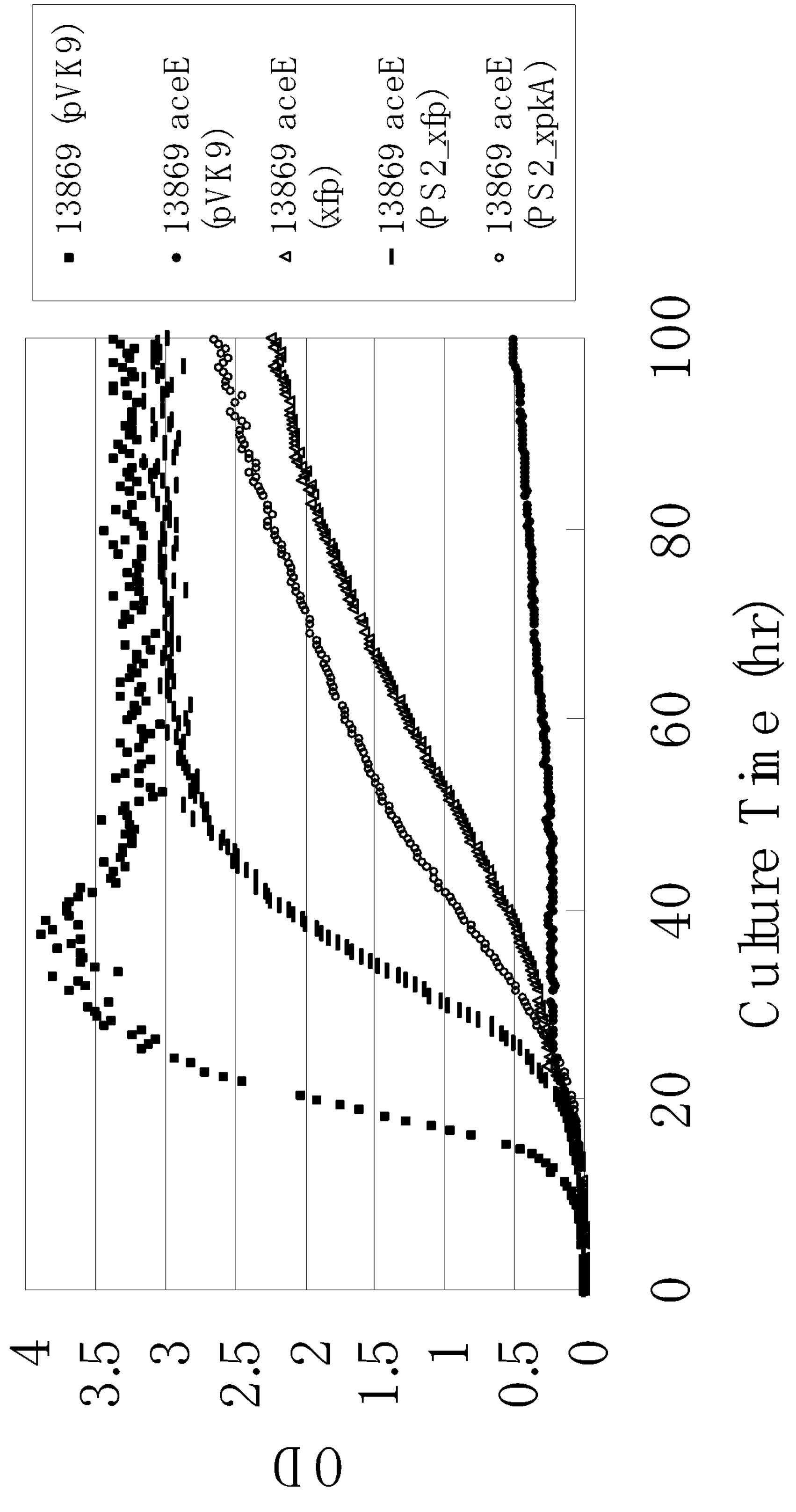
FIG. 6 shows the growth curves of phosphoketolase gene-amplified strains and a control strain in a minimum medium.

These strains were cultured in a micro-shaker ("Biophotorecorder TN-1506", product of ADVANTEC) while measuring OD with the function of time. Two mediums are employed here, that is, a minimum liquid medium (composed of 10 g/L of glucose, 2.5 g/L of $(NH_4)_2SO_4$, 0.5 g/L of $KH_2PO_4$, 0.25 g/L of $MgSO_4.7H_2O$, 0.01 g/L of $FeSO_4.7H_2O$, 0.01 g/L of $MnSO_4.7H_2O$, 2 g/L of urea, 50 μg/L of Biotin, 100 mL of VB1-HCl, 15 mg/L of protocatechuic acid, 0.02 mg/L of $CuSO_4$, 10 mg/L of $CaCl_2$, and 40 g/L of MOPS, adjusted to pH 7.0 by KOH) containing 25 mg/ml of kanamycin, and a minimum liquid medium containing acetate (2 g/L of sodium acetate). The results of the cultivation on the minimum medium and the results of the cultivation on the minimum medium containing acetate are illustrated in FIGS. 6 and 5, respectively. The ATCC13869ΔaceE(pVK9) strain could grow on the minimum medium containing acetate, but could not grow on the minimum medium, and thus exhibited acetate-auxotrophy. The ATCC13869ΔaceE strains carrying pvK9-xfp, pVK9-PS2_xfp, and pVK9-PS2_xpkA, respectively could grow even on the minimum medium, indicating that introduction of xfp or xpkA results in compensation for the acetate-auxotrophy of the PDH-defective strain. Accordingly, the physiological activity of phosphoketolase which had been introduced into *C. glutamicum* was confirmed.

Example 7

Confirmation of Enzyme Activity of Phosphoketolase

The *Coryneform* bacterium can produce L-glutamic acid under conditions where biotin is limited, or penicillin or surfactant is added in the medium (refer to WO95/34672). It is known, on the other hand, that the strain which was modified to decrease α-ketoglutarate dehydrogenase activity (E1.2.4.2 sucA; 2-oxoglutarate dehydrogenase) can produce L-glutamic acid even not under such conditions (Kimura E., Adv. Biochem. Eng. Biotechnol., 79, 37-57 (2003), "Metabolic engineering of glutamic acid production"). Accordingly, we studied the improvement in the fermentation yield of L-glutamic acid by the introduction of a phosphoketolase gene using a sucA-deficient strain *C. glutamicum* ATCC13869.

(7-1) Construction of the ATCC13869ΔsucA Strain (1) Cloning of a Fragment for Disruption of sucA Gene A sucA-deleted fragment derived from the strain *C. glutamicum* ATCC13869 was obtained by the overlap PCR method using as primers synthetic DNAs designed based on the nucleotide sequence sucA gene of *C. glutamicum* ATCC13032 (GenBank Database Accession No. NC_003450; SEQ ID NO: 48).

First, PCR was performed by using a chromosomal DNA of *C. glutamicum* ATCC13869 as a template and the synthetic DNAs of SEQ ID NO: 32 and No: 33 as primers to obtain an amplification product of the N-terminus of the sucA gene. Then, in order to obtain an amplification product of the C-terminus of the sucA gene, PCR was performed using the chromosomal DNA of *C. glutamicum* ATCC13869 as a template and the synthetic DNAs of SEQ ID NO: 34 and NO: 35 as primers. The sequences of SEQ ID NO: 33 and NO: 34 are complementary to each other.

Then, in order to obtain a sucA fragment in which its internal sequence is deleted, the aforementioned gene fragments of the N- and C-terminus were mixed in substantially equimolar amounts, and PCR was performed using this mixture as a template and the synthetic DNAs of SEQ ID NO: 36 and NO: 37 as primers.

The resulting PCR product was purified in a conventional manner and digested with BamHI. The digested PCR product was ligated by using Ligation Kit (product of Takara Bio Inc) to the above-described pBS3 which had been digested with BamHI. The ligation mixture was used to transform competent cells of *Escherichia coli* DH5α (product of Takara Bio Inc.). The cells were plated on LB medium (10 g of bacto-tryptone, 5 g of bacto-yeast extract and 10 g of NaCl in 1 L)

containing 100 μM of IPTG, 40 mg/ml of X-Gal and 25 mg/ml of Km and cultured overnight. Then, the white colonies which emerged were selected and separated into single colonies to obtain transformants. The target plasmid pBS3ΔsucA was isolated from the transformants.

(2) Preparation of a sucA-Disrupted Strain

The pBS3ΔsucA prepared in (A) does not contain a region autonomously replicable in the cells of coryneform bacterium. Therefore, if a *corynebacterium* is transformed with this plasmid, a strain having this plasmid integrated into its chromosome by homologous recombination would appear as a transformant although it occurs at an extremely low frequency. *C. glutamicum* ATCC13869 was transformed with a high concentration of the plasmid pBS3ΔsucA by the electric pulse method, plated on CM-Dex medium (5 g/L of glucose, 10 g/L of polypeptone, 10 g/L of yeast extract, 1 g/L of $KH_2PO_4$, 0.4 g/L of $MgSO_4.7H_2O$, 0.01 g/L of $FeSO_4.7H_2O$, 0.01 g/L of $MnSO_4.7H_2O$, 3 g/L of urea, 1.2 g/L of soybean hydrolysate and 10 μg/L of biotin, adjusted to pH 7.5 by NaOH) containing 25 mg/ml of kanamycin, and cultured at 31.5° C. for about 30 hours, and then, the colonies which emerged were isolated as transformants. These transformants have both the kanamycin-resistance gene and the SacB gene derived from the plasmid, as a result of homologous recombination between the sucA gene fragment of the plasmid and the native gene on the chromosome.

Next, the obtained first recombinant strain was cultured overnight on a kanamycin-free CM-Dex liquid medium at 31.5° C. After appropriate dilution, the cultured transformant was plated on the kanamycin-free Dex-S10 medium (10 g/L of sucrose, 10 g/L of polypeptone, 10 g/L of yeast extract, 1 g/L of $KH_2PO_4$, 0.4 g/L of $MgSO_4.7H_2O$, 0.01 g/L of $FeSO_4.7H_2O$, 0.01 g/L of $MnSO_4.4H_2O$, 3 g/L of urea, 1.2 g/L of soybean hydrolysate, and 10 μg/L of biotin, adjusted to pH 7.5 by KOH) containing 10% sucrose, cultured at 31.5° C. for about 30 hours, and the colony which emerged was isolated as a transformant. As a result of the second cross-over homologous recombination, a strain which has lost the SacB gene from the chromosome and is not sensitive to sucrose was obtained.

The strains obtained in this manner include those having a disrupted-type of sucA gene and those having a wild-type sucA gene. Whether the sucA gene is the disrupted-type or the wild-type was confirmed by a direct PCR reaction using the cells obtained by culturing on a Dex-S10 agar medium. The strain having a disrupted-type of sucA gene was selected.

The production of L-glutamic acid by the sucA-disrupted strain was evaluated by the following method. The cells of the sucA-disrupted strain obtained by culturing on a CM2B plate medium were inoculated into a flask containing 80 g of glucose, 1 g of $KH_2PO_4$, 0.4 g of $MgSO_4$, 30 g of $(NH_4)_2SO_4$, 0.01 g of $FeSO_4.7H_2O$, 0.01 g of $MnSO_4.7H_2O$, 15 ml of soybean hydrolysate solution, 200 mg of thiamine hydrochloride, 60 μg of biotin and 50 g of $CaCO_3$ in 1 L of pure water (adjusted to pH 8.0 with KOH) and cultured at 31.5° C. with shaking until the sugar was completely consumed. After completion of the culture, the amount of accumulated L-glutamic acid in the culture broth was measured. The sucA-disrupted strain which can produce a greater fermentation yield of L-glutamic acid than ATCC13869 was selected as the sucA-disrupted strain of ATCC13869 and named ATCC13869ΔsucA.

(7-2) Confirmation of Phosphoketolase Gene Expression and Enzyme Activity in sucA-Disrupted ATCC13869 Strain Expression of a phosphoketolase gene and its enzyme activity was investigated by using the strain which had been modified to enhance the expression of phosphoketolase.

pVK9 (plasmid for control), pVK9-xfp (plasmid for amplifying xfp gene of *Bifidobacterium animalis*), pVK9-tac_xfp (plasmid for amplifying xfp gene of *Bifidobacterium animalis*, in which its native promoter is replaced with a tac promoter), pVK9-PS2_xfp (plasmid for amplifying xfp gene of *Bifidobacterium animalis*, in which its native promoter is replaced with a PS2 promoter), and pVK9-PS2_xpkA (plasmid for amplifying xpkA gene of *Lactobacillus pentosus*, in which its native promoter is replaced with a PS2 promoter) were each introduced into the above-described *C. glutamicum* ATCC13869ΔsucA to obtain phosphoketolase-expressing strains. Specifically, the ATCC138694 sucA strain was transformed with the each of the plasmids by the electric pulse method, plated on a CM-Dex medium (5 g/L of glucose, 10 g/L of polypeptone, 10 g/L of yeast extract, 1 g/L of $KH_2PO_4$, 0.4 g/L of $MgSO_4.7H_2O$, 0.01 g/L of $FeSO_4.7H_2O$, 0.01 g/L of $MnSO_4.7H_2O$, 3 g/L of urea, 1.2 g/L of soybean hydrolysate and 10 μg/L of biotin, adjusted to pH 7.5 by NaOH) containing 25 mg/ml of kanamycin and cultured at 31.5° C. for about 30 hours. The colonies which emerged were isolated as transformants and designated as ATCC13869ΔsucA(pVK9), ATCC13869ΔsucA(pVK9-xfp), ATCC13869ΔsucA(pVK9-tac_xfp), ATCC13869ΔsucA (pVK9-PS2_xfp), and ATCC13869ΔsucA(pVK9-PS2_xpkA), respectively.

In order to obtain a crude enzyme solution, the cells of the aforementioned strains obtained by culturing each strain on a CM-Dex plate medium were inoculated into a Flask containing 30 g of glucose, 1 g of $KH_2PO_4$, 0.4 g of $MgSO_4$, 15 g of $(NH_4)_2SO_4$, 0.01 g of $FeSO_4.7H_2O$, 0.01 g of $MnSO_4.7H_2O$, 13.7 ml of a soybean hydrolysate solution, 200 mg of thiamine hydrochloride, 300 μg of biotin, and 50 g of $CaCO_3$ in 1 L of pure water (adjusted to pH 8.0 with KOH) and cultured at 31.5° C. with shaking. The cultivation was terminated when the OD620 of cell concentration became 15, as measured by "Hitachi Spectrophotometer U-2000A". After removal of calcium carbonate by moderate centrifugation at 3000 rpm for 30 seconds, the cells were collected. The following procedures were carried out at 0 to 4° C. The collected cells were washed twice with a 0.85N NaCl solution and resuspended in 4 ml/g (wet weight) of buffer A (100 mM $KPO_4$ (pH 6.5), 30 mM KCl, 0.1 mM EDTA, 1 mM $MgCl_2$, 0.2 mM PMSF, 2 mM DTT). The cells were disrupted by an ultrasonic cell disruptor ("Bioruptor"). The undisrupted cells were removed by centrifugation (15,000 g, 60 min) to obtain a crude enzyme solution. The protein concentration in the crude enzyme solution was quantified by using a CBB solution (protein assay CBB solution, product of Nacalai Tesque) with bovine serum albumin as a standard sample.

By SDS-PAGE, the protein in the crude enzyme solution was separated. The specific procedure of the separation will be described next. The crude enzyme solution was mixed, after concentration adjustment, with a sample buffer ("Laemmli sample buffer", product of BIORAD) at 1:1. After heating at 95° C. for 2 minutes, the resulting mixture was applied to "Ready Gel J 10%" (product of BIORAD) so that the applied protein amount was 10 μg, followed by electrophoresis for 40 minutes in a MiniProtean III Cell phoresis tank (product of BIORAD) at a constant voltage of 200V. As an electrophoresis buffer, tris/glycine/SDS (BIORAD) was used. For staining, Coomassie Brilliant Blue ("Bio Safe Coomassei", BIORAD) was used. The results are shown below in FIG. 7 (marker: product of BIORAD, precision plus protein standards (#161-0363)).

Figure 7:
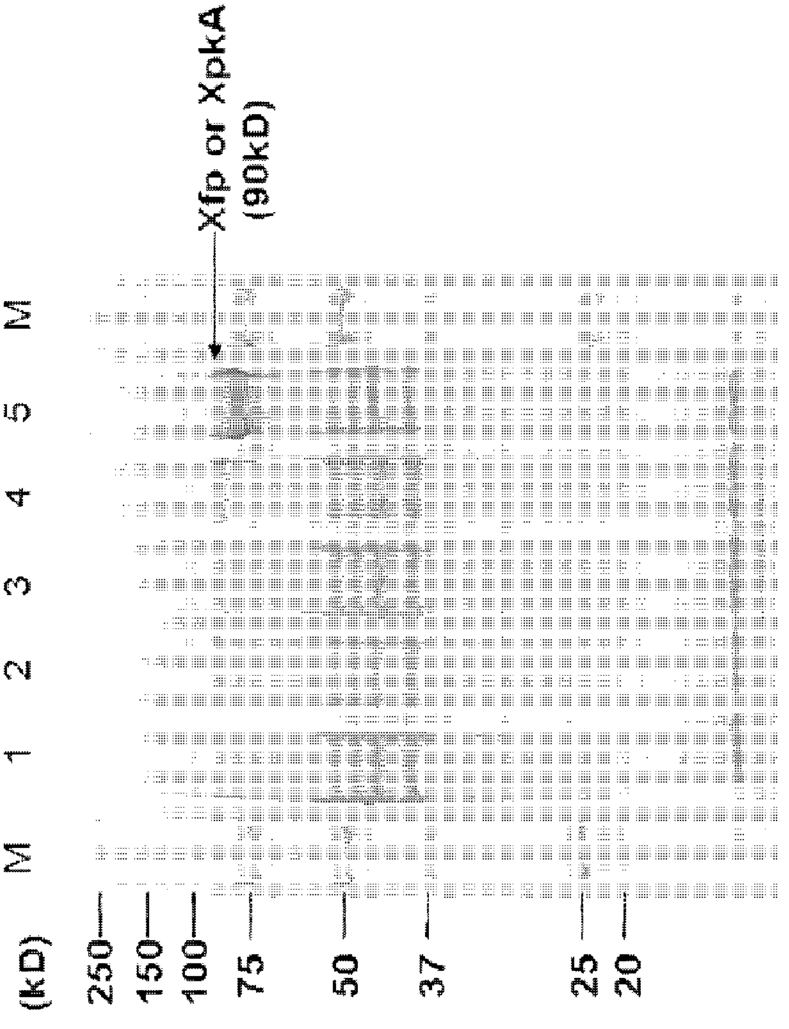
FIG. 7 shows the electrophoresis of cell extracts containing phosphoketolase protein.

Lanes 1 to 5 of FIG. 7 show ATCC13869ΔsucA(pVK9), ATCC13869ΔsucA(pVK9-xfp), ATCC13869ΔsucA(pVK9-tac_xfp), ATCC13869ΔsucA(pVK9-PS2_xfp), and ATCC13869ΔsucA(pVK9-PS2_xpkA)), respectively. Compared with the control band (pVK9), approximately 90 kD band which corresponds to that of the phosphoketolase gene product becomes denser in the strain which was modified to enhance the activity of phosphoketolase. This clearly suggests that a sufficient amount of expression of the phosphoketolase gene occurs in the coryneform bacterium.

In accordance with Meile's method (L. Meile, L. M. Rohr, T. A. Geissmann, M. Herensperger and M. Teuber, J. Bacteriol. 183, 2929-2936 (2001)), the enzyme activity of phosphoketolase gene was measured. After reaction with 0.075 ml of a crude enzyme solution (33.3 mM $KPO_4$ (pH 6.5), 1.9 mM L-cystein hydrochloride, 23 mM sodium fluoride, 8 mM sodium iodoacetate, and 27 mM D-fructose 6-phosphate) at 37° C. for 30 minutes, 0.075 ml of hydroxylamine hydrochloride (2M, pH 6.5) was added. The mixture was allowed to react for 10 minutes at room temperature and then was stained with 0.05 ml of 15% (wt/vol) of trichloroacetic acid, 0.05 ml of 4M HCl and 0.05 ml of $FeCl_3.6H_2O$ (in 0.1 m HCl, 5% wt/vol). After removal of crystals by centrifugal separation, the OD505 was measured using an enzyme activity reader ("Spectra max 190", product of Molecular Devices).

The results are shown below in Table 3. No enzyme activity was detected in control (pVK9), while enzyme activity was detected in the strains in which phosphoketolase activity had been enhanced.

TABLE 3

| | pVK9 | xfp | PS2_xfp | PS2_xpkA |
|---|---|---|---|---|
| ΔABS/mg/hr | Trace | 1.00 | 2.68 | 2.38 |

Example 8

Figure 8:
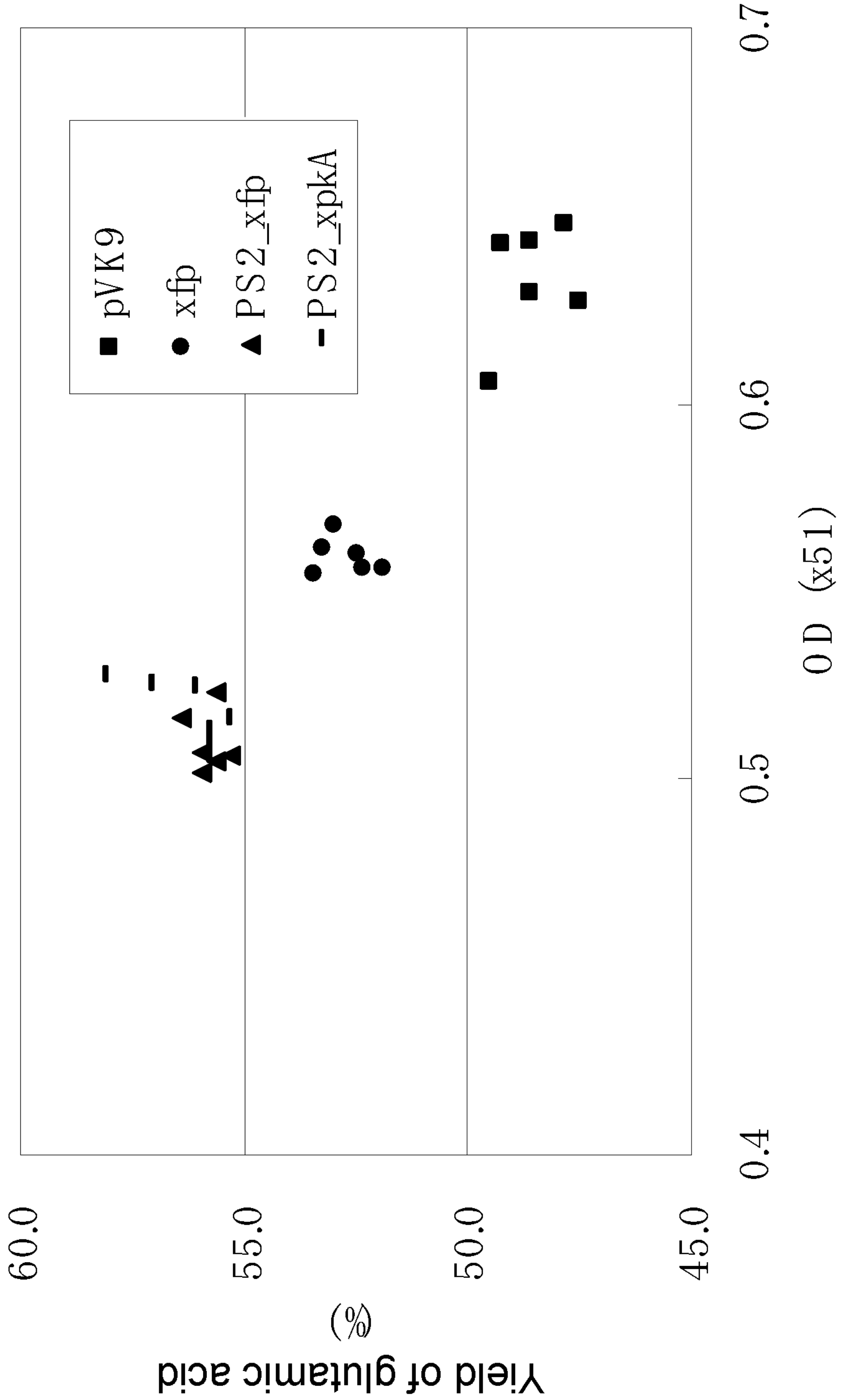
FIG. 8 shows the production of L-glutamic acid using phosphoketolase gene-amplified strains under biotin-sufficient conditions.

Evaluation of L-Glutamic Acid-Producing Ability of the Bacterium Having Enhanced Phosphoketolase Activity (8-1) Evaluation Under a Condition Containing a Sufficient Amount of Biotin By using the strain *C. glutamicum* ATCC 13869 ΔsucA, the effect of the introduction of a phosphoketolase gene on the fermentation yield of L-glutamic acid was evaluated. The cells of the ATCC13869ΔsucA(pVK9), ATCC13869ΔsucA (pVK9-xfp), ATCC13869ΔsucA(pVK9-PS2_xfp) and ATCC13869ΔsucA(pVK9-PS2_xpkA) strains obtained by culturing on a CM-Dex plate medium were inoculated into the Flask containing 30 g of glucose, 1 g of $KH_2PO_4$.0.4 g of $MgSO_4$, 15 g of $(NH_4)_2SO_4$, 0.01 g of $FeSO_4.7H_2O$, 0.01 g of $MnSO_4.7H_2O$, 13.7 ml of a soybean hydrolysate solution, 200 mg of thiamine hydrochloride, 300 μg of biotin, and 50 g of $CaCO_3$ in 1 L of pure water (adjusted to pH 8.0 with KOH) and cultured at 31.5° C. with shaking until the sugar was completely consumed. After completion of the culture, the amount of accumulated L-glutamic acid and OD in the culture broth were measured. The results are shown in FIG. 8. The results show that all of the strains in which xfp gene is amplified show high L-glutamic acid yield compared to the control.

(8-2) Evaluation when Penicillin is Added

Figure 9:
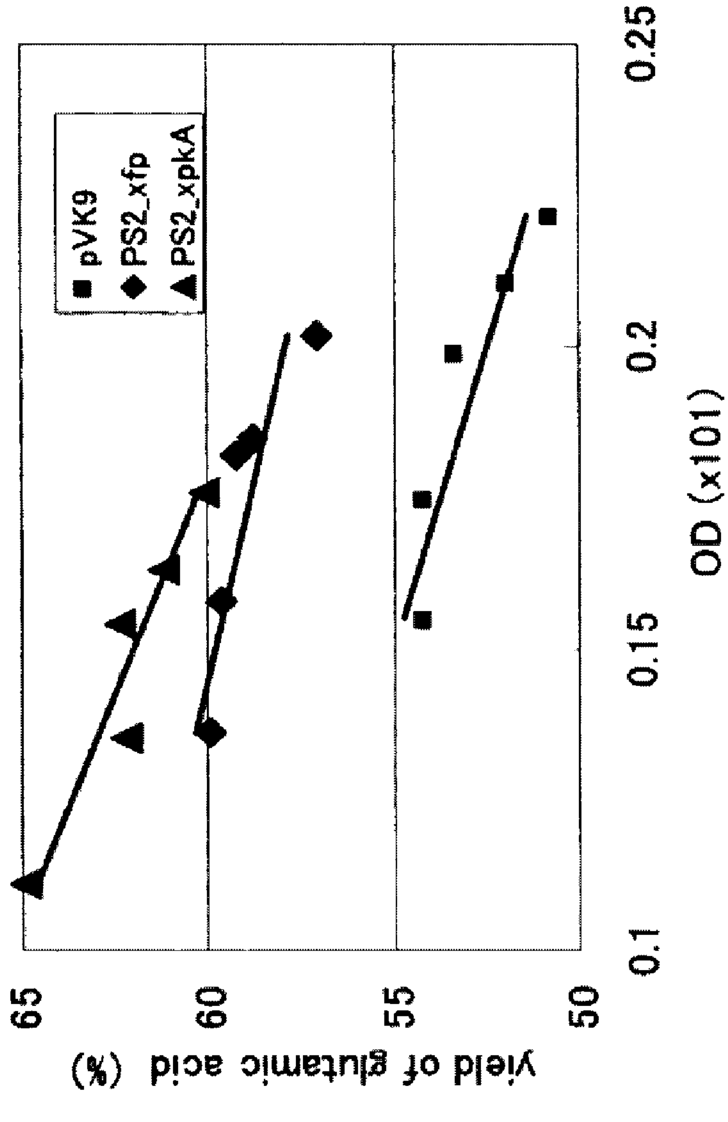
FIG. 9 shows the production of L-glutamic acid using phosphoketolase gene-amplified strains with the addition of penicillin.

In order to evaluate under the equalized final OD, the proliferation of cells was stopped by adding penicillin G. The yield of L-glutamic acid was compared by adding penicillin G to the medium as described in the above (1) so that its final concentration was 4 U/ml at plural growth points when the OD became within a range from 10 to 14 after the culture was started. The results are shown in FIG. 9. These results show that even if the yield of L-glutamic acid was compared among them at a point when their final cell counts were equal, the L-glutamic acid yield was higher in the xfp gene- or xpk gene-amplified strains compared with the control strain. The above-described results show that the introduction of phosphoketolase is effective for improving L-glutamic acid fermentation yield.

Example 9

Effect of expression of xfp gene of *B. animalis* on L-Glutamic Acid Accumulation by *Pantoea ananatis* Strain pVK9-PS2-xfp plasmid expressing xfp gene of *Bifidobacterium animalis* and control pVK9 shuttle vector were introduced to NP106/RSFCPG L-glutamic acid producing strain by electroporation using Bio-Rad MicroPulser. NP106/RSFCPG strain was obtained by curing pSTVCB plasmid from AJ13601 strain (FERM BP-7207; European patent publication 1078989) by plating the AJ13601 strain on the medium which does not contain chloramphenicol as a selection marker.

To transform NP106/RSFCPG strain with pVK9-PS2-xfp plasmid or pVK9 vector, cells obtained by overnight culture on LBG-M9 medium (trypton (10 g/L), yeast extract (5 g/L), NaCl (5 g/L), glucose (5 g/L), 0.5×M9 salt solution) with addition of tetracycline (10 μg/ml) was diluted 1:100 by fresh LBG-M9 medium and incubated at 34° C. with aeration up to $OD_{595}$=0.6. Cells from 10 ml of the culture were harvested by centrifugation, washed three times with ice-cold de-ionized water and with ice-cold 10% glycerol and resuspended in 10% glycerol. 10 ng of plasmid DNA were added to cell suspension and electric pulse (E=20 kV/cm, t=5 msec) was applied. 1 ml of LBG-M9 medium was added immediately after electroporation. Cells were incubated at 34° C. under aeration for 2 hours and plated on solid LBG-M9 medium containing 40 ng/ml of kanamycin. Plates were incubated at 34° C. for 48 hours. Grown clones were inoculated in 2 ml of LBG-MES medium (trypton (10 g/L), yeast extract (5 g/L), NaCl (5 g/L), glucose (5 g/L), MES 0.1M, pH7.0) containing 40 μg/ml kanamycin and 10 μg/ml tetracycline and incubated at 34° C. under aeration overnight. 80 μl of the overnight-cultured medium containing the bacterial cells were inoculated in 2 ml of fermentation medium (glucose (40 g/L), $MgSO_4.7H_2O$ (0.5 g/L), $(NH_4)_2SO_4$ (16 g/L), $KH_2PO_4$ (0.3 g/L), KCl (1.0 g/L), MES (10 g/L), betaine (1.0 g/L), $FeSO_4.7H_2O$ (10 mg/L), $MnSO_4.5H_2O$ (10 mg/L), lysine, methionine, and DAP 100 mg/L of each, trypton (1 g/L), yeast extract (1 g/L), calcium pantothenate (10 mg/L), $CaCO_3$ (30 g/L)) in test-tubes and incubated for 26 hours with aeration. The amount of accumulated L-glutamic acid was determined by the TLC method. Average data of 4 independent experiments are represented in Table 4.

TABLE 4

| Strain | $OD_{540}$ | Glu, g/L | Yield, % |
|---|---|---|---|
| NP106 RSFCPG/pVK9 | 21.8 | 9.8 | 24.4 |
| NP106 RSFCPG/pVK9-PS2-xfp | 20.7 | 12.4 | 30.9 |

As could be seen from Table 4, the strain carrying pVK9-PS2-xfp plasmid showed L-glutamic acid accumulation approximately 2.6 g/L higher than the control strain transformed with vector pVK9, which corresponds to at least a 6% increase in yield.

Example 10

Improvement of Fermentation Yield of L-Glutamic Acid by a Combination of the Enhancement of Phosphoketolase Activity and the Reduction of 6-Phosphofructokinase (PFK) Activity 10-1. Preparation of a sucA and PFK Double-Disrupted Strain (1) Construction of a Plasmid for Disruption of pfk Gene Gene fragments lacking the ORF of pfk derived from the strain ATCC13869 were obtained by the overlap PCR method using synthetic DNA as primers designed based on the nucleotide sequence of the corresponding gene of *Corynebacterium glutamicum* ATCC 13032 (GenBank Database Accession No. NC_003450; SEQ ID NO: 61). Specifically, the amplification products of the N-terminal region of the pfk gene were obtained by a conventional PCR method using chromosomal DNA of the *C. glutamicum* strain ATCC13869 as a template, and synthetic DNAs of SEQ ID NO: 50 and NO: 51 as primers. On the other hand, in order to obtain amplification products of the C-terminal region of the pfk gene, a conventional PCR was performed using chromosomal DNA of the strain ATCC13869 as a template and synthetic DNAs of SEQ ID NO: 52 and NO: 53 as primers. The sequences of SEQ ID NO: 51 and NO: 53 are complimentary to each other.

Then, in order to obtain a pfk gene fragment in which its internal sequence is deleted, the aforementioned amplification products of the N-terminal and C-terminal region of the pfk were mixed in substantially equimolar amounts, and gene amplification products were obtained by a conventional PCR using this mixture as a template and synthetic DNAs of SEQ ID NO: 54 and NO: 55 as primers. The PCR product was purified in an ordinary way and then digested with BamH I, and was inserted at the BamH I site of the above-described pBS5T. This DNA was used to transform competent cells of *Escherichia coli* DH5α (product of Takara Bio Inc.), and the cells were plated and cultivated overnight on LB medium supplemented with 100 μM of IPTG, 40 μg/ml of X-Gal, and 25 μg/ml of kanamycin. Then, white colonies that emerged were picked and separated into single colonies to obtain transformants. Plasmids were isolated from the obtained transformants, and the plasmid having an insert of the target PCR product was selected and named pBS5T-Δpfk.

(2) Preparation of a Disrupted Strain

The aforementioned strain ATCC13869ΔsucA was first transformed with a high concentration of the plasmid pBS5T-Δpfk by the electric pulse method, and plated on CM-Dex medium (5 g/L of glucose, 10 g/L of polypeptone, 10 g/L of yeast extract, 1 g/L of $KH_2PO_4$, 0.4 g/L of $MgSO_4.7H_2O$, 0.01 g/L of $FeSO_4.7H_2O$, 0.01 g/L of $MnSO_4.7H_2O$, 3 g/L of urea, 1.2 g/L of soybean hydrolysate, and 10 μg/L of biotin, adjusted to pH7.5 by NaOH) supplemented with 25 μg/ml of kanamycin, and cultivated for about 60 hours at 25° C. The resultant transformants were cultivated with shaking overnight at 34° C., and then suitably diluted, and plated and cultivated for 30 hours on CM-Dex medium supplemented with 25 μg/ml of kanamycin. The strain that can grow on this medium is a strain in which the kanamycin-resistance gene and the SacB gene derived from said plasmid are integrated into its chromosome, as a result of homologous recombination between the pfk gene fragment on said plasmid and the same gene located on the chromosome of the strain ATCC13869.

Then the first recombinants were cultivated overnight in kanamycin-free liquid CM-Dex medium at 31.5° C., and after an appropriate dilution, they were plated on kanamycin-free and 10% sucrose-containing Dex-S10 medium (10 g/L of glucose, 10 g/L of polypeptone, 10 g/L of yeast extract, 1 g/L of $KH_2PO_4$, 0.4 g/L of $MgSO_4.7H_2O$, 0.01 g/L of $FeSO_4.7H_2O$, 0.01 g/L of $MnSO_4$. $7H_2O$, 3 g/L of urea, 1.2 g/L of soybean hydrolysate, 10 μg/L of biotin, and 2 g/L of sodium acetate, adjusted to pH7.5 by KOH), and cultivated for about 30 hours at 34° C. As a result, a strain was obtained that seems to have lost the SacB gene and become insensitive to sucrose because of the second homologous recombination.

The obtained strains include those having the disrupted type of pfk gene derived from pBS5T-Δpfk, and those having the wild-type pfk gene. To confirm whether the pfk gene was disrupted type or wild-type, direct PCR analysis was performed using the bacterial cells cultivated on a Dex-10 agar medium. The strain having only the disrupted-type of pfk was selected and named ATCC13869 ΔsucA Δpfk.

10-2 Acquisition of Mutant Pfk Genes Encoding PFK Having Reduced Activity (1) Mutant PFK Having Reduced Activity As PFK with reduced activity, PFK*1(SEQ ID NO: 57) and PFK*2 (SEQ ID NO: 59) were obtained. PFK*1 is generated by substituting lysine for glutamic acid at position 171 of the wild-type PFK (SEQ ID NO: 61). PFK*2 is generated by substituting arginine for glutamic acid at position 171 of the wild-type PFK (SEQ ID NO: 61). These sequences can be obtained by crossover PCR using the wild-type pfk gene as a template and synthetic DNAs for introducing such a mutation as primers.

(2) Construction of Expression Vector for the Mutant pfk Gene and the Phosphoketolase Gene In order to construct a PFK expression vector, a conventional PCR was performed using chromosomal DNA of the *C. glutamicum* strain ATCC13869 as a template, and synthetic DNAs of SEQ ID NO: 54 and NO: 55 as primers. The PCR product was purified in an ordinary way and then digested with Xba I and Kpn I, and the gene fragment containing the pfk gene was inserted at the Xba I-Kpn I site of the above-described pVK9. This DNA was used to transform competent cells of *Escherichia coli* DH5α (product of Takara Bio Inc.), and the cells were plated and cultivated overnight on LB medium supplemented with 100 μM of IPTG, 40 μg/ml of X-Gal, and 25 μg/ml of Km. Then, white colonies that emerged were picked and separated into single colonies to obtain transformants. Plasmids were isolated from the obtained transformants, and the plasmid having an insert of the target gene was selected and named pVK9-PFK.

Then, in order to construct a plasmid that expresses both the mutant PFK and the phosphoketolase at the same time, the above-mentioned pVK9-PS2_xfp was digested with Xba I, and then the gene fragment containing the PS2_xfp was purified and inserted into Xba I site of the pVK9-PFK. This DNA was used to transform competent cells of *Escherichia coli* DH5α (product of Takara Bio Inc.), and the cells were plated and cultivated overnight on LB medium supplemented with 100 μM of IPTG, 40 μg/ml of X-Gal, and 25 μg/ml of Km. Then, white colonies that emerged were picked and separated into single colonies to obtain transformants. Plasmids were isolated from the obtained transformants, and the plasmid having an insert of the PS2_xfp and pfk was selected and named pVK9-PS2_xfp_PFK.

In order to construct a plasmid that expresses both the mutant pfk gene and the phosphoketolase gene at the same time, pVK9-PS2_xfp_PFK*1 and pVK9-PS2_xfp_PFK* were generated according to the same procedure as employed in construction of pVK9-PS2_xfp_PFK.

(3) Analysis of the Activity

The aforementioned expression plasmids for PFK and phosphoketolase (pVK9-PS2_xfp_PFK, pVK9-PS2_xfp_PFK*1, and pVK9-PS2_xfp_PFK*2) were used to transform the above-mentioned strain ATCC13869 ΔsucA Δpfk to examine the enzymatic activity of PFK. The transformation was performed by the electric pulse method, and the transformants were obtained by plating the bacterial cells on CM-Dex medium (5 g/L of glucose, 10 g/L of polypeptone, 10 g/L of yeast extract, 1 g/L of $KH_2PO_4$, 0.4 g/L of $MgSO_4.7H_2O$, 0.01 g/L of $FeSO_4.7H_2O$, 0.01 g/L of $MnSO_4.7H_2O$, 3 g/L of urea, 1.2 g/L of soybean hydrolysate, and 10 μg/L of biotin, adjusted to pH7.5 by NaOH) supplemented with 25 μg/ml of kanamycin, and cultivating them for about 30 hours at 31.5° C.

Crude enzyme solution was obtained in the following way. Bacterial cells in a logarithmic phase were collected, washed by 100 mM Kpi buffer (pH8.2), and then dissolved in the same buffer, followed by ultrasonic disruption. The soluble fraction was separated by ultracentrifugation (60000 rpm, 30 min) to obtain crude enzyme solution. The procedure for quantifying protein concentration in the crude enzyme solution is shown below. The crude enzyme solution and the BSA solution of known concentration for generating a standard curve were each reacted with CBB solution (protein assay CBB solution, Nacalai Tesque) to develop color, and followed by measuring OD595 nm using spectra max 190 (Molecular Divices).

Then, PFK activity was measured according to the conventional method (Denise Kotlars and Henri Buc, Methods in Enzymology (1982) 90: 60-70). The specific procedure is shown below. Enzymatic activity was determined by adding crude enzyme solution to 100 mM Tris-HCl (pH8.2), 10 mM $MgCl_2$, 1 mM ATP, 1 U/ml glycerol-3-phosphate dehydrogenase, 1 U/ml triosephosphate isomerase, 1 U/ml aldolase, 0.2 mM NADH, and 10 mM fructose-6-phosphate, followed by measuring time-course changes in OD340 nm using spectra max 190 (Molecular Devices). Relative activity of the reduced PFK when the activity of wild-type PFK is set at 1, is shown in the following Table 5.

TABLE 5

| | pVK9-PS2_xfp_PFK | pVK9-PS2_xfp_PFK*1 | pVK9-PS2_xfp_PFK*2 |
|---|---|---|---|
| Relative PFK activity | 1 | 0.33 | 0.41 |

Figure 10:
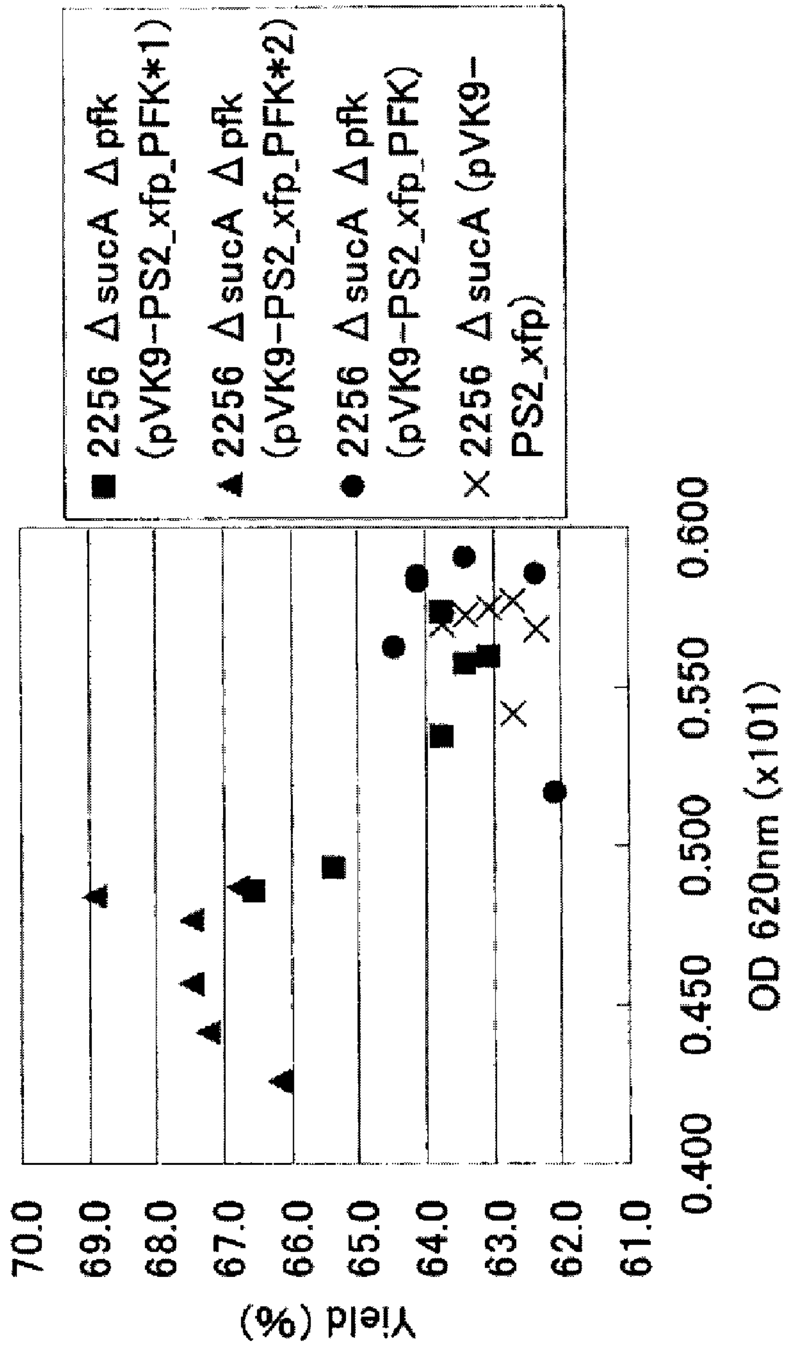
FIG. 10 shows the production of L-glutamic acid using a strain in which a phosphoketolase gene is introduced and 6-phosphofructokinase activity is reduced.

10-3 Increase in Yield of L-Glutamic Acid by Reducing PFK Activity (1) Evaluation Under a Condition Containing a Sufficient Amount of Biotin By using the strain *C. glutamicum* ATCC13869 ΔsucA Δpfk, the effect of reduction in PFK activity on the fermentation yield of L-glutamic acid was evaluated. Cells of each strain obtained by cultivating the strain on a CM-Dex plate was inoculated into a medium containing 30 g of glucose, 1 g of $KH_2PO_4$, 0.4 g of $MgSO_4$, 15 g of $(NH_4)_2SO_4$, 0.01 g of $FeSO_4.7H_2O$, 0.01 g of $MnSO_4.7H_2O$, 13.7 ml of a soybean hydrolysate solution, 200 μg of thiamine hydrochloride, 300 μg of biotin, and 50 g of $CaCO_3$ in 1 L of pure water (adjusted to pH 8.0 with KOH), and cultivated at 31.5° C. After completion of the culture, the amount of accumulated L-glutamic acid and bacterial cell concentration (OD) in the culture broth was measured. The result is shown in FIG. 10. The result shows that the strain expressing the mutant pfk gene exhibited higher L-glutamic acid yield compared to the strain expressing the wild-type pfk gene.

(2) Evaluation when Penicillin is Added

Figure 11:
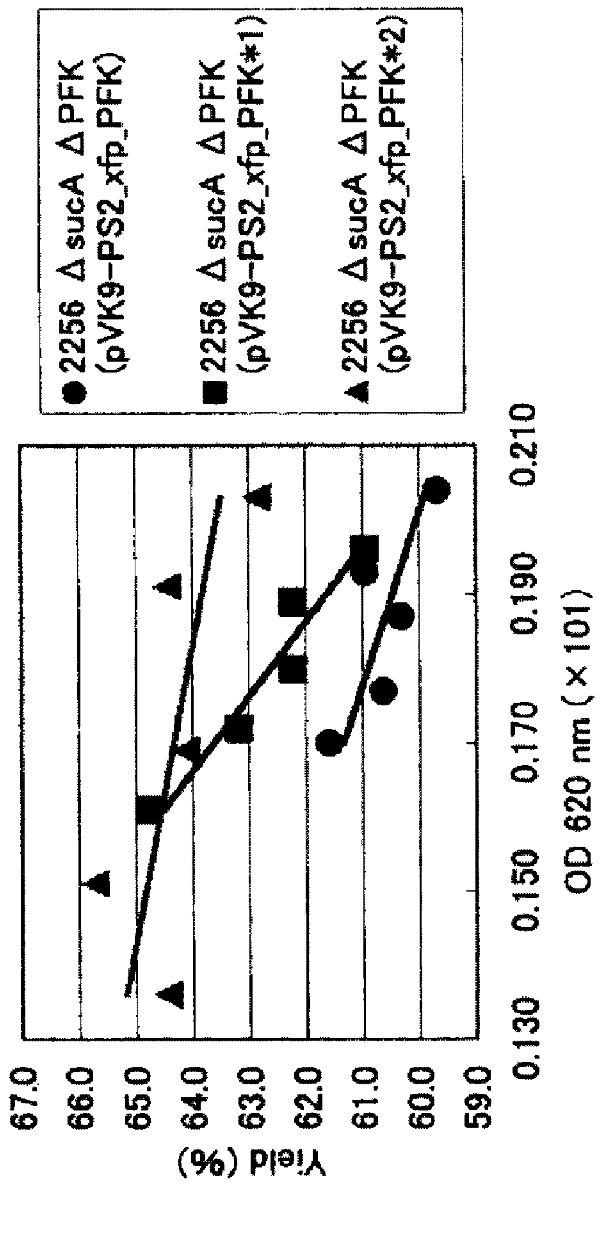
FIG. 11 shows the production of L-glutamic acid using a strain in which a phosphoketolase gene is introduced and 6-phosphofructokinase activity is reduced in the presence of penicillin.

The yield of L-glutamic acid was compared by adding penicillin G to a final concentration of 4 U/ml to the above-described medium in order to stop cell growth to obtain an equalized final bacterial amount, at plural growth points when the OD became within a range from 10 to 14 after start of the culture. The result is shown in FIG. 11. The above-described results show that the reduction in PFK activity in phosphoketolase-introduced strains is effective for improving fermentation yield of L-glutamic acid.

Example 11

Evaluation of L-Glutamine-Production Using a Bacterium in which Phosphoketolase Activity is Enhanced By using the strain *B. flavum* AJ11576 (JP56-16479A), the effect of the introduction of a phosphoketolase gene on the improvement of fermentation yield of L-glutamine was evaluated. The AJ11576 strain is resistant to compounds which have vitamin P activity. This strain was deposited at the National Institute of Bioscience and Human-Technology, Agency of Industrial Science and Technology, Ministry of International Trade and Industry (currently, National Institute of Advanced Industrial Science and Technology, International Patent Organism Depositary, Central 6, 1-1, Higashi 1-Chome, Tsukuba-shi, Ibaraki-ken, 305-8566, Japan) and received an accession number of FERM BP-10381.

The pVK9 (plasmid for control) and pVK9-PS2_xfp (plasmid for amplifying xfp gene of *Bifidobacterium animalis*, in which the native promoter is replaced with a PS2 promoter) were each introduced into the above-described strain *B. flavum* AJ11576 to obtain phosphoketolase-expressing strains. Specifically, the strain was transformed with the each of the plasmids by the electric pulse method, plated on a CM2G medium (5 g/L of glucose, 10 g/L of polypeptone, 10 g/L of yeast extract, 5 g/L NaCl, adjusted to pH 7.0 by KOH) containing 25 mg/ml of kanamycin and cultured at 31.5° C. for about 30 hours. The emerged colonies were isolated as transformants and designated AJ11576 (pVK9) and AJ11576 (pVK9-PS2_xfp), respectively.

Figure 12:
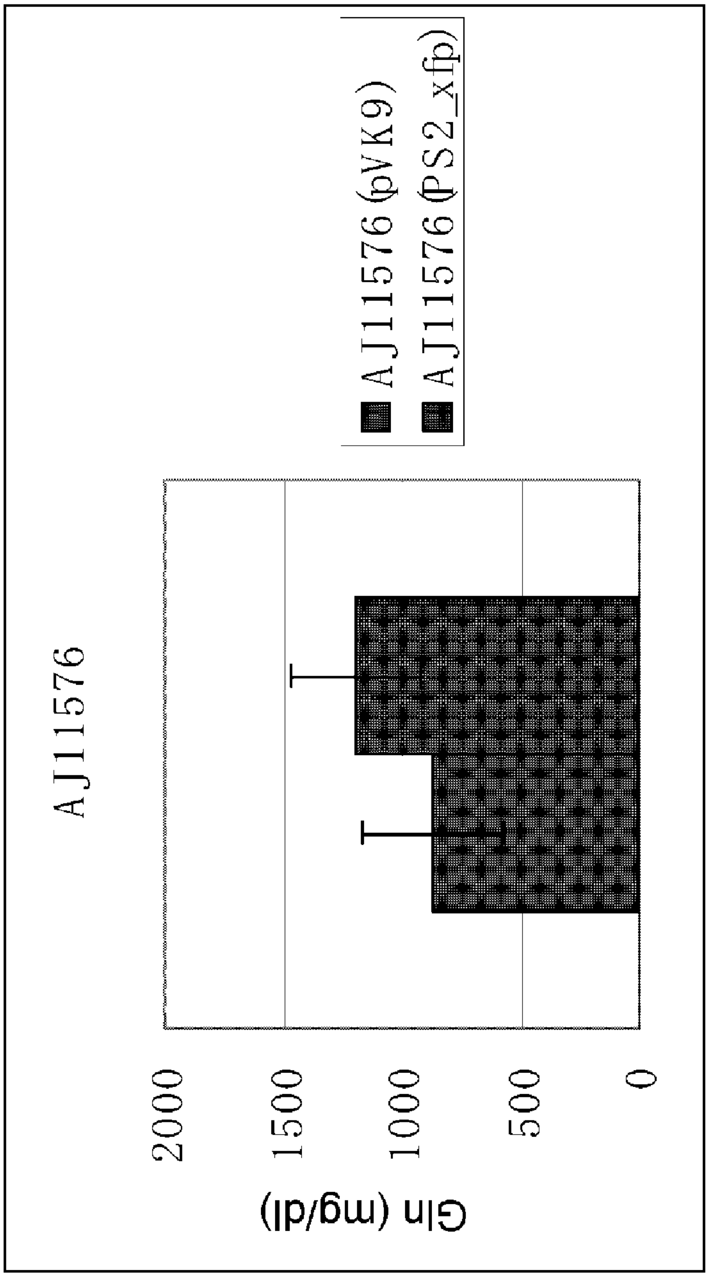
FIG. 12 shows the production of L-glutamine (Gln) using a phosphoketolase gene-amplified strain.

The cells of the AJ11576 (pVK9) and AJ11576 (pVK9-PS2_xfp) strains obtained by culturing on a CM2G plate medium were inoculated into the Flask culture medium containing 100 g of glucose, 2.5 g of $KH_2PO_4$, 0.4 g of $MgSO_4$, 60 g of $(NH_4)_2SO_4$, 0.01 g of $FeSO_4.7H_2O$, 5.7 ml of a soybean hydrolysate solution, 2 mg of thiamine hydrochloride, 4 μg of biotin, 0.02 ml GD-113 and 50 g of $CaCO_3$ in 1 L of pure water (adjusted to pH 6.8 with NaOH) and cultured at 31.5° C. with shaking until the sugar was completely consumed. After completion of the culture, the amount of accumulated L-glutamine and OD in the culture broth were measured. The results are shown in FIG. 12. It has been revealed that all of the xfp-gene amplified strains exhibited high L-glutamine production compared to the control strain.

While the invention has been described in detail with reference to preferred embodiments thereof, it will be apparent to one skilled in the art that various changes can be made, and equivalents employed, without departing from the scope of the invention. All the references cited herein, including the priority documents, RU 2004124226 and U.S. 60/644,562, are incorporated as a part of this application by reference.

The invention claimed is:

1. A method for producing L-glutamic acid comprising cultivating a bacterium in a culture medium to produce L-glutamic acid in the culture medium and/or the bacterium, and collecting L-glutamic acid from the culture medium and/or the bacterium, wherein said bacterium is modified to have D-xylulose-5-phosphate phosphoketolase and/or fructose-6-phosphate phosphoketolase activities, wherein the bacterium is selected from the group consisting of *Pantoea ananatis* and coryneform bacterium.

2. The method according to claim 1, wherein the bacterium inherently does not have an activity of D-xylulose-5-phosphate phosphoketolase and fructose-6-phosphate phosphoketolase, and wherein said bacterium is modified by introducing a DNA fragment coding for D-xylulose-5-phosphate phosphoketolase and/or fructose-6-phosphate phosphoketolase.

3. The method according to claim 1, wherein the bacterium is further modified to have a reduced activity of 6-phosphofructokinase.

4. The method according to claim 2, wherein said DNA fragment coding for D-xylulose-5-phosphate phosphoketolase, fructose-6-phosphate phosphoketolase, or both is derived from a bacterium belonging to the genus *Acetobacter, Bifidobacterium, Chlorobium, Brucella, Methylococus*, or *Gardnerella*, or yeast belonging to the genus *Rhodotorula, Candida*, or *Saccharomyces*.

5. The method according to claim 2, wherein said DNA fragment coding for D-xylulose-5-phosphate phosphoketolase, fructose-6-phosphate phosphoketolase, or both is derived from *Bifidobacterium longum*.

6. The method according to claim 2, wherein said DNA fragment coding for D-xylulose-5-phosphate phosphoketolase, fructose-6-phosphate phosphoketolase, or both codes for the amino acid sequence of SEQ ID NO: 73.

* * * * *

SEQUENCE LISTING

```
<160> NUMBER OF SEQ ID NOS: 81

<210> SEQ ID NO 1
<211> LENGTH: 2367
<212> TYPE: DNA
<213> ORGANISM: Lactobacillus pentosus
<220> FEATURE:
<221> NAME/KEY: CDS
<222> LOCATION: (1)..(2367)

<400> SEQUENCE: 1

atg tct aca gat tac tca tca cca gca tat ttg caa aaa gtt gat aag       48
Met Ser Thr Asp Tyr Ser Ser Pro Ala Tyr Leu Gln Lys Val Asp Lys
1               5                   10                  15

tac tgg cgt gct gcc aac tat tta tca gtt ggt caa ctt tat tta aaa       96
Tyr Trp Arg Ala Ala Asn Tyr Leu Ser Val Gly Gln Leu Tyr Leu Lys
            20                  25                  30

gat aat cct tta tta caa cgg cca tta aag gct agt gac gtt aag gtt      144
Asp Asn Pro Leu Leu Gln Arg Pro Leu Lys Ala Ser Asp Val Lys Val
        35                  40                  45

cac cca atc ggt cac tgg ggc acg att gcc ggc caa aac ttc atc tat      192
His Pro Ile Gly His Trp Gly Thr Ile Ala Gly Gln Asn Phe Ile Tyr
    50                  55                  60

gcg cat ctt aac cgg gtc atc aac aag tac ggt ttg aag atg ttc tac      240
Ala His Leu Asn Arg Val Ile Asn Lys Tyr Gly Leu Lys Met Phe Tyr
65                  70                  75                  80

gtt gaa ggt cca ggt cat ggt ggc caa gtg atg gtc tcc aac tca tac      288
Val Glu Gly Pro Gly His Gly Gly Gln Val Met Val Ser Asn Ser Tyr
                85                  90                  95

ctt gat ggg act tac acg gat att tat cct gaa att acg cag gat gtt      336
Leu Asp Gly Thr Tyr Thr Asp Ile Tyr Pro Glu Ile Thr Gln Asp Val
            100                 105                 110

gaa ggg atg caa aaa ctc ttc aag caa ttc tca ttc cca ggt ggc gtg      384
Glu Gly Met Gln Lys Leu Phe Lys Gln Phe Ser Phe Pro Gly Gly Val
        115                 120                 125

gct tcc cat gct gct cct gaa aca cca ggc tca atc cac gaa ggt ggc      432
Ala Ser His Ala Ala Pro Glu Thr Pro Gly Ser Ile His Glu Gly Gly
    130                 135                 140

gaa ctt ggt tac tca att tca cac ggt gtt ggg gca atc ctt gac aac      480
Glu Leu Gly Tyr Ser Ile Ser His Gly Val Gly Ala Ile Leu Asp Asn
145                 150                 155                 160

cct gat gaa atc gcc gca gtc gtt gtt ggt gat ggg gaa tcc gaa acc      528
Pro Asp Glu Ile Ala Ala Val Val Val Gly Asp Gly Glu Ser Glu Thr
                165                 170                 175

ggc cca tta gca act tca tgg caa tca acg aag ttc atc aac cca atc      576
Gly Pro Leu Ala Thr Ser Trp Gln Ser Thr Lys Phe Ile Asn Pro Ile
            180                 185                 190

aac gat ggg gca gtg tta cca atc ttg aac ctt aac ggc ttt aag att      624
Asn Asp Gly Ala Val Leu Pro Ile Leu Asn Leu Asn Gly Phe Lys Ile
        195                 200                 205

tct aac cca acg att ttt ggt cgg act tct gat gaa aag atc aag caa      672
Ser Asn Pro Thr Ile Phe Gly Arg Thr Ser Asp Glu Lys Ile Lys Gln
    210                 215                 220

tac ttc gaa agc atg aac tgg gaa cca atc ttt gtt gaa ggt gac gat      720
Tyr Phe Glu Ser Met Asn Trp Glu Pro Ile Phe Val Glu Gly Asp Asp
225                 230                 235                 240

cct gaa aag gtt cac cca gct tta gct aag gcc atg gat gaa gcc gtc      768
Pro Glu Lys Val His Pro Ala Leu Ala Lys Ala Met Asp Glu Ala Val
                245                 250                 255

gaa aag atc aaa gcc att caa aag aac gct cgt gaa aac gat gac gct      816
```

-continued

```
Glu Lys Ile Lys Ala Ile Gln Lys Asn Ala Arg Glu Asn Asp Asp Ala
            260                 265                 270

act tta cca gta tgg ccg atg atc gtc ttc cgc gca cct aag ggc tgg      864
Thr Leu Pro Val Trp Pro Met Ile Val Phe Arg Ala Pro Lys Gly Trp
        275                 280                 285

act ggt cct aag tca tgg gat ggc gac aag atc gaa ggt tca ttc cga      912
Thr Gly Pro Lys Ser Trp Asp Gly Asp Lys Ile Glu Gly Ser Phe Arg
    290                 295                 300

gct cac caa att cca att cct gtt gac caa acc gac atg gaa cat gcc      960
Ala His Gln Ile Pro Ile Pro Val Asp Gln Thr Asp Met Glu His Ala
305                 310                 315                 320

gat gcg tta gtt gac tgg ttg gaa tca tat caa cca aag gaa ctc ttc     1008
Asp Ala Leu Val Asp Trp Leu Glu Ser Tyr Gln Pro Lys Glu Leu Phe
                325                 330                 335

aat gaa gat ggt tct ttg aag gat gat atc aaa gaa att atc cca act     1056
Asn Glu Asp Gly Ser Leu Lys Asp Asp Ile Lys Glu Ile Ile Pro Thr
            340                 345                 350

ggc gat gca cgg atg gcc gct aac cca atc act aat ggt ggg gtt gat     1104
Gly Asp Ala Arg Met Ala Ala Asn Pro Ile Thr Asn Gly Gly Val Asp
        355                 360                 365

cca aag gcc ttg aac tta cct aac ttc cgt gat tac gcc gtt gat acg     1152
Pro Lys Ala Leu Asn Leu Pro Asn Phe Arg Asp Tyr Ala Val Asp Thr
    370                 375                 380

tct aag cat ggt gcc aac gtt aag caa gat atg atc gtt tgg tca gac     1200
Ser Lys His Gly Ala Asn Val Lys Gln Asp Met Ile Val Trp Ser Asp
385                 390                 395                 400

tac ttg cgt gat gtt atc aag aag aac cca gat aac ttc cgg tta ttt     1248
Tyr Leu Arg Asp Val Ile Lys Lys Asn Pro Asp Asn Phe Arg Leu Phe
                405                 410                 415

ggc cct gat gaa acc atg tca aac cgg tta tat ggt gtc ttt gaa acc     1296
Gly Pro Asp Glu Thr Met Ser Asn Arg Leu Tyr Gly Val Phe Glu Thr
            420                 425                 430

act aac cgt caa tgg atg gaa gat att cac cca gat agt gac caa tac     1344
Thr Asn Arg Gln Trp Met Glu Asp Ile His Pro Asp Ser Asp Gln Tyr
        435                 440                 445

gaa gca cct gct ggc cgg gtc ttg gat gct caa tta tct gaa cac caa     1392
Glu Ala Pro Ala Gly Arg Val Leu Asp Ala Gln Leu Ser Glu His Gln
    450                 455                 460

gct gaa ggt tgg tta gaa ggt tac gtc tta act ggt cgt cat ggc ttg     1440
Ala Glu Gly Trp Leu Glu Gly Tyr Val Leu Thr Gly Arg His Gly Leu
465                 470                 475                 480

ttt gca agt tac gaa gcc ttc tta cgg gtt gtc gac tca atg ttg acg     1488
Phe Ala Ser Tyr Glu Ala Phe Leu Arg Val Val Asp Ser Met Leu Thr
                485                 490                 495

caa cac ttc aag tgg tta cgt aag gcc aac gaa ctt gac tgg cgg aag     1536
Gln His Phe Lys Trp Leu Arg Lys Ala Asn Glu Leu Asp Trp Arg Lys
            500                 505                 510

aag tac ccg tca ctc aac att atc gcg gct tca act gtg ttc caa caa     1584
Lys Tyr Pro Ser Leu Asn Ile Ile Ala Ala Ser Thr Val Phe Gln Gln
        515                 520                 525

gac cat aat ggg tac acc cac caa gat cca ggt gcc ttg act cat ttg     1632
Asp His Asn Gly Tyr Thr His Gln Asp Pro Gly Ala Leu Thr His Leu
    530                 535                 540

gct gaa aag aag cct gaa tat atc cgc gaa tat tta cca gcc gac gcc     1680
Ala Glu Lys Lys Pro Glu Tyr Ile Arg Glu Tyr Leu Pro Ala Asp Ala
545                 550                 555                 560

aac tcc ttg tta gct gtt ggg gac gtc atc ttc cgt agc caa gaa aag     1728
Asn Ser Leu Leu Ala Val Gly Asp Val Ile Phe Arg Ser Gln Glu Lys
                565                 570                 575

atc aac tac gtg gtt acg tcg aag cac cca cgt caa caa tgg ttc agc     1776
```

```
Ile Asn Tyr Val Val Thr Ser Lys His Pro Arg Gln Gln Trp Phe Ser
            580                 585                 590

att gaa gaa gct aag caa tta gtt gac aac ggt ctt ggt atc att gac      1824
Ile Glu Glu Ala Lys Gln Leu Val Asp Asn Gly Leu Gly Ile Ile Asp
        595                 600                 605

tgg gca agc acg gac caa ggt agc gaa cca gat atc gtg ttt gct gct      1872
Trp Ala Ser Thr Asp Gln Gly Ser Glu Pro Asp Ile Val Phe Ala Ala
    610                 615                 620

gcc gga acg gaa cca acg ctt gaa acg ttg gct gca atc caa ttg ctc      1920
Ala Gly Thr Glu Pro Thr Leu Glu Thr Leu Ala Ala Ile Gln Leu Leu
625                 630                 635                 640

cat gat agc ttc cca gac atg aag att cgt ttc gtg aac gtg gtc gac      1968
His Asp Ser Phe Pro Asp Met Lys Ile Arg Phe Val Asn Val Val Asp
                645                 650                 655

atc ttg aag tta cgt agc cct gaa aag gac cct cgt ggc ttg tca gat      2016
Ile Leu Lys Leu Arg Ser Pro Glu Lys Asp Pro Arg Gly Leu Ser Asp
            660                 665                 670

gct gaa ttt gac cat tac ttc act aag gac aaa cca gtt gtc ttc gcc      2064
Ala Glu Phe Asp His Tyr Phe Thr Lys Asp Lys Pro Val Val Phe Ala
        675                 680                 685

ttc cat ggt tac gaa gac ctg gtt cgt gac atc ttc ttt gat cgt cac      2112
Phe His Gly Tyr Glu Asp Leu Val Arg Asp Ile Phe Phe Asp Arg His
    690                 695                 700

aac cac aac tta cac gtg cat ggc tac cgt gaa aat ggt gac att acg      2160
Asn His Asn Leu His Val His Gly Tyr Arg Glu Asn Gly Asp Ile Thr
705                 710                 715                 720

aca cca ttc gat gtc cgg gtc atg aac caa atg gac cgt ttc gac tta      2208
Thr Pro Phe Asp Val Arg Val Met Asn Gln Met Asp Arg Phe Asp Leu
                725                 730                 735

gca aaa tct gca att gcg gcg caa cca gca atg gaa aac acc ggt gca      2256
Ala Lys Ser Ala Ile Ala Ala Gln Pro Ala Met Glu Asn Thr Gly Ala
            740                 745                 750

gcc ttt gtt caa gac atg gat aac atg ctt gca aaa cac aac gca tac      2304
Ala Phe Val Gln Asp Met Asp Asn Met Leu Ala Lys His Asn Ala Tyr
        755                 760                 765

atc cgt gac gcc gga acc gac ttg cca gaa gtt aac gac tgg caa tgg      2352
Ile Arg Asp Ala Gly Thr Asp Leu Pro Glu Val Asn Asp Trp Gln Trp
    770                 775                 780

aaa ggt ttg aaa taa                                                  2367
Lys Gly Leu Lys
785


<210> SEQ ID NO 2
<211> LENGTH: 788
<212> TYPE: PRT
<213> ORGANISM: Lactobacillus pentosus

<400> SEQUENCE: 2

Met Ser Thr Asp Tyr Ser Ser Pro Ala Tyr Leu Gln Lys Val Asp Lys
1               5                   10                  15

Tyr Trp Arg Ala Ala Asn Tyr Leu Ser Val Gly Gln Leu Tyr Leu Lys
            20                  25                  30

Asp Asn Pro Leu Leu Gln Arg Pro Leu Lys Ala Ser Asp Val Lys Val
        35                  40                  45

His Pro Ile Gly His Trp Gly Thr Ile Ala Gly Gln Asn Phe Ile Tyr
    50                  55                  60

Ala His Leu Asn Arg Val Ile Asn Lys Tyr Gly Leu Lys Met Phe Tyr
65                  70                  75                  80

Val Glu Gly Pro Gly His Gly Gly Gln Val Met Val Ser Asn Ser Tyr
                85                  90                  95
```

-continued

```
Leu Asp Gly Thr Tyr Thr Asp Ile Tyr Pro Glu Ile Thr Gln Asp Val
            100                 105                 110

Glu Gly Met Gln Lys Leu Phe Lys Gln Phe Ser Phe Pro Gly Gly Val
        115                 120                 125

Ala Ser His Ala Ala Pro Glu Thr Pro Gly Ser Ile His Glu Gly Gly
    130                 135                 140

Glu Leu Gly Tyr Ser Ile Ser His Gly Val Gly Ala Ile Leu Asp Asn
145                 150                 155                 160

Pro Asp Glu Ile Ala Ala Val Val Val Gly Asp Gly Glu Ser Glu Thr
                165                 170                 175

Gly Pro Leu Ala Thr Ser Trp Gln Ser Thr Lys Phe Ile Asn Pro Ile
            180                 185                 190

Asn Asp Gly Ala Val Leu Pro Ile Leu Asn Leu Asn Gly Phe Lys Ile
        195                 200                 205

Ser Asn Pro Thr Ile Phe Gly Arg Thr Ser Asp Glu Lys Ile Lys Gln
    210                 215                 220

Tyr Phe Glu Ser Met Asn Trp Glu Pro Ile Phe Val Glu Gly Asp Asp
225                 230                 235                 240

Pro Glu Lys Val His Pro Ala Leu Ala Lys Ala Met Asp Glu Ala Val
                245                 250                 255

Glu Lys Ile Lys Ala Ile Gln Lys Asn Ala Arg Glu Asn Asp Asp Ala
            260                 265                 270

Thr Leu Pro Val Trp Pro Met Ile Val Phe Arg Ala Pro Lys Gly Trp
        275                 280                 285

Thr Gly Pro Lys Ser Trp Asp Gly Asp Lys Ile Glu Gly Ser Phe Arg
    290                 295                 300

Ala His Gln Ile Pro Ile Pro Val Asp Gln Thr Asp Met Glu His Ala
305                 310                 315                 320

Asp Ala Leu Val Asp Trp Leu Glu Ser Tyr Gln Pro Lys Glu Leu Phe
                325                 330                 335

Asn Glu Asp Gly Ser Leu Lys Asp Asp Ile Lys Glu Ile Ile Pro Thr
            340                 345                 350

Gly Asp Ala Arg Met Ala Ala Asn Pro Ile Thr Asn Gly Gly Val Asp
        355                 360                 365

Pro Lys Ala Leu Asn Leu Pro Asn Phe Arg Asp Tyr Ala Val Asp Thr
    370                 375                 380

Ser Lys His Gly Ala Asn Val Lys Gln Asp Met Ile Val Trp Ser Asp
385                 390                 395                 400

Tyr Leu Arg Asp Val Ile Lys Lys Asn Pro Asp Asn Phe Arg Leu Phe
                405                 410                 415

Gly Pro Asp Glu Thr Met Ser Asn Arg Leu Tyr Gly Val Phe Glu Thr
            420                 425                 430

Thr Asn Arg Gln Trp Met Glu Asp Ile His Pro Asp Ser Asp Gln Tyr
        435                 440                 445

Glu Ala Pro Ala Gly Arg Val Leu Asp Ala Gln Leu Ser Glu His Gln
    450                 455                 460

Ala Glu Gly Trp Leu Glu Gly Tyr Val Leu Thr Gly Arg His Gly Leu
465                 470                 475                 480

Phe Ala Ser Tyr Glu Ala Phe Leu Arg Val Val Asp Ser Met Leu Thr
                485                 490                 495

Gln His Phe Lys Trp Leu Arg Lys Ala Asn Glu Leu Asp Trp Arg Lys
            500                 505                 510

Lys Tyr Pro Ser Leu Asn Ile Ile Ala Ala Ser Thr Val Phe Gln Gln
```

```
        515                 520                 525

Asp His Asn Gly Tyr Thr His Gln Asp Pro Gly Ala Leu Thr His Leu
    530                 535                 540

Ala Glu Lys Lys Pro Glu Tyr Ile Arg Glu Tyr Leu Pro Ala Asp Ala
545                 550                 555                 560

Asn Ser Leu Leu Ala Val Gly Asp Val Ile Phe Arg Ser Gln Glu Lys
                565                 570                 575

Ile Asn Tyr Val Val Thr Ser Lys His Pro Arg Gln Gln Trp Phe Ser
            580                 585                 590

Ile Glu Glu Ala Lys Gln Leu Val Asp Asn Gly Leu Gly Ile Ile Asp
        595                 600                 605

Trp Ala Ser Thr Asp Gln Gly Ser Glu Pro Asp Ile Val Phe Ala Ala
    610                 615                 620

Ala Gly Thr Glu Pro Thr Leu Glu Thr Leu Ala Ala Ile Gln Leu Leu
625                 630                 635                 640

His Asp Ser Phe Pro Asp Met Lys Ile Arg Phe Val Asn Val Val Asp
                645                 650                 655

Ile Leu Lys Leu Arg Ser Pro Glu Lys Asp Pro Arg Gly Leu Ser Asp
            660                 665                 670

Ala Glu Phe Asp His Tyr Phe Thr Lys Asp Lys Pro Val Val Phe Ala
        675                 680                 685

Phe His Gly Tyr Glu Asp Leu Val Arg Asp Ile Phe Phe Asp Arg His
    690                 695                 700

Asn His Asn Leu His Val His Gly Tyr Arg Glu Asn Gly Asp Ile Thr
705                 710                 715                 720

Thr Pro Phe Asp Val Arg Val Met Asn Gln Met Asp Arg Phe Asp Leu
                725                 730                 735

Ala Lys Ser Ala Ile Ala Ala Gln Pro Ala Met Glu Asn Thr Gly Ala
            740                 745                 750

Ala Phe Val Gln Asp Met Asp Asn Met Leu Ala Lys His Asn Ala Tyr
        755                 760                 765

Ile Arg Asp Ala Gly Thr Asp Leu Pro Glu Val Asn Asp Trp Gln Trp
    770                 775                 780

Lys Gly Leu Lys
785


<210> SEQ ID NO 3
<211> LENGTH: 2367
<212> TYPE: DNA
<213> ORGANISM: Lactobacillus plantarum
<220> FEATURE:
<221> NAME/KEY: CDS
<222> LOCATION: (1)..(2367)

<400> SEQUENCE: 3

atg aca aca gat tac tca tca cca gca tat ttg caa aaa gtt gat aag        48
Met Thr Thr Asp Tyr Ser Ser Pro Ala Tyr Leu Gln Lys Val Asp Lys
1               5                   10                  15

tac tgg cgt gct gcc aac tac tta tca gtt ggt caa ctt tat tta aaa        96
Tyr Trp Arg Ala Ala Asn Tyr Leu Ser Val Gly Gln Leu Tyr Leu Lys
            20                  25                  30

gat aat cca cta tta caa cgg cca ttg aag gcc agt gac gtt aag gtt       144
Asp Asn Pro Leu Leu Gln Arg Pro Leu Lys Ala Ser Asp Val Lys Val
        35                  40                  45

cat cca att ggt cac tgg ggg acg att gcc ggt caa aac ttt atc tat       192
His Pro Ile Gly His Trp Gly Thr Ile Ala Gly Gln Asn Phe Ile Tyr
    50                  55                  60
```

-continued

```
gct cat ctt aac cgg gtc atc aac aag tac ggt ttg aag atg ttc tac      240
Ala His Leu Asn Arg Val Ile Asn Lys Tyr Gly Leu Lys Met Phe Tyr
65                  70                  75                  80

gtt gaa ggt cca ggt cat ggt ggt caa gtg atg gtt tca aac tct tac      288
Val Glu Gly Pro Gly His Gly Gly Gln Val Met Val Ser Asn Ser Tyr
                85                  90                  95

ctt gac ggt act tac acc gat att tat cca gaa att acg cag gat gtt      336
Leu Asp Gly Thr Tyr Thr Asp Ile Tyr Pro Glu Ile Thr Gln Asp Val
            100                 105                 110

gaa ggg atg caa aag ctc ttc aag caa ttc tca ttc cca ggt ggg gtt      384
Glu Gly Met Gln Lys Leu Phe Lys Gln Phe Ser Phe Pro Gly Gly Val
        115                 120                 125

gct tcc cat gcg gca cct gaa aca ccc ggt tca atc cac gaa ggt ggc      432
Ala Ser His Ala Ala Pro Glu Thr Pro Gly Ser Ile His Glu Gly Gly
    130                 135                 140

gaa ctt ggt tac tca att tca cac ggg gtt ggg gca att ctt gac aat      480
Glu Leu Gly Tyr Ser Ile Ser His Gly Val Gly Ala Ile Leu Asp Asn
145                 150                 155                 160

cct gac gaa atc gcc gcg gtt gtt gtt ggt gat ggg gaa tcc gaa acg      528
Pro Asp Glu Ile Ala Ala Val Val Val Gly Asp Gly Glu Ser Glu Thr
                165                 170                 175

ggt cca tta gca act tca tgg caa tca acg aag ttc att aac cca atc      576
Gly Pro Leu Ala Thr Ser Trp Gln Ser Thr Lys Phe Ile Asn Pro Ile
            180                 185                 190

aac gac ggg gct gtt tta cca atc ttg aac tta aat ggt ttt aag att      624
Asn Asp Gly Ala Val Leu Pro Ile Leu Asn Leu Asn Gly Phe Lys Ile
        195                 200                 205

tct aat cca acg att ttt ggt cgg act tct gat gct aag att aag gaa      672
Ser Asn Pro Thr Ile Phe Gly Arg Thr Ser Asp Ala Lys Ile Lys Glu
    210                 215                 220

tac ttc gaa agc atg aat tgg gaa cca atc ttc gtt gaa ggt gac gat      720
Tyr Phe Glu Ser Met Asn Trp Glu Pro Ile Phe Val Glu Gly Asp Asp
225                 230                 235                 240

cct gaa aag gtt cac cca gcc tta gct aag gcc atg gat gaa gcc gtt      768
Pro Glu Lys Val His Pro Ala Leu Ala Lys Ala Met Asp Glu Ala Val
                245                 250                 255

gaa aag atc aag gca atc cag aag cat gct cgc gaa aat aac gat gca      816
Glu Lys Ile Lys Ala Ile Gln Lys His Ala Arg Glu Asn Asn Asp Ala
            260                 265                 270

aca ttg cca gta tgg cca atg atc gtc ttc cgc gca cct aag ggc tgg      864
Thr Leu Pro Val Trp Pro Met Ile Val Phe Arg Ala Pro Lys Gly Trp
        275                 280                 285

act ggt ccg aag tca tgg gac ggt gat aag atc gaa ggt tca ttc cgt      912
Thr Gly Pro Lys Ser Trp Asp Gly Asp Lys Ile Glu Gly Ser Phe Arg
    290                 295                 300

gct cat caa att ccg att cct gtt gat caa aat gac atg gaa cat gcg      960
Ala His Gln Ile Pro Ile Pro Val Asp Gln Asn Asp Met Glu His Ala
305                 310                 315                 320

gat gct tta gtt gat tgg ctc gaa tca tat caa cca aaa gaa ctc ttc     1008
Asp Ala Leu Val Asp Trp Leu Glu Ser Tyr Gln Pro Lys Glu Leu Phe
                325                 330                 335

aat gaa gat ggc tct ttg aag gat gat att aaa gaa att att cct act     1056
Asn Glu Asp Gly Ser Leu Lys Asp Asp Ile Lys Glu Ile Ile Pro Thr
            340                 345                 350

ggg gac agt cgg atg gct gct aac cca atc acc aat ggt ggg gtc gat     1104
Gly Asp Ser Arg Met Ala Ala Asn Pro Ile Thr Asn Gly Gly Val Asp
        355                 360                 365

ccg aaa gcc ttg aac tta cca aac ttc cgt gat tat gcg gtc gat acg     1152
Pro Lys Ala Leu Asn Leu Pro Asn Phe Arg Asp Tyr Ala Val Asp Thr
    370                 375                 380
```

-continued

```
tcc aaa gaa ggc gcg aat gtt aag caa gat atg atc gtt tgg tca gac      1200
Ser Lys Glu Gly Ala Asn Val Lys Gln Asp Met Ile Val Trp Ser Asp
385                 390                 395                 400

tat ttg cgg gat gtc atc aag aaa aat cct gat aac ttc cgg ttg ttc      1248
Tyr Leu Arg Asp Val Ile Lys Lys Asn Pro Asp Asn Phe Arg Leu Phe
                405                 410                 415

gga cct gat gaa acc atg tct aac cgt tta tat ggt gtc ttc gaa acc      1296
Gly Pro Asp Glu Thr Met Ser Asn Arg Leu Tyr Gly Val Phe Glu Thr
            420                 425                 430

act aat cgt caa tgg atg gaa gac att cat cca gat agt gac caa tat      1344
Thr Asn Arg Gln Trp Met Glu Asp Ile His Pro Asp Ser Asp Gln Tyr
        435                 440                 445

gaa gca cca gct ggc cgg gtc tta gat gct cag tta tct gaa cac caa      1392
Glu Ala Pro Ala Gly Arg Val Leu Asp Ala Gln Leu Ser Glu His Gln
    450                 455                 460

gct gaa ggt tgg tta gaa ggt tac gtc tta act gga cgt cat ggg tta      1440
Ala Glu Gly Trp Leu Glu Gly Tyr Val Leu Thr Gly Arg His Gly Leu
465                 470                 475                 480

ttt gcc agt tat gaa gcc ttc cta cgc gtt gtg gac tca atg ttg acg      1488
Phe Ala Ser Tyr Glu Ala Phe Leu Arg Val Val Asp Ser Met Leu Thr
                485                 490                 495

caa cac ttc aag tgg tta cgt aaa gcc aat gaa ctt gat tgg cgt aaa      1536
Gln His Phe Lys Trp Leu Arg Lys Ala Asn Glu Leu Asp Trp Arg Lys
            500                 505                 510

aag tac cca tca ctt aac att atc gcg gct tca act gta ttc caa caa      1584
Lys Tyr Pro Ser Leu Asn Ile Ile Ala Ala Ser Thr Val Phe Gln Gln
        515                 520                 525

gac cat aat ggt tat acc cac caa gat cca ggt gca tta act cat ttg      1632
Asp His Asn Gly Tyr Thr His Gln Asp Pro Gly Ala Leu Thr His Leu
    530                 535                 540

gcc gaa aag aaa cca gaa tac att cgt gaa tat tta cca gcc gat gcc      1680
Ala Glu Lys Lys Pro Glu Tyr Ile Arg Glu Tyr Leu Pro Ala Asp Ala
545                 550                 555                 560

aac acg tta tta gct gtc ggt gac gtc att ttc cgg agc caa gaa aag      1728
Asn Thr Leu Leu Ala Val Gly Asp Val Ile Phe Arg Ser Gln Glu Lys
                565                 570                 575

atc aac tac gtg gtt acg tca aaa cac cca cgt caa caa tgg ttc agc      1776
Ile Asn Tyr Val Val Thr Ser Lys His Pro Arg Gln Gln Trp Phe Ser
            580                 585                 590

att gaa gaa gct aag caa tta gtt gac aat ggt ctt ggt atc att gat      1824
Ile Glu Glu Ala Lys Gln Leu Val Asp Asn Gly Leu Gly Ile Ile Asp
        595                 600                 605

tgg gca agt acg gac caa ggt agc gaa cca gac att gtc ttt gca gct      1872
Trp Ala Ser Thr Asp Gln Gly Ser Glu Pro Asp Ile Val Phe Ala Ala
    610                 615                 620

gct ggg acg gaa cca acg ctt gaa acg ttg gct gcc atc caa tta cta      1920
Ala Gly Thr Glu Pro Thr Leu Glu Thr Leu Ala Ala Ile Gln Leu Leu
625                 630                 635                 640

cac gac agt ttc cca gag atg aag att cgt ttc gtg aac gtg gtc gac      1968
His Asp Ser Phe Pro Glu Met Lys Ile Arg Phe Val Asn Val Val Asp
                645                 650                 655

atc ttg aag tta cgt agt cct gaa aag gat ccg cgg ggc ttg tca gat      2016
Ile Leu Lys Leu Arg Ser Pro Glu Lys Asp Pro Arg Gly Leu Ser Asp
            660                 665                 670

gct gag ttt gac cat tac ttt act aag gac aaa cca gtg gtc ttt gct      2064
Ala Glu Phe Asp His Tyr Phe Thr Lys Asp Lys Pro Val Val Phe Ala
        675                 680                 685

ttc cac ggt tac gaa gac tta gtt cgt gac atc ttc ttt gat cgt cac      2112
Phe His Gly Tyr Glu Asp Leu Val Arg Asp Ile Phe Phe Asp Arg His
    690                 695                 700
```

```
aac cat aac tta tac gtc cac ggt tac cgt gaa aat ggt gat att acc      2160
Asn His Asn Leu Tyr Val His Gly Tyr Arg Glu Asn Gly Asp Ile Thr
705                 710                 715                 720

aca cca ttc gac gta cgg gtc atg aac cag atg gac cgc ttc gac tta      2208
Thr Pro Phe Asp Val Arg Val Met Asn Gln Met Asp Arg Phe Asp Leu
                725                 730                 735

gct aag tcg gca att gcg gcg caa cca gca atg gaa aac act ggt gcg      2256
Ala Lys Ser Ala Ile Ala Ala Gln Pro Ala Met Glu Asn Thr Gly Ala
            740                 745                 750

gcc ttc gtt caa tcc atg gat aat atg ctt gct aaa cac aat gcc tat      2304
Ala Phe Val Gln Ser Met Asp Asn Met Leu Ala Lys His Asn Ala Tyr
        755                 760                 765

atc cgg gat gcc gga act gac ttg cca gaa gtt aat gat tgg caa tgg      2352
Ile Arg Asp Ala Gly Thr Asp Leu Pro Glu Val Asn Asp Trp Gln Trp
    770                 775                 780

aag ggt tta aaa taa                                                  2367
Lys Gly Leu Lys
785


<210> SEQ ID NO 4
<211> LENGTH: 788
<212> TYPE: PRT
<213> ORGANISM: Lactobacillus plantarum

<400> SEQUENCE: 4

Met Thr Thr Asp Tyr Ser Ser Pro Ala Tyr Leu Gln Lys Val Asp Lys
1               5                   10                  15

Tyr Trp Arg Ala Ala Asn Tyr Leu Ser Val Gly Gln Leu Tyr Leu Lys
            20                  25                  30

Asp Asn Pro Leu Leu Gln Arg Pro Leu Lys Ala Ser Asp Val Lys Val
        35                  40                  45

His Pro Ile Gly His Trp Gly Thr Ile Ala Gly Gln Asn Phe Ile Tyr
    50                  55                  60

Ala His Leu Asn Arg Val Ile Asn Lys Tyr Gly Leu Lys Met Phe Tyr
65                  70                  75                  80

Val Glu Gly Pro Gly His Gly Gly Gln Val Met Val Ser Asn Ser Tyr
                85                  90                  95

Leu Asp Gly Thr Tyr Thr Asp Ile Tyr Pro Glu Ile Thr Gln Asp Val
            100                 105                 110

Glu Gly Met Gln Lys Leu Phe Lys Gln Phe Ser Phe Pro Gly Gly Val
        115                 120                 125

Ala Ser His Ala Ala Pro Glu Thr Pro Gly Ser Ile His Glu Gly Gly
    130                 135                 140

Glu Leu Gly Tyr Ser Ile Ser His Gly Val Gly Ala Ile Leu Asp Asn
145                 150                 155                 160

Pro Asp Glu Ile Ala Ala Val Val Val Gly Asp Gly Glu Ser Glu Thr
                165                 170                 175

Gly Pro Leu Ala Thr Ser Trp Gln Ser Thr Lys Phe Ile Asn Pro Ile
            180                 185                 190

Asn Asp Gly Ala Val Leu Pro Ile Leu Asn Leu Asn Gly Phe Lys Ile
        195                 200                 205

Ser Asn Pro Thr Ile Phe Gly Arg Thr Ser Asp Ala Lys Ile Lys Glu
    210                 215                 220

Tyr Phe Glu Ser Met Asn Trp Glu Pro Ile Phe Val Glu Gly Asp Asp
225                 230                 235                 240

Pro Glu Lys Val His Pro Ala Leu Ala Lys Ala Met Asp Glu Ala Val
                245                 250                 255
```

-continued

```
Glu Lys Ile Lys Ala Ile Gln Lys His Ala Arg Glu Asn Asn Asp Ala
            260                 265                 270

Thr Leu Pro Val Trp Pro Met Ile Val Phe Arg Ala Pro Lys Gly Trp
        275                 280                 285

Thr Gly Pro Lys Ser Trp Asp Gly Asp Lys Ile Glu Gly Ser Phe Arg
    290                 295                 300

Ala His Gln Ile Pro Ile Pro Val Asp Gln Asn Asp Met Glu His Ala
305                 310                 315                 320

Asp Ala Leu Val Asp Trp Leu Glu Ser Tyr Gln Pro Lys Glu Leu Phe
                325                 330                 335

Asn Glu Asp Gly Ser Leu Lys Asp Asp Ile Lys Glu Ile Ile Pro Thr
            340                 345                 350

Gly Asp Ser Arg Met Ala Ala Asn Pro Ile Thr Asn Gly Gly Val Asp
        355                 360                 365

Pro Lys Ala Leu Asn Leu Pro Asn Phe Arg Asp Tyr Ala Val Asp Thr
    370                 375                 380

Ser Lys Glu Gly Ala Asn Val Lys Gln Asp Met Ile Val Trp Ser Asp
385                 390                 395                 400

Tyr Leu Arg Asp Val Ile Lys Lys Asn Pro Asp Asn Phe Arg Leu Phe
                405                 410                 415

Gly Pro Asp Glu Thr Met Ser Asn Arg Leu Tyr Gly Val Phe Glu Thr
            420                 425                 430

Thr Asn Arg Gln Trp Met Glu Asp Ile His Pro Asp Ser Asp Gln Tyr
        435                 440                 445

Glu Ala Pro Ala Gly Arg Val Leu Asp Ala Gln Leu Ser Glu His Gln
    450                 455                 460

Ala Glu Gly Trp Leu Glu Gly Tyr Val Leu Thr Gly Arg His Gly Leu
465                 470                 475                 480

Phe Ala Ser Tyr Glu Ala Phe Leu Arg Val Val Asp Ser Met Leu Thr
                485                 490                 495

Gln His Phe Lys Trp Leu Arg Lys Ala Asn Glu Leu Asp Trp Arg Lys
            500                 505                 510

Lys Tyr Pro Ser Leu Asn Ile Ile Ala Ala Ser Thr Val Phe Gln Gln
        515                 520                 525

Asp His Asn Gly Tyr Thr His Gln Asp Pro Gly Ala Leu Thr His Leu
    530                 535                 540

Ala Glu Lys Lys Pro Glu Tyr Ile Arg Glu Tyr Leu Pro Ala Asp Ala
545                 550                 555                 560

Asn Thr Leu Leu Ala Val Gly Asp Val Ile Phe Arg Ser Gln Glu Lys
                565                 570                 575

Ile Asn Tyr Val Val Thr Ser Lys His Pro Arg Gln Gln Trp Phe Ser
            580                 585                 590

Ile Glu Glu Ala Lys Gln Leu Val Asp Asn Gly Leu Gly Ile Ile Asp
        595                 600                 605

Trp Ala Ser Thr Asp Gln Gly Ser Glu Pro Asp Ile Val Phe Ala Ala
    610                 615                 620

Ala Gly Thr Glu Pro Thr Leu Glu Thr Leu Ala Ala Ile Gln Leu Leu
625                 630                 635                 640

His Asp Ser Phe Pro Glu Met Lys Ile Arg Phe Val Asn Val Val Asp
                645                 650                 655

Ile Leu Lys Leu Arg Ser Pro Glu Lys Asp Pro Arg Gly Leu Ser Asp
            660                 665                 670

Ala Glu Phe Asp His Tyr Phe Thr Lys Asp Lys Pro Val Val Phe Ala
        675                 680                 685
```

```
Phe His Gly Tyr Glu Asp Leu Val Arg Asp Ile Phe Phe Asp Arg His
    690                 695                 700

Asn His Asn Leu Tyr Val His Gly Tyr Arg Glu Asn Gly Asp Ile Thr
705                 710                 715                 720

Thr Pro Phe Asp Val Arg Val Met Asn Gln Met Asp Arg Phe Asp Leu
                725                 730                 735

Ala Lys Ser Ala Ile Ala Ala Gln Pro Ala Met Glu Asn Thr Gly Ala
            740                 745                 750

Ala Phe Val Gln Ser Met Asp Asn Met Leu Ala Lys His Asn Ala Tyr
        755                 760                 765

Ile Arg Asp Ala Gly Thr Asp Leu Pro Glu Val Asn Asp Trp Gln Trp
    770                 775                 780

Lys Gly Leu Lys
785


<210> SEQ ID NO 5
<211> LENGTH: 2660
<212> TYPE: DNA
<213> ORGANISM: Bifidobacterium lactis
<220> FEATURE:
<221> NAME/KEY: CDS
<222> LOCATION: (128)..(2605)

<400> SEQUENCE: 5

aggtcagcgt attcgcgtaa cataatcagc gatcgggcac ggagaccggc ctgcaggaca      60

gcgccgaagc ccgtgcccaa cggaataaac aaatcgcaca tttatgtgca ggagtacagg     120

agcacac atg act aat cct gtt att ggt acc cca tgg cag aag ctg gat       169
        Met Thr Asn Pro Val Ile Gly Thr Pro Trp Gln Lys Leu Asp
        1               5                   10

cgt ccg gtt tcc gaa gag gcc atc gaa ggc atg gac aag tac tgg cgc       217
Arg Pro Val Ser Glu Glu Ala Ile Glu Gly Met Asp Lys Tyr Trp Arg
15                  20                  25                  30

gtc gcc aac tac atg tct atc ggc cag atc tac ctg cgt agc aac ccg       265
Val Ala Asn Tyr Met Ser Ile Gly Gln Ile Tyr Leu Arg Ser Asn Pro
                35                  40                  45

ctg atg aag gag ccc ttc acc cgc gat gac gtg aag cac cgt ctg gtc       313
Leu Met Lys Glu Pro Phe Thr Arg Asp Asp Val Lys His Arg Leu Val
            50                  55                  60

ggc cac tgg ggc acc acc ccg ggc ctg aac ttc ctt ctc gcc cac atc       361
Gly His Trp Gly Thr Thr Pro Gly Leu Asn Phe Leu Leu Ala His Ile
        65                  70                  75

aac cgc ctg atc gcc gat cac cag cag aac acc gtg ttc atc atg ggt       409
Asn Arg Leu Ile Ala Asp His Gln Gln Asn Thr Val Phe Ile Met Gly
    80                  85                  90

cct ggc cac ggc ggc cct gca ggt acc gct cag tcc tac atc gac ggc       457
Pro Gly His Gly Gly Pro Ala Gly Thr Ala Gln Ser Tyr Ile Asp Gly
95                  100                 105                 110

acc tac acc gag tac tac ccg aac atc acc aag gac gaa gct ggc ctg       505
Thr Tyr Thr Glu Tyr Tyr Pro Asn Ile Thr Lys Asp Glu Ala Gly Leu
                115                 120                 125

cag aag ttc ttc cgc cag ttc tcc tac ccg ggt ggc att cct tcc cac       553
Gln Lys Phe Phe Arg Gln Phe Ser Tyr Pro Gly Gly Ile Pro Ser His
            130                 135                 140

ttc gct ccg gag acg ccg ggc tcc atc cac gaa ggc ggc gag ctg ggc       601
Phe Ala Pro Glu Thr Pro Gly Ser Ile His Glu Gly Gly Glu Leu Gly
        145                 150                 155

tac gcc ctg tcg cac gcc tac ggc gcg atc atg gac aac ccg agc ctc       649
Tyr Ala Leu Ser His Ala Tyr Gly Ala Ile Met Asp Asn Pro Ser Leu
    160                 165                 170
```

```
ttc gtc ccg tgc atc atc ggt gac ggc gaa gcc gag acc ggc cct ctg      697
Phe Val Pro Cys Ile Ile Gly Asp Gly Glu Ala Glu Thr Gly Pro Leu
175                 180                 185                 190

gcc acc ggc tgg cag tcc aac aag ctc gtc aac ccg cgc acc gac ggc      745
Ala Thr Gly Trp Gln Ser Asn Lys Leu Val Asn Pro Arg Thr Asp Gly
                195                 200                 205

atc gtc ctg ccg atc ctg cac ctc aac ggc tac aag atc gcc aac ccg      793
Ile Val Leu Pro Ile Leu His Leu Asn Gly Tyr Lys Ile Ala Asn Pro
            210                 215                 220

acg atc ctc gcc cgc atc tcc gac gag gag ctg cac gac ttc ttc cgc      841
Thr Ile Leu Ala Arg Ile Ser Asp Glu Glu Leu His Asp Phe Phe Arg
        225                 230                 235

ggc atg ggt tac cac ccg tac gag ttc gtc gcc ggc ttc gac aac gag      889
Gly Met Gly Tyr His Pro Tyr Glu Phe Val Ala Gly Phe Asp Asn Glu
    240                 245                 250

gat cac ctg tcg atc cac cgt cgc ttc gcc gag ctc ttc gag acc atc      937
Asp His Leu Ser Ile His Arg Arg Phe Ala Glu Leu Phe Glu Thr Ile
255                 260                 265                 270

ttc gac gag atc tgc gat atc aag gct gcg gct cag acc gac gac atg      985
Phe Asp Glu Ile Cys Asp Ile Lys Ala Ala Ala Gln Thr Asp Asp Met
                275                 280                 285

acc cgt ccg ttc tac ccg atg ctc atc ttc cgc acc ccg aag ggc tgg     1033
Thr Arg Pro Phe Tyr Pro Met Leu Ile Phe Arg Thr Pro Lys Gly Trp
            290                 295                 300

acc tgc ccg aag ttc atc gac ggc aag aag acc gaa ggc tcc tgg cgt     1081
Thr Cys Pro Lys Phe Ile Asp Gly Lys Lys Thr Glu Gly Ser Trp Arg
        305                 310                 315

gca cac cag gtc ccg ctg gct tcc gcc cgc gac acc gag gcc cac ttc     1129
Ala His Gln Val Pro Leu Ala Ser Ala Arg Asp Thr Glu Ala His Phe
    320                 325                 330

gaa gtc ctc aag ggc tgg atg gaa tcc tac aag ccg gag gag ctc ttc     1177
Glu Val Leu Lys Gly Trp Met Glu Ser Tyr Lys Pro Glu Glu Leu Phe
335                 340                 345                 350

aac gcc gac ggc tcc atc aag gag gac gtc acc gca ttc atg cct aag     1225
Asn Ala Asp Gly Ser Ile Lys Glu Asp Val Thr Ala Phe Met Pro Lys
                355                 360                 365

ggc gaa ctg cgc atc ggc gcc aac ccg aat gcc aac ggc ggc cgc atc     1273
Gly Glu Leu Arg Ile Gly Ala Asn Pro Asn Ala Asn Gly Gly Arg Ile
            370                 375                 380

cgc gag gat ctg aag ctc cct gag ctc gat cag tac gag atc acc ggc     1321
Arg Glu Asp Leu Lys Leu Pro Glu Leu Asp Gln Tyr Glu Ile Thr Gly
        385                 390                 395

gtc aag gaa tac ggc cac ggt tgg ggc cag gtc gag gct ccg cgt tcc     1369
Val Lys Glu Tyr Gly His Gly Trp Gly Gln Val Glu Ala Pro Arg Ser
    400                 405                 410

ctc ggc gcg tac tgc cgc gac atc atc aag aac aac ccg gat tcg ttc     1417
Leu Gly Ala Tyr Cys Arg Asp Ile Ile Lys Asn Asn Pro Asp Ser Phe
415                 420                 425                 430

cgc gtc ttc gga cct gac gag acc gcg tcc aac cgt ctg aac gcg acc     1465
Arg Val Phe Gly Pro Asp Glu Thr Ala Ser Asn Arg Leu Asn Ala Thr
                435                 440                 445

tac gag gtc acc aag aag cag tgg gac aac gga tac ctc tcg gct ctc     1513
Tyr Glu Val Thr Lys Lys Gln Trp Asp Asn Gly Tyr Leu Ser Ala Leu
            450                 455                 460

gtc gac gag aac atg gcc gtc acc ggc cag gtt gtc gag cag ctc tcc     1561
Val Asp Glu Asn Met Ala Val Thr Gly Gln Val Val Glu Gln Leu Ser
        465                 470                 475

gag cat cag tgc gaa ggc ttc ctc gag gcc tac ctg ctc acc ggc cgt     1609
Glu His Gln Cys Glu Gly Phe Leu Glu Ala Tyr Leu Leu Thr Gly Arg
    480                 485                 490
```

-continued

```
cac ggc atc tgg agc tcc tac gag tcc ttc gtg cac gtg atc gac tcc     1657
His Gly Ile Trp Ser Ser Tyr Glu Ser Phe Val His Val Ile Asp Ser
495                 500                 505                 510

atg ctg aac cag cat gcg aag tgg ctc gag gcc acc gtc cgc gag atc     1705
Met Leu Asn Gln His Ala Lys Trp Leu Glu Ala Thr Val Arg Glu Ile
                515                 520                 525

ccg tgg cgt aag ccg atc tcc tcg gtg aac ctc ctg gtc tcc tcg cac     1753
Pro Trp Arg Lys Pro Ile Ser Ser Val Asn Leu Leu Val Ser Ser His
            530                 535                 540

gtg tgg cgt cag gat cac aac ggc ttc tcg cac cag gat ccg ggt gtg     1801
Val Trp Arg Gln Asp His Asn Gly Phe Ser His Gln Asp Pro Gly Val
        545                 550                 555

acc tcc gtc ctg ctg aac aag acg ttc aac aac gac cac gtg acg aac     1849
Thr Ser Val Leu Leu Asn Lys Thr Phe Asn Asn Asp His Val Thr Asn
    560                 565                 570

atc tac ttc gcg acc gat gcc aac atg ctg ctg gcc atc gcc gag aag     1897
Ile Tyr Phe Ala Thr Asp Ala Asn Met Leu Leu Ala Ile Ala Glu Lys
575                 580                 585                 590

tgc ttc aag tcc acc aac aag atc aac gca atc ttc gcc ggc aag cag     1945
Cys Phe Lys Ser Thr Asn Lys Ile Asn Ala Ile Phe Ala Gly Lys Gln
                595                 600                 605

ccg gcc gcg acg tgg atc acc ctc gac gag gta cgc gcc gag ctc gag     1993
Pro Ala Ala Thr Trp Ile Thr Leu Asp Glu Val Arg Ala Glu Leu Glu
            610                 615                 620

gct ggt gcc gcc gag tgg aag tgg gct tcc aac gcc aag agc aac gac     2041
Ala Gly Ala Ala Glu Trp Lys Trp Ala Ser Asn Ala Lys Ser Asn Asp
        625                 630                 635

gag gtc cag gtt gtc ctc gcc gcc gcc ggc gac gtc ccg acc cag gag     2089
Glu Val Gln Val Val Leu Ala Ala Ala Gly Asp Val Pro Thr Gln Glu
    640                 645                 650

atc atg gcc gct tcc gat gcc ctc aac aag atg ggc atc aag ttc aag     2137
Ile Met Ala Ala Ser Asp Ala Leu Asn Lys Met Gly Ile Lys Phe Lys
655                 660                 665                 670

gtc gtc aac gtc gtg gac ctc atc aag ctg cag tcc tcg aag gag aac     2185
Val Val Asn Val Val Asp Leu Ile Lys Leu Gln Ser Ser Lys Glu Asn
                675                 680                 685

gac gag gcc atg tct gac gag gac ttc gcc gac ctg ttc acc gcg gac     2233
Asp Glu Ala Met Ser Asp Glu Asp Phe Ala Asp Leu Phe Thr Ala Asp
            690                 695                 700

aag ccg gtc ctc ttc gcc tac cac tcc tat gcc cag gac gtt cgt ggc     2281
Lys Pro Val Leu Phe Ala Tyr His Ser Tyr Ala Gln Asp Val Arg Gly
        705                 710                 715

ctc atc tac gac cgc ccg aac cac gac aac ttc acc gtt gtc gga tac     2329
Leu Ile Tyr Asp Arg Pro Asn His Asp Asn Phe Thr Val Val Gly Tyr
    720                 725                 730

aag gag cag ggc tcc acg acg acg ccg ttc gac atg gtg cgt gtc aac     2377
Lys Glu Gln Gly Ser Thr Thr Thr Pro Phe Asp Met Val Arg Val Asn
735                 740                 745                 750

gac atg gat cgc tac gcc ctt cag gcc aag gcc ctc gag ctc atc gac     2425
Asp Met Asp Arg Tyr Ala Leu Gln Ala Lys Ala Leu Glu Leu Ile Asp
                755                 760                 765

gcc gac aag tat gcc gac aag atc aac gag ctc aac gag ttc cgc aag     2473
Ala Asp Lys Tyr Ala Asp Lys Ile Asn Glu Leu Asn Glu Phe Arg Lys
            770                 775                 780

acc gcg ttc cag ttc gcc gtc gac aat ggc tat gac att cct gag ttc     2521
Thr Ala Phe Gln Phe Ala Val Asp Asn Gly Tyr Asp Ile Pro Glu Phe
        785                 790                 795

acc gat tgg gtg tac ccg gat gtc aag gtc gac gag acc tcc atg ctc     2569
Thr Asp Trp Val Tyr Pro Asp Val Lys Val Asp Glu Thr Ser Met Leu
    800                 805                 810
```

```
tcc gcc acc gcc gcg acc gcc ggc gac aac gag tga gcatagtctc          2615
Ser Ala Thr Ala Ala Thr Ala Gly Asp Asn Glu
815                 820                 825

atcgcttagc cgatgaaagg cccgggtgtc cgcacccggg ccttt                   2660


<210> SEQ ID NO 6
<211> LENGTH: 825
<212> TYPE: PRT
<213> ORGANISM: Bifidobacterium lactis

<400> SEQUENCE: 6

Met Thr Asn Pro Val Ile Gly Thr Pro Trp Gln Lys Leu Asp Arg Pro
1               5                   10                  15

Val Ser Glu Glu Ala Ile Glu Gly Met Asp Lys Tyr Trp Arg Val Ala
            20                  25                  30

Asn Tyr Met Ser Ile Gly Gln Ile Tyr Leu Arg Ser Asn Pro Leu Met
        35                  40                  45

Lys Glu Pro Phe Thr Arg Asp Asp Val Lys His Arg Leu Val Gly His
    50                  55                  60

Trp Gly Thr Thr Pro Gly Leu Asn Phe Leu Leu Ala His Ile Asn Arg
65                  70                  75                  80

Leu Ile Ala Asp His Gln Gln Asn Thr Val Phe Ile Met Gly Pro Gly
                85                  90                  95

His Gly Gly Pro Ala Gly Thr Ala Gln Ser Tyr Ile Asp Gly Thr Tyr
            100                 105                 110

Thr Glu Tyr Tyr Pro Asn Ile Thr Lys Asp Glu Ala Gly Leu Gln Lys
        115                 120                 125

Phe Phe Arg Gln Phe Ser Tyr Pro Gly Gly Ile Pro Ser His Phe Ala
    130                 135                 140

Pro Glu Thr Pro Gly Ser Ile His Glu Gly Gly Glu Leu Gly Tyr Ala
145                 150                 155                 160

Leu Ser His Ala Tyr Gly Ala Ile Met Asp Asn Pro Ser Leu Phe Val
                165                 170                 175

Pro Cys Ile Ile Gly Asp Gly Glu Ala Glu Thr Gly Pro Leu Ala Thr
            180                 185                 190

Gly Trp Gln Ser Asn Lys Leu Val Asn Pro Arg Thr Asp Gly Ile Val
        195                 200                 205

Leu Pro Ile Leu His Leu Asn Gly Tyr Lys Ile Ala Asn Pro Thr Ile
    210                 215                 220

Leu Ala Arg Ile Ser Asp Glu Glu Leu His Asp Phe Phe Arg Gly Met
225                 230                 235                 240

Gly Tyr His Pro Tyr Glu Phe Val Ala Gly Phe Asp Asn Glu Asp His
                245                 250                 255

Leu Ser Ile His Arg Arg Phe Ala Glu Leu Phe Glu Thr Ile Phe Asp
            260                 265                 270

Glu Ile Cys Asp Ile Lys Ala Ala Ala Gln Thr Asp Asp Met Thr Arg
        275                 280                 285

Pro Phe Tyr Pro Met Leu Ile Phe Arg Thr Pro Lys Gly Trp Thr Cys
    290                 295                 300

Pro Lys Phe Ile Asp Gly Lys Lys Thr Glu Gly Ser Trp Arg Ala His
305                 310                 315                 320

Gln Val Pro Leu Ala Ser Ala Arg Asp Thr Glu Ala His Phe Glu Val
                325                 330                 335

Leu Lys Gly Trp Met Glu Ser Tyr Lys Pro Glu Glu Leu Phe Asn Ala
            340                 345                 350
```

Asp Gly Ser Ile Lys Glu Asp Val Thr Ala Phe Met Pro Lys Gly Glu
        355                 360                 365

Leu Arg Ile Gly Ala Asn Pro Asn Ala Asn Gly Gly Arg Ile Arg Glu
    370                 375                 380

Asp Leu Lys Leu Pro Glu Leu Asp Gln Tyr Glu Ile Thr Gly Val Lys
385                 390                 395                 400

Glu Tyr Gly His Gly Trp Gly Gln Val Glu Ala Pro Arg Ser Leu Gly
                405                 410                 415

Ala Tyr Cys Arg Asp Ile Ile Lys Asn Asn Pro Asp Ser Phe Arg Val
            420                 425                 430

Phe Gly Pro Asp Glu Thr Ala Ser Asn Arg Leu Asn Ala Thr Tyr Glu
        435                 440                 445

Val Thr Lys Lys Gln Trp Asp Asn Gly Tyr Leu Ser Ala Leu Val Asp
    450                 455                 460

Glu Asn Met Ala Val Thr Gly Gln Val Val Glu Gln Leu Ser Glu His
465                 470                 475                 480

Gln Cys Glu Gly Phe Leu Glu Ala Tyr Leu Leu Thr Gly Arg His Gly
                485                 490                 495

Ile Trp Ser Ser Tyr Glu Ser Phe Val His Val Ile Asp Ser Met Leu
            500                 505                 510

Asn Gln His Ala Lys Trp Leu Glu Ala Thr Val Arg Glu Ile Pro Trp
        515                 520                 525

Arg Lys Pro Ile Ser Ser Val Asn Leu Leu Val Ser Ser His Val Trp
    530                 535                 540

Arg Gln Asp His Asn Gly Phe Ser His Gln Asp Pro Gly Val Thr Ser
545                 550                 555                 560

Val Leu Leu Asn Lys Thr Phe Asn Asn Asp His Val Thr Asn Ile Tyr
                565                 570                 575

Phe Ala Thr Asp Ala Asn Met Leu Leu Ala Ile Ala Glu Lys Cys Phe
            580                 585                 590

Lys Ser Thr Asn Lys Ile Asn Ala Ile Phe Ala Gly Lys Gln Pro Ala
        595                 600                 605

Ala Thr Trp Ile Thr Leu Asp Glu Val Arg Ala Glu Leu Glu Ala Gly
    610                 615                 620

Ala Ala Glu Trp Lys Trp Ala Ser Asn Ala Lys Ser Asn Asp Glu Val
625                 630                 635                 640

Gln Val Val Leu Ala Ala Ala Gly Asp Val Pro Thr Gln Glu Ile Met
                645                 650                 655

Ala Ala Ser Asp Ala Leu Asn Lys Met Gly Ile Lys Phe Lys Val Val
            660                 665                 670

Asn Val Val Asp Leu Ile Lys Leu Gln Ser Ser Lys Glu Asn Asp Glu
        675                 680                 685

Ala Met Ser Asp Glu Asp Phe Ala Asp Leu Phe Thr Ala Asp Lys Pro
    690                 695                 700

Val Leu Phe Ala Tyr His Ser Tyr Ala Gln Asp Val Arg Gly Leu Ile
705                 710                 715                 720

Tyr Asp Arg Pro Asn His Asp Asn Phe Thr Val Val Gly Tyr Lys Glu
                725                 730                 735

Gln Gly Ser Thr Thr Thr Pro Phe Asp Met Val Arg Val Asn Asp Met
            740                 745                 750

Asp Arg Tyr Ala Leu Gln Ala Lys Ala Leu Glu Leu Ile Asp Ala Asp
        755                 760                 765

Lys Tyr Ala Asp Lys Ile Asn Glu Leu Asn Glu Phe Arg Lys Thr Ala

-continued

```
    770                 775                 780

Phe Gln Phe Ala Val Asp Asn Gly Tyr Asp Ile Pro Glu Phe Thr Asp
785                 790                 795                 800

Trp Val Tyr Pro Asp Val Lys Val Asp Glu Thr Ser Met Leu Ser Ala
                805                 810                 815

Thr Ala Ala Thr Ala Gly Asp Asn Glu
            820                 825


<210> SEQ ID NO 7
<211> LENGTH: 31
<212> TYPE: DNA
<213> ORGANISM: Artificial sequence
<220> FEATURE:
<222> LOCATION:
<223> OTHER INFORMATION: primer

<400> SEQUENCE: 7

ctgaagcttg tgaaaagcaa attaaggagt g                                   31


<210> SEQ ID NO 8
<211> LENGTH: 31
<212> TYPE: DNA
<213> ORGANISM: Artificial sequence
<220> FEATURE:
<222> LOCATION:
<223> OTHER INFORMATION: primer

<400> SEQUENCE: 8

tcagaattct tattttaaac ccttccattg c                                   31


<210> SEQ ID NO 9
<211> LENGTH: 2841
<212> TYPE: DNA
<213> ORGANISM: Bifidobacterium animalis
<220> FEATURE:
<221> NAME/KEY: CDS
<222> LOCATION: (320)..(2797)

<400> SEQUENCE: 9

ttttcaacac gccgcgcaat atcctcacaa accgcacgcg acaacgacgg cgaaaacgct     60

tgcattcgtt ggtatttcaa cgtttctcgc ctttattcac tgattttcca ttttcacaaa    120

tcgcccgagc aatctcccaa attcgcaaat tatgcgcaca gattcgctca cactgtttca    180

aaaactgcaa aaaggtcagc gtattcgcgt aacataatca gcgatcgggc acggagaccg    240

gcctgcagga cagcgccgaa gcccgtgccc aacggaataa acaaatcgca catttatgtg    300

caggagtaca ggagcacac atg act aat cct gtt att ggt acc cca tgg cag     352
                    Met Thr Asn Pro Val Ile Gly Thr Pro Trp Gln
                    1               5                   10

aag ctg gat cgt ccg gtt tcc gaa gag gcc atc gaa ggc atg gac aag      400
Lys Leu Asp Arg Pro Val Ser Glu Glu Ala Ile Glu Gly Met Asp Lys
            15                  20                  25

tac tgg cgc gtc gcc aac tac atg tct atc ggc cag atc tac ctg cgt      448
Tyr Trp Arg Val Ala Asn Tyr Met Ser Ile Gly Gln Ile Tyr Leu Arg
        30                  35                  40

agc aac ccg ctg atg aag gag ccc ttc acc cgc gat gac gtg aag cac      496
Ser Asn Pro Leu Met Lys Glu Pro Phe Thr Arg Asp Asp Val Lys His
    45                  50                  55

cgt ctg gtc ggc cac tgg ggc acc acc ccg ggc ctg aac ttc ctt ctc      544
Arg Leu Val Gly His Trp Gly Thr Thr Pro Gly Leu Asn Phe Leu Leu
60                  65                  70                  75

gcc cac atc aac cgc ctg atc gcc gat cac cag cag aac acc gtg ttc      592
Ala His Ile Asn Arg Leu Ile Ala Asp His Gln Gln Asn Thr Val Phe
```

-continued

```
                80                  85                  90

atc atg ggt cct ggc cac ggc ggc cct gca ggt acc gct cag tcc tac      640
Ile Met Gly Pro Gly His Gly Gly Pro Ala Gly Thr Ala Gln Ser Tyr
            95                  100                 105

atc gac ggc acc tac acc gag tac tac ccg aac atc acc aag gac gaa      688
Ile Asp Gly Thr Tyr Thr Glu Tyr Tyr Pro Asn Ile Thr Lys Asp Glu
        110                 115                 120

gct ggc ctg cag aag ttc ttc cgc cag ttc tcc tac ccg ggt ggc att      736
Ala Gly Leu Gln Lys Phe Phe Arg Gln Phe Ser Tyr Pro Gly Gly Ile
    125                 130                 135

cct tcc cac ttc gct ccg gag acg ccg ggc tcc atc cac gaa ggc ggc      784
Pro Ser His Phe Ala Pro Glu Thr Pro Gly Ser Ile His Glu Gly Gly
140                 145                 150                 155

gag ctg ggc tac gcc ctg tcg cac gcc tac ggc gcg atc atg gac aac      832
Glu Leu Gly Tyr Ala Leu Ser His Ala Tyr Gly Ala Ile Met Asp Asn
                160                 165                 170

ccg agc ctc ttc gtc ccg tgc atc atc ggt gac ggc gaa gcc gag acc      880
Pro Ser Leu Phe Val Pro Cys Ile Ile Gly Asp Gly Glu Ala Glu Thr
            175                 180                 185

ggc cct ctg gcc acc ggc tgg cag tcc aac aag ctc gtc aac ccg cgc      928
Gly Pro Leu Ala Thr Gly Trp Gln Ser Asn Lys Leu Val Asn Pro Arg
        190                 195                 200

acc gac ggc atc gtc ctg ccg atc ctg cac ctc aac ggc tac aag atc      976
Thr Asp Gly Ile Val Leu Pro Ile Leu His Leu Asn Gly Tyr Lys Ile
    205                 210                 215

gcc aac ccg acg atc ctc gcc cgc atc tcc gac gag gag ctg cac gac     1024
Ala Asn Pro Thr Ile Leu Ala Arg Ile Ser Asp Glu Glu Leu His Asp
220                 225                 230                 235

ttc ttc cgc ggc atg ggt tac cac ccg tac gag ttc gtc gcc ggc ttc     1072
Phe Phe Arg Gly Met Gly Tyr His Pro Tyr Glu Phe Val Ala Gly Phe
                240                 245                 250

gac aac gag gat cac ctg tcg atc cac cgt cgc ttc gcc gag ctc ttc     1120
Asp Asn Glu Asp His Leu Ser Ile His Arg Arg Phe Ala Glu Leu Phe
            255                 260                 265

gag acc atc ttc gac gag atc tgc gat atc aag gct gcg gct cag acc     1168
Glu Thr Ile Phe Asp Glu Ile Cys Asp Ile Lys Ala Ala Ala Gln Thr
        270                 275                 280

gac gac atg acc cgt ccg ttc tac ccg atg ctc atc ttc cgc acc ccg     1216
Asp Asp Met Thr Arg Pro Phe Tyr Pro Met Leu Ile Phe Arg Thr Pro
    285                 290                 295

aag ggc tgg acc tgc ccg aag ttc atc gac ggc aag aag acc gaa ggc     1264
Lys Gly Trp Thr Cys Pro Lys Phe Ile Asp Gly Lys Lys Thr Glu Gly
300                 305                 310                 315

tcc tgg cgt gca cac cag gtc ccg ctg gct tcc gcc cgc gac acc gag     1312
Ser Trp Arg Ala His Gln Val Pro Leu Ala Ser Ala Arg Asp Thr Glu
                320                 325                 330

gcc cac ttc gaa gtc ctc aag ggc tgg atg gaa tcc tac aag ccg gag     1360
Ala His Phe Glu Val Leu Lys Gly Trp Met Glu Ser Tyr Lys Pro Glu
            335                 340                 345

gag ctc ttc aac gcc gac ggc tcc atc aag gag gac gtc acc gca ttc     1408
Glu Leu Phe Asn Ala Asp Gly Ser Ile Lys Glu Asp Val Thr Ala Phe
        350                 355                 360

atg cct aag ggc gaa ctg cgc atc ggc gcc aac ccg aat gcc aac ggc     1456
Met Pro Lys Gly Glu Leu Arg Ile Gly Ala Asn Pro Asn Ala Asn Gly
    365                 370                 375

ggc cgc atc cgc gag gat ctg aag ctc cct gag ctc gat cag tac gag     1504
Gly Arg Ile Arg Glu Asp Leu Lys Leu Pro Glu Leu Asp Gln Tyr Glu
380                 385                 390                 395

atc acc ggc gtc aag gaa tac ggc cac ggt tgg ggc cag gtc gag gct     1552
Ile Thr Gly Val Lys Glu Tyr Gly His Gly Trp Gly Gln Val Glu Ala
```

-continued

```
                400                 405                 410

ccg cgt tcc ctc ggc gcg tac tgc cgc gac atc atc aag aac aac ccg     1600
Pro Arg Ser Leu Gly Ala Tyr Cys Arg Asp Ile Ile Lys Asn Asn Pro
            415                 420                 425

gat tcg ttc cgc gtc ttc gga cct gac gag acc gcg tcc aac cgt ctg     1648
Asp Ser Phe Arg Val Phe Gly Pro Asp Glu Thr Ala Ser Asn Arg Leu
        430                 435                 440

aac gcg acc tac gag gtc acc aag aag cag tgg gac aac gga tac ctc     1696
Asn Ala Thr Tyr Glu Val Thr Lys Lys Gln Trp Asp Asn Gly Tyr Leu
    445                 450                 455

tcg gct ctc gtc gac gag aac atg gcc gtc acc ggc cag gtt gtc gag     1744
Ser Ala Leu Val Asp Glu Asn Met Ala Val Thr Gly Gln Val Val Glu
460                 465                 470                 475

cag ctc tcc gag cat cag tgc gaa ggc ttc ctc gag gcc tac ctg ctc     1792
Gln Leu Ser Glu His Gln Cys Glu Gly Phe Leu Glu Ala Tyr Leu Leu
                480                 485                 490

acc ggc cgt cac ggc atc tgg agc tcc tac gag tcc ttc gtg cac gtg     1840
Thr Gly Arg His Gly Ile Trp Ser Ser Tyr Glu Ser Phe Val His Val
            495                 500                 505

atc gac tcc atg ctg aac cag cat gcg aag tgg ctc gag gcc acc gtc     1888
Ile Asp Ser Met Leu Asn Gln His Ala Lys Trp Leu Glu Ala Thr Val
        510                 515                 520

cgc gag atc ccg tgg cgt aag ccg atc tcc tcg gtg aac ctc ctg gtc     1936
Arg Glu Ile Pro Trp Arg Lys Pro Ile Ser Ser Val Asn Leu Leu Val
    525                 530                 535

tcc tcg cac gtg tgg cgt cag gat cac aac ggc ttc tcg cac cag gat     1984
Ser Ser His Val Trp Arg Gln Asp His Asn Gly Phe Ser His Gln Asp
540                 545                 550                 555

ccg ggt gtg acc tcc gtc ctg ctg aac aag acg ttc aac aac gac cac     2032
Pro Gly Val Thr Ser Val Leu Leu Asn Lys Thr Phe Asn Asn Asp His
                560                 565                 570

gtg acg aac atc tac ttc gcg acc gat gcc aac atg ctg ctg gcc atc     2080
Val Thr Asn Ile Tyr Phe Ala Thr Asp Ala Asn Met Leu Leu Ala Ile
            575                 580                 585

gcc gag aag tgc ttc aag tcc acc aac aag atc aac gca atc ttc gcc     2128
Ala Glu Lys Cys Phe Lys Ser Thr Asn Lys Ile Asn Ala Ile Phe Ala
        590                 595                 600

ggc aag cag ccg gcc gcg acg tgg atc acc ctc gac gag gca cgc gcc     2176
Gly Lys Gln Pro Ala Ala Thr Trp Ile Thr Leu Asp Glu Ala Arg Ala
    605                 610                 615

gag ctc gag gct ggt gcc gcc gag tgg aag tgg gct tcc aac gcc aag     2224
Glu Leu Glu Ala Gly Ala Ala Glu Trp Lys Trp Ala Ser Asn Ala Lys
620                 625                 630                 635

agc aac gac gag gtc cag gtt gtc ctc gcc gcc gcc ggc gac gtc ccg     2272
Ser Asn Asp Glu Val Gln Val Val Leu Ala Ala Ala Gly Asp Val Pro
                640                 645                 650

acc cag gag atc atg gcc gct tcc gat gcc ctc aac aag atg ggc atc     2320
Thr Gln Glu Ile Met Ala Ala Ser Asp Ala Leu Asn Lys Met Gly Ile
            655                 660                 665

aag ttc aag gtc gtc aac gtc gtg gac ctc atc aag ctg cag tcc tcg     2368
Lys Phe Lys Val Val Asn Val Val Asp Leu Ile Lys Leu Gln Ser Ser
        670                 675                 680

aag gag aac gac gag gcc atg tct gac gag gac ttc gcc gac ctg ttc     2416
Lys Glu Asn Asp Glu Ala Met Ser Asp Glu Asp Phe Ala Asp Leu Phe
    685                 690                 695

acc gcg gac aag ccg gtc ctc ttc gcc tac cac tcc tat gcc cag gac     2464
Thr Ala Asp Lys Pro Val Leu Phe Ala Tyr His Ser Tyr Ala Gln Asp
700                 705                 710                 715

gtt cgt ggc ctc atc tac gac cgc ccg aac cac gac aac ttc acc gtt     2512
Val Arg Gly Leu Ile Tyr Asp Arg Pro Asn His Asp Asn Phe Thr Val
```

```
                720                 725                 730

gtc gga tac aag gag cag ggc tcc acg acg acg ccg ttc gac atg gtg      2560
Val Gly Tyr Lys Glu Gln Gly Ser Thr Thr Thr Pro Phe Asp Met Val
            735                 740                 745

cgt gtc aac gac atg gat cgc tac gcc ctt cag gcc aag gcc ctc gag      2608
Arg Val Asn Asp Met Asp Arg Tyr Ala Leu Gln Ala Lys Ala Leu Glu
        750                 755                 760

ctc atc gac gcc gac aag tat gcc gac aag atc aac gag ctc aac gag      2656
Leu Ile Asp Ala Asp Lys Tyr Ala Asp Lys Ile Asn Glu Leu Asn Glu
    765                 770                 775

ttc cgc aag acc gcg ttc cag ttc gcc gtc gac aat ggc tat gac att      2704
Phe Arg Lys Thr Ala Phe Gln Phe Ala Val Asp Asn Gly Tyr Asp Ile
780                 785                 790                 795

cct gag ttc acc gat tgg gtg tac ccg gat gtc aag gtc gac gag acc      2752
Pro Glu Phe Thr Asp Trp Val Tyr Pro Asp Val Lys Val Asp Glu Thr
                800                 805                 810

tcc atg ctc tcc gcc acc gcc gcg acc gcc ggc gac aac gag tga          2797
Ser Met Leu Ser Ala Thr Ala Ala Thr Ala Gly Asp Asn Glu
            815                 820                 825

gcatagtctc atcgcttagc cgatgaaagg ccaagggcga attc                     2841


<210> SEQ ID NO 10
<211> LENGTH: 825
<212> TYPE: PRT
<213> ORGANISM: Bifidobacterium animalis

<400> SEQUENCE: 10

Met Thr Asn Pro Val Ile Gly Thr Pro Trp Gln Lys Leu Asp Arg Pro
1               5                   10                  15

Val Ser Glu Glu Ala Ile Glu Gly Met Asp Lys Tyr Trp Arg Val Ala
            20                  25                  30

Asn Tyr Met Ser Ile Gly Gln Ile Tyr Leu Arg Ser Asn Pro Leu Met
        35                  40                  45

Lys Glu Pro Phe Thr Arg Asp Asp Val Lys His Arg Leu Val Gly His
    50                  55                  60

Trp Gly Thr Thr Pro Gly Leu Asn Phe Leu Leu Ala His Ile Asn Arg
65                  70                  75                  80

Leu Ile Ala Asp His Gln Gln Asn Thr Val Phe Ile Met Gly Pro Gly
                85                  90                  95

His Gly Gly Pro Ala Gly Thr Ala Gln Ser Tyr Ile Asp Gly Thr Tyr
            100                 105                 110

Thr Glu Tyr Tyr Pro Asn Ile Thr Lys Asp Glu Ala Gly Leu Gln Lys
        115                 120                 125

Phe Phe Arg Gln Phe Ser Tyr Pro Gly Gly Ile Pro Ser His Phe Ala
    130                 135                 140

Pro Glu Thr Pro Gly Ser Ile His Glu Gly Gly Glu Leu Gly Tyr Ala
145                 150                 155                 160

Leu Ser His Ala Tyr Gly Ala Ile Met Asp Asn Pro Ser Leu Phe Val
                165                 170                 175

Pro Cys Ile Ile Gly Asp Gly Glu Ala Glu Thr Gly Pro Leu Ala Thr
            180                 185                 190

Gly Trp Gln Ser Asn Lys Leu Val Asn Pro Arg Thr Asp Gly Ile Val
        195                 200                 205

Leu Pro Ile Leu His Leu Asn Gly Tyr Lys Ile Ala Asn Pro Thr Ile
    210                 215                 220

Leu Ala Arg Ile Ser Asp Glu Glu Leu His Asp Phe Phe Arg Gly Met
225                 230                 235                 240
```

-continued

```
Gly Tyr His Pro Tyr Glu Phe Val Ala Gly Phe Asp Asn Glu Asp His
                245                 250                 255

Leu Ser Ile His Arg Arg Phe Ala Glu Leu Phe Glu Thr Ile Phe Asp
            260                 265                 270

Glu Ile Cys Asp Ile Lys Ala Ala Ala Gln Thr Asp Asp Met Thr Arg
        275                 280                 285

Pro Phe Tyr Pro Met Leu Ile Phe Arg Thr Pro Lys Gly Trp Thr Cys
    290                 295                 300

Pro Lys Phe Ile Asp Gly Lys Lys Thr Glu Gly Ser Trp Arg Ala His
305                 310                 315                 320

Gln Val Pro Leu Ala Ser Ala Arg Asp Thr Glu Ala His Phe Glu Val
                325                 330                 335

Leu Lys Gly Trp Met Glu Ser Tyr Lys Pro Glu Glu Leu Phe Asn Ala
            340                 345                 350

Asp Gly Ser Ile Lys Glu Asp Val Thr Ala Phe Met Pro Lys Gly Glu
        355                 360                 365

Leu Arg Ile Gly Ala Asn Pro Asn Ala Asn Gly Gly Arg Ile Arg Glu
    370                 375                 380

Asp Leu Lys Leu Pro Glu Leu Asp Gln Tyr Glu Ile Thr Gly Val Lys
385                 390                 395                 400

Glu Tyr Gly His Gly Trp Gly Gln Val Glu Ala Pro Arg Ser Leu Gly
                405                 410                 415

Ala Tyr Cys Arg Asp Ile Ile Lys Asn Asn Pro Asp Ser Phe Arg Val
            420                 425                 430

Phe Gly Pro Asp Glu Thr Ala Ser Asn Arg Leu Asn Ala Thr Tyr Glu
        435                 440                 445

Val Thr Lys Lys Gln Trp Asp Asn Gly Tyr Leu Ser Ala Leu Val Asp
    450                 455                 460

Glu Asn Met Ala Val Thr Gly Gln Val Val Glu Gln Leu Ser Glu His
465                 470                 475                 480

Gln Cys Glu Gly Phe Leu Glu Ala Tyr Leu Leu Thr Gly Arg His Gly
                485                 490                 495

Ile Trp Ser Ser Tyr Glu Ser Phe Val His Val Ile Asp Ser Met Leu
            500                 505                 510

Asn Gln His Ala Lys Trp Leu Glu Ala Thr Val Arg Glu Ile Pro Trp
        515                 520                 525

Arg Lys Pro Ile Ser Ser Val Asn Leu Leu Val Ser Ser His Val Trp
    530                 535                 540

Arg Gln Asp His Asn Gly Phe Ser His Gln Asp Pro Gly Val Thr Ser
545                 550                 555                 560

Val Leu Leu Asn Lys Thr Phe Asn Asn Asp His Val Thr Asn Ile Tyr
                565                 570                 575

Phe Ala Thr Asp Ala Asn Met Leu Leu Ala Ile Ala Glu Lys Cys Phe
            580                 585                 590

Lys Ser Thr Asn Lys Ile Asn Ala Ile Phe Ala Gly Lys Gln Pro Ala
        595                 600                 605

Ala Thr Trp Ile Thr Leu Asp Glu Ala Arg Ala Glu Leu Glu Ala Gly
    610                 615                 620

Ala Ala Glu Trp Lys Trp Ala Ser Asn Ala Lys Ser Asn Asp Glu Val
625                 630                 635                 640

Gln Val Val Leu Ala Ala Ala Gly Asp Val Pro Thr Gln Glu Ile Met
                645                 650                 655

Ala Ala Ser Asp Ala Leu Asn Lys Met Gly Ile Lys Phe Lys Val Val
```

```
            660                 665                 670

Asn Val Val Asp Leu Ile Lys Leu Gln Ser Ser Lys Glu Asn Asp Glu
        675                 680                 685

Ala Met Ser Asp Glu Asp Phe Ala Asp Leu Phe Thr Ala Asp Lys Pro
    690                 695                 700

Val Leu Phe Ala Tyr His Ser Tyr Ala Gln Asp Val Arg Gly Leu Ile
705                 710                 715                 720

Tyr Asp Arg Pro Asn His Asp Asn Phe Thr Val Val Gly Tyr Lys Glu
                725                 730                 735

Gln Gly Ser Thr Thr Thr Pro Phe Asp Met Val Arg Val Asn Asp Met
            740                 745                 750

Asp Arg Tyr Ala Leu Gln Ala Lys Ala Leu Glu Leu Ile Asp Ala Asp
        755                 760                 765

Lys Tyr Ala Asp Lys Ile Asn Glu Leu Asn Glu Phe Arg Lys Thr Ala
    770                 775                 780

Phe Gln Phe Ala Val Asp Asn Gly Tyr Asp Ile Pro Glu Phe Thr Asp
785                 790                 795                 800

Trp Val Tyr Pro Asp Val Lys Val Asp Glu Thr Ser Met Leu Ser Ala
                805                 810                 815

Thr Ala Ala Thr Ala Gly Asp Asn Glu
            820                 825


<210> SEQ ID NO 11
<211> LENGTH: 2841
<212> TYPE: DNA
<213> ORGANISM: Bifidobacterium animalis
<220> FEATURE:
<221> NAME/KEY: CDS
<222> LOCATION: (320)..(2797)

<400> SEQUENCE: 11

ttttcaacac gccgcgcaat atcctcacaa accgcacgcg acaacgacgg cgaaaatgct      60

tgcattcgtt ggaatctcaa cgtttctcgc ctttattcac tgattttcca ttttcacaaa     120

tcgctcgagc aatcgcccaa attcgcaaat tatgcgcaca gattcgccca cactgtttca     180

aaaactgcaa aaaggtcagc gtattcgcgt aacataatca gcgatcggac acggaaaccg     240

gcctgcagga cagcaccgaa gcccgtgtcc aatggaataa acaaatcgca catttatgtg     300

caggagtaca ggagcacac atg act aat cct gtt att ggt acc cca tgg cag      352
                     Met Thr Asn Pro Val Ile Gly Thr Pro Trp Gln
                     1               5                   10

aag ctg gac cgt ccg gtt tcc gaa gag gcc atc gaa ggc atg gac aag      400
Lys Leu Asp Arg Pro Val Ser Glu Glu Ala Ile Glu Gly Met Asp Lys
            15                  20                  25

tac tgg cgc gtc gcc aac tac atg tcc atc ggc cag atc tac ctg cgt      448
Tyr Trp Arg Val Ala Asn Tyr Met Ser Ile Gly Gln Ile Tyr Leu Arg
        30                  35                  40

agc aac ccg ctg atg aag gag ccc ttc acc cgc gat gac gtg aag cac      496
Ser Asn Pro Leu Met Lys Glu Pro Phe Thr Arg Asp Asp Val Lys His
    45                  50                  55

cgt ctg gtc ggc cac tgg ggc acc acc ccg ggc ctg aac ttc ctt ctc      544
Arg Leu Val Gly His Trp Gly Thr Thr Pro Gly Leu Asn Phe Leu Leu
60                  65                  70                  75

gcc cat atc aac cgc ctg atc gcc gat cac cag cag aac acc gtg ttc      592
Ala His Ile Asn Arg Leu Ile Ala Asp His Gln Gln Asn Thr Val Phe
                80                  85                  90

atc atg ggt cct ggc cac ggc ggc cct gca ggt acc gct cag tcc tac      640
Ile Met Gly Pro Gly His Gly Gly Pro Ala Gly Thr Ala Gln Ser Tyr
            95                  100                 105
```

```
atc gac ggc acc tac acc gag tac tac ccg aac atc acc aag gac gag      688
Ile Asp Gly Thr Tyr Thr Glu Tyr Tyr Pro Asn Ile Thr Lys Asp Glu
        110                 115                 120

gct ggc ctg cag aag ttc ttc cgc cag ttc tcc tac ccg ggt ggc att      736
Ala Gly Leu Gln Lys Phe Phe Arg Gln Phe Ser Tyr Pro Gly Gly Ile
    125                 130                 135

cct tcc cac ttc gct ccg gag acg cca ggc tcc atc cac gaa ggc ggc      784
Pro Ser His Phe Ala Pro Glu Thr Pro Gly Ser Ile His Glu Gly Gly
140                 145                 150                 155

gag ctg ggc tac gcc ctg tcg cac gcc tac ggc gcg atc atg aac aac      832
Glu Leu Gly Tyr Ala Leu Ser His Ala Tyr Gly Ala Ile Met Asn Asn
                160                 165                 170

ccg agc ctc ttc gtc ccg tgc atc atc ggt gac ggc gaa gcc gag acc      880
Pro Ser Leu Phe Val Pro Cys Ile Ile Gly Asp Gly Glu Ala Glu Thr
            175                 180                 185

ggc cct ctg gcc acc ggc tgg cag tcc aac aag ctc gtc aac ccg cgc      928
Gly Pro Leu Ala Thr Gly Trp Gln Ser Asn Lys Leu Val Asn Pro Arg
        190                 195                 200

acc gac ggc atc gtg ctg ccg atc ctg cac ctc aac ggc tac aag atc      976
Thr Asp Gly Ile Val Leu Pro Ile Leu His Leu Asn Gly Tyr Lys Ile
    205                 210                 215

gcc aac ccg acg ctc ctc gcc cgc atc tcc gac gag gag ctg cac gac     1024
Ala Asn Pro Thr Leu Leu Ala Arg Ile Ser Asp Glu Glu Leu His Asp
220                 225                 230                 235

ttc ttc cgc ggt atg ggt tac cac ccg tac gag ttc gtc gcc ggc ttc     1072
Phe Phe Arg Gly Met Gly Tyr His Pro Tyr Glu Phe Val Ala Gly Phe
                240                 245                 250

gac aac gag gat cac ctg tcg atc cac cgt cgc ttc gcc gag ctc ttc     1120
Asp Asn Glu Asp His Leu Ser Ile His Arg Arg Phe Ala Glu Leu Phe
            255                 260                 265

gag acc atc ttc gac gag atc tgc gat atc aag gct gcg gct cag acc     1168
Glu Thr Ile Phe Asp Glu Ile Cys Asp Ile Lys Ala Ala Ala Gln Thr
        270                 275                 280

gac gac atg acc cgt ccg ttc tac ccg atg ctc atc ttc cgc acc ccg     1216
Asp Asp Met Thr Arg Pro Phe Tyr Pro Met Leu Ile Phe Arg Thr Pro
    285                 290                 295

aag ggc tgg acc tgc ccg aag ttc atc gac ggc aag aag acc gaa ggc     1264
Lys Gly Trp Thr Cys Pro Lys Phe Ile Asp Gly Lys Lys Thr Glu Gly
300                 305                 310                 315

tcc tgg cgt gca cac cag gtc ccg ctg gct tcc gcc cgc gac acc gag     1312
Ser Trp Arg Ala His Gln Val Pro Leu Ala Ser Ala Arg Asp Thr Glu
                320                 325                 330

gcc cac ttc gaa gtc ctc aag ggc tgg atg gaa tcc tac aag ccg gag     1360
Ala His Phe Glu Val Leu Lys Gly Trp Met Glu Ser Tyr Lys Pro Glu
            335                 340                 345

gag ctc ttc aac gcc gac ggc tcc atc aag gac gac gtc acc gca ttc     1408
Glu Leu Phe Asn Ala Asp Gly Ser Ile Lys Asp Asp Val Thr Ala Phe
        350                 355                 360

atg cct aag ggc gaa ctg cgc atc ggc gcc aac ccg aac gcc aac ggt     1456
Met Pro Lys Gly Glu Leu Arg Ile Gly Ala Asn Pro Asn Ala Asn Gly
    365                 370                 375

ggc cgc atc cgc gag gat ctg aag ctc cct gag ctc gat cag tac gag     1504
Gly Arg Ile Arg Glu Asp Leu Lys Leu Pro Glu Leu Asp Gln Tyr Glu
380                 385                 390                 395

atc acc ggc gtc aag gaa tac ggc cat ggc tgg ggc cag gtc gag gct     1552
Ile Thr Gly Val Lys Glu Tyr Gly His Gly Trp Gly Gln Val Glu Ala
                400                 405                 410

ccg cgc tcc ctc ggc gcg tac tgc cgc gac atc atc aag aac aac ccg     1600
Pro Arg Ser Leu Gly Ala Tyr Cys Arg Asp Ile Ile Lys Asn Asn Pro
            415                 420                 425
```

-continued

```
gat tcg ttc cgc atc ttc gga cct gat gag acc gca tcc aac cgt ctg      1648
Asp Ser Phe Arg Ile Phe Gly Pro Asp Glu Thr Ala Ser Asn Arg Leu
        430                 435                 440

aac gcg acc tac gag gtc acc aag aag cag tgg gac aac ggc tat ctc      1696
Asn Ala Thr Tyr Glu Val Thr Lys Lys Gln Trp Asp Asn Gly Tyr Leu
    445                 450                 455

tcg gct ctc gtc gac gag aac atg gct gtc acc ggc cag gtt gtc gag      1744
Ser Ala Leu Val Asp Glu Asn Met Ala Val Thr Gly Gln Val Val Glu
460                 465                 470                 475

cag ctc tcc gag cat cag tgc gaa ggc ttc ctc gag gcc tac ctg ctc      1792
Gln Leu Ser Glu His Gln Cys Glu Gly Phe Leu Glu Ala Tyr Leu Leu
                480                 485                 490

acg ggc cgc cac ggc atg tgg agc acc tat gag tcc ttc gcc cac gtg      1840
Thr Gly Arg His Gly Met Trp Ser Thr Tyr Glu Ser Phe Ala His Val
            495                 500                 505

atc gac tcg atg ctc aac cag cat gcg aag tgg ctc gag gcg acc gtc      1888
Ile Asp Ser Met Leu Asn Gln His Ala Lys Trp Leu Glu Ala Thr Val
        510                 515                 520

cgc gag atc ccg tgg cgc aag ccg atc tcc tcg gtc aac ctc ctc gtc      1936
Arg Glu Ile Pro Trp Arg Lys Pro Ile Ser Ser Val Asn Leu Leu Val
    525                 530                 535

tcc tcg cac gtg tgg cgt cag gac cac aac ggc ttc tcg cat cag gac      1984
Ser Ser His Val Trp Arg Gln Asp His Asn Gly Phe Ser His Gln Asp
540                 545                 550                 555

ccg ggt gtc acc tcc gtc ctg atc aac aag acg ttc aac aac gac cac      2032
Pro Gly Val Thr Ser Val Leu Ile Asn Lys Thr Phe Asn Asn Asp His
                560                 565                 570

gtg acg aac atc tac ttc gcg acc gac gcc aac atg ctg ctc gcg atc      2080
Val Thr Asn Ile Tyr Phe Ala Thr Asp Ala Asn Met Leu Leu Ala Ile
            575                 580                 585

gcc gag aag tgc ttc aag tcc acc aac aag atc aac gcg atc ttc tcc      2128
Ala Glu Lys Cys Phe Lys Ser Thr Asn Lys Ile Asn Ala Ile Phe Ser
        590                 595                 600

ggc aag cag ccg gct ccg acc tgg att acc ctc gac gag gct cgt gcc      2176
Gly Lys Gln Pro Ala Pro Thr Trp Ile Thr Leu Asp Glu Ala Arg Ala
    605                 610                 615

gag ctc gag gcc ggc gcc gcc gag tgg aag tgg gct tcc aac gcc aag      2224
Glu Leu Glu Ala Gly Ala Ala Glu Trp Lys Trp Ala Ser Asn Ala Lys
620                 625                 630                 635

agc aac gac gag gtc cag att gtc ctc gcc gcc gca ggc gat gtc ccg      2272
Ser Asn Asp Glu Val Gln Ile Val Leu Ala Ala Ala Gly Asp Val Pro
                640                 645                 650

acc cag gag atc atg gcc gct tcc gat gcc ctg aac aag gat ggc atc      2320
Thr Gln Glu Ile Met Ala Ala Ser Asp Ala Leu Asn Lys Asp Gly Ile
            655                 660                 665

aag ttc aag gtc gtc aac gtt gtt gac ctc ctg aag ctg cag tcc ccg      2368
Lys Phe Lys Val Val Asn Val Val Asp Leu Leu Lys Leu Gln Ser Pro
        670                 675                 680

gag aac aac gac gag gcc atg tcg aac gaa gac ttc acc gag ctc ttc      2416
Glu Asn Asn Asp Glu Ala Met Ser Asn Glu Asp Phe Thr Glu Leu Phe
    685                 690                 695

acc gcc gac aaa ccg gtt ctg ttc gcc tac cac tcc tat gcc cag gac      2464
Thr Ala Asp Lys Pro Val Leu Phe Ala Tyr His Ser Tyr Ala Gln Asp
700                 705                 710                 715

gtt cgt ggt ctt atc tac gac cgc ccg aac cac gac aac ttc aac gtt      2512
Val Arg Gly Leu Ile Tyr Asp Arg Pro Asn His Asp Asn Phe Asn Val
                720                 725                 730

gtc ggc tac aag gag cag ggc tcc acg acc acg ccg ttc gac atg gtc      2560
Val Gly Tyr Lys Glu Gln Gly Ser Thr Thr Thr Pro Phe Asp Met Val
            735                 740                 745
```

```
cgc gtc aac gac atg gat cgc tac gcg ctc gaa gct cag gct ctc gag     2608
Arg Val Asn Asp Met Asp Arg Tyr Ala Leu Glu Ala Gln Ala Leu Glu
        750                 755                 760

ctg atc gac gcc gac aag tat gcc gac aag atc gac gag ctc aac gcg     2656
Leu Ile Asp Ala Asp Lys Tyr Ala Asp Lys Ile Asp Glu Leu Asn Ala
    765                 770                 775

ttc cgc aag acc gcg ttc cag ttc gcc gtc gac aac ggc tac gac atc     2704
Phe Arg Lys Thr Ala Phe Gln Phe Ala Val Asp Asn Gly Tyr Asp Ile
780                 785                 790                 795

ccg gag ttc acc gac tgg gtg tac ccg gac gtc aag gtc gac gag acg     2752
Pro Glu Phe Thr Asp Trp Val Tyr Pro Asp Val Lys Val Asp Glu Thr
                800                 805                 810

cag atg ctc tcc gcg acc gcg gcg acc gct ggc gac aac gag tga         2797
Gln Met Leu Ser Ala Thr Ala Ala Thr Ala Gly Asp Asn Glu
            815                 820                 825

gcatagtctc atcgcttagc cgatgaaagg ccaagggcga attc                    2841


<210> SEQ ID NO 12
<211> LENGTH: 825
<212> TYPE: PRT
<213> ORGANISM: Bifidobacterium animalis

<400> SEQUENCE: 12

Met Thr Asn Pro Val Ile Gly Thr Pro Trp Gln Lys Leu Asp Arg Pro
1               5                   10                  15

Val Ser Glu Glu Ala Ile Glu Gly Met Asp Lys Tyr Trp Arg Val Ala
            20                  25                  30

Asn Tyr Met Ser Ile Gly Gln Ile Tyr Leu Arg Ser Asn Pro Leu Met
        35                  40                  45

Lys Glu Pro Phe Thr Arg Asp Asp Val Lys His Arg Leu Val Gly His
    50                  55                  60

Trp Gly Thr Thr Pro Gly Leu Asn Phe Leu Leu Ala His Ile Asn Arg
65                  70                  75                  80

Leu Ile Ala Asp His Gln Gln Asn Thr Val Phe Ile Met Gly Pro Gly
                85                  90                  95

His Gly Gly Pro Ala Gly Thr Ala Gln Ser Tyr Ile Asp Gly Thr Tyr
            100                 105                 110

Thr Glu Tyr Tyr Pro Asn Ile Thr Lys Asp Glu Ala Gly Leu Gln Lys
        115                 120                 125

Phe Phe Arg Gln Phe Ser Tyr Pro Gly Gly Ile Pro Ser His Phe Ala
    130                 135                 140

Pro Glu Thr Pro Gly Ser Ile His Glu Gly Gly Glu Leu Gly Tyr Ala
145                 150                 155                 160

Leu Ser His Ala Tyr Gly Ala Ile Met Asn Asn Pro Ser Leu Phe Val
                165                 170                 175

Pro Cys Ile Ile Gly Asp Gly Glu Ala Glu Thr Gly Pro Leu Ala Thr
            180                 185                 190

Gly Trp Gln Ser Asn Lys Leu Val Asn Pro Arg Thr Asp Gly Ile Val
        195                 200                 205

Leu Pro Ile Leu His Leu Asn Gly Tyr Lys Ile Ala Asn Pro Thr Leu
    210                 215                 220

Leu Ala Arg Ile Ser Asp Glu Glu Leu His Asp Phe Phe Arg Gly Met
225                 230                 235                 240

Gly Tyr His Pro Tyr Glu Phe Val Ala Gly Phe Asp Asn Glu Asp His
                245                 250                 255

Leu Ser Ile His Arg Arg Phe Ala Glu Leu Phe Glu Thr Ile Phe Asp
```

-continued

```
            260                 265                 270

Glu Ile Cys Asp Ile Lys Ala Ala Ala Gln Thr Asp Asp Met Thr Arg
        275                 280                 285

Pro Phe Tyr Pro Met Leu Ile Phe Arg Thr Pro Lys Gly Trp Thr Cys
    290                 295                 300

Pro Lys Phe Ile Asp Gly Lys Lys Thr Glu Gly Ser Trp Arg Ala His
305                 310                 315                 320

Gln Val Pro Leu Ala Ser Ala Arg Asp Thr Glu Ala His Phe Glu Val
                325                 330                 335

Leu Lys Gly Trp Met Glu Ser Tyr Lys Pro Glu Glu Leu Phe Asn Ala
            340                 345                 350

Asp Gly Ser Ile Lys Asp Asp Val Thr Ala Phe Met Pro Lys Gly Glu
        355                 360                 365

Leu Arg Ile Gly Ala Asn Pro Asn Ala Asn Gly Gly Arg Ile Arg Glu
    370                 375                 380

Asp Leu Lys Leu Pro Glu Leu Asp Gln Tyr Glu Ile Thr Gly Val Lys
385                 390                 395                 400

Glu Tyr Gly His Gly Trp Gly Gln Val Glu Ala Pro Arg Ser Leu Gly
                405                 410                 415

Ala Tyr Cys Arg Asp Ile Ile Lys Asn Asn Pro Asp Ser Phe Arg Ile
            420                 425                 430

Phe Gly Pro Asp Glu Thr Ala Ser Asn Arg Leu Asn Ala Thr Tyr Glu
        435                 440                 445

Val Thr Lys Lys Gln Trp Asp Asn Gly Tyr Leu Ser Ala Leu Val Asp
    450                 455                 460

Glu Asn Met Ala Val Thr Gly Gln Val Val Glu Gln Leu Ser Glu His
465                 470                 475                 480

Gln Cys Glu Gly Phe Leu Glu Ala Tyr Leu Leu Thr Gly Arg His Gly
                485                 490                 495

Met Trp Ser Thr Tyr Glu Ser Phe Ala His Val Ile Asp Ser Met Leu
            500                 505                 510

Asn Gln His Ala Lys Trp Leu Glu Ala Thr Val Arg Glu Ile Pro Trp
        515                 520                 525

Arg Lys Pro Ile Ser Ser Val Asn Leu Leu Val Ser Ser His Val Trp
    530                 535                 540

Arg Gln Asp His Asn Gly Phe Ser His Gln Asp Pro Gly Val Thr Ser
545                 550                 555                 560

Val Leu Ile Asn Lys Thr Phe Asn Asn Asp His Val Thr Asn Ile Tyr
                565                 570                 575

Phe Ala Thr Asp Ala Asn Met Leu Leu Ala Ile Ala Glu Lys Cys Phe
            580                 585                 590

Lys Ser Thr Asn Lys Ile Asn Ala Ile Phe Ser Gly Lys Gln Pro Ala
        595                 600                 605

Pro Thr Trp Ile Thr Leu Asp Glu Ala Arg Ala Glu Leu Glu Ala Gly
    610                 615                 620

Ala Ala Glu Trp Lys Trp Ala Ser Asn Ala Lys Ser Asn Asp Glu Val
625                 630                 635                 640

Gln Ile Val Leu Ala Ala Ala Gly Asp Val Pro Thr Gln Glu Ile Met
                645                 650                 655

Ala Ala Ser Asp Ala Leu Asn Lys Asp Gly Ile Lys Phe Lys Val Val
            660                 665                 670

Asn Val Val Asp Leu Leu Lys Leu Gln Ser Pro Glu Asn Asn Asp Glu
        675                 680                 685
```

```
Ala Met Ser Asn Glu Asp Phe Thr Glu Leu Phe Thr Ala Asp Lys Pro
    690                 695                 700

Val Leu Phe Ala Tyr His Ser Tyr Ala Gln Asp Val Arg Gly Leu Ile
705                 710                 715                 720

Tyr Asp Arg Pro Asn His Asp Asn Phe Asn Val Val Gly Tyr Lys Glu
                725                 730                 735

Gln Gly Ser Thr Thr Thr Pro Phe Asp Met Val Arg Val Asn Asp Met
            740                 745                 750

Asp Arg Tyr Ala Leu Glu Ala Gln Ala Leu Glu Leu Ile Asp Ala Asp
        755                 760                 765

Lys Tyr Ala Asp Lys Ile Asp Glu Leu Asn Ala Phe Arg Lys Thr Ala
    770                 775                 780

Phe Gln Phe Ala Val Asp Asn Gly Tyr Asp Ile Pro Glu Phe Thr Asp
785                 790                 795                 800

Trp Val Tyr Pro Asp Val Lys Val Asp Glu Thr Gln Met Leu Ser Ala
                805                 810                 815

Thr Ala Ala Thr Ala Gly Asp Asn Glu
            820                 825


<210> SEQ ID NO 13
<211> LENGTH: 34
<212> TYPE: DNA
<213> ORGANISM: Artificial sequence
<220> FEATURE:
<223> OTHER INFORMATION: primer

<400> SEQUENCE: 13

ctagtctaga ttttcaacac gccgcgcaat atcc                                34


<210> SEQ ID NO 14
<211> LENGTH: 41
<212> TYPE: DNA
<213> ORGANISM: Artificial sequence
<220> FEATURE:
<223> OTHER INFORMATION: primer

<400> SEQUENCE: 14

ctagtctaga gaattcgccc ttggcctttc atcggctaag c                        41


<210> SEQ ID NO 15
<211> LENGTH: 24
<212> TYPE: DNA
<213> ORGANISM: Artificial Sequence
<220> FEATURE:
<223> OTHER INFORMATION: primer

<400> SEQUENCE: 15

aaattcctgt gaattagctg attt                                           24


<210> SEQ ID NO 16
<211> LENGTH: 48
<212> TYPE: DNA
<213> ORGANISM: Artificial Sequence
<220> FEATURE:
<223> OTHER INFORMATION: primer

<400> SEQUENCE: 16

ggtaccaata acaggattag tcatagaggc gaaggctcct tgaatagg                 48


<210> SEQ ID NO 17
<211> LENGTH: 34
<212> TYPE: DNA
<213> ORGANISM: Artificial Sequence
```

<220> FEATURE:
<223> OTHER INFORMATION: primer

<400> SEQUENCE: 17
ctagtctaga gaattcgccc ttggcctttc atcg 34

<210> SEQ ID NO 18
<211> LENGTH: 48
<212> TYPE: DNA
<213> ORGANISM: Artificial sequence
<220> FEATURE:
<223> OTHER INFORMATION: primer

<400> SEQUENCE: 18
cctattcaag gagccttcgc ctctatgact aatcctgtta ttggtacc 48

<210> SEQ ID NO 19
<211> LENGTH: 44
<212> TYPE: DNA
<213> ORGANISM: Artificial sequence
<220> FEATURE:
<223> OTHER INFORMATION: primer

<400> SEQUENCE: 19
ctattctaga aaattcctgt gaattagctg atttagtact tttc 44

<210> SEQ ID NO 20
<211> LENGTH: 48
<212> TYPE: DNA
<213> ORGANISM: Artificial sequence
<220> FEATURE:
<223> OTHER INFORMATION: primer

<400> SEQUENCE: 20
ggtaccaata acaggattag tcataattct gtttcctgtg tgaaattg 48

<210> SEQ ID NO 21
<211> LENGTH: 34
<212> TYPE: DNA
<213> ORGANISM: Artificial sequence
<220> FEATURE:
<223> OTHER INFORMATION: primer

<400> SEQUENCE: 21
cggttctaga ggatccggag cttatcgact gcac 34

<210> SEQ ID NO 22
<211> LENGTH: 48
<212> TYPE: DNA
<213> ORGANISM: Artificial sequence
<220> FEATURE:
<223> OTHER INFORMATION: primer

<400> SEQUENCE: 22
caatttcaca caggaaacag aattatgact aatcctgtta ttggtacc 48

<210> SEQ ID NO 23
<211> LENGTH: 49
<212> TYPE: DNA
<213> ORGANISM: Artificial sequence
<220> FEATURE:
<223> OTHER INFORMATION: primer

<400> SEQUENCE: 23
ctggtgatga gtaatctgta gacatagagg cgaaggctcc ttgaatagg 49

<210> SEQ ID NO 24
<211> LENGTH: 34
<212> TYPE: DNA
<213> ORGANISM: Artificial sequence
<220> FEATURE:
<223> OTHER INFORMATION: primer

<400> SEQUENCE: 24
ctagtctaga ttatttcaaa cctttccatt gcca 34

<210> SEQ ID NO 25
<211> LENGTH: 49
<212> TYPE: DNA
<213> ORGANISM: Artificial sequence
<220> FEATURE:
<223> OTHER INFORMATION: primer

<400> SEQUENCE: 25
cctattcaag gagccttcgc ctctatgtct acagattact catcaccag 49

<210> SEQ ID NO 26
<211> LENGTH: 48
<212> TYPE: DNA
<213> ORGANISM: Artificial sequence
<220> FEATURE:
<223> OTHER INFORMATION: primer

<400> SEQUENCE: 26
ttatctgtcc cttgaggtga tttattccac acctcctgtt ggaatgtt 48

<210> SEQ ID NO 27
<211> LENGTH: 23
<212> TYPE: DNA
<213> ORGANISM: Artificial sequence
<220> FEATURE:
<223> OTHER INFORMATION: primer

<400> SEQUENCE: 27
caaggtacaa cgcaacgatg cag 23

<210> SEQ ID NO 28
<211> LENGTH: 48
<212> TYPE: DNA
<213> ORGANISM: Artificial sequence
<220> FEATURE:
<223> OTHER INFORMATION: primer

<400> SEQUENCE: 28
aacattccaa caggaggtgt ggaataaatc acctcaaggg acagataa 48

<210> SEQ ID NO 29
<211> LENGTH: 24
<212> TYPE: DNA
<213> ORGANISM: Artificial sequence
<220> FEATURE:
<223> OTHER INFORMATION: primer

<400> SEQUENCE: 29
gatggtttgc tcgcaggtat tttg 24

<210> SEQ ID NO 30
<211> LENGTH: 34
<212> TYPE: DNA
<213> ORGANISM: Artificial sequence
<220> FEATURE:
<223> OTHER INFORMATION: primer

<400> SEQUENCE: 30
cgcacccggg cagagaagcc ttggaggtga tctg 34

<210> SEQ ID NO 31
<211> LENGTH: 32
<212> TYPE: DNA
<213> ORGANISM: Artificial sequence
<220> FEATURE:
<223> OTHER INFORMATION: primer

<400> SEQUENCE: 31
aggtcccggg accatgattg cgttgtggtc gg 32

<210> SEQ ID NO 32
<211> LENGTH: 20
<212> TYPE: DNA
<213> ORGANISM: Artificial sequence
<220> FEATURE:
<223> OTHER INFORMATION: primer

<400> SEQUENCE: 32
ccaggcactc gtcctcggtt 20

<210> SEQ ID NO 33
<211> LENGTH: 48
<212> TYPE: DNA
<213> ORGANISM: Artificial sequence
<220> FEATURE:
<223> OTHER INFORMATION: primer

<400> SEQUENCE: 33
aggctagtgc aggactataa agaccagttc tcctaaaaat aacgtgtc 48

<210> SEQ ID NO 34
<211> LENGTH: 48
<212> TYPE: DNA
<213> ORGANISM: Artificial sequence
<220> FEATURE:
<223> OTHER INFORMATION: primer

<400> SEQUENCE: 34
gacacgttat ttttaggaga actggtcttt atagtcctgc actagcct 48

<210> SEQ ID NO 35
<211> LENGTH: 20
<212> TYPE: DNA
<213> ORGANISM: Artificial sequence
<220> FEATURE:
<223> OTHER INFORMATION: primer

<400> SEQUENCE: 35
tccatcgtgg ccaccgatcc 20

<210> SEQ ID NO 36
<211> LENGTH: 25
<212> TYPE: DNA
<213> ORGANISM: Artificial sequence
<220> FEATURE:
<223> OTHER INFORMATION: primer

<400> SEQUENCE: 36
cgggatcccc accggcgtac tcgtg 25

<210> SEQ ID NO 37
<211> LENGTH: 28
<212> TYPE: DNA
<213> ORGANISM: Artificial sequence -continued
<220> FEATURE:
<223> OTHER INFORMATION: primer

<400> SEQUENCE: 37
ccacggatcc ttccaatgct attggttg 28

<210> SEQ ID NO 38
<211> LENGTH: 2769
<212> TYPE: DNA
<213> ORGANISM: Corynebacterium glutamicum
<220> FEATURE:
<221> NAME/KEY: CDS
<222> LOCATION: (1)..(2769)
<223> OTHER INFORMATION: aceE

<400> SEQUENCE: 38

```
atg gcc gat caa gca aaa ctt ggt ggc aag ccc tcg gat gac tct aac       48
Met Ala Asp Gln Ala Lys Leu Gly Gly Lys Pro Ser Asp Asp Ser Asn
1               5                   10                  15

ttc gcg atg atc cgc gat ggc gtg gca tct tat ttg aac gac tca gat       96
Phe Ala Met Ile Arg Asp Gly Val Ala Ser Tyr Leu Asn Asp Ser Asp
            20                  25                  30

ccg gag gag acc aac gag tgg atg gat tca ctc gac gga tta ctc cag      144
Pro Glu Glu Thr Asn Glu Trp Met Asp Ser Leu Asp Gly Leu Leu Gln
        35                  40                  45

gag tct tct cca gaa cgt gct cgt tac ctc atg ctt cgt ttg ctt gag      192
Glu Ser Ser Pro Glu Arg Ala Arg Tyr Leu Met Leu Arg Leu Leu Glu
    50                  55                  60

cgt gca tct gca aag cgc gta tct ctt ccc cca atg acg tca acc gac      240
Arg Ala Ser Ala Lys Arg Val Ser Leu Pro Pro Met Thr Ser Thr Asp
65                  70                  75                  80

tac gtc aac acc att cca acc tct atg gaa cct gaa ttc cca ggc gat      288
Tyr Val Asn Thr Ile Pro Thr Ser Met Glu Pro Glu Phe Pro Gly Asp
                85                  90                  95

gag gaa atg gag aag cgt tac cgt cgt tgg att cgc tgg aac gca gcc      336
Glu Glu Met Glu Lys Arg Tyr Arg Arg Trp Ile Arg Trp Asn Ala Ala
            100                 105                 110

atc atg gtt cac cgc gct cag cga cca ggc atc ggc gtc ggc gga cac      384
Ile Met Val His Arg Ala Gln Arg Pro Gly Ile Gly Val Gly Gly His
        115                 120                 125

att tcc act tac gca ggc gca gcc cct ctg tac gaa gtt ggc ttc aac      432
Ile Ser Thr Tyr Ala Gly Ala Ala Pro Leu Tyr Glu Val Gly Phe Asn
    130                 135                 140

cac ttc ttc cgc ggc aag gat cac cca ggc ggc ggc gac cag atc ttc      480
His Phe Phe Arg Gly Lys Asp His Pro Gly Gly Gly Asp Gln Ile Phe
145                 150                 155                 160

ttc cag ggc cac gca tca cca ggt atg tac gca cgt gca ttc atg gag      528
Phe Gln Gly His Ala Ser Pro Gly Met Tyr Ala Arg Ala Phe Met Glu
                165                 170                 175

ggt cgc ctt tct gaa gac gat ctc gat ggc ttc cgt cag gaa gtt tcc      576
Gly Arg Leu Ser Glu Asp Asp Leu Asp Gly Phe Arg Gln Glu Val Ser
            180                 185                 190

cgt gag cag ggt ggc att ccg tcc tac cct cac cca cac ggt atg aag      624
Arg Glu Gln Gly Gly Ile Pro Ser Tyr Pro His Pro His Gly Met Lys
        195                 200                 205

gac ttc tgg gag ttc cca act gtg tcc atg ggt ctt ggc cca atg gat      672
Asp Phe Trp Glu Phe Pro Thr Val Ser Met Gly Leu Gly Pro Met Asp
    210                 215                 220

gcc att tac cag gca cgt ttc aac cgc tac ctc gaa aac cgt ggc atc      720
Ala Ile Tyr Gln Ala Arg Phe Asn Arg Tyr Leu Glu Asn Arg Gly Ile
225                 230                 235                 240

aag gac acc tct gac cag cac gtc tgg gcc ttc ctt ggc gac ggc gaa      768
```

```
Lys Asp Thr Ser Asp Gln His Val Trp Ala Phe Leu Gly Asp Gly Glu
                245                 250                 255

atg gac gag cca gaa tca cgt ggt ctc atc cag cag gct gca ctg aac      816
Met Asp Glu Pro Glu Ser Arg Gly Leu Ile Gln Gln Ala Ala Leu Asn
            260                 265                 270

aac ctg gac aac ctg acc ttc gtg gtt aac tgc aac ctg cag cgt ctc      864
Asn Leu Asp Asn Leu Thr Phe Val Val Asn Cys Asn Leu Gln Arg Leu
        275                 280                 285

gac gga cct gtc cgc ggt aac acc aag atc atc cag gaa ctc gag tcc      912
Asp Gly Pro Val Arg Gly Asn Thr Lys Ile Ile Gln Glu Leu Glu Ser
    290                 295                 300

ttc ttc cgt ggc gca ggc tgg tct gtg atc aag gtt gtt tgg ggt cgc      960
Phe Phe Arg Gly Ala Gly Trp Ser Val Ile Lys Val Val Trp Gly Arg
305                 310                 315                 320

gag tgg gat gaa ctt ctg gag aag gac cag gat ggt gca ctt gtt gag     1008
Glu Trp Asp Glu Leu Leu Glu Lys Asp Gln Asp Gly Ala Leu Val Glu
                325                 330                 335

atc atg aac aac acc tcc gat ggt gac tac cag acc ttc aag gct aac     1056
Ile Met Asn Asn Thr Ser Asp Gly Asp Tyr Gln Thr Phe Lys Ala Asn
            340                 345                 350

gac ggc gca tat gtt cgt gag cac ttc ttc gga cgt gac cca cgc acc     1104
Asp Gly Ala Tyr Val Arg Glu His Phe Phe Gly Arg Asp Pro Arg Thr
        355                 360                 365

gca aag ctc gtt gag aac atg acc gac gaa gaa atc tgg aag ctt cca     1152
Ala Lys Leu Val Glu Asn Met Thr Asp Glu Glu Ile Trp Lys Leu Pro
    370                 375                 380

cgt ggc ggc cac gat tac cgc aag gtt tac gca gcc tac aag cga gct     1200
Arg Gly Gly His Asp Tyr Arg Lys Val Tyr Ala Ala Tyr Lys Arg Ala
385                 390                 395                 400

ctt gag acc aag gat cgc cca acc gtc atc ctt gct cac acc att aag     1248
Leu Glu Thr Lys Asp Arg Pro Thr Val Ile Leu Ala His Thr Ile Lys
                405                 410                 415

ggc tac gga ctc ggc cac aac ttc gaa ggc cgt aac gca acc cac cag     1296
Gly Tyr Gly Leu Gly His Asn Phe Glu Gly Arg Asn Ala Thr His Gln
            420                 425                 430

atg aag aag ctg acg ctt gat gat ctg aag ttg ttc cgc gac aag cag     1344
Met Lys Lys Leu Thr Leu Asp Asp Leu Lys Leu Phe Arg Asp Lys Gln
        435                 440                 445

ggc atc cca atc acc gat gag cag ctg gag aag gat cct tac ctt cct     1392
Gly Ile Pro Ile Thr Asp Glu Gln Leu Glu Lys Asp Pro Tyr Leu Pro
    450                 455                 460

cct tac tac cac cca ggt gaa gac gct cct gaa atc aag tac atg aag     1440
Pro Tyr Tyr His Pro Gly Glu Asp Ala Pro Glu Ile Lys Tyr Met Lys
465                 470                 475                 480

gaa cgt cgc gca gcg ctc ggt ggc tac ctg cca gag cgt cgt gag aac     1488
Glu Arg Arg Ala Ala Leu Gly Gly Tyr Leu Pro Glu Arg Arg Glu Asn
                485                 490                 495

tac gat cca att cag gtt cca cca ctg gat aag ctt cgc tct gtc cgt     1536
Tyr Asp Pro Ile Gln Val Pro Pro Leu Asp Lys Leu Arg Ser Val Arg
            500                 505                 510

aag ggc tcc ggc aag cag cag atc gct acc acc atg gcg act gtt cgt     1584
Lys Gly Ser Gly Lys Gln Gln Ile Ala Thr Thr Met Ala Thr Val Arg
        515                 520                 525

acc ttc aag gaa ctg atg cgc gat aag ggc ttg gct gat cgc ctt gtc     1632
Thr Phe Lys Glu Leu Met Arg Asp Lys Gly Leu Ala Asp Arg Leu Val
    530                 535                 540

cca atc att cct gat gag gca cgt acc ttc ggt ctt gac tct tgg ttc     1680
Pro Ile Ile Pro Asp Glu Ala Arg Thr Phe Gly Leu Asp Ser Trp Phe
545                 550                 555                 560

cca acc ttg aag atc tac aac ccg cac ggt cag aac tac gtg cct gtt     1728
```

```
Pro Thr Leu Lys Ile Tyr Asn Pro His Gly Gln Asn Tyr Val Pro Val
                565                 570                 575

gac cac gac ctg atg ctc tcc tac cgt gag gca cct gaa gga cag atc      1776
Asp His Asp Leu Met Leu Ser Tyr Arg Glu Ala Pro Glu Gly Gln Ile
            580                 585                 590

ctg cac gaa ggc atc aac gag gct ggt tcc gtg gca tcg ttc atc gct      1824
Leu His Glu Gly Ile Asn Glu Ala Gly Ser Val Ala Ser Phe Ile Ala
        595                 600                 605

gcg ggt acc tcc tac gcc acc cac ggc aag gcc atg att ccg ctg tac      1872
Ala Gly Thr Ser Tyr Ala Thr His Gly Lys Ala Met Ile Pro Leu Tyr
    610                 615                 620

atc ttc tac tcg atg ttc gga ttc cag cgc acc ggt gac tcc atc tgg      1920
Ile Phe Tyr Ser Met Phe Gly Phe Gln Arg Thr Gly Asp Ser Ile Trp
625                 630                 635                 640

gca gca gcc gat cag atg gca cgt ggc ttc ctc ttg ggc gct acc gca      1968
Ala Ala Ala Asp Gln Met Ala Arg Gly Phe Leu Leu Gly Ala Thr Ala
                645                 650                 655

ggt cgc acc acc ctg acc ggt gaa ggc ctc cag cac atg gat gga cac      2016
Gly Arg Thr Thr Leu Thr Gly Glu Gly Leu Gln His Met Asp Gly His
            660                 665                 670

tcc cct gtc ttg gct tcc acc aac gag ggt gtc gag acc tac gac cca      2064
Ser Pro Val Leu Ala Ser Thr Asn Glu Gly Val Glu Thr Tyr Asp Pro
        675                 680                 685

tcc ttt gcg tac gag atc gca cac ctg gtt cac cgt ggc atc gac cgc      2112
Ser Phe Ala Tyr Glu Ile Ala His Leu Val His Arg Gly Ile Asp Arg
    690                 695                 700

atg tac ggc cca ggc aag ggt gaa gat gtt atc tac tac atc acc atc      2160
Met Tyr Gly Pro Gly Lys Gly Glu Asp Val Ile Tyr Tyr Ile Thr Ile
705                 710                 715                 720

tac aac gag cca acc cca cag cca gct gag cca gaa gga ctg gac gta      2208
Tyr Asn Glu Pro Thr Pro Gln Pro Ala Glu Pro Glu Gly Leu Asp Val
                725                 730                 735

gaa ggc ctg cac aag ggc atc tac ctc tac tcc cgc ggt gaa ggc acc      2256
Glu Gly Leu His Lys Gly Ile Tyr Leu Tyr Ser Arg Gly Glu Gly Thr
            740                 745                 750

ggc cat gag gca aac atc ttg gct tcc ggt gtt ggt atg cag tgg gct      2304
Gly His Glu Ala Asn Ile Leu Ala Ser Gly Val Gly Met Gln Trp Ala
        755                 760                 765

ctc aag gct gca tcc atc ctt gag gct gac tac gga gtt cgt gcc aac      2352
Leu Lys Ala Ala Ser Ile Leu Glu Ala Asp Tyr Gly Val Arg Ala Asn
    770                 775                 780

att tac tcc gct act tct tgg gtt aac ttg gct cgc gat ggc gct gct      2400
Ile Tyr Ser Ala Thr Ser Trp Val Asn Leu Ala Arg Asp Gly Ala Ala
785                 790                 795                 800

cgt aac aag gca cag ctg cgc aac cca ggt gca gat gct ggc gag gca      2448
Arg Asn Lys Ala Gln Leu Arg Asn Pro Gly Ala Asp Ala Gly Glu Ala
                805                 810                 815

ttc gta acc acc cag ctg aag cag acc tcc ggc cca tac gtt gca gtg      2496
Phe Val Thr Thr Gln Leu Lys Gln Thr Ser Gly Pro Tyr Val Ala Val
            820                 825                 830

tct gac ttc tcc act gat ctg cca aac cag atc cgt gaa tgg gtc cca      2544
Ser Asp Phe Ser Thr Asp Leu Pro Asn Gln Ile Arg Glu Trp Val Pro
        835                 840                 845

ggc gac tac acc gtt ctc ggt gca gat ggc ttc ggt ttc tct gat acc      2592
Gly Asp Tyr Thr Val Leu Gly Ala Asp Gly Phe Gly Phe Ser Asp Thr
    850                 855                 860

cgc cca gct gct cgt cgc ttc ttc aac atc gac gct gag tcc att gtt      2640
Arg Pro Ala Ala Arg Arg Phe Phe Asn Ile Asp Ala Glu Ser Ile Val
865                 870                 875                 880

gtt gca gtg ctg aac tcc ctg gca cgc gaa ggc aag atc gac gtc tcc      2688
```

-continued

```
Val Ala Val Leu Asn Ser Leu Ala Arg Glu Gly Lys Ile Asp Val Ser
            885                 890                 895

gtt gct gct cag gct gct gag aag ttc aag ttg gat gat cct acg agt     2736
Val Ala Ala Gln Ala Ala Glu Lys Phe Lys Leu Asp Asp Pro Thr Ser
            900                 905                 910

gtt tcc gta gat cca aac gct cct gag gaa taa                         2769
Val Ser Val Asp Pro Asn Ala Pro Glu Glu
        915                 920


<210> SEQ ID NO 39
<211> LENGTH: 922
<212> TYPE: PRT
<213> ORGANISM: Corynebacterium glutamicum

<400> SEQUENCE: 39

Met Ala Asp Gln Ala Lys Leu Gly Gly Lys Pro Ser Asp Asp Ser Asn
1               5                   10                  15

Phe Ala Met Ile Arg Asp Gly Val Ala Ser Tyr Leu Asn Asp Ser Asp
            20                  25                  30

Pro Glu Glu Thr Asn Glu Trp Met Asp Ser Leu Asp Gly Leu Leu Gln
        35                  40                  45

Glu Ser Ser Pro Glu Arg Ala Arg Tyr Leu Met Leu Arg Leu Leu Glu
    50                  55                  60

Arg Ala Ser Ala Lys Arg Val Ser Leu Pro Pro Met Thr Ser Thr Asp
65                  70                  75                  80

Tyr Val Asn Thr Ile Pro Thr Ser Met Glu Pro Glu Phe Pro Gly Asp
                85                  90                  95

Glu Glu Met Glu Lys Arg Tyr Arg Arg Trp Ile Arg Trp Asn Ala Ala
            100                 105                 110

Ile Met Val His Arg Ala Gln Arg Pro Gly Ile Gly Val Gly Gly His
        115                 120                 125

Ile Ser Thr Tyr Ala Gly Ala Ala Pro Leu Tyr Glu Val Gly Phe Asn
    130                 135                 140

His Phe Phe Arg Gly Lys Asp His Pro Gly Gly Gly Asp Gln Ile Phe
145                 150                 155                 160

Phe Gln Gly His Ala Ser Pro Gly Met Tyr Ala Arg Ala Phe Met Glu
                165                 170                 175

Gly Arg Leu Ser Glu Asp Asp Leu Asp Gly Phe Arg Gln Glu Val Ser
            180                 185                 190

Arg Glu Gln Gly Gly Ile Pro Ser Tyr Pro His Pro His Gly Met Lys
        195                 200                 205

Asp Phe Trp Glu Phe Pro Thr Val Ser Met Gly Leu Gly Pro Met Asp
    210                 215                 220

Ala Ile Tyr Gln Ala Arg Phe Asn Arg Tyr Leu Glu Asn Arg Gly Ile
225                 230                 235                 240

Lys Asp Thr Ser Asp Gln His Val Trp Ala Phe Leu Gly Asp Gly Glu
                245                 250                 255

Met Asp Glu Pro Glu Ser Arg Gly Leu Ile Gln Gln Ala Ala Leu Asn
            260                 265                 270

Asn Leu Asp Asn Leu Thr Phe Val Val Asn Cys Asn Leu Gln Arg Leu
        275                 280                 285

Asp Gly Pro Val Arg Gly Asn Thr Lys Ile Ile Gln Glu Leu Glu Ser
    290                 295                 300

Phe Phe Arg Gly Ala Gly Trp Ser Val Ile Lys Val Val Trp Gly Arg
305                 310                 315                 320

Glu Trp Asp Glu Leu Leu Glu Lys Asp Gln Asp Gly Ala Leu Val Glu
```

```
                325                 330                 335

Ile Met Asn Asn Thr Ser Asp Gly Asp Tyr Gln Thr Phe Lys Ala Asn
            340                 345                 350

Asp Gly Ala Tyr Val Arg Glu His Phe Phe Gly Arg Asp Pro Arg Thr
        355                 360                 365

Ala Lys Leu Val Glu Asn Met Thr Asp Glu Glu Ile Trp Lys Leu Pro
    370                 375                 380

Arg Gly Gly His Asp Tyr Arg Lys Val Tyr Ala Ala Tyr Lys Arg Ala
385                 390                 395                 400

Leu Glu Thr Lys Asp Arg Pro Thr Val Ile Leu Ala His Thr Ile Lys
                405                 410                 415

Gly Tyr Gly Leu Gly His Asn Phe Glu Gly Arg Asn Ala Thr His Gln
            420                 425                 430

Met Lys Lys Leu Thr Leu Asp Asp Leu Lys Leu Phe Arg Asp Lys Gln
        435                 440                 445

Gly Ile Pro Ile Thr Asp Glu Gln Leu Glu Lys Asp Pro Tyr Leu Pro
    450                 455                 460

Pro Tyr Tyr His Pro Gly Glu Asp Ala Pro Glu Ile Lys Tyr Met Lys
465                 470                 475                 480

Glu Arg Arg Ala Ala Leu Gly Gly Tyr Leu Pro Glu Arg Arg Glu Asn
                485                 490                 495

Tyr Asp Pro Ile Gln Val Pro Pro Leu Asp Lys Leu Arg Ser Val Arg
            500                 505                 510

Lys Gly Ser Gly Lys Gln Gln Ile Ala Thr Thr Met Ala Thr Val Arg
        515                 520                 525

Thr Phe Lys Glu Leu Met Arg Asp Lys Gly Leu Ala Asp Arg Leu Val
    530                 535                 540

Pro Ile Ile Pro Asp Glu Ala Arg Thr Phe Gly Leu Asp Ser Trp Phe
545                 550                 555                 560

Pro Thr Leu Lys Ile Tyr Asn Pro His Gly Gln Asn Tyr Val Pro Val
                565                 570                 575

Asp His Asp Leu Met Leu Ser Tyr Arg Glu Ala Pro Glu Gly Gln Ile
            580                 585                 590

Leu His Glu Gly Ile Asn Glu Ala Gly Ser Val Ala Ser Phe Ile Ala
        595                 600                 605

Ala Gly Thr Ser Tyr Ala Thr His Gly Lys Ala Met Ile Pro Leu Tyr
    610                 615                 620

Ile Phe Tyr Ser Met Phe Gly Phe Gln Arg Thr Gly Asp Ser Ile Trp
625                 630                 635                 640

Ala Ala Ala Asp Gln Met Ala Arg Gly Phe Leu Leu Gly Ala Thr Ala
                645                 650                 655

Gly Arg Thr Thr Leu Thr Gly Glu Gly Leu Gln His Met Asp Gly His
            660                 665                 670

Ser Pro Val Leu Ala Ser Thr Asn Glu Gly Val Glu Thr Tyr Asp Pro
        675                 680                 685

Ser Phe Ala Tyr Glu Ile Ala His Leu Val His Arg Gly Ile Asp Arg
    690                 695                 700

Met Tyr Gly Pro Gly Lys Gly Glu Asp Val Ile Tyr Tyr Ile Thr Ile
705                 710                 715                 720

Tyr Asn Glu Pro Thr Pro Gln Pro Ala Glu Pro Glu Gly Leu Asp Val
                725                 730                 735

Glu Gly Leu His Lys Gly Ile Tyr Leu Tyr Ser Arg Gly Glu Gly Thr
            740                 745                 750
```

```
Gly His Glu Ala Asn Ile Leu Ala Ser Gly Val Gly Met Gln Trp Ala
        755                 760                 765

Leu Lys Ala Ala Ser Ile Leu Glu Ala Asp Tyr Gly Val Arg Ala Asn
    770                 775                 780

Ile Tyr Ser Ala Thr Ser Trp Val Asn Leu Ala Arg Asp Gly Ala Ala
785                 790                 795                 800

Arg Asn Lys Ala Gln Leu Arg Asn Pro Gly Ala Asp Ala Gly Glu Ala
                805                 810                 815

Phe Val Thr Thr Gln Leu Lys Gln Thr Ser Gly Pro Tyr Val Ala Val
            820                 825                 830

Ser Asp Phe Ser Thr Asp Leu Pro Asn Gln Ile Arg Glu Trp Val Pro
        835                 840                 845

Gly Asp Tyr Thr Val Leu Gly Ala Asp Gly Phe Gly Phe Ser Asp Thr
    850                 855                 860

Arg Pro Ala Ala Arg Arg Phe Phe Asn Ile Asp Ala Glu Ser Ile Val
865                 870                 875                 880

Val Ala Val Leu Asn Ser Leu Ala Arg Glu Gly Lys Ile Asp Val Ser
                885                 890                 895

Val Ala Ala Gln Ala Ala Glu Lys Phe Lys Leu Asp Asp Pro Thr Ser
            900                 905                 910

Val Ser Val Asp Pro Asn Ala Pro Glu Glu
        915                 920


<210> SEQ ID NO 40
<211> LENGTH: 2014
<212> TYPE: DNA
<213> ORGANISM: Bacillus subtilis
<220> FEATURE:
<221> NAME/KEY: CDS
<222> LOCATION: (464)..(1885)
<223> OTHER INFORMATION: sacB

<400> SEQUENCE: 40

gatccttttt aacccatcac atatacctgc cgttcactat tatttagtga aatgagatat      60

tatgatattt tctgaattgt gattaaaaag gcaactttat gcccatgcaa cagaaactat     120

aaaaaataca gagaatgaaa agaaacagat agatttttta gttctttagg cccgtagtct     180

gcaaatcctt ttatgatttt ctatcaaaca aaagaggaaa atagaccagt tgcaatccaa     240

acgagagtct aatagaatga ggtcgaaaag taaatcgcgc gggtttgtta ctgataaagc     300

aggcaagacc taaaatgtgt aaagggcaaa gtgtatactt tggcgtcacc ccttacatat     360

tttaggtctt tttttattgt gcgtaactaa cttgccatct tcaaacagga gggctggaag     420

aagcagaccg ctaacacagt acataaaaaa ggagacatga acg atg aac atc aaa      475
                                                Met Asn Ile Lys
                                                1

aag ttt gca aaa caa gca aca gta tta acc ttt act acc gca ctg ctg      523
Lys Phe Ala Lys Gln Ala Thr Val Leu Thr Phe Thr Thr Ala Leu Leu
5                   10                  15                  20

gca gga ggc gca act caa gcg ttt gcg aaa gaa acg aac caa aag cca      571
Ala Gly Gly Ala Thr Gln Ala Phe Ala Lys Glu Thr Asn Gln Lys Pro
                25                  30                  35

tat aag gaa aca tac ggc att tcc cat att aca cgc cat gat atg ctg      619
Tyr Lys Glu Thr Tyr Gly Ile Ser His Ile Thr Arg His Asp Met Leu
            40                  45                  50

caa atc cct gaa cag caa aaa aat gaa aaa tat caa gtt cct gaa ttc      667
Gln Ile Pro Glu Gln Gln Lys Asn Glu Lys Tyr Gln Val Pro Glu Phe
        55                  60                  65

gat tcg tcc aca att aaa aat atc tct tct gca aaa ggc ctg gac gtt      715
```

-continued

```
Asp Ser Ser Thr Ile Lys Asn Ile Ser Ser Ala Lys Gly Leu Asp Val
    70                  75                  80

tgg gac agc tgg cca tta caa aac gct gac ggc act gtc gca aac tat      763
Trp Asp Ser Trp Pro Leu Gln Asn Ala Asp Gly Thr Val Ala Asn Tyr
85                  90                  95                  100

cac ggc tac cac atc gtc ttt gca tta gcc gga gat cct aaa aat gcg      811
His Gly Tyr His Ile Val Phe Ala Leu Ala Gly Asp Pro Lys Asn Ala
                105                 110                 115

gat gac aca tcg att tac atg ttc tat caa aaa gtc ggc gaa act tct      859
Asp Asp Thr Ser Ile Tyr Met Phe Tyr Gln Lys Val Gly Glu Thr Ser
            120                 125                 130

att gac agc tgg aaa aac gct ggc cgc gtc ttt aaa gac agc gac aaa      907
Ile Asp Ser Trp Lys Asn Ala Gly Arg Val Phe Lys Asp Ser Asp Lys
        135                 140                 145

ttc gat gca aat gat tct atc cta aaa gac caa aca caa gaa tgg tca      955
Phe Asp Ala Asn Asp Ser Ile Leu Lys Asp Gln Thr Gln Glu Trp Ser
    150                 155                 160

ggt tca gcc aca ttt aca tct gac gga aaa atc cgt tta ttc tac act     1003
Gly Ser Ala Thr Phe Thr Ser Asp Gly Lys Ile Arg Leu Phe Tyr Thr
165                 170                 175                 180

gat ttc tcc ggt aaa cat tac ggc aaa caa aca ctg aca act gca caa     1051
Asp Phe Ser Gly Lys His Tyr Gly Lys Gln Thr Leu Thr Thr Ala Gln
                185                 190                 195

gtt aac gta tca gca tca gac agc tct ttg aac atc aac ggt gta gag     1099
Val Asn Val Ser Ala Ser Asp Ser Ser Leu Asn Ile Asn Gly Val Glu
            200                 205                 210

gat tat aaa tca atc ttt gac ggt gac gga aaa acg tat caa aat gta     1147
Asp Tyr Lys Ser Ile Phe Asp Gly Asp Gly Lys Thr Tyr Gln Asn Val
        215                 220                 225

cag cag ttc atc gat gaa ggc aac tac agc tca ggc gac aac cat acg     1195
Gln Gln Phe Ile Asp Glu Gly Asn Tyr Ser Ser Gly Asp Asn His Thr
    230                 235                 240

ctg aga gat cct cac tac gta gaa gat aaa ggc cac aaa tac tta gta     1243
Leu Arg Asp Pro His Tyr Val Glu Asp Lys Gly His Lys Tyr Leu Val
245                 250                 255                 260

ttt gaa gca aac act gga act gaa gat ggc tac caa ggc gaa gaa tct     1291
Phe Glu Ala Asn Thr Gly Thr Glu Asp Gly Tyr Gln Gly Glu Glu Ser
                265                 270                 275

tta ttt aac aaa gca tac tat ggc aaa agc aca tca ttc ttc cgt caa     1339
Leu Phe Asn Lys Ala Tyr Tyr Gly Lys Ser Thr Ser Phe Phe Arg Gln
            280                 285                 290

gaa agt caa aaa ctt ctg caa agc gat aaa aaa cgc acg gct gag tta     1387
Glu Ser Gln Lys Leu Leu Gln Ser Asp Lys Lys Arg Thr Ala Glu Leu
        295                 300                 305

gca aac ggc gct ctc ggt atg att gag cta aac gat gat tac aca ctg     1435
Ala Asn Gly Ala Leu Gly Met Ile Glu Leu Asn Asp Asp Tyr Thr Leu
    310                 315                 320

aaa aaa gtg atg aaa ccg ctg att gca tct aac aca gta aca gat gaa     1483
Lys Lys Val Met Lys Pro Leu Ile Ala Ser Asn Thr Val Thr Asp Glu
325                 330                 335                 340

att gaa cgc gcg aac gtc ttt aaa atg aac ggc aaa tgg tac ctg ttc     1531
Ile Glu Arg Ala Asn Val Phe Lys Met Asn Gly Lys Trp Tyr Leu Phe
                345                 350                 355

act gac tcc cgc gga tca aaa atg acg att gac ggc att acg tct aac     1579
Thr Asp Ser Arg Gly Ser Lys Met Thr Ile Asp Gly Ile Thr Ser Asn
            360                 365                 370

gat att tac atg ctt ggt tat gtt tct aat tct tta act ggc cca tac     1627
Asp Ile Tyr Met Leu Gly Tyr Val Ser Asn Ser Leu Thr Gly Pro Tyr
        375                 380                 385

aag ccg ctg aac aaa act ggc ctt gtg tta aaa atg gat ctt gat cct     1675
```

-continued

```
Lys Pro Leu Asn Lys Thr Gly Leu Val Leu Lys Met Asp Leu Asp Pro
    390                 395                 400

aac gat gta acc ttt act tac tca cac ttc gct gta cct caa gcg aaa      1723
Asn Asp Val Thr Phe Thr Tyr Ser His Phe Ala Val Pro Gln Ala Lys
405                 410                 415                 420

gga aac aat gtc gtg att aca agc tat atg aca aac aga gga ttc tac      1771
Gly Asn Asn Val Val Ile Thr Ser Tyr Met Thr Asn Arg Gly Phe Tyr
                425                 430                 435

gca gac aaa caa tca acg ttt gcg cca agc ttc ctg ctg aac atc aaa      1819
Ala Asp Lys Gln Ser Thr Phe Ala Pro Ser Phe Leu Leu Asn Ile Lys
            440                 445                 450

ggc aag aaa aca tct gtt gtc aaa gac agc atc ctt gaa caa gga caa      1867
Gly Lys Lys Thr Ser Val Val Lys Asp Ser Ile Leu Glu Gln Gly Gln
        455                 460                 465

tta aca gtt aac aaa taa aaacgcaaaa gaaaatgccg atatcctatt            1915
Leu Thr Val Asn Lys
    470

ggcattttct tttatttctt atcaacataa aggtgaatcc catatgaact atataaaagc   1975

aggcaaatgg ctaaccgtat tcctaacctt ttgaagatc                          2014


<210> SEQ ID NO 41
<211> LENGTH: 473
<212> TYPE: PRT
<213> ORGANISM: Bacillus subtilis

<400> SEQUENCE: 41

Met Asn Ile Lys Lys Phe Ala Lys Gln Ala Thr Val Leu Thr Phe Thr
1               5                   10                  15

Thr Ala Leu Leu Ala Gly Gly Ala Thr Gln Ala Phe Ala Lys Glu Thr
            20                  25                  30

Asn Gln Lys Pro Tyr Lys Glu Thr Tyr Gly Ile Ser His Ile Thr Arg
        35                  40                  45

His Asp Met Leu Gln Ile Pro Glu Gln Gln Lys Asn Glu Lys Tyr Gln
    50                  55                  60

Val Pro Glu Phe Asp Ser Ser Thr Ile Lys Asn Ile Ser Ser Ala Lys
65                  70                  75                  80

Gly Leu Asp Val Trp Asp Ser Trp Pro Leu Gln Asn Ala Asp Gly Thr
                85                  90                  95

Val Ala Asn Tyr His Gly Tyr His Ile Val Phe Ala Leu Ala Gly Asp
            100                 105                 110

Pro Lys Asn Ala Asp Asp Thr Ser Ile Tyr Met Phe Tyr Gln Lys Val
        115                 120                 125

Gly Glu Thr Ser Ile Asp Ser Trp Lys Asn Ala Gly Arg Val Phe Lys
    130                 135                 140

Asp Ser Asp Lys Phe Asp Ala Asn Asp Ser Ile Leu Lys Asp Gln Thr
145                 150                 155                 160

Gln Glu Trp Ser Gly Ser Ala Thr Phe Thr Ser Asp Gly Lys Ile Arg
                165                 170                 175

Leu Phe Tyr Thr Asp Phe Ser Gly Lys His Tyr Gly Lys Gln Thr Leu
            180                 185                 190

Thr Thr Ala Gln Val Asn Val Ser Ala Ser Asp Ser Ser Leu Asn Ile
        195                 200                 205

Asn Gly Val Glu Asp Tyr Lys Ser Ile Phe Asp Gly Asp Gly Lys Thr
    210                 215                 220

Tyr Gln Asn Val Gln Gln Phe Ile Asp Glu Gly Asn Tyr Ser Ser Gly
225                 230                 235                 240
```

-continued

```
Asp Asn His Thr Leu Arg Asp Pro His Tyr Val Glu Asp Lys Gly His
                245                 250                 255

Lys Tyr Leu Val Phe Glu Ala Asn Thr Gly Thr Glu Asp Gly Tyr Gln
            260                 265                 270

Gly Glu Glu Ser Leu Phe Asn Lys Ala Tyr Tyr Gly Lys Ser Thr Ser
        275                 280                 285

Phe Phe Arg Gln Glu Ser Gln Lys Leu Leu Gln Ser Asp Lys Lys Arg
    290                 295                 300

Thr Ala Glu Leu Ala Asn Gly Ala Leu Gly Met Ile Glu Leu Asn Asp
305                 310                 315                 320

Asp Tyr Thr Leu Lys Lys Val Met Lys Pro Leu Ile Ala Ser Asn Thr
                325                 330                 335

Val Thr Asp Glu Ile Glu Arg Ala Asn Val Phe Lys Met Asn Gly Lys
            340                 345                 350

Trp Tyr Leu Phe Thr Asp Ser Arg Gly Ser Lys Met Thr Ile Asp Gly
        355                 360                 365

Ile Thr Ser Asn Asp Ile Tyr Met Leu Gly Tyr Val Ser Asn Ser Leu
    370                 375                 380

Thr Gly Pro Tyr Lys Pro Leu Asn Lys Thr Gly Leu Val Leu Lys Met
385                 390                 395                 400

Asp Leu Asp Pro Asn Asp Val Thr Phe Thr Tyr Ser His Phe Ala Val
                405                 410                 415

Pro Gln Ala Lys Gly Asn Asn Val Val Ile Thr Ser Tyr Met Thr Asn
            420                 425                 430

Arg Gly Phe Tyr Ala Asp Lys Gln Ser Thr Phe Ala Pro Ser Phe Leu
        435                 440                 445

Leu Asn Ile Lys Gly Lys Lys Thr Ser Val Val Lys Asp Ser Ile Leu
    450                 455                 460

Glu Gln Gly Gln Leu Thr Val Asn Lys
465                 470
```

<210> SEQ ID NO 42
<211> LENGTH: 24
<212> TYPE: DNA
<213> ORGANISM: Artificial sequence
<220> FEATURE:
<223> OTHER INFORMATION: primer

<400> SEQUENCE: 42
cgggatcctt tttaacccat caca 24

<210> SEQ ID NO 43
<211> LENGTH: 29
<212> TYPE: DNA
<213> ORGANISM: Artificial sequence
<220> FEATURE:
<223> OTHER INFORMATION: primer

<400> SEQUENCE: 43
gaagatcttc aaaaggttag gaatacggt 29

<210> SEQ ID NO 44
<211> LENGTH: 23
<212> TYPE: DNA
<213> ORGANISM: Artificial sequence
<220> FEATURE:
<223> OTHER INFORMATION: primer

<400> SEQUENCE: 44
ccttttgaag atcgaccagt tgg 23

-continued

<210> SEQ ID NO 45
<211> LENGTH: 44
<212> TYPE: DNA
<213> ORGANISM: Artificial sequence
<220> FEATURE:
<223> OTHER INFORMATION: primer

<400> SEQUENCE: 45
tacctggaat gctgttttcc cagggatcgc agtggtgagt aacc 44

<210> SEQ ID NO 46
<211> LENGTH: 28
<212> TYPE: DNA
<213> ORGANISM: Artificial sequence
<220> FEATURE:
<223> OTHER INFORMATION: primer

<400> SEQUENCE: 46
cctgggaaaa cagcattcca ggtattag 28

<210> SEQ ID NO 47
<211> LENGTH: 23
<212> TYPE: DNA
<213> ORGANISM: Artificial sequence
<220> FEATURE:
<223> OTHER INFORMATION: primer

<400> SEQUENCE: 47
tgcaggtcga ctctagagga tcc 23

<210> SEQ ID NO 48
<211> LENGTH: 3774
<212> TYPE: DNA
<213> ORGANISM: Corynebacterium glutamicum
<220> FEATURE:
<221> NAME/KEY: CDS
<222> LOCATION: (1)..(3774)
<223> OTHER INFORMATION: sucA

<400> SEQUENCE: 48 atg cta caa ctg ggg ctt agg cat aat cag cca acg acc aac gtt aca 48
Met Leu Gln Leu Gly Leu Arg His Asn Gln Pro Thr Thr Asn Val Thr
1 5 10 15 gtg gat aaa aca aag ctc aat aaa ccc tca aga agc aag gaa aag agg 96
Val Asp Lys Thr Lys Leu Asn Lys Pro Ser Arg Ser Lys Glu Lys Arg
20 25 30 cga gta cct gcc gtg agc agc gct agt act ttc ggc cag aat gcg tgg 144
Arg Val Pro Ala Val Ser Ser Ala Ser Thr Phe Gly Gln Asn Ala Trp
35 40 45 ctg gta gac gag atg ttc cag cag ttc cag aag gac ccc aag tcc gtg 192
Leu Val Asp Glu Met Phe Gln Gln Phe Gln Lys Asp Pro Lys Ser Val
50 55 60 gac aag gaa tgg aga gaa ctc ttt gag gcg cag ggg gga cca aat act 240
Asp Lys Glu Trp Arg Glu Leu Phe Glu Ala Gln Gly Gly Pro Asn Thr
65 70 75 80 acc ccc gct aca aca gaa gca cag cct tca gcg ccc aag gag tct gcg 288
Thr Pro Ala Thr Thr Glu Ala Gln Pro Ser Ala Pro Lys Glu Ser Ala
85 90 95 aaa cca gca cca aag gct gcc cct gca gcc aag gca gca ccg cgc gta 336
Lys Pro Ala Pro Lys Ala Ala Pro Ala Ala Lys Ala Ala Pro Arg Val
100 105 110 gaa acc aag ccg gcc gac aag acc gcc cct aag gcc aag gag tcc tca 384
Glu Thr Lys Pro Ala Asp Lys Thr Ala Pro Lys Ala Lys Glu Ser Ser
115 120 125

-continued

```
gtg cca cag caa cct aag ctt ccg gag cca gga caa acc cca atc agg      432
Val Pro Gln Gln Pro Lys Leu Pro Glu Pro Gly Gln Thr Pro Ile Arg
    130                 135                 140

ggt att ttc aag tcc atc gcg aag aac atg gat atc tcc ctg gaa atc      480
Gly Ile Phe Lys Ser Ile Ala Lys Asn Met Asp Ile Ser Leu Glu Ile
145                 150                 155                 160

cca acc gca acc tcg gtt cgc gat atg cca gct cgc ctc atg ttc gaa      528
Pro Thr Ala Thr Ser Val Arg Asp Met Pro Ala Arg Leu Met Phe Glu
                165                 170                 175

aac cgc gcg atg gtc aac gat cag ctc aag cgc acc cgc ggt ggc aag      576
Asn Arg Ala Met Val Asn Asp Gln Leu Lys Arg Thr Arg Gly Gly Lys
            180                 185                 190

atc tcc ttc acc cac atc att ggc tac gcc atg gtg aag gca gtc atg      624
Ile Ser Phe Thr His Ile Ile Gly Tyr Ala Met Val Lys Ala Val Met
        195                 200                 205

gct cac ccg gac atg aac aac tcc tac gac gtc atc gac ggc aag cca      672
Ala His Pro Asp Met Asn Asn Ser Tyr Asp Val Ile Asp Gly Lys Pro
    210                 215                 220

acc ctg atc gtg cct gag cac atc aac ctg ggc ctt gct atc gac ctt      720
Thr Leu Ile Val Pro Glu His Ile Asn Leu Gly Leu Ala Ile Asp Leu
225                 230                 235                 240

cct cag aag gac ggc tcc cgc gca ctt gtc gta gca gcc atc aag gaa      768
Pro Gln Lys Asp Gly Ser Arg Ala Leu Val Val Ala Ala Ile Lys Glu
                245                 250                 255

acc gag aag atg aac ttc tcc gag ttc ctc gca gcc tac gaa gac atc      816
Thr Glu Lys Met Asn Phe Ser Glu Phe Leu Ala Ala Tyr Glu Asp Ile
            260                 265                 270

gtg gca cgc tcc cgc aag ggc aag ctc acc atg gat gac tac cag ggc      864
Val Ala Arg Ser Arg Lys Gly Lys Leu Thr Met Asp Asp Tyr Gln Gly
        275                 280                 285

gtt acc gtt tcc ttg acc aac cca ggt ggc atc ggt acc cgc cac tct      912
Val Thr Val Ser Leu Thr Asn Pro Gly Gly Ile Gly Thr Arg His Ser
    290                 295                 300

gtt cca cgt cta acc aag ggc cag ggc acc atc atc ggt gtc ggt tcc      960
Val Pro Arg Leu Thr Lys Gly Gln Gly Thr Ile Ile Gly Val Gly Ser
305                 310                 315                 320

atg gat tac cca gca gag ttc cag ggc gct tca gaa gac cgc ctt gca     1008
Met Asp Tyr Pro Ala Glu Phe Gln Gly Ala Ser Glu Asp Arg Leu Ala
                325                 330                 335

gag ctc ggc gtt ggc aaa ctt gtc acc atc acc tcc acc tac gat cac     1056
Glu Leu Gly Val Gly Lys Leu Val Thr Ile Thr Ser Thr Tyr Asp His
            340                 345                 350

cgc gtg atc cag ggt gct gtg tcc ggt gaa ttc ctg cgc acc atg tct     1104
Arg Val Ile Gln Gly Ala Val Ser Gly Glu Phe Leu Arg Thr Met Ser
        355                 360                 365

cgc ctg ctc acc gat gat tcc ttc tgg gat gag atc ttc gac gca atg     1152
Arg Leu Leu Thr Asp Asp Ser Phe Trp Asp Glu Ile Phe Asp Ala Met
    370                 375                 380

aac gtt cct tac acc cca atg cgt tgg gca cag gac gtt cca aac acc     1200
Asn Val Pro Tyr Thr Pro Met Arg Trp Ala Gln Asp Val Pro Asn Thr
385                 390                 395                 400

ggt gtt gat aag aac acc cgc gtc atg cag ctc att gag gca tac cgc     1248
Gly Val Asp Lys Asn Thr Arg Val Met Gln Leu Ile Glu Ala Tyr Arg
                405                 410                 415

tcc cgt gga cac ctc atc gct gac acc aac cca ctt tca tgg gtt cag     1296
Ser Arg Gly His Leu Ile Ala Asp Thr Asn Pro Leu Ser Trp Val Gln
            420                 425                 430

cct ggc atg cca gtt cca gac cac cgc gac ctc gac atc gag acc cac     1344
Pro Gly Met Pro Val Pro Asp His Arg Asp Leu Asp Ile Glu Thr His
        435                 440                 445
```

```
aac ctg acc atc tgg gat ctg gac cgt acc ttc aac gtc ggt ggc ttc      1392
Asn Leu Thr Ile Trp Asp Leu Asp Arg Thr Phe Asn Val Gly Gly Phe
    450                 455                 460

ggc ggc aag gag acc atg acc ctg cgc gag gta ctg tcc cgc ctc cgc      1440
Gly Gly Lys Glu Thr Met Thr Leu Arg Glu Val Leu Ser Arg Leu Arg
465                 470                 475                 480

gct gcg tac acc ctc aag gtc ggc tcc gaa tac acc cac atc ctg gac      1488
Ala Ala Tyr Thr Leu Lys Val Gly Ser Glu Tyr Thr His Ile Leu Asp
                485                 490                 495

cgc gac gag cgc acc tgg ctg cag gac cgc ctc gag gcc gga atg cca      1536
Arg Asp Glu Arg Thr Trp Leu Gln Asp Arg Leu Glu Ala Gly Met Pro
            500                 505                 510

aag cca acc cag gca gag cag aag tac atc ctg cag aag ctg aac gcc      1584
Lys Pro Thr Gln Ala Glu Gln Lys Tyr Ile Leu Gln Lys Leu Asn Ala
        515                 520                 525

gcg gag gct ttc gag aac ttc ctg cag acc aag tac gtc ggc cag aag      1632
Ala Glu Ala Phe Glu Asn Phe Leu Gln Thr Lys Tyr Val Gly Gln Lys
    530                 535                 540

cgc ttc tcc ctc gaa ggt gca gaa gca ctt atc cca ctg atg gac tcc      1680
Arg Phe Ser Leu Glu Gly Ala Glu Ala Leu Ile Pro Leu Met Asp Ser
545                 550                 555                 560

gcc atc gac acc gcc gca ggc caa ggc ctc gac gaa gtt gtc atc ggt      1728
Ala Ile Asp Thr Ala Ala Gly Gln Gly Leu Asp Glu Val Val Ile Gly
                565                 570                 575

atg cca cac cgt ggt cgc ctc aac gtg ctg ttc aac atc gtg ggc aag      1776
Met Pro His Arg Gly Arg Leu Asn Val Leu Phe Asn Ile Val Gly Lys
            580                 585                 590

cca ctg gca tcc atc ttc aac gag ttt gaa ggc caa atg gag cag ggc      1824
Pro Leu Ala Ser Ile Phe Asn Glu Phe Glu Gly Gln Met Glu Gln Gly
        595                 600                 605

cag atc ggt ggc tcc ggt gac gtg aag tac cac ctc ggt tcc gaa ggc      1872
Gln Ile Gly Gly Ser Gly Asp Val Lys Tyr His Leu Gly Ser Glu Gly
    610                 615                 620

cag cac ctg cag atg ttc ggc gac ggc gag atc aag gtc tcc ctg act      1920
Gln His Leu Gln Met Phe Gly Asp Gly Glu Ile Lys Val Ser Leu Thr
625                 630                 635                 640

gct aac ccg tcc cac ctg gaa gct gtt aac cca gtg atg gaa ggt atc      1968
Ala Asn Pro Ser His Leu Glu Ala Val Asn Pro Val Met Glu Gly Ile
                645                 650                 655

gtc cgc gca aag cag gac tac ctg gac aag ggc gta gac ggc aag act      2016
Val Arg Ala Lys Gln Asp Tyr Leu Asp Lys Gly Val Asp Gly Lys Thr
            660                 665                 670

gtt gtg cca ctg ctg ctc cac ggt gac gct gca ttc gca ggc ctg ggc      2064
Val Val Pro Leu Leu Leu His Gly Asp Ala Ala Phe Ala Gly Leu Gly
        675                 680                 685

atc gtg cca gaa acc atc aac ctg gct aag ctg cgt ggc tac gac gtc      2112
Ile Val Pro Glu Thr Ile Asn Leu Ala Lys Leu Arg Gly Tyr Asp Val
    690                 695                 700

ggc ggc acc atc cac atc gtg gtg aac aac cag atc ggc ttc acc acc      2160
Gly Gly Thr Ile His Ile Val Val Asn Asn Gln Ile Gly Phe Thr Thr
705                 710                 715                 720

acc cca gac tcc agc cgc tcc atg cac tac gca acc gac tac gcc aag      2208
Thr Pro Asp Ser Ser Arg Ser Met His Tyr Ala Thr Asp Tyr Ala Lys
                725                 730                 735

gca ttc ggc tgc cca gtc ttc cac gtc aac ggc gac gac cca gag gca      2256
Ala Phe Gly Cys Pro Val Phe His Val Asn Gly Asp Asp Pro Glu Ala
            740                 745                 750

gtt gtc tgg gtt ggc cag ctg gcc acc gag tac cgt cgt cgc ttc ggc      2304
Val Val Trp Val Gly Gln Leu Ala Thr Glu Tyr Arg Arg Arg Phe Gly
        755                 760                 765
```

-continued

```
aag gac gtc ttc atc gac ctc gtc tgc tac cgc ctc cgc ggc cac aac     2352
Lys Asp Val Phe Ile Asp Leu Val Cys Tyr Arg Leu Arg Gly His Asn
    770                 775                 780

gaa gct gat gat cct tcc atg acc cag cca aag atg tat gag ctc atc     2400
Glu Ala Asp Asp Pro Ser Met Thr Gln Pro Lys Met Tyr Glu Leu Ile
785                 790                 795                 800

acc ggc cgc gag acc gtt cgt gct cag tac acc gaa gac ctg ctc gga     2448
Thr Gly Arg Glu Thr Val Arg Ala Gln Tyr Thr Glu Asp Leu Leu Gly
                805                 810                 815

cgt gga gac ctc tcc aac gaa gat gca gaa gca gtc gtc cgc gac ttc     2496
Arg Gly Asp Leu Ser Asn Glu Asp Ala Glu Ala Val Val Arg Asp Phe
            820                 825                 830

cac gac cag atg gaa tct gtg ttc aac gaa gtc aag gaa ggc ggc aag     2544
His Asp Gln Met Glu Ser Val Phe Asn Glu Val Lys Glu Gly Gly Lys
        835                 840                 845

aag cag gct gag gca cag acc ggc atc acc ggc tcc cag aag ctt cca     2592
Lys Gln Ala Glu Ala Gln Thr Gly Ile Thr Gly Ser Gln Lys Leu Pro
    850                 855                 860

cac ggc ctt gag acc aac atc tcc cgt gaa gag ctc ctg gaa ctg gga     2640
His Gly Leu Glu Thr Asn Ile Ser Arg Glu Glu Leu Leu Glu Leu Gly
865                 870                 875                 880

cag gct ttc gcc aac acc cca gaa ggc ttc aac tac cac cca cgt gtg     2688
Gln Ala Phe Ala Asn Thr Pro Glu Gly Phe Asn Tyr His Pro Arg Val
                885                 890                 895

gct ccc gtt gct aag aag cgc gtc tcc tct gtc acc gaa ggt ggc atc     2736
Ala Pro Val Ala Lys Lys Arg Val Ser Ser Val Thr Glu Gly Gly Ile
            900                 905                 910

gac tgg gca tgg ggc gag ctc ctc gcc ttc ggt tcc ctg gct aac tcc     2784
Asp Trp Ala Trp Gly Glu Leu Leu Ala Phe Gly Ser Leu Ala Asn Ser
        915                 920                 925

ggc cgc ttg gtt cgc ctt gca ggt gaa gat tcc cgc cgc ggt acc ttc     2832
Gly Arg Leu Val Arg Leu Ala Gly Glu Asp Ser Arg Arg Gly Thr Phe
    930                 935                 940

acc cag cgc cac gca gtt gcc atc gac cca gcg acc gct gaa gag ttc     2880
Thr Gln Arg His Ala Val Ala Ile Asp Pro Ala Thr Ala Glu Glu Phe
945                 950                 955                 960

aac cca ctc cac gag ctt gca cag tcc aag ggc aac aac ggt aag ttc     2928
Asn Pro Leu His Glu Leu Ala Gln Ser Lys Gly Asn Asn Gly Lys Phe
                965                 970                 975

ctg gtc tac aac tcc gca ctg acc gag tac gca ggc atg ggc ttc gag     2976
Leu Val Tyr Asn Ser Ala Leu Thr Glu Tyr Ala Gly Met Gly Phe Glu
            980                 985                 990

tac ggc tac tcc gta gga aac gaa  gac tcc atc gtt gca  tgg gaa gca   3024
Tyr Gly Tyr Ser Val Gly Asn Glu  Asp Ser Ile Val Ala  Trp Glu Ala
        995                 1000                1005

cag ttc  ggc gac ttc gcc aac  ggc gct cag acc atc  atc gat gag     3069
Gln Phe  Gly Asp Phe Ala Asn  Gly Ala Gln Thr Ile  Ile Asp Glu
    1010                1015                1020

tac gtc  tcc tca ggc gaa gct  aag tgg ggc cag acc  tcc aag ctg     3114
Tyr Val  Ser Ser Gly Glu Ala  Lys Trp Gly Gln Thr  Ser Lys Leu
    1025                1030                1035

atc ctt  ctg ctg cct cac ggc  tac gaa ggc cag ggc  cca gac cac     3159
Ile Leu  Leu Leu Pro His Gly  Tyr Glu Gly Gln Gly  Pro Asp His
    1040                1045                1050

tct tcc  gca cgt atc gag cgc  ttc ctg cag ctg tgc  gct gag ggt     3204
Ser Ser  Ala Arg Ile Glu Arg  Phe Leu Gln Leu Cys  Ala Glu Gly
    1055                1060                1065

tcc atg  act gtt gct cag cca  tcc acc cca gca aac  cac ttc cac     3249
Ser Met  Thr Val Ala Gln Pro  Ser Thr Pro Ala Asn  His Phe His
    1070                1075                1080
```

```
cta ctg  cgt cgt cac gct ctg  tcc gac ctg aag cgt  cca ctg gtt      3294
Leu Leu  Arg Arg His Ala Leu  Ser Asp Leu Lys Arg  Pro Leu Val
    1085                 1090                 1095

atc ttc  acc ccg aag tcc atg  ctg cgt aac aag gct  gct gcc tcc      3339
Ile Phe  Thr Pro Lys Ser Met  Leu Arg Asn Lys Ala  Ala Ala Ser
    1100                 1105                 1110

gca cca  gaa gac ttc act gag  gtc acc aag ttc cag  tcc gtg atc      3384
Ala Pro  Glu Asp Phe Thr Glu  Val Thr Lys Phe Gln  Ser Val Ile
    1115                 1120                 1125

aac gat  cca aac gtt gca gat  gca gcc aag gtg aag  aag gtc atg      3429
Asn Asp  Pro Asn Val Ala Asp  Ala Ala Lys Val Lys  Lys Val Met
    1130                 1135                 1140

ctg gtc  tcc ggc aag ctg tac  tac gaa ttg gca aag  cgc aag gag      3474
Leu Val  Ser Gly Lys Leu Tyr  Tyr Glu Leu Ala Lys  Arg Lys Glu
    1145                 1150                 1155

aag gac  gga cgc gac gac atc  gcg atc gtt cgt atc  gaa atg ctc      3519
Lys Asp  Gly Arg Asp Asp Ile  Ala Ile Val Arg Ile  Glu Met Leu
    1160                 1165                 1170

cac cca  att ccg ttc aac cgc  atc tcc gag gct ctt  gcc ggc tac      3564
His Pro  Ile Pro Phe Asn Arg  Ile Ser Glu Ala Leu  Ala Gly Tyr
    1175                 1180                 1185

cct aac  gct gag gaa gtc ctc  ttc gtt cag gat gag  cca gca aac      3609
Pro Asn  Ala Glu Glu Val Leu  Phe Val Gln Asp Glu  Pro Ala Asn
    1190                 1195                 1200

cag ggc  cca tgg ccg ttc tac  cag gag cac ctc cca  gag ctg atc      3654
Gln Gly  Pro Trp Pro Phe Tyr  Gln Glu His Leu Pro  Glu Leu Ile
    1205                 1210                 1215

ccg aac  atg cca aag atg cgc  cgc gtt tcc cgc cgc  gct cag tcc      3699
Pro Asn  Met Pro Lys Met Arg  Arg Val Ser Arg Arg  Ala Gln Ser
    1220                 1225                 1230

tcc acc  gca act ggt gtt gcc  aag gtg cac cag ctg  gag gag aag      3744
Ser Thr  Ala Thr Gly Val Ala  Lys Val His Gln Leu  Glu Glu Lys
    1235                 1240                 1245

cag ctt  atc gac gag gct ttc  gag gct taa                          3774
Gln Leu  Ile Asp Glu Ala Phe  Glu Ala
    1250                 1255


<210> SEQ ID NO 49
<211> LENGTH: 1257
<212> TYPE: PRT
<213> ORGANISM: Corynebacterium glutamicum

<400> SEQUENCE: 49

Met Leu Gln Leu Gly Leu Arg His Asn Gln Pro Thr Thr Asn Val Thr
1               5                   10                  15

Val Asp Lys Thr Lys Leu Asn Lys Pro Ser Arg Ser Lys Glu Lys Arg
            20                  25                  30

Arg Val Pro Ala Val Ser Ser Ala Ser Thr Phe Gly Gln Asn Ala Trp
        35                  40                  45

Leu Val Asp Glu Met Phe Gln Gln Phe Gln Lys Asp Pro Lys Ser Val
    50                  55                  60

Asp Lys Glu Trp Arg Glu Leu Phe Glu Ala Gln Gly Gly Pro Asn Thr
65                  70                  75                  80

Thr Pro Ala Thr Thr Glu Ala Gln Pro Ser Ala Pro Lys Glu Ser Ala
                85                  90                  95

Lys Pro Ala Pro Lys Ala Ala Pro Ala Ala Lys Ala Ala Pro Arg Val
            100                 105                 110

Glu Thr Lys Pro Ala Asp Lys Thr Ala Pro Lys Ala Lys Glu Ser Ser
        115                 120                 125
```

```
Val Pro Gln Gln Pro Lys Leu Pro Glu Pro Gly Gln Thr Pro Ile Arg
    130                 135                 140

Gly Ile Phe Lys Ser Ile Ala Lys Asn Met Asp Ile Ser Leu Glu Ile
145                 150                 155                 160

Pro Thr Ala Thr Ser Val Arg Asp Met Pro Ala Arg Leu Met Phe Glu
                165                 170                 175

Asn Arg Ala Met Val Asn Asp Gln Leu Lys Arg Thr Arg Gly Gly Lys
            180                 185                 190

Ile Ser Phe Thr His Ile Ile Gly Tyr Ala Met Val Lys Ala Val Met
        195                 200                 205

Ala His Pro Asp Met Asn Asn Ser Tyr Asp Val Ile Asp Gly Lys Pro
    210                 215                 220

Thr Leu Ile Val Pro Glu His Ile Asn Leu Gly Leu Ala Ile Asp Leu
225                 230                 235                 240

Pro Gln Lys Asp Gly Ser Arg Ala Leu Val Val Ala Ala Ile Lys Glu
                245                 250                 255

Thr Glu Lys Met Asn Phe Ser Glu Phe Leu Ala Ala Tyr Glu Asp Ile
            260                 265                 270

Val Ala Arg Ser Arg Lys Gly Lys Leu Thr Met Asp Asp Tyr Gln Gly
        275                 280                 285

Val Thr Val Ser Leu Thr Asn Pro Gly Gly Ile Gly Thr Arg His Ser
    290                 295                 300

Val Pro Arg Leu Thr Lys Gly Gln Gly Thr Ile Ile Gly Val Gly Ser
305                 310                 315                 320

Met Asp Tyr Pro Ala Glu Phe Gln Gly Ala Ser Glu Asp Arg Leu Ala
                325                 330                 335

Glu Leu Gly Val Gly Lys Leu Val Thr Ile Thr Ser Thr Tyr Asp His
            340                 345                 350

Arg Val Ile Gln Gly Ala Val Ser Gly Glu Phe Leu Arg Thr Met Ser
        355                 360                 365

Arg Leu Leu Thr Asp Asp Ser Phe Trp Asp Glu Ile Phe Asp Ala Met
    370                 375                 380

Asn Val Pro Tyr Thr Pro Met Arg Trp Ala Gln Asp Val Pro Asn Thr
385                 390                 395                 400

Gly Val Asp Lys Asn Thr Arg Val Met Gln Leu Ile Glu Ala Tyr Arg
                405                 410                 415

Ser Arg Gly His Leu Ile Ala Asp Thr Asn Pro Leu Ser Trp Val Gln
            420                 425                 430

Pro Gly Met Pro Val Pro Asp His Arg Asp Leu Asp Ile Glu Thr His
        435                 440                 445

Asn Leu Thr Ile Trp Asp Leu Asp Arg Thr Phe Asn Val Gly Gly Phe
    450                 455                 460

Gly Gly Lys Glu Thr Met Thr Leu Arg Glu Val Leu Ser Arg Leu Arg
465                 470                 475                 480

Ala Ala Tyr Thr Leu Lys Val Gly Ser Glu Tyr Thr His Ile Leu Asp
                485                 490                 495

Arg Asp Glu Arg Thr Trp Leu Gln Asp Arg Leu Glu Ala Gly Met Pro
            500                 505                 510

Lys Pro Thr Gln Ala Glu Gln Lys Tyr Ile Leu Gln Lys Leu Asn Ala
        515                 520                 525

Ala Glu Ala Phe Glu Asn Phe Leu Gln Thr Lys Tyr Val Gly Gln Lys
    530                 535                 540

Arg Phe Ser Leu Glu Gly Ala Glu Ala Leu Ile Pro Leu Met Asp Ser
```

```
545                 550                 555                 560

Ala Ile Asp Thr Ala Ala Gly Gln Gly Leu Asp Glu Val Val Ile Gly
                565                 570                 575

Met Pro His Arg Gly Arg Leu Asn Val Leu Phe Asn Ile Val Gly Lys
            580                 585                 590

Pro Leu Ala Ser Ile Phe Asn Glu Phe Glu Gly Gln Met Glu Gln Gly
        595                 600                 605

Gln Ile Gly Gly Ser Gly Asp Val Lys Tyr His Leu Gly Ser Glu Gly
    610                 615                 620

Gln His Leu Gln Met Phe Gly Asp Gly Glu Ile Lys Val Ser Leu Thr
625                 630                 635                 640

Ala Asn Pro Ser His Leu Glu Ala Val Asn Pro Val Met Glu Gly Ile
                645                 650                 655

Val Arg Ala Lys Gln Asp Tyr Leu Asp Lys Gly Val Asp Gly Lys Thr
            660                 665                 670

Val Val Pro Leu Leu Leu His Gly Asp Ala Ala Phe Ala Gly Leu Gly
        675                 680                 685

Ile Val Pro Glu Thr Ile Asn Leu Ala Lys Leu Arg Gly Tyr Asp Val
    690                 695                 700

Gly Gly Thr Ile His Ile Val Val Asn Asn Gln Ile Gly Phe Thr Thr
705                 710                 715                 720

Thr Pro Asp Ser Ser Arg Ser Met His Tyr Ala Thr Asp Tyr Ala Lys
                725                 730                 735

Ala Phe Gly Cys Pro Val Phe His Val Asn Gly Asp Asp Pro Glu Ala
            740                 745                 750

Val Val Trp Val Gly Gln Leu Ala Thr Glu Tyr Arg Arg Arg Phe Gly
        755                 760                 765

Lys Asp Val Phe Ile Asp Leu Val Cys Tyr Arg Leu Arg Gly His Asn
    770                 775                 780

Glu Ala Asp Asp Pro Ser Met Thr Gln Pro Lys Met Tyr Glu Leu Ile
785                 790                 795                 800

Thr Gly Arg Glu Thr Val Arg Ala Gln Tyr Thr Glu Asp Leu Leu Gly
                805                 810                 815

Arg Gly Asp Leu Ser Asn Glu Asp Ala Glu Ala Val Val Arg Asp Phe
            820                 825                 830

His Asp Gln Met Glu Ser Val Phe Asn Glu Val Lys Glu Gly Gly Lys
        835                 840                 845

Lys Gln Ala Glu Ala Gln Thr Gly Ile Thr Gly Ser Gln Lys Leu Pro
    850                 855                 860

His Gly Leu Glu Thr Asn Ile Ser Arg Glu Glu Leu Leu Glu Leu Gly
865                 870                 875                 880

Gln Ala Phe Ala Asn Thr Pro Glu Gly Phe Asn Tyr His Pro Arg Val
                885                 890                 895

Ala Pro Val Ala Lys Lys Arg Val Ser Ser Val Thr Glu Gly Gly Ile
            900                 905                 910

Asp Trp Ala Trp Gly Glu Leu Leu Ala Phe Gly Ser Leu Ala Asn Ser
        915                 920                 925

Gly Arg Leu Val Arg Leu Ala Gly Glu Asp Ser Arg Arg Gly Thr Phe
    930                 935                 940

Thr Gln Arg His Ala Val Ala Ile Asp Pro Ala Thr Ala Glu Glu Phe
945                 950                 955                 960

Asn Pro Leu His Glu Leu Ala Gln Ser Lys Gly Asn Asn Gly Lys Phe
                965                 970                 975
```

-continued

```
Leu Val Tyr Asn Ser Ala Leu Thr Glu Tyr Ala Gly Met Gly Phe Glu
            980                 985                 990

Tyr Gly Tyr Ser Val Gly Asn Glu  Asp Ser Ile Val Ala  Trp Glu Ala
        995                 1000                 1005

Gln Phe  Gly Asp Phe Ala Asn  Gly Ala Gln Thr Ile  Ile Asp Glu
    1010                 1015                 1020

Tyr Val  Ser Ser Gly Glu Ala  Lys Trp Gly Gln Thr  Ser Lys Leu
    1025                 1030                 1035

Ile Leu  Leu Leu Pro His Gly  Tyr Glu Gly Gln Gly  Pro Asp His
    1040                 1045                 1050

Ser Ser  Ala Arg Ile Glu Arg  Phe Leu Gln Leu Cys  Ala Glu Gly
    1055                 1060                 1065

Ser Met  Thr Val Ala Gln Pro  Ser Thr Pro Ala Asn  His Phe His
    1070                 1075                 1080

Leu Leu  Arg Arg His Ala Leu  Ser Asp Leu Lys Arg  Pro Leu Val
    1085                 1090                 1095

Ile Phe  Thr Pro Lys Ser Met  Leu Arg Asn Lys Ala  Ala Ala Ser
    1100                 1105                 1110

Ala Pro  Glu Asp Phe Thr Glu  Val Thr Lys Phe Gln  Ser Val Ile
    1115                 1120                 1125

Asn Asp  Pro Asn Val Ala Asp  Ala Ala Lys Val Lys  Lys Val Met
    1130                 1135                 1140

Leu Val  Ser Gly Lys Leu Tyr  Tyr Glu Leu Ala Lys  Arg Lys Glu
    1145                 1150                 1155

Lys Asp  Gly Arg Asp Asp Ile  Ala Ile Val Arg Ile  Glu Met Leu
    1160                 1165                 1170

His Pro  Ile Pro Phe Asn Arg  Ile Ser Glu Ala Leu  Ala Gly Tyr
    1175                 1180                 1185

Pro Asn  Ala Glu Glu Val Leu  Phe Val Gln Asp Glu  Pro Ala Asn
    1190                 1195                 1200

Gln Gly  Pro Trp Pro Phe Tyr  Gln Glu His Leu Pro  Glu Leu Ile
    1205                 1210                 1215

Pro Asn  Met Pro Lys Met Arg  Arg Val Ser Arg Arg  Ala Gln Ser
    1220                 1225                 1230

Ser Thr  Ala Thr Gly Val Ala  Lys Val His Gln Leu  Glu Glu Lys
    1235                 1240                 1245

Gln Leu  Ile Asp Glu Ala Phe  Glu Ala
    1250                 1255
```

<210> SEQ ID NO 50
<211> LENGTH: 30
<212> TYPE: DNA
<213> ORGANISM: Artificial sequence
<220> FEATURE:
<223> OTHER INFORMATION: primer pfk50

<400> SEQUENCE: 50
acccgcaatt ttcgcagcct tagaacacct 30

<210> SEQ ID NO 51
<211> LENGTH: 49
<212> TYPE: DNA
<213> ORGANISM: Artificial sequence
<220> FEATURE:
<223> OTHER INFORMATION: primer pfk51

<400> SEQUENCE: 51
ctgttgataa aagcccgaaa aactaattaa acccatcaca acacccgcg 49

<210> SEQ ID NO 52
<211> LENGTH: 32
<212> TYPE: DNA
<213> ORGANISM: Artificial sequence
<220> FEATURE:
<223> OTHER INFORMATION: primer pfk52

<400> SEQUENCE: 52
agcttctgca gaatctcaaa cgcacgctta cc 32

<210> SEQ ID NO 53
<211> LENGTH: 49
<212> TYPE: DNA
<213> ORGANISM: Artificial sequence
<220> FEATURE:
<223> OTHER INFORMATION: primer pfk53

<400> SEQUENCE: 53
cgcgggtgtt gtgatgggtt taattagttt ttcgggcttt tatcaacag 49

<210> SEQ ID NO 54
<211> LENGTH: 40
<212> TYPE: DNA
<213> ORGANISM: Artificial sequence
<220> FEATURE:
<223> OTHER INFORMATION: primer pfk54

<400> SEQUENCE: 54
gcaaggatcc agggcaaggg gttctagaaa gaccaacgga 40

<210> SEQ ID NO 55
<211> LENGTH: 44
<212> TYPE: DNA
<213> ORGANISM: Artificial sequence
<220> FEATURE:
<223> OTHER INFORMATION: primer pfk55

<400> SEQUENCE: 55
ttctggatcc tctcaaacgc acgcttaccg atctcttgta cgtg 44

<210> SEQ ID NO 56
<211> LENGTH: 1041
<212> TYPE: DNA
<213> ORGANISM: Corynebacterium glutamicum
<220> FEATURE:
<221> NAME/KEY: CDS
<222> LOCATION: (1)..(1041)
<223> OTHER INFORMATION: pfk*1

<400> SEQUENCE: 56

```
atg gaa gac atg cga att gct act ctc acg tca ggc ggc gac tgc ccc       48
Met Glu Asp Met Arg Ile Ala Thr Leu Thr Ser Gly Gly Asp Cys Pro
1               5                   10                  15

gga cta aat gcc gtc atc cga gga atc gtc cgc aca gcc agc aat gaa       96
Gly Leu Asn Ala Val Ile Arg Gly Ile Val Arg Thr Ala Ser Asn Glu
            20                  25                  30

ttt ggc tcc acc gtc gtt ggt tat caa gac ggt tgg gaa gga ctg tta      144
Phe Gly Ser Thr Val Val Gly Tyr Gln Asp Gly Trp Glu Gly Leu Leu
        35                  40                  45

gcc gat cgt cgc gta cag ctg tat gac gat gaa gat att gac cga atc      192
Ala Asp Arg Arg Val Gln Leu Tyr Asp Asp Glu Asp Ile Asp Arg Ile
    50                  55                  60

ctc ctt cga ggc ggc acc att ttg ggc act ggt cgc ctc cat ccg gac      240
Leu Leu Arg Gly Gly Thr Ile Leu Gly Thr Gly Arg Leu His Pro Asp
65                  70                  75                  80
```

```
aag ttt aag gcc gga att gat cag att aag gcc aac tta gaa gac gcc      288
Lys Phe Lys Ala Gly Ile Asp Gln Ile Lys Ala Asn Leu Glu Asp Ala
                85                  90                  95

ggc atc gat gcc ctt atc cca atc ggt ggc gaa gga acc ctg aag ggt      336
Gly Ile Asp Ala Leu Ile Pro Ile Gly Gly Glu Gly Thr Leu Lys Gly
            100                 105                 110

gcc aag tgg ctg tct gat aac ggt atc cct gtt gtc ggt gtc cca aag      384
Ala Lys Trp Leu Ser Asp Asn Gly Ile Pro Val Val Gly Val Pro Lys
        115                 120                 125

acc att gac aat gac gtg aat ggc act gac ttc acc ttc ggt ttc gat      432
Thr Ile Asp Asn Asp Val Asn Gly Thr Asp Phe Thr Phe Gly Phe Asp
    130                 135                 140

act gct gtg gca gtg gct acc gac gct gtt gac cgc ctg cac acc acc      480
Thr Ala Val Ala Val Ala Thr Asp Ala Val Asp Arg Leu His Thr Thr
145                 150                 155                 160

gct gaa tct cac aac cgt gtg atg atc gtg aag gtc atg ggc cgc cac      528
Ala Glu Ser His Asn Arg Val Met Ile Val Lys Val Met Gly Arg His
                165                 170                 175

gtg ggt tgg att gct ctg cac gca ggt atg gcg ggc ggt gct cac tac      576
Val Gly Trp Ile Ala Leu His Ala Gly Met Ala Gly Gly Ala His Tyr
            180                 185                 190

acc gtt att cca gaa gta cct ttc gat att gca gag atc tgc aag gcg      624
Thr Val Ile Pro Glu Val Pro Phe Asp Ile Ala Glu Ile Cys Lys Ala
        195                 200                 205

atg gaa cgt cgc ttc cag atg ggc gag aag tac ggc att atc gtc gtt      672
Met Glu Arg Arg Phe Gln Met Gly Glu Lys Tyr Gly Ile Ile Val Val
    210                 215                 220

gcg gaa ggt gcg ttg cca cgc gaa ggc acc atg gag ctt cgt gaa ggc      720
Ala Glu Gly Ala Leu Pro Arg Glu Gly Thr Met Glu Leu Arg Glu Gly
225                 230                 235                 240

cac att gac cag ttc ggt cac aag acc ttc acg gga att gga cag cag      768
His Ile Asp Gln Phe Gly His Lys Thr Phe Thr Gly Ile Gly Gln Gln
                245                 250                 255

atc gct gat gag atc cac gtg cgc ctc ggc cac gat gtt cgt acg acc      816
Ile Ala Asp Glu Ile His Val Arg Leu Gly His Asp Val Arg Thr Thr
            260                 265                 270

gtt ctt ggc cac att caa cgt ggt gga acc cca act gct ttc gac cgt      864
Val Leu Gly His Ile Gln Arg Gly Gly Thr Pro Thr Ala Phe Asp Arg
        275                 280                 285

gtt ctg gcc act cgt tat ggt gtt cgt gca gct cgt gcg tgc cat gag      912
Val Leu Ala Thr Arg Tyr Gly Val Arg Ala Ala Arg Ala Cys His Glu
    290                 295                 300

gga agc ttt gac aag gtt gtt gct ttg aag ggt gag agc att gag atg      960
Gly Ser Phe Asp Lys Val Val Ala Leu Lys Gly Glu Ser Ile Glu Met
305                 310                 315                 320

atc acc ttt gaa gaa gcc gtc gga acc ttg aag gaa gtc cca ttc gaa     1008
Ile Thr Phe Glu Glu Ala Val Gly Thr Leu Lys Glu Val Pro Phe Glu
                325                 330                 335

cgc tgg gtt act gcc cag gca atg ttt gga tag                         1041
Arg Trp Val Thr Ala Gln Ala Met Phe Gly
            340                 345
```

<210> SEQ ID NO 57
<211> LENGTH: 346
<212> TYPE: PRT
<213> ORGANISM: Corynebacterium glutamicum

<400> SEQUENCE: 57

```
Met Glu Asp Met Arg Ile Ala Thr Leu Thr Ser Gly Gly Asp Cys Pro
1               5                   10                  15
```

-continued

```
Gly Leu Asn Ala Val Ile Arg Gly Ile Val Arg Thr Ala Ser Asn Glu
            20                  25                  30

Phe Gly Ser Thr Val Val Gly Tyr Gln Asp Gly Trp Glu Gly Leu Leu
        35                  40                  45

Ala Asp Arg Arg Val Gln Leu Tyr Asp Asp Glu Asp Ile Asp Arg Ile
    50                  55                  60

Leu Leu Arg Gly Gly Thr Ile Leu Gly Thr Gly Arg Leu His Pro Asp
65                  70                  75                  80

Lys Phe Lys Ala Gly Ile Asp Gln Ile Lys Ala Asn Leu Glu Asp Ala
                85                  90                  95

Gly Ile Asp Ala Leu Ile Pro Ile Gly Gly Glu Gly Thr Leu Lys Gly
            100                 105                 110

Ala Lys Trp Leu Ser Asp Asn Gly Ile Pro Val Val Gly Val Pro Lys
        115                 120                 125

Thr Ile Asp Asn Asp Val Asn Gly Thr Asp Phe Thr Phe Gly Phe Asp
    130                 135                 140

Thr Ala Val Ala Val Ala Thr Asp Ala Val Asp Arg Leu His Thr Thr
145                 150                 155                 160

Ala Glu Ser His Asn Arg Val Met Ile Val Lys Val Met Gly Arg His
                165                 170                 175

Val Gly Trp Ile Ala Leu His Ala Gly Met Ala Gly Gly Ala His Tyr
            180                 185                 190

Thr Val Ile Pro Glu Val Pro Phe Asp Ile Ala Glu Ile Cys Lys Ala
        195                 200                 205

Met Glu Arg Arg Phe Gln Met Gly Glu Lys Tyr Gly Ile Ile Val Val
    210                 215                 220

Ala Glu Gly Ala Leu Pro Arg Glu Gly Thr Met Glu Leu Arg Glu Gly
225                 230                 235                 240

His Ile Asp Gln Phe Gly His Lys Thr Phe Thr Gly Ile Gly Gln Gln
                245                 250                 255

Ile Ala Asp Glu Ile His Val Arg Leu Gly His Asp Val Arg Thr Thr
            260                 265                 270

Val Leu Gly His Ile Gln Arg Gly Gly Thr Pro Thr Ala Phe Asp Arg
        275                 280                 285

Val Leu Ala Thr Arg Tyr Gly Val Arg Ala Ala Arg Ala Cys His Glu
    290                 295                 300

Gly Ser Phe Asp Lys Val Val Ala Leu Lys Gly Glu Ser Ile Glu Met
305                 310                 315                 320

Ile Thr Phe Glu Glu Ala Val Gly Thr Leu Lys Glu Val Pro Phe Glu
                325                 330                 335

Arg Trp Val Thr Ala Gln Ala Met Phe Gly
            340                 345


<210> SEQ ID NO 58
<211> LENGTH: 1041
<212> TYPE: DNA
<213> ORGANISM: Corynebacterium glutamicum
<220> FEATURE:
<221> NAME/KEY: CDS
<222> LOCATION: (1)..(1041)
<223> OTHER INFORMATION: pfk*2

<400> SEQUENCE: 58

atg gaa gac atg cga att gct act ctc acg tca ggc ggc gac tgc ccc       48
Met Glu Asp Met Arg Ile Ala Thr Leu Thr Ser Gly Gly Asp Cys Pro
1               5                   10                  15

gga cta aat gcc gtc atc cga gga atc gtc cgc aca gcc agc aat gaa       96
```

-continued

```
Gly Leu Asn Ala Val Ile Arg Gly Ile Val Arg Thr Ala Ser Asn Glu
            20                  25                  30

ttt ggc tcc acc gtc gtt ggt tat caa gac ggt tgg gaa gga ctg tta      144
Phe Gly Ser Thr Val Val Gly Tyr Gln Asp Gly Trp Glu Gly Leu Leu
        35                  40                  45

gcc gat cgt cgc gta cag ctg tat gac gat gaa gat att gac cga atc      192
Ala Asp Arg Arg Val Gln Leu Tyr Asp Asp Glu Asp Ile Asp Arg Ile
    50                  55                  60

ctc ctt cga ggc ggc acc att ttg ggc act ggt cgc ctc cat ccg gac      240
Leu Leu Arg Gly Gly Thr Ile Leu Gly Thr Gly Arg Leu His Pro Asp
65                  70                  75                  80

aag ttt aag gcc gga att gat cag att aag gcc aac tta gaa gac gcc      288
Lys Phe Lys Ala Gly Ile Asp Gln Ile Lys Ala Asn Leu Glu Asp Ala
                85                  90                  95

ggc atc gat gcc ctt atc cca atc ggt ggc gaa gga acc ctg aag ggt      336
Gly Ile Asp Ala Leu Ile Pro Ile Gly Gly Glu Gly Thr Leu Lys Gly
            100                 105                 110

gcc aag tgg ctg tct gat aac ggt atc cct gtt gtc ggt gtc cca aag      384
Ala Lys Trp Leu Ser Asp Asn Gly Ile Pro Val Val Gly Val Pro Lys
        115                 120                 125

acc att gac aat gac gtg aat ggc act gac ttc acc ttc ggt ttc gat      432
Thr Ile Asp Asn Asp Val Asn Gly Thr Asp Phe Thr Phe Gly Phe Asp
    130                 135                 140

act gct gtg gca gtg gct acc gac gct gtt gac cgc ctg cac acc acc      480
Thr Ala Val Ala Val Ala Thr Asp Ala Val Asp Arg Leu His Thr Thr
145                 150                 155                 160

gct gaa tct cac aac cgt gtg atg atc gtg agg gtc atg ggc cgc cac      528
Ala Glu Ser His Asn Arg Val Met Ile Val Arg Val Met Gly Arg His
                165                 170                 175

gtg ggt tgg att gct ctg cac gca ggt atg gcg ggc ggt gct cac tac      576
Val Gly Trp Ile Ala Leu His Ala Gly Met Ala Gly Gly Ala His Tyr
            180                 185                 190

acc gtt att cca gaa gta cct ttc gat att gca gag atc tgc aag gcg      624
Thr Val Ile Pro Glu Val Pro Phe Asp Ile Ala Glu Ile Cys Lys Ala
        195                 200                 205

atg gaa cgt cgc ttc cag atg ggc gag aag tac ggc att atc gtc gtt      672
Met Glu Arg Arg Phe Gln Met Gly Glu Lys Tyr Gly Ile Ile Val Val
    210                 215                 220

gcg gaa ggt gcg ttg cca cgc gaa ggc acc atg gag ctt cgt gaa ggc      720
Ala Glu Gly Ala Leu Pro Arg Glu Gly Thr Met Glu Leu Arg Glu Gly
225                 230                 235                 240

cac att gac cag ttc ggt cac aag acc ttc acg gga att gga cag cag      768
His Ile Asp Gln Phe Gly His Lys Thr Phe Thr Gly Ile Gly Gln Gln
                245                 250                 255

atc gct gat gag atc cac gtg cgc ctc ggc cac gat gtt cgt acg acc      816
Ile Ala Asp Glu Ile His Val Arg Leu Gly His Asp Val Arg Thr Thr
            260                 265                 270

gtt ctt ggc cac att caa cgt ggt gga acc cca act gct ttc gac cgt      864
Val Leu Gly His Ile Gln Arg Gly Gly Thr Pro Thr Ala Phe Asp Arg
        275                 280                 285

gtt ctg gcc act cgt tat ggt gtt cgt gca gct cgt gcg tgc cat gag      912
Val Leu Ala Thr Arg Tyr Gly Val Arg Ala Ala Arg Ala Cys His Glu
    290                 295                 300

gga agc ttt gac aag gtt gtt gct ttg aag ggt gag agc att gag atg      960
Gly Ser Phe Asp Lys Val Val Ala Leu Lys Gly Glu Ser Ile Glu Met
305                 310                 315                 320

atc acc ttt gaa gaa gcc gtc gga acc ttg aag gaa gtc cca ttc gaa     1008
Ile Thr Phe Glu Glu Ala Val Gly Thr Leu Lys Glu Val Pro Phe Glu
                325                 330                 335

cgc tgg gtt act gcc cag gca atg ttt gga tag                         1041
```

-continued

```
Arg Trp Val Thr Ala Gln Ala Met Phe Gly
            340                 345


<210> SEQ ID NO 59
<211> LENGTH: 346
<212> TYPE: PRT
<213> ORGANISM: Corynebacterium glutamicum

<400> SEQUENCE: 59

Met Glu Asp Met Arg Ile Ala Thr Leu Thr Ser Gly Gly Asp Cys Pro
1               5                   10                  15

Gly Leu Asn Ala Val Ile Arg Gly Ile Val Arg Thr Ala Ser Asn Glu
            20                  25                  30

Phe Gly Ser Thr Val Val Gly Tyr Gln Asp Gly Trp Glu Gly Leu Leu
        35                  40                  45

Ala Asp Arg Arg Val Gln Leu Tyr Asp Asp Glu Asp Ile Asp Arg Ile
    50                  55                  60

Leu Leu Arg Gly Gly Thr Ile Leu Gly Thr Gly Arg Leu His Pro Asp
65                  70                  75                  80

Lys Phe Lys Ala Gly Ile Asp Gln Ile Lys Ala Asn Leu Glu Asp Ala
                85                  90                  95

Gly Ile Asp Ala Leu Ile Pro Ile Gly Gly Glu Gly Thr Leu Lys Gly
            100                 105                 110

Ala Lys Trp Leu Ser Asp Asn Gly Ile Pro Val Val Gly Val Pro Lys
        115                 120                 125

Thr Ile Asp Asn Asp Val Asn Gly Thr Asp Phe Thr Phe Gly Phe Asp
    130                 135                 140

Thr Ala Val Ala Val Ala Thr Asp Ala Val Asp Arg Leu His Thr Thr
145                 150                 155                 160

Ala Glu Ser His Asn Arg Val Met Ile Val Arg Val Met Gly Arg His
                165                 170                 175

Val Gly Trp Ile Ala Leu His Ala Gly Met Ala Gly Gly Ala His Tyr
            180                 185                 190

Thr Val Ile Pro Glu Val Pro Phe Asp Ile Ala Glu Ile Cys Lys Ala
        195                 200                 205

Met Glu Arg Arg Phe Gln Met Gly Glu Lys Tyr Gly Ile Ile Val Val
    210                 215                 220

Ala Glu Gly Ala Leu Pro Arg Glu Gly Thr Met Glu Leu Arg Glu Gly
225                 230                 235                 240

His Ile Asp Gln Phe Gly His Lys Thr Phe Thr Gly Ile Gly Gln Gln
                245                 250                 255

Ile Ala Asp Glu Ile His Val Arg Leu Gly His Asp Val Arg Thr Thr
            260                 265                 270

Val Leu Gly His Ile Gln Arg Gly Gly Thr Pro Thr Ala Phe Asp Arg
        275                 280                 285

Val Leu Ala Thr Arg Tyr Gly Val Arg Ala Ala Arg Ala Cys His Glu
    290                 295                 300

Gly Ser Phe Asp Lys Val Val Ala Leu Lys Gly Glu Ser Ile Glu Met
305                 310                 315                 320

Ile Thr Phe Glu Glu Ala Val Gly Thr Leu Lys Glu Val Pro Phe Glu
                325                 330                 335

Arg Trp Val Thr Ala Gln Ala Met Phe Gly
            340                 345


<210> SEQ ID NO 60
<211> LENGTH: 1041
```

```
<212> TYPE: DNA
<213> ORGANISM: Corynebacterium glutamicum
<220> FEATURE:
<221> NAME/KEY: CDS
<222> LOCATION: (1)..(1041)
<223> OTHER INFORMATION: pfk

<400> SEQUENCE: 60

atg gaa gac atg cga att gct act ctc acg tca ggc ggc gac tgc ccc       48
Met Glu Asp Met Arg Ile Ala Thr Leu Thr Ser Gly Gly Asp Cys Pro
1               5                   10                  15

gga cta aat gcc gtc atc cga gga atc gtc cgc aca gcc agc aat gaa       96
Gly Leu Asn Ala Val Ile Arg Gly Ile Val Arg Thr Ala Ser Asn Glu
            20                  25                  30

ttt ggc tcc acc gtc gtt ggt tat caa gac ggt tgg gaa gga ctg tta      144
Phe Gly Ser Thr Val Val Gly Tyr Gln Asp Gly Trp Glu Gly Leu Leu
        35                  40                  45

gcc gat cgt cgc gta cag ctg tat gac gat gaa gat att gac cga atc      192
Ala Asp Arg Arg Val Gln Leu Tyr Asp Asp Glu Asp Ile Asp Arg Ile
    50                  55                  60

ctc ctt cga ggc ggc acc att ttg ggc act ggt cgc ctc cat ccg gac      240
Leu Leu Arg Gly Gly Thr Ile Leu Gly Thr Gly Arg Leu His Pro Asp
65                  70                  75                  80

aag ttt aag gcc gga att gat cag att aag gcc aac tta gaa gac gcc      288
Lys Phe Lys Ala Gly Ile Asp Gln Ile Lys Ala Asn Leu Glu Asp Ala
                85                  90                  95

ggc atc gat gcc ctt atc cca atc ggt ggc gaa gga acc ctg aag ggt      336
Gly Ile Asp Ala Leu Ile Pro Ile Gly Gly Glu Gly Thr Leu Lys Gly
            100                 105                 110

gcc aag tgg ctg tct gat aac ggt atc cct gtt gtc ggt gtc cca aag      384
Ala Lys Trp Leu Ser Asp Asn Gly Ile Pro Val Val Gly Val Pro Lys
        115                 120                 125

acc att gac aat gac gtg aat ggc act gac ttc acc ttc ggt ttc gat      432
Thr Ile Asp Asn Asp Val Asn Gly Thr Asp Phe Thr Phe Gly Phe Asp
    130                 135                 140

act gct gtg gca gtg gct acc gac gct gtt gac cgc ctg cac acc acc      480
Thr Ala Val Ala Val Ala Thr Asp Ala Val Asp Arg Leu His Thr Thr
145                 150                 155                 160

gct gaa tct cac aac cgt gtg atg atc gtg gag gtc atg ggc cgc cac      528
Ala Glu Ser His Asn Arg Val Met Ile Val Glu Val Met Gly Arg His
                165                 170                 175

gtg ggt tgg att gct ctg cac gca ggt atg gcg ggc ggt gct cac tac      576
Val Gly Trp Ile Ala Leu His Ala Gly Met Ala Gly Gly Ala His Tyr
            180                 185                 190

acc gtt att cca gaa gta cct ttc gat att gca gag atc tgc aag gcg      624
Thr Val Ile Pro Glu Val Pro Phe Asp Ile Ala Glu Ile Cys Lys Ala
        195                 200                 205

atg gaa cgt cgc ttc cag atg ggc gag aag tac ggc att atc gtc gtt      672
Met Glu Arg Arg Phe Gln Met Gly Glu Lys Tyr Gly Ile Ile Val Val
    210                 215                 220

gcg gaa ggt gcg ttg cca cgc gaa ggc acc atg gag ctt cgt gaa ggc      720
Ala Glu Gly Ala Leu Pro Arg Glu Gly Thr Met Glu Leu Arg Glu Gly
225                 230                 235                 240

cac att gac cag ttc ggt cac aag acc ttc acg gga att gga cag cag      768
His Ile Asp Gln Phe Gly His Lys Thr Phe Thr Gly Ile Gly Gln Gln
                245                 250                 255

atc gct gat gag atc cac gtg cgc ctc ggc cac gat gtt cgt acg acc      816
Ile Ala Asp Glu Ile His Val Arg Leu Gly His Asp Val Arg Thr Thr
            260                 265                 270

gtt ctt ggc cac att caa cgt ggt gga acc cca act gct ttc gac cgt      864
Val Leu Gly His Ile Gln Arg Gly Gly Thr Pro Thr Ala Phe Asp Arg
        275                 280                 285
```

```
gtt ctg gcc act cgt tat ggt gtt cgt gca gct cgt gcg tgc cat gag      912
Val Leu Ala Thr Arg Tyr Gly Val Arg Ala Ala Arg Ala Cys His Glu
    290                 295                 300

gga agc ttt gac aag gtt gtt gct ttg aag ggt gag agc att gag atg      960
Gly Ser Phe Asp Lys Val Val Ala Leu Lys Gly Glu Ser Ile Glu Met
305                 310                 315                 320

atc acc ttt gaa gaa gcc gtc gga acc ttg aag gaa gtc cca ttc gaa     1008
Ile Thr Phe Glu Glu Ala Val Gly Thr Leu Lys Glu Val Pro Phe Glu
                325                 330                 335

cgc tgg gtt act gcc cag gca atg ttt gga tag                         1041
Arg Trp Val Thr Ala Gln Ala Met Phe Gly
            340                 345


<210> SEQ ID NO 61
<211> LENGTH: 346
<212> TYPE: PRT
<213> ORGANISM: Corynebacterium glutamicum

<400> SEQUENCE: 61

Met Glu Asp Met Arg Ile Ala Thr Leu Thr Ser Gly Gly Asp Cys Pro
1               5                   10                  15

Gly Leu Asn Ala Val Ile Arg Gly Ile Val Arg Thr Ala Ser Asn Glu
            20                  25                  30

Phe Gly Ser Thr Val Val Gly Tyr Gln Asp Gly Trp Glu Gly Leu Leu
        35                  40                  45

Ala Asp Arg Arg Val Gln Leu Tyr Asp Asp Glu Asp Ile Asp Arg Ile
    50                  55                  60

Leu Leu Arg Gly Gly Thr Ile Leu Gly Thr Gly Arg Leu His Pro Asp
65                  70                  75                  80

Lys Phe Lys Ala Gly Ile Asp Gln Ile Lys Ala Asn Leu Glu Asp Ala
                85                  90                  95

Gly Ile Asp Ala Leu Ile Pro Ile Gly Gly Glu Gly Thr Leu Lys Gly
            100                 105                 110

Ala Lys Trp Leu Ser Asp Asn Gly Ile Pro Val Val Gly Val Pro Lys
        115                 120                 125

Thr Ile Asp Asn Asp Val Asn Gly Thr Asp Phe Thr Phe Gly Phe Asp
    130                 135                 140

Thr Ala Val Ala Val Ala Thr Asp Ala Val Asp Arg Leu His Thr Thr
145                 150                 155                 160

Ala Glu Ser His Asn Arg Val Met Ile Val Glu Val Met Gly Arg His
                165                 170                 175

Val Gly Trp Ile Ala Leu His Ala Gly Met Ala Gly Gly Ala His Tyr
            180                 185                 190

Thr Val Ile Pro Glu Val Pro Phe Asp Ile Ala Glu Ile Cys Lys Ala
        195                 200                 205

Met Glu Arg Arg Phe Gln Met Gly Glu Lys Tyr Gly Ile Ile Val Val
    210                 215                 220

Ala Glu Gly Ala Leu Pro Arg Glu Gly Thr Met Glu Leu Arg Glu Gly
225                 230                 235                 240

His Ile Asp Gln Phe Gly His Lys Thr Phe Thr Gly Ile Gly Gln Gln
                245                 250                 255

Ile Ala Asp Glu Ile His Val Arg Leu Gly His Asp Val Arg Thr Thr
            260                 265                 270

Val Leu Gly His Ile Gln Arg Gly Gly Thr Pro Thr Ala Phe Asp Arg
        275                 280                 285

Val Leu Ala Thr Arg Tyr Gly Val Arg Ala Ala Arg Ala Cys His Glu
```

-continued 290 295 300

Gly Ser Phe Asp Lys Val Val Ala Leu Lys Gly Glu Ser Ile Glu Met
305 310 315 320

Ile Thr Phe Glu Glu Ala Val Gly Thr Leu Lys Glu Val Pro Phe Glu
325 330 335

Arg Trp Val Thr Ala Gln Ala Met Phe Gly
340 345

<210> SEQ ID NO 62
<211> LENGTH: 2412
<212> TYPE: DNA
<213> ORGANISM: Lactobacillus plantarum
<220> FEATURE:
<221> NAME/KEY: CDS
<222> LOCATION: (1)..(2412)
<223> OTHER INFORMATION: xpk

<400> SEQUENCE: 62 ttg caa agg agt tgc aaa ata atg agt gaa gca att aaa tcc aaa aca 48
Leu Gln Arg Ser Cys Lys Ile Met Ser Glu Ala Ile Lys Ser Lys Thr
1 5 10 15 gtt gat tac tct tct gat gaa tat cta aaa cgc gtt gat gaa tat tgg 96
Val Asp Tyr Ser Ser Asp Glu Tyr Leu Lys Arg Val Asp Glu Tyr Trp
20 25 30 cgt gct gct aac tac atc tca gtt ggt caa ctc tat cta cta aat aac 144
Arg Ala Ala Asn Tyr Ile Ser Val Gly Gln Leu Tyr Leu Leu Asn Asn
35 40 45 ccg tta ctt cgg gaa cca cta aag gcg acc gac gtg aaa gtt cat cca 192
Pro Leu Leu Arg Glu Pro Leu Lys Ala Thr Asp Val Lys Val His Pro
50 55 60 atc ggc cat tgg ggc acg att gct ggt caa aac ttt att tat gcc cat 240
Ile Gly His Trp Gly Thr Ile Ala Gly Gln Asn Phe Ile Tyr Ala His
65 70 75 80 tta aac cgg gca atc aat aag tat ggc ttg aac atg ttc tac att gaa 288
Leu Asn Arg Ala Ile Asn Lys Tyr Gly Leu Asn Met Phe Tyr Ile Glu
85 90 95 ggc cct ggt cat ggt ggt caa gta atg gtt tct aac tcc tac tta gat 336
Gly Pro Gly His Gly Gly Gln Val Met Val Ser Asn Ser Tyr Leu Asp
100 105 110 ggc acc tat acg gaa acg tat cct aaa atc acc caa gac aaa gct ggg 384
Gly Thr Tyr Thr Glu Thr Tyr Pro Lys Ile Thr Gln Asp Lys Ala Gly
115 120 125 atg aaa cgc tta ttc aag caa ttc tca ttc cca ggc ggg gtt gct tcc 432
Met Lys Arg Leu Phe Lys Gln Phe Ser Phe Pro Gly Gly Val Ala Ser
130 135 140 cat gcc gat cct aag acg cct ggt tcg atc cat gaa ggt ggc gaa ctt 480
His Ala Asp Pro Lys Thr Pro Gly Ser Ile His Glu Gly Gly Glu Leu
145 150 155 160 ggc tac tca atc ctg cat ggt gct ggt gca gta tta gat aat cca ggt 528
Gly Tyr Ser Ile Leu His Gly Ala Gly Ala Val Leu Asp Asn Pro Gly
165 170 175 tta att gcc gct acc gtt gtt ggt gat ggt gaa tct gaa act ggg cca 576
Leu Ile Ala Ala Thr Val Val Gly Asp Gly Glu Ser Glu Thr Gly Pro
180 185 190 ttg gca act tct tgg caa gtt aac aag ttc ctt aac cca att aca gac 624
Leu Ala Thr Ser Trp Gln Val Asn Lys Phe Leu Asn Pro Ile Thr Asp
195 200 205 ggg aca gtc ttg cca atc ttg aac tta aac ggc ttc aag att tct aat 672
Gly Thr Val Leu Pro Ile Leu Asn Leu Asn Gly Phe Lys Ile Ser Asn
210 215 220 cca aca gtt ctt tca cgt gaa tca cat gaa gaa ctt gaa gac tac ttt 720

```
Pro Thr Val Leu Ser Arg Glu Ser His Glu Glu Leu Glu Asp Tyr Phe
225                 230                 235                 240

aaa ggt cta ggc tgg gat cca cac ttt gtt gaa ggt aca gac cct gcc      768
Lys Gly Leu Gly Trp Asp Pro His Phe Val Glu Gly Thr Asp Pro Ala
                245                 250                 255

aag atg cac aaa att atg gct gaa gaa ttg gat aaa gtc att gaa gaa      816
Lys Met His Lys Ile Met Ala Glu Glu Leu Asp Lys Val Ile Glu Glu
            260                 265                 270

atc cac gca att cgt aag aac gcc aag gat aac aat gat gaa tct cgt      864
Ile His Ala Ile Arg Lys Asn Ala Lys Asp Asn Asn Asp Glu Ser Arg
        275                 280                 285

cct aag tgg cca atg att gtt ttc cgg gca cct aag ggc tgg acc ggt      912
Pro Lys Trp Pro Met Ile Val Phe Arg Ala Pro Lys Gly Trp Thr Gly
    290                 295                 300

cct aag agt tgg gac ggc gaa cca att gaa ggt tca ttc cgg gct cac      960
Pro Lys Ser Trp Asp Gly Glu Pro Ile Glu Gly Ser Phe Arg Ala His
305                 310                 315                 320

caa att cca att cct gtc gat cgc aat cac atg gaa cac gcc gac aaa     1008
Gln Ile Pro Ile Pro Val Asp Arg Asn His Met Glu His Ala Asp Lys
                325                 330                 335

tta gtt gac tgg ctc aaa tca tac aaa cca gaa gaa tta ttt gat gaa     1056
Leu Val Asp Trp Leu Lys Ser Tyr Lys Pro Glu Glu Leu Phe Asp Glu
            340                 345                 350

aat ggt act tta aaa cca gaa att gcc gca atc atc cct gaa ggc caa     1104
Asn Gly Thr Leu Lys Pro Glu Ile Ala Ala Ile Ile Pro Glu Gly Gln
        355                 360                 365

gct cgt atg gct gct aac ccc gtt act aac ggc ggt aag tta act aaa     1152
Ala Arg Met Ala Ala Asn Pro Val Thr Asn Gly Gly Lys Leu Thr Lys
    370                 375                 380

gac tta att aca cca aat atc gat gat tat gct ttg gac aac aag agt     1200
Asp Leu Ile Thr Pro Asn Ile Asp Asp Tyr Ala Leu Asp Asn Lys Ser
385                 390                 395                 400

cac ggt aag gaa gac ggt tca gac atg act gaa ctt ggt aag tat atc     1248
His Gly Lys Glu Asp Gly Ser Asp Met Thr Glu Leu Gly Lys Tyr Ile
                405                 410                 415

cgt gat tta att gag ttg aac aaa gac aac aag aac ttc cgt ggc tgg     1296
Arg Asp Leu Ile Glu Leu Asn Lys Asp Asn Lys Asn Phe Arg Gly Trp
            420                 425                 430

ggt cct gac gaa acc tta tct aac aaa cta ggc gct gct ttt gaa gat     1344
Gly Pro Asp Glu Thr Leu Ser Asn Lys Leu Gly Ala Ala Phe Glu Asp
        435                 440                 445

acc aaa cgt cag tgg atg gaa cca atc cac gaa cct aat gat gct ttg     1392
Thr Lys Arg Gln Trp Met Glu Pro Ile His Glu Pro Asn Asp Ala Leu
    450                 455                 460

tta gca cct caa ggc cgg att att gac tcc atg ttg tca gaa cac atg     1440
Leu Ala Pro Gln Gly Arg Ile Ile Asp Ser Met Leu Ser Glu His Met
465                 470                 475                 480

gat gaa ggg atg ttg gaa gct tac aat tta acc gga cgt tac ggt ttc     1488
Asp Glu Gly Met Leu Glu Ala Tyr Asn Leu Thr Gly Arg Tyr Gly Phe
                485                 490                 495

ttc gca agt tat gaa tca ttc ctg cgc gtt gtg gat tca atg tta acc     1536
Phe Ala Ser Tyr Glu Ser Phe Leu Arg Val Val Asp Ser Met Leu Thr
            500                 505                 510

caa cac ttc aag tgg tta cgg aat tct cac gaa gaa acc cct tgg cgg     1584
Gln His Phe Lys Trp Leu Arg Asn Ser His Glu Glu Thr Pro Trp Arg
        515                 520                 525

gct gat gta cct tca ctg aat gtg att gca tca tca aca gcc ttc caa     1632
Ala Asp Val Pro Ser Leu Asn Val Ile Ala Ser Ser Thr Ala Phe Gln
    530                 535                 540

caa gat cac aat ggt tac tct cac caa gat cca ggt atc att tca cac     1680
```

```
Gln Asp His Asn Gly Tyr Ser His Gln Asp Pro Gly Ile Ile Ser His
545                 550                 555                 560

ttg gct gaa aag aag acc gaa tac gtt cgt gcc tat ctt cca ggt gat     1728
Leu Ala Glu Lys Lys Thr Glu Tyr Val Arg Ala Tyr Leu Pro Gly Asp
                565                 570                 575

gcc aat act ttg att gca acc ttt gat aag gct atc caa agc aaa caa     1776
Ala Asn Thr Leu Ile Ala Thr Phe Asp Lys Ala Ile Gln Ser Lys Gln
            580                 585                 590

ttg att aat tta atc att gcc agc aag cac cct cgt cca caa tgg ttc     1824
Leu Ile Asn Leu Ile Ile Ala Ser Lys His Pro Arg Pro Gln Trp Phe
        595                 600                 605

aca atg gac gaa gct aag cgc tta gtt cgt gat ggc ctt ggt gtt gtt     1872
Thr Met Asp Glu Ala Lys Arg Leu Val Arg Asp Gly Leu Gly Val Val
    610                 615                 620

gat tgg gca agc act gat cat ggt gaa gaa ccc gac gtt gtc ttc gca     1920
Asp Trp Ala Ser Thr Asp His Gly Glu Glu Pro Asp Val Val Phe Ala
625                 630                 635                 640

act gcc ggc tct gaa cca acg act gaa agc tta gct gcc gta tca atc     1968
Thr Ala Gly Ser Glu Pro Thr Thr Glu Ser Leu Ala Ala Val Ser Ile
                645                 650                 655

ttg cat gca cgc ttc cct gaa atg aag att cgc ttc att aac gtt gtt     2016
Leu His Ala Arg Phe Pro Glu Met Lys Ile Arg Phe Ile Asn Val Val
            660                 665                 670

gat ctt ctg aag ctg aag aaa gac gac cct cgt ggt tta tca gat gct     2064
Asp Leu Leu Lys Leu Lys Lys Asp Asp Pro Arg Gly Leu Ser Asp Ala
        675                 680                 685

gaa ttt gat gct ttc ttc act aag gac aaa cca gtt atc ttt gct tat     2112
Glu Phe Asp Ala Phe Phe Thr Lys Asp Lys Pro Val Ile Phe Ala Tyr
    690                 695                 700

cat gca tac gac gac tta gta aag acc atc ttc ttc gat cgc cat aac     2160
His Ala Tyr Asp Asp Leu Val Lys Thr Ile Phe Phe Asp Arg His Asn
705                 710                 715                 720

cat aac tta cac gtt cat ggt tac cgc gaa gaa ggc gac att aca acg     2208
His Asn Leu His Val His Gly Tyr Arg Glu Glu Gly Asp Ile Thr Thr
                725                 730                 735

cca ttc gac atg cgt gtt cgc aac gaa ctc gat cgt ttc cac tta gtc     2256
Pro Phe Asp Met Arg Val Arg Asn Glu Leu Asp Arg Phe His Leu Val
            740                 745                 750

aaa gct gcc tta tta gca acg cca gct tat gcc gaa aaa ggt gcc cat     2304
Lys Ala Ala Leu Leu Ala Thr Pro Ala Tyr Ala Glu Lys Gly Ala His
        755                 760                 765

gtc att caa gag atg aac agc att tta gac aag cat cat gac tat atc     2352
Val Ile Gln Glu Met Asn Ser Ile Leu Asp Lys His His Asp Tyr Ile
    770                 775                 780

cgt gct gaa ggt acc gat att cca gaa gtt gaa aac tgg aaa tgg act     2400
Arg Ala Glu Gly Thr Asp Ile Pro Glu Val Glu Asn Trp Lys Trp Thr
785                 790                 795                 800

gca ttg aag tag                                                     2412
Ala Leu Lys


<210> SEQ ID NO 63
<211> LENGTH: 803
<212> TYPE: PRT
<213> ORGANISM: Lactobacillus plantarum

<400> SEQUENCE: 63

Leu Gln Arg Ser Cys Lys Ile Met Ser Glu Ala Ile Lys Ser Lys Thr
1               5                   10                  15

Val Asp Tyr Ser Ser Asp Glu Tyr Leu Lys Arg Val Asp Glu Tyr Trp
            20                  25                  30
```

-continued

```
Arg Ala Ala Asn Tyr Ile Ser Val Gly Gln Leu Tyr Leu Leu Asn Asn
        35                  40                  45

Pro Leu Leu Arg Glu Pro Leu Lys Ala Thr Asp Val Lys Val His Pro
    50                  55                  60

Ile Gly His Trp Gly Thr Ile Ala Gly Gln Asn Phe Ile Tyr Ala His
65                  70                  75                  80

Leu Asn Arg Ala Ile Asn Lys Tyr Gly Leu Asn Met Phe Tyr Ile Glu
                85                  90                  95

Gly Pro Gly His Gly Gly Gln Val Met Val Ser Asn Ser Tyr Leu Asp
            100                 105                 110

Gly Thr Tyr Thr Glu Thr Tyr Pro Lys Ile Thr Gln Asp Lys Ala Gly
        115                 120                 125

Met Lys Arg Leu Phe Lys Gln Phe Ser Phe Pro Gly Gly Val Ala Ser
    130                 135                 140

His Ala Asp Pro Lys Thr Pro Gly Ser Ile His Glu Gly Gly Glu Leu
145                 150                 155                 160

Gly Tyr Ser Ile Leu His Gly Ala Gly Ala Val Leu Asp Asn Pro Gly
                165                 170                 175

Leu Ile Ala Ala Thr Val Val Gly Asp Gly Glu Ser Glu Thr Gly Pro
            180                 185                 190

Leu Ala Thr Ser Trp Gln Val Asn Lys Phe Leu Asn Pro Ile Thr Asp
        195                 200                 205

Gly Thr Val Leu Pro Ile Leu Asn Leu Asn Gly Phe Lys Ile Ser Asn
    210                 215                 220

Pro Thr Val Leu Ser Arg Glu Ser His Glu Glu Leu Glu Asp Tyr Phe
225                 230                 235                 240

Lys Gly Leu Gly Trp Asp Pro His Phe Val Glu Gly Thr Asp Pro Ala
                245                 250                 255

Lys Met His Lys Ile Met Ala Glu Glu Leu Asp Lys Val Ile Glu Glu
            260                 265                 270

Ile His Ala Ile Arg Lys Asn Ala Lys Asp Asn Asn Asp Glu Ser Arg
        275                 280                 285

Pro Lys Trp Pro Met Ile Val Phe Arg Ala Pro Lys Gly Trp Thr Gly
    290                 295                 300

Pro Lys Ser Trp Asp Gly Glu Pro Ile Glu Gly Ser Phe Arg Ala His
305                 310                 315                 320

Gln Ile Pro Ile Pro Val Asp Arg Asn His Met Glu His Ala Asp Lys
                325                 330                 335

Leu Val Asp Trp Leu Lys Ser Tyr Lys Pro Glu Glu Leu Phe Asp Glu
            340                 345                 350

Asn Gly Thr Leu Lys Pro Glu Ile Ala Ala Ile Ile Pro Glu Gly Gln
        355                 360                 365

Ala Arg Met Ala Ala Asn Pro Val Thr Asn Gly Gly Lys Leu Thr Lys
    370                 375                 380

Asp Leu Ile Thr Pro Asn Ile Asp Asp Tyr Ala Leu Asp Asn Lys Ser
385                 390                 395                 400

His Gly Lys Glu Asp Gly Ser Asp Met Thr Glu Leu Gly Lys Tyr Ile
                405                 410                 415

Arg Asp Leu Ile Glu Leu Asn Lys Asp Asn Lys Asn Phe Arg Gly Trp
            420                 425                 430

Gly Pro Asp Glu Thr Leu Ser Asn Lys Leu Gly Ala Ala Phe Glu Asp
        435                 440                 445

Thr Lys Arg Gln Trp Met Glu Pro Ile His Glu Pro Asn Asp Ala Leu
    450                 455                 460
```

```
Leu Ala Pro Gln Gly Arg Ile Ile Asp Ser Met Leu Ser Glu His Met
465                 470                 475                 480

Asp Glu Gly Met Leu Glu Ala Tyr Asn Leu Thr Gly Arg Tyr Gly Phe
                485                 490                 495

Phe Ala Ser Tyr Glu Ser Phe Leu Arg Val Val Asp Ser Met Leu Thr
            500                 505                 510

Gln His Phe Lys Trp Leu Arg Asn Ser His Glu Glu Thr Pro Trp Arg
        515                 520                 525

Ala Asp Val Pro Ser Leu Asn Val Ile Ala Ser Ser Thr Ala Phe Gln
    530                 535                 540

Gln Asp His Asn Gly Tyr Ser His Gln Asp Pro Gly Ile Ile Ser His
545                 550                 555                 560

Leu Ala Glu Lys Lys Thr Glu Tyr Val Arg Ala Tyr Leu Pro Gly Asp
                565                 570                 575

Ala Asn Thr Leu Ile Ala Thr Phe Asp Lys Ala Ile Gln Ser Lys Gln
            580                 585                 590

Leu Ile Asn Leu Ile Ile Ala Ser Lys His Pro Arg Pro Gln Trp Phe
        595                 600                 605

Thr Met Asp Glu Ala Lys Arg Leu Val Arg Asp Gly Leu Gly Val Val
    610                 615                 620

Asp Trp Ala Ser Thr Asp His Gly Glu Glu Pro Asp Val Val Phe Ala
625                 630                 635                 640

Thr Ala Gly Ser Glu Pro Thr Thr Glu Ser Leu Ala Ala Val Ser Ile
                645                 650                 655

Leu His Ala Arg Phe Pro Glu Met Lys Ile Arg Phe Ile Asn Val Val
            660                 665                 670

Asp Leu Leu Lys Leu Lys Lys Asp Asp Pro Arg Gly Leu Ser Asp Ala
        675                 680                 685

Glu Phe Asp Ala Phe Phe Thr Lys Asp Lys Pro Val Ile Phe Ala Tyr
    690                 695                 700

His Ala Tyr Asp Asp Leu Val Lys Thr Ile Phe Phe Asp Arg His Asn
705                 710                 715                 720

His Asn Leu His Val His Gly Tyr Arg Glu Glu Gly Asp Ile Thr Thr
                725                 730                 735

Pro Phe Asp Met Arg Val Arg Asn Glu Leu Asp Arg Phe His Leu Val
            740                 745                 750

Lys Ala Ala Leu Leu Ala Thr Pro Ala Tyr Ala Glu Lys Gly Ala His
        755                 760                 765

Val Ile Gln Glu Met Asn Ser Ile Leu Asp Lys His His Asp Tyr Ile
    770                 775                 780

Arg Ala Glu Gly Thr Asp Ile Pro Glu Val Glu Asn Trp Lys Trp Thr
785                 790                 795                 800

Ala Leu Lys


<210> SEQ ID NO 64
<211> LENGTH: 2379
<212> TYPE: DNA
<213> ORGANISM: Streptococcus agalactiae
<220> FEATURE:
<221> NAME/KEY: CDS
<222> LOCATION: (1)..(2379)
<223> OTHER INFORMATION: xpk

<400> SEQUENCE: 64

atg tca gaa ttt gat aca aaa tca tat tta gaa aaa ctt gat gca tgg       48
Met Ser Glu Phe Asp Thr Lys Ser Tyr Leu Glu Lys Leu Asp Ala Trp
```

-continued

```
1               5                   10                  15

tgg aga gca gct aat tat att tct gca gca caa atg tat cta aag gat        96
Trp Arg Ala Ala Asn Tyr Ile Ser Ala Ala Gln Met Tyr Leu Lys Asp
            20                  25                  30

aat cct ctc ttg aga cga gag cta gtt gaa aac gac tta aag gtt cat       144
Asn Pro Leu Leu Arg Arg Glu Leu Val Glu Asn Asp Leu Lys Val His
        35                  40                  45

cca att ggt cac tgg ggc act gta cct gga caa aac ttt atc tat gct       192
Pro Ile Gly His Trp Gly Thr Val Pro Gly Gln Asn Phe Ile Tyr Ala
    50                  55                  60

cac tta aat cgc gct att aat aaa tac gat tta gac atg ttc tat att       240
His Leu Asn Arg Ala Ile Asn Lys Tyr Asp Leu Asp Met Phe Tyr Ile
65                  70                  75                  80

gaa ggt cca ggt cat ggt ggt caa gtt atg gta tct aat tca tat tta       288
Glu Gly Pro Gly His Gly Gly Gln Val Met Val Ser Asn Ser Tyr Leu
                85                  90                  95

gat ggt tca tat act gaa tta aac cca aat att gag caa aca gag gat       336
Asp Gly Ser Tyr Thr Glu Leu Asn Pro Asn Ile Glu Gln Thr Glu Asp
            100                 105                 110

ggc ttt aag cag tta tgt aaa atc ttc tct ttc cca ggt gga att gca       384
Gly Phe Lys Gln Leu Cys Lys Ile Phe Ser Phe Pro Gly Gly Ile Ala
        115                 120                 125

tcc cat gca gca cca gaa aca cca ggg tca att cat gaa ggt ggt gaa       432
Ser His Ala Ala Pro Glu Thr Pro Gly Ser Ile His Glu Gly Gly Glu
    130                 135                 140

ctt ggt tac gca ctt tct cat gcg aca ggt gcc atc cta gac aat cca       480
Leu Gly Tyr Ala Leu Ser His Ala Thr Gly Ala Ile Leu Asp Asn Pro
145                 150                 155                 160

gat gtt att gct gcg act gtt att ggt gat ggt gaa ggt gaa aca gga       528
Asp Val Ile Ala Ala Thr Val Ile Gly Asp Gly Glu Gly Glu Thr Gly
                165                 170                 175

cca ctt atg gct ggt tgg cta tct aat acc ttt atc aat cca gta aat       576
Pro Leu Met Ala Gly Trp Leu Ser Asn Thr Phe Ile Asn Pro Val Asn
            180                 185                 190

gat ggt gct gtt cta cca atc ttc tat tta aat ggt ggt aaa atc cat       624
Asp Gly Ala Val Leu Pro Ile Phe Tyr Leu Asn Gly Gly Lys Ile His
        195                 200                 205

aac cca act atc ttt gaa cgt aag aca gat gaa gaa tta tct cag ttt       672
Asn Pro Thr Ile Phe Glu Arg Lys Thr Asp Glu Glu Leu Ser Gln Phe
    210                 215                 220

ttt gaa gga tta ggt tgg aaa cct att ttt gca gat gtt gtt gaa ctc       720
Phe Glu Gly Leu Gly Trp Lys Pro Ile Phe Ala Asp Val Val Glu Leu
225                 230                 235                 240

tct gag gat cat gcg gct gct cat gct ttg ttt gca gaa aaa tta gat       768
Ser Glu Asp His Ala Ala Ala His Ala Leu Phe Ala Glu Lys Leu Asp
                245                 250                 255

caa gct att caa gag att aaa acc att caa tca gaa gca cga caa aaa       816
Gln Ala Ile Gln Glu Ile Lys Thr Ile Gln Ser Glu Ala Arg Gln Lys
            260                 265                 270

cca gca gaa gaa gct atc caa gca aaa ttc cct gtc ttg gtt gca cgt       864
Pro Ala Glu Glu Ala Ile Gln Ala Lys Phe Pro Val Leu Val Ala Arg
        275                 280                 285

att cct aag ggg tgg act ggt cca aaa gct tgg gaa gga aca cca att       912
Ile Pro Lys Gly Trp Thr Gly Pro Lys Ala Trp Glu Gly Thr Pro Ile
    290                 295                 300

gaa ggt ggc ttc cgc gct cac caa gta cca att cca gta gat gcc cac       960
Glu Gly Gly Phe Arg Ala His Gln Val Pro Ile Pro Val Asp Ala His
305                 310                 315                 320

cat atg gaa cat gtc gat tct ctt ttg tca tgg ctt caa tca tac cgt      1008
His Met Glu His Val Asp Ser Leu Leu Ser Trp Leu Gln Ser Tyr Arg
```

```
                325                 330                 335

cca gaa gaa tta ttt gat gaa agt ggt aaa atc gtt gat gag att gct      1056
Pro Glu Glu Leu Phe Asp Glu Ser Gly Lys Ile Val Asp Glu Ile Ala
            340                 345                 350

gct att tca cca aaa ggt gat cgt cgc atg tcc atg aat cca ata acc      1104
Ala Ile Ser Pro Lys Gly Asp Arg Arg Met Ser Met Asn Pro Ile Thr
        355                 360                 365

aat gct ggt att gtt aaa gca atg gat aca gca gat tgg aag aaa ttt      1152
Asn Ala Gly Ile Val Lys Ala Met Asp Thr Ala Asp Trp Lys Lys Phe
    370                 375                 380

gct ctt gat att aat gtt cca ggt caa att atg gca caa gat atg att      1200
Ala Leu Asp Ile Asn Val Pro Gly Gln Ile Met Ala Gln Asp Met Ile
385                 390                 395                 400

gaa ttt gga aaa tat gca gca gat ttg gta gat gct aat cca gat aat      1248
Glu Phe Gly Lys Tyr Ala Ala Asp Leu Val Asp Ala Asn Pro Asp Asn
                405                 410                 415

ttc cgt att ttt ggt cca gat gaa acg aaa tca aat cgt ctt caa gaa      1296
Phe Arg Ile Phe Gly Pro Asp Glu Thr Lys Ser Asn Arg Leu Gln Glu
            420                 425                 430

gtg ttt aca cgt act agc cgt caa tgg ctt ggt cgt cgt aaa cca gat      1344
Val Phe Thr Arg Thr Ser Arg Gln Trp Leu Gly Arg Arg Lys Pro Asp
        435                 440                 445

tat gac gaa gct tta agt cca gct gga cgt gtt att gat tcc caa ttg      1392
Tyr Asp Glu Ala Leu Ser Pro Ala Gly Arg Val Ile Asp Ser Gln Leu
    450                 455                 460

tct gaa cat caa gca gaa ggt ttc tta gaa ggt tat gtt tta act ggt      1440
Ser Glu His Gln Ala Glu Gly Phe Leu Glu Gly Tyr Val Leu Thr Gly
465                 470                 475                 480

cgt cac ggc ttc ttt gct tca tac gaa tca ttc ctt cgc gtt gta gat      1488
Arg His Gly Phe Phe Ala Ser Tyr Glu Ser Phe Leu Arg Val Val Asp
                485                 490                 495

tca atg gta aca caa cat ttc aaa tgg tta cgt aaa tca aaa aca cac      1536
Ser Met Val Thr Gln His Phe Lys Trp Leu Arg Lys Ser Lys Thr His
            500                 505                 510

aca aca tgg cgt aaa aat tat cca gcg ctt aac tta att gca gct tca      1584
Thr Thr Trp Arg Lys Asn Tyr Pro Ala Leu Asn Leu Ile Ala Ala Ser
        515                 520                 525

act gtt ttc caa caa gat cat aat ggt tac act cac caa gat cca ggt      1632
Thr Val Phe Gln Gln Asp His Asn Gly Tyr Thr His Gln Asp Pro Gly
    530                 535                 540

atc tta act cac tta gct gaa aaa aca cct gaa tac att cgt gaa tat      1680
Ile Leu Thr His Leu Ala Glu Lys Thr Pro Glu Tyr Ile Arg Glu Tyr
545                 550                 555                 560

tta cca gca gat act aac tca ctt cta gct gtt atg gat aaa gcg ttt      1728
Leu Pro Ala Asp Thr Asn Ser Leu Leu Ala Val Met Asp Lys Ala Phe
                565                 570                 575

aaa gct gaa gat aaa att aat tta att gtg aca tct aag cac cct cgt      1776
Lys Ala Glu Asp Lys Ile Asn Leu Ile Val Thr Ser Lys His Pro Arg
            580                 585                 590

cca caa ttt tac tct att gct gaa gca gaa gag tta gtg gca gaa gga      1824
Pro Gln Phe Tyr Ser Ile Ala Glu Ala Glu Glu Leu Val Ala Glu Gly
        595                 600                 605

tat aag gtg att gac tgg gct tca aat gtg tcg ctt aat caa gag cca      1872
Tyr Lys Val Ile Asp Trp Ala Ser Asn Val Ser Leu Asn Gln Glu Pro
    610                 615                 620

gat gtt gtc ttt gct gcg gcg gga aca gaa cct aac tta gaa gct ttg      1920
Asp Val Val Phe Ala Ala Ala Gly Thr Glu Pro Asn Leu Glu Ala Leu
625                 630                 635                 640

gca gct att agt att ctt cat aag gct ttc cca gaa ctt aag att aga      1968
Ala Ala Ile Ser Ile Leu His Lys Ala Phe Pro Glu Leu Lys Ile Arg
```

-continued

```
                645                 650                 655

ttt gtt aat gta tta gac atc cta aaa ctt cgt cat cct tca caa gat      2016
Phe Val Asn Val Leu Asp Ile Leu Lys Leu Arg His Pro Ser Gln Asp
            660                 665                 670

gct cgc ggt tta tca gat gaa gag ttt gac aaa gtc ttt acc aca gat      2064
Ala Arg Gly Leu Ser Asp Glu Glu Phe Asp Lys Val Phe Thr Thr Asp
        675                 680                 685

aaa cct gtt att ttt gct ttc cat agt tat gaa gat atg att cga gat      2112
Lys Pro Val Ile Phe Ala Phe His Ser Tyr Glu Asp Met Ile Arg Asp
    690                 695                 700

att ttc ttt agt cgt cac aat cat aat ttg cat acg cat ggt tac cgt      2160
Ile Phe Phe Ser Arg His Asn His Asn Leu His Thr His Gly Tyr Arg
705                 710                 715                 720

gaa aat ggt gat atc aca aca cca ttt gat atg cgc gtg atg tca gaa      2208
Glu Asn Gly Asp Ile Thr Thr Pro Phe Asp Met Arg Val Met Ser Glu
                725                 730                 735

ttg gac cga ttc cat ctg gca cag gat gca gct ctt gct tct tta gga      2256
Leu Asp Arg Phe His Leu Ala Gln Asp Ala Ala Leu Ala Ser Leu Gly
            740                 745                 750

aat gaa gca caa gcc ttc agt gat gaa atg aat caa atg gtt gct tat      2304
Asn Glu Ala Gln Ala Phe Ser Asp Glu Met Asn Gln Met Val Ala Tyr
        755                 760                 765

cac aaa gac tat att cgt gaa cac gga gac gat att cca gaa gtg caa      2352
His Lys Asp Tyr Ile Arg Glu His Gly Asp Asp Ile Pro Glu Val Gln
    770                 775                 780

aat tgg aaa tgg gaa aat atc aag tag                                  2379
Asn Trp Lys Trp Glu Asn Ile Lys
785                 790


<210> SEQ ID NO 65
<211> LENGTH: 792
<212> TYPE: PRT
<213> ORGANISM: Streptococcus agalactiae

<400> SEQUENCE: 65

Met Ser Glu Phe Asp Thr Lys Ser Tyr Leu Glu Lys Leu Asp Ala Trp
1               5                   10                  15

Trp Arg Ala Ala Asn Tyr Ile Ser Ala Ala Gln Met Tyr Leu Lys Asp
            20                  25                  30

Asn Pro Leu Leu Arg Arg Glu Leu Val Glu Asn Asp Leu Lys Val His
        35                  40                  45

Pro Ile Gly His Trp Gly Thr Val Pro Gly Gln Asn Phe Ile Tyr Ala
    50                  55                  60

His Leu Asn Arg Ala Ile Asn Lys Tyr Asp Leu Asp Met Phe Tyr Ile
65                  70                  75                  80

Glu Gly Pro Gly His Gly Gly Gln Val Met Val Ser Asn Ser Tyr Leu
                85                  90                  95

Asp Gly Ser Tyr Thr Glu Leu Asn Pro Asn Ile Glu Gln Thr Glu Asp
            100                 105                 110

Gly Phe Lys Gln Leu Cys Lys Ile Phe Ser Phe Pro Gly Gly Ile Ala
        115                 120                 125

Ser His Ala Ala Pro Glu Thr Pro Gly Ser Ile His Glu Gly Gly Glu
    130                 135                 140

Leu Gly Tyr Ala Leu Ser His Ala Thr Gly Ala Ile Leu Asp Asn Pro
145                 150                 155                 160

Asp Val Ile Ala Ala Thr Val Ile Gly Asp Gly Glu Gly Glu Thr Gly
                165                 170                 175

Pro Leu Met Ala Gly Trp Leu Ser Asn Thr Phe Ile Asn Pro Val Asn
```

-continued

```
            180                 185                 190

Asp Gly Ala Val Leu Pro Ile Phe Tyr Leu Asn Gly Gly Lys Ile His
        195                 200                 205

Asn Pro Thr Ile Phe Glu Arg Lys Thr Asp Glu Glu Leu Ser Gln Phe
    210                 215                 220

Phe Glu Gly Leu Gly Trp Lys Pro Ile Phe Ala Asp Val Val Glu Leu
225                 230                 235                 240

Ser Glu Asp His Ala Ala Ala His Ala Leu Phe Ala Glu Lys Leu Asp
                245                 250                 255

Gln Ala Ile Gln Glu Ile Lys Thr Ile Gln Ser Glu Ala Arg Gln Lys
            260                 265                 270

Pro Ala Glu Glu Ala Ile Gln Ala Lys Phe Pro Val Leu Val Ala Arg
        275                 280                 285

Ile Pro Lys Gly Trp Thr Gly Pro Lys Ala Trp Glu Gly Thr Pro Ile
    290                 295                 300

Glu Gly Gly Phe Arg Ala His Gln Val Pro Ile Pro Val Asp Ala His
305                 310                 315                 320

His Met Glu His Val Asp Ser Leu Leu Ser Trp Leu Gln Ser Tyr Arg
                325                 330                 335

Pro Glu Glu Leu Phe Asp Glu Ser Gly Lys Ile Val Asp Glu Ile Ala
            340                 345                 350

Ala Ile Ser Pro Lys Gly Asp Arg Arg Met Ser Met Asn Pro Ile Thr
        355                 360                 365

Asn Ala Gly Ile Val Lys Ala Met Asp Thr Ala Asp Trp Lys Lys Phe
    370                 375                 380

Ala Leu Asp Ile Asn Val Pro Gly Gln Ile Met Ala Gln Asp Met Ile
385                 390                 395                 400

Glu Phe Gly Lys Tyr Ala Ala Asp Leu Val Asp Ala Asn Pro Asp Asn
                405                 410                 415

Phe Arg Ile Phe Gly Pro Asp Glu Thr Lys Ser Asn Arg Leu Gln Glu
            420                 425                 430

Val Phe Thr Arg Thr Ser Arg Gln Trp Leu Gly Arg Arg Lys Pro Asp
        435                 440                 445

Tyr Asp Glu Ala Leu Ser Pro Ala Gly Arg Val Ile Asp Ser Gln Leu
    450                 455                 460

Ser Glu His Gln Ala Glu Gly Phe Leu Glu Gly Tyr Val Leu Thr Gly
465                 470                 475                 480

Arg His Gly Phe Phe Ala Ser Tyr Glu Ser Phe Leu Arg Val Val Asp
                485                 490                 495

Ser Met Val Thr Gln His Phe Lys Trp Leu Arg Lys Ser Lys Thr His
            500                 505                 510

Thr Thr Trp Arg Lys Asn Tyr Pro Ala Leu Asn Leu Ile Ala Ala Ser
        515                 520                 525

Thr Val Phe Gln Gln Asp His Asn Gly Tyr Thr His Gln Asp Pro Gly
    530                 535                 540

Ile Leu Thr His Leu Ala Glu Lys Thr Pro Glu Tyr Ile Arg Glu Tyr
545                 550                 555                 560

Leu Pro Ala Asp Thr Asn Ser Leu Leu Ala Val Met Asp Lys Ala Phe
                565                 570                 575

Lys Ala Glu Asp Lys Ile Asn Leu Ile Val Thr Ser Lys His Pro Arg
            580                 585                 590

Pro Gln Phe Tyr Ser Ile Ala Glu Ala Glu Glu Leu Val Ala Glu Gly
        595                 600                 605
```

-continued

```
Tyr Lys Val Ile Asp Trp Ala Ser Asn Val Ser Leu Asn Gln Glu Pro
    610                 615                 620

Asp Val Val Phe Ala Ala Ala Gly Thr Glu Pro Asn Leu Glu Ala Leu
625                 630                 635                 640

Ala Ala Ile Ser Ile Leu His Lys Ala Phe Pro Glu Leu Lys Ile Arg
                645                 650                 655

Phe Val Asn Val Leu Asp Ile Leu Lys Leu Arg His Pro Ser Gln Asp
            660                 665                 670

Ala Arg Gly Leu Ser Asp Glu Glu Phe Asp Lys Val Phe Thr Thr Asp
        675                 680                 685

Lys Pro Val Ile Phe Ala Phe His Ser Tyr Glu Asp Met Ile Arg Asp
    690                 695                 700

Ile Phe Phe Ser Arg His Asn His Asn Leu His Thr His Gly Tyr Arg
705                 710                 715                 720

Glu Asn Gly Asp Ile Thr Thr Pro Phe Asp Met Arg Val Met Ser Glu
                725                 730                 735

Leu Asp Arg Phe His Leu Ala Gln Asp Ala Ala Leu Ala Ser Leu Gly
            740                 745                 750

Asn Glu Ala Gln Ala Phe Ser Asp Glu Met Asn Gln Met Val Ala Tyr
        755                 760                 765

His Lys Asp Tyr Ile Arg Glu His Gly Asp Asp Ile Pro Glu Val Gln
    770                 775                 780

Asn Trp Lys Trp Glu Asn Ile Lys
785                 790


<210> SEQ ID NO 66
<211> LENGTH: 2469
<212> TYPE: DNA
<213> ORGANISM: Lactococcus lactis
<220> FEATURE:
<221> NAME/KEY: CDS
<222> LOCATION: (1)..(2469)
<223> OTHER INFORMATION: xpk

<400> SEQUENCE: 66

atg aca gaa tat aat tca gaa gct tat ttg aaa aag ctt gat aaa tgg       48
Met Thr Glu Tyr Asn Ser Glu Ala Tyr Leu Lys Lys Leu Asp Lys Trp
1               5                   10                  15

tgg cga gca gca act tat ctt gga gca gga atg atc ttc ttg aaa gaa       96
Trp Arg Ala Ala Thr Tyr Leu Gly Ala Gly Met Ile Phe Leu Lys Glu
            20                  25                  30

aat cca ttg ttc tct gtg aca ggt act cca att aaa gcg gaa aac ctt      144
Asn Pro Leu Phe Ser Val Thr Gly Thr Pro Ile Lys Ala Glu Asn Leu
        35                  40                  45

aaa gcc aat cct att ggg cac tgg ggg acg gtt tca gga caa act ttc      192
Lys Ala Asn Pro Ile Gly His Trp Gly Thr Val Ser Gly Gln Thr Phe
    50                  55                  60

ctc tat gct cat gct aat cgt cta atc aat aaa tat gat caa aag atg      240
Leu Tyr Ala His Ala Asn Arg Leu Ile Asn Lys Tyr Asp Gln Lys Met
65                  70                  75                  80

ttt tac atg ggt ggc ccc gga cat ggt gga caa gct atg gtt gtt cct      288
Phe Tyr Met Gly Gly Pro Gly His Gly Gly Gln Ala Met Val Val Pro
                85                  90                  95

tct tat ctt gat ggc tca tat aca gaa gct tat cca gag att acc caa      336
Ser Tyr Leu Asp Gly Ser Tyr Thr Glu Ala Tyr Pro Glu Ile Thr Gln
            100                 105                 110

gat ttg gaa gga atg tca cgt ttg ttt aaa cgt ttc tca ttt cct gga      384
Asp Leu Glu Gly Met Ser Arg Leu Phe Lys Arg Phe Ser Phe Pro Gly
        115                 120                 125
```

```
gga ata ggg tcg cat atg aca gca caa acc cct ggt tca ctt cat gaa      432
Gly Ile Gly Ser His Met Thr Ala Gln Thr Pro Gly Ser Leu His Glu
    130                 135                 140

gga ggt gag ttg ggt tat gtg cta tca cat gca aca ggg gct att ctt      480
Gly Gly Glu Leu Gly Tyr Val Leu Ser His Ala Thr Gly Ala Ile Leu
145                 150                 155                 160

gat caa cct gaa cag att gct ttt gct gtt gtt ggg gat gga gaa gct      528
Asp Gln Pro Glu Gln Ile Ala Phe Ala Val Val Gly Asp Gly Glu Ala
                165                 170                 175

gaa act gga ccg ttg atg aca agt tgg cac tct att aaa ttc att aat      576
Glu Thr Gly Pro Leu Met Thr Ser Trp His Ser Ile Lys Phe Ile Asn
            180                 185                 190

cct aag aat gat ggg gcg att tta cca att ctt gat tta aat ggt ttt      624
Pro Lys Asn Asp Gly Ala Ile Leu Pro Ile Leu Asp Leu Asn Gly Phe
        195                 200                 205

aaa att tca aat cct act ttg ttc gct cga act tca gat gtt gat att      672
Lys Ile Ser Asn Pro Thr Leu Phe Ala Arg Thr Ser Asp Val Asp Ile
    210                 215                 220

cgt aaa ttc ttt gaa gga ctg ggt tac tca cct cgt tat att gaa aat      720
Arg Lys Phe Phe Glu Gly Leu Gly Tyr Ser Pro Arg Tyr Ile Glu Asn
225                 230                 235                 240

gat gat att cat gat tac atg gct tat cat aaa tta gca gct gaa gtt      768
Asp Asp Ile His Asp Tyr Met Ala Tyr His Lys Leu Ala Ala Glu Val
                245                 250                 255

ttt gat aaa gcg att gaa gac att cat caa att cag aaa gat gcg cgt      816
Phe Asp Lys Ala Ile Glu Asp Ile His Gln Ile Gln Lys Asp Ala Arg
            260                 265                 270

gaa gat aat cgt tat caa aat gga gag att cca gct tgg cca att gtt      864
Glu Asp Asn Arg Tyr Gln Asn Gly Glu Ile Pro Ala Trp Pro Ile Val
        275                 280                 285

atc gca cgt tta cca aaa ggt tgg ggt ggt cca cgt tat aat gat tgg      912
Ile Ala Arg Leu Pro Lys Gly Trp Gly Gly Pro Arg Tyr Asn Asp Trp
    290                 295                 300

tca ggt cct aaa ttt gac ggt aag gga atg cca att gaa cat agt ttc      960
Ser Gly Pro Lys Phe Asp Gly Lys Gly Met Pro Ile Glu His Ser Phe
305                 310                 315                 320

cgt gcg cat caa gtt cca ctt ccg tta tct tct aaa aat atg gga act     1008
Arg Ala His Gln Val Pro Leu Pro Leu Ser Ser Lys Asn Met Gly Thr
                325                 330                 335

tta cca gaa ttt gta aaa tgg atg act tct tac caa cca gaa act tta     1056
Leu Pro Glu Phe Val Lys Trp Met Thr Ser Tyr Gln Pro Glu Thr Leu
            340                 345                 350

ttt aat gct gat gga agt ttg aaa gaa gag ttg cgt gat ttt gca cca     1104
Phe Asn Ala Asp Gly Ser Leu Lys Glu Glu Leu Arg Asp Phe Ala Pro
        355                 360                 365

aaa ggt gag atg cga atg gct tca aac cct gta aca aat ggg gga gtt     1152
Lys Gly Glu Met Arg Met Ala Ser Asn Pro Val Thr Asn Gly Gly Val
    370                 375                 380

gat tct tct aat ttg gtt tta cca gat tgg caa gaa ttt gca aat cca     1200
Asp Ser Ser Asn Leu Val Leu Pro Asp Trp Gln Glu Phe Ala Asn Pro
385                 390                 395                 400

att tct gaa aat aat cga ggg aaa tta ctc cct gat aca aat gac aat     1248
Ile Ser Glu Asn Asn Arg Gly Lys Leu Leu Pro Asp Thr Asn Asp Asn
                405                 410                 415

atg gat atg aat gtt ttg tca aaa tat ttt gct gaa ata gtc aaa ctt     1296
Met Asp Met Asn Val Leu Ser Lys Tyr Phe Ala Glu Ile Val Lys Leu
            420                 425                 430

aat cct acg cgt ttc cgt ttg ttt ggt cct gat gaa acc atg tct aat     1344
Asn Pro Thr Arg Phe Arg Leu Phe Gly Pro Asp Glu Thr Met Ser Asn
        435                 440                 445
```

```
cgt ttt tgg gaa atg ttt aag gtg acg aat cgt cag tgg atg caa gtc      1392
Arg Phe Trp Glu Met Phe Lys Val Thr Asn Arg Gln Trp Met Gln Val
    450                 455                 460

ata aaa aat cca aat gat gaa ttt atc tca cct gag ggt cgc att att      1440
Ile Lys Asn Pro Asn Asp Glu Phe Ile Ser Pro Glu Gly Arg Ile Ile
465                 470                 475                 480

gat tct caa tta tca gaa cac caa gca gaa ggt tgg ctt gaa ggt tat      1488
Asp Ser Gln Leu Ser Glu His Gln Ala Glu Gly Trp Leu Glu Gly Tyr
                485                 490                 495

act tta acc gga cgc aca gga gca ttt gca agt tat gaa tca ttc ttg      1536
Thr Leu Thr Gly Arg Thr Gly Ala Phe Ala Ser Tyr Glu Ser Phe Leu
            500                 505                 510

cga gtc gta gat tca atg tta act caa cat ttc aaa tgg att cgt caa      1584
Arg Val Val Asp Ser Met Leu Thr Gln His Phe Lys Trp Ile Arg Gln
        515                 520                 525

gct gca gac caa aaa tgg cgc cat gat tat cct tcg ctt aat gtt att      1632
Ala Ala Asp Gln Lys Trp Arg His Asp Tyr Pro Ser Leu Asn Val Ile
    530                 535                 540

tcg acc tca acc gtt ttc caa caa gac cat aat ggt tat act cac caa      1680
Ser Thr Ser Thr Val Phe Gln Gln Asp His Asn Gly Tyr Thr His Gln
545                 550                 555                 560

gat cct gga atg ttg act cat ttg gct gaa aag aaa tct gat ttt atc      1728
Asp Pro Gly Met Leu Thr His Leu Ala Glu Lys Lys Ser Asp Phe Ile
                565                 570                 575

aga caa tac ttg ccg gct gat ggg aat act ttg ctt gcc gta ttt gac      1776
Arg Gln Tyr Leu Pro Ala Asp Gly Asn Thr Leu Leu Ala Val Phe Asp
            580                 585                 590

cgt gct ttt caa gat aga agt aaa att aat cat att gta gcc tct aaa      1824
Arg Ala Phe Gln Asp Arg Ser Lys Ile Asn His Ile Val Ala Ser Lys
        595                 600                 605

caa cct cgt caa caa tgg ttt act aaa gaa gaa gct gaa aaa ttg gcg      1872
Gln Pro Arg Gln Gln Trp Phe Thr Lys Glu Glu Ala Glu Lys Leu Ala
    610                 615                 620

act gac gga att gca aca att gat tgg gct tca acg gct aaa gat gga      1920
Thr Asp Gly Ile Ala Thr Ile Asp Trp Ala Ser Thr Ala Lys Asp Gly
625                 630                 635                 640

gaa gca gta gat tta gtt ttt gcc tca gca gga gct gag cct aca att      1968
Glu Ala Val Asp Leu Val Phe Ala Ser Ala Gly Ala Glu Pro Thr Ile
                645                 650                 655

gaa aca ctg gca gct tta cat ctt gta aac gaa gtt ttc cca cag gca      2016
Glu Thr Leu Ala Ala Leu His Leu Val Asn Glu Val Phe Pro Gln Ala
            660                 665                 670

aaa ttc cgt tat gtg aac gtg gtt gaa ttg ggt cgg ttg caa aag aaa      2064
Lys Phe Arg Tyr Val Asn Val Val Glu Leu Gly Arg Leu Gln Lys Lys
        675                 680                 685

aag gga gca ctc aat caa gaa cgt gaa ctc tca gat gaa gaa ttt gaa      2112
Lys Gly Ala Leu Asn Gln Glu Arg Glu Leu Ser Asp Glu Glu Phe Glu
    690                 695                 700

aaa tac ttt ggc cct tca ggc act cca gta att ttt gga ttc cat gga      2160
Lys Tyr Phe Gly Pro Ser Gly Thr Pro Val Ile Phe Gly Phe His Gly
705                 710                 715                 720

tat gaa gat tta atc gaa tcc att ttc tat caa aga gga cat gat ggt      2208
Tyr Glu Asp Leu Ile Glu Ser Ile Phe Tyr Gln Arg Gly His Asp Gly
                725                 730                 735

ttg att gtt cat ggt tac cgt gaa gat ggt gac atc acg acg act tat      2256
Leu Ile Val His Gly Tyr Arg Glu Asp Gly Asp Ile Thr Thr Thr Tyr
            740                 745                 750

gat atg cgg gtt tac tct gag ctt gac cgt ttc cac caa gcg att gat      2304
Asp Met Arg Val Tyr Ser Glu Leu Asp Arg Phe His Gln Ala Ile Asp
        755                 760                 765
```

```
gcc atg caa gtt cta tat gtc aac cga aaa gtt aat caa ggt cta gcg      2352
Ala Met Gln Val Leu Tyr Val Asn Arg Lys Val Asn Gln Gly Leu Ala
    770                 775                 780

aaa gct ttc att gac cga atg aaa cgg aca cta gtt aaa cac ttt gaa      2400
Lys Ala Phe Ile Asp Arg Met Lys Arg Thr Leu Val Lys His Phe Glu
785                 790                 795                 800

gtg aca aga aat gaa gga gtt gat att cct gat ttt act gaa tgg gtt      2448
Val Thr Arg Asn Glu Gly Val Asp Ile Pro Asp Phe Thr Glu Trp Val
                805                 810                 815

tgg tcg gat tta aag aaa tag                                          2469
Trp Ser Asp Leu Lys Lys
            820


<210> SEQ ID NO 67
<211> LENGTH: 822
<212> TYPE: PRT
<213> ORGANISM: Lactococcus lactis

<400> SEQUENCE: 67

Met Thr Glu Tyr Asn Ser Glu Ala Tyr Leu Lys Lys Leu Asp Lys Trp
1               5                   10                  15

Trp Arg Ala Ala Thr Tyr Leu Gly Ala Gly Met Ile Phe Leu Lys Glu
            20                  25                  30

Asn Pro Leu Phe Ser Val Thr Gly Thr Pro Ile Lys Ala Glu Asn Leu
        35                  40                  45

Lys Ala Asn Pro Ile Gly His Trp Gly Thr Val Ser Gly Gln Thr Phe
    50                  55                  60

Leu Tyr Ala His Ala Asn Arg Leu Ile Asn Lys Tyr Asp Gln Lys Met
65                  70                  75                  80

Phe Tyr Met Gly Gly Pro Gly His Gly Gly Gln Ala Met Val Val Pro
                85                  90                  95

Ser Tyr Leu Asp Gly Ser Tyr Thr Glu Ala Tyr Pro Glu Ile Thr Gln
            100                 105                 110

Asp Leu Glu Gly Met Ser Arg Leu Phe Lys Arg Phe Ser Phe Pro Gly
        115                 120                 125

Gly Ile Gly Ser His Met Thr Ala Gln Thr Pro Gly Ser Leu His Glu
    130                 135                 140

Gly Gly Glu Leu Gly Tyr Val Leu Ser His Ala Thr Gly Ala Ile Leu
145                 150                 155                 160

Asp Gln Pro Glu Gln Ile Ala Phe Ala Val Val Gly Asp Gly Glu Ala
                165                 170                 175

Glu Thr Gly Pro Leu Met Thr Ser Trp His Ser Ile Lys Phe Ile Asn
            180                 185                 190

Pro Lys Asn Asp Gly Ala Ile Leu Pro Ile Leu Asp Leu Asn Gly Phe
        195                 200                 205

Lys Ile Ser Asn Pro Thr Leu Phe Ala Arg Thr Ser Asp Val Asp Ile
    210                 215                 220

Arg Lys Phe Phe Glu Gly Leu Gly Tyr Ser Pro Arg Tyr Ile Glu Asn
225                 230                 235                 240

Asp Asp Ile His Asp Tyr Met Ala Tyr His Lys Leu Ala Ala Glu Val
                245                 250                 255

Phe Asp Lys Ala Ile Glu Asp Ile His Gln Ile Gln Lys Asp Ala Arg
            260                 265                 270

Glu Asp Asn Arg Tyr Gln Asn Gly Glu Ile Pro Ala Trp Pro Ile Val
        275                 280                 285

Ile Ala Arg Leu Pro Lys Gly Trp Gly Gly Pro Arg Tyr Asn Asp Trp
    290                 295                 300
```

```
Ser Gly Pro Lys Phe Asp Gly Lys Gly Met Pro Ile Glu His Ser Phe
305                 310                 315                 320

Arg Ala His Gln Val Pro Leu Pro Leu Ser Ser Lys Asn Met Gly Thr
                325                 330                 335

Leu Pro Glu Phe Val Lys Trp Met Thr Ser Tyr Gln Pro Glu Thr Leu
            340                 345                 350

Phe Asn Ala Asp Gly Ser Leu Lys Glu Glu Leu Arg Asp Phe Ala Pro
        355                 360                 365

Lys Gly Glu Met Arg Met Ala Ser Asn Pro Val Thr Asn Gly Gly Val
    370                 375                 380

Asp Ser Ser Asn Leu Val Leu Pro Asp Trp Gln Glu Phe Ala Asn Pro
385                 390                 395                 400

Ile Ser Glu Asn Asn Arg Gly Lys Leu Leu Pro Asp Thr Asn Asp Asn
                405                 410                 415

Met Asp Met Asn Val Leu Ser Lys Tyr Phe Ala Glu Ile Val Lys Leu
            420                 425                 430

Asn Pro Thr Arg Phe Arg Leu Phe Gly Pro Asp Glu Thr Met Ser Asn
        435                 440                 445

Arg Phe Trp Glu Met Phe Lys Val Thr Asn Arg Gln Trp Met Gln Val
    450                 455                 460

Ile Lys Asn Pro Asn Asp Glu Phe Ile Ser Pro Glu Gly Arg Ile Ile
465                 470                 475                 480

Asp Ser Gln Leu Ser Glu His Gln Ala Glu Gly Trp Leu Glu Gly Tyr
                485                 490                 495

Thr Leu Thr Gly Arg Thr Gly Ala Phe Ala Ser Tyr Glu Ser Phe Leu
            500                 505                 510

Arg Val Val Asp Ser Met Leu Thr Gln His Phe Lys Trp Ile Arg Gln
        515                 520                 525

Ala Ala Asp Gln Lys Trp Arg His Asp Tyr Pro Ser Leu Asn Val Ile
    530                 535                 540

Ser Thr Ser Thr Val Phe Gln Gln Asp His Asn Gly Tyr Thr His Gln
545                 550                 555                 560

Asp Pro Gly Met Leu Thr His Leu Ala Glu Lys Lys Ser Asp Phe Ile
                565                 570                 575

Arg Gln Tyr Leu Pro Ala Asp Gly Asn Thr Leu Leu Ala Val Phe Asp
            580                 585                 590

Arg Ala Phe Gln Asp Arg Ser Lys Ile Asn His Ile Val Ala Ser Lys
        595                 600                 605

Gln Pro Arg Gln Gln Trp Phe Thr Lys Glu Glu Ala Glu Lys Leu Ala
    610                 615                 620

Thr Asp Gly Ile Ala Thr Ile Asp Trp Ala Ser Thr Ala Lys Asp Gly
625                 630                 635                 640

Glu Ala Val Asp Leu Val Phe Ala Ser Ala Gly Ala Glu Pro Thr Ile
                645                 650                 655

Glu Thr Leu Ala Ala Leu His Leu Val Asn Glu Val Phe Pro Gln Ala
            660                 665                 670

Lys Phe Arg Tyr Val Asn Val Val Glu Leu Gly Arg Leu Gln Lys Lys
        675                 680                 685

Lys Gly Ala Leu Asn Gln Glu Arg Glu Leu Ser Asp Glu Glu Phe Glu
    690                 695                 700

Lys Tyr Phe Gly Pro Ser Gly Thr Pro Val Ile Phe Gly Phe His Gly
705                 710                 715                 720

Tyr Glu Asp Leu Ile Glu Ser Ile Phe Tyr Gln Arg Gly His Asp Gly
```

```
                725                 730                 735

Leu Ile Val His Gly Tyr Arg Glu Asp Gly Asp Ile Thr Thr Thr Tyr
            740                 745                 750

Asp Met Arg Val Tyr Ser Glu Leu Asp Arg Phe His Gln Ala Ile Asp
        755                 760                 765

Ala Met Gln Val Leu Tyr Val Asn Arg Lys Val Asn Gln Gly Leu Ala
    770                 775                 780

Lys Ala Phe Ile Asp Arg Met Lys Arg Thr Leu Val Lys His Phe Glu
785                 790                 795                 800

Val Thr Arg Asn Glu Gly Val Asp Ile Pro Asp Phe Thr Glu Trp Val
                805                 810                 815

Trp Ser Asp Leu Lys Lys
            820


<210> SEQ ID NO 68
<211> LENGTH: 2406
<212> TYPE: DNA
<213> ORGANISM: Lactobacillus johnsonii
<220> FEATURE:
<221> NAME/KEY: CDS
<222> LOCATION: (1)..(2406)
<223> OTHER INFORMATION: xpk

<400> SEQUENCE: 68

atg gca gta aat tac gat tct caa gaa tac tta aag agt gtt gac gca       48
Met Ala Val Asn Tyr Asp Ser Gln Glu Tyr Leu Lys Ser Val Asp Ala
1               5                   10                  15

tac tgg cgt gca gct aac tac tta tca gtg gga caa tta ttt tta atg       96
Tyr Trp Arg Ala Ala Asn Tyr Leu Ser Val Gly Gln Leu Phe Leu Met
            20                  25                  30

aat aat cct tta ctt aaa aga gaa tta aag gca gaa gat gta aaa cct      144
Asn Asn Pro Leu Leu Lys Arg Glu Leu Lys Ala Glu Asp Val Lys Pro
        35                  40                  45

aag cca att ggt cac tgg ggt aca att gtg ccg caa aac ttt att tat      192
Lys Pro Ile Gly His Trp Gly Thr Ile Val Pro Gln Asn Phe Ile Tyr
    50                  55                  60

gga cat tta aat cgt gca att aag aaa tat gat tta aac atg ttc tac      240
Gly His Leu Asn Arg Ala Ile Lys Lys Tyr Asp Leu Asn Met Phe Tyr
65                  70                  75                  80

att gaa ggt tct ggt cac ggt ggt caa gta atg gta tcg aac tca tat      288
Ile Glu Gly Ser Gly His Gly Gly Gln Val Met Val Ser Asn Ser Tyr
                85                  90                  95

tta gat ggt tct tat act gaa cgc tac cca gaa att act caa gat gaa      336
Leu Asp Gly Ser Tyr Thr Glu Arg Tyr Pro Glu Ile Thr Gln Asp Glu
            100                 105                 110

aag gga atg gct aag tta ttt aag caa ttt agt ttt cca ggt gga gtt      384
Lys Gly Met Ala Lys Leu Phe Lys Gln Phe Ser Phe Pro Gly Gly Val
        115                 120                 125

gcg tct cat gct gct cca gaa act cct gga tca atc cat gaa ggt gga      432
Ala Ser His Ala Ala Pro Glu Thr Pro Gly Ser Ile His Glu Gly Gly
    130                 135                 140

gaa tta ggc tac tca cta tct cat ggt gtt ggt gca att tta gac aat      480
Glu Leu Gly Tyr Ser Leu Ser His Gly Val Gly Ala Ile Leu Asp Asn
145                 150                 155                 160

cca gat gta att gct gca gtt gaa att ggt gac ggt gaa tca gag act      528
Pro Asp Val Ile Ala Ala Val Glu Ile Gly Asp Gly Glu Ser Glu Thr
                165                 170                 175

ggt cca ctt gct act tct tgg ttt tca agt aag ttc att aat cca att      576
Gly Pro Leu Ala Thr Ser Trp Phe Ser Ser Lys Phe Ile Asn Pro Ile
            180                 185                 190
```

-continued

```
aaa gat ggt gca gtt att cct atc ttg caa atc aat ggc ttt aag att       624
Lys Asp Gly Ala Val Ile Pro Ile Leu Gln Ile Asn Gly Phe Lys Ile
        195                 200                 205

tct aac cca act atc gtt tct aga atg agt gac gaa gac tta act aag       672
Ser Asn Pro Thr Ile Val Ser Arg Met Ser Asp Glu Asp Leu Thr Lys
    210                 215                 220

tac ttt gaa gga atg ggt tgg aag cca tac ttt gtt tct gca tat aaa       720
Tyr Phe Glu Gly Met Gly Trp Lys Pro Tyr Phe Val Ser Ala Tyr Lys
225                 230                 235                 240

gac ggt gaa ttt aat ggg tat aaa gac cac atg gaa gtt cac caa gaa       768
Asp Gly Glu Phe Asn Gly Tyr Lys Asp His Met Glu Val His Gln Glu
                245                 250                 255

atg gca aag aca atg gac gaa gtt gtt gaa gaa att aaa gct att caa       816
Met Ala Lys Thr Met Asp Glu Val Val Glu Glu Ile Lys Ala Ile Gln
            260                 265                 270

aag cat gcg cgt gaa aac aat gat gat tcc tta gtg aag tgg cca atg       864
Lys His Ala Arg Glu Asn Asn Asp Asp Ser Leu Val Lys Trp Pro Met
        275                 280                 285

att gtc ttt aga gta cct aag ggt tgg acg ggt cca aaa ttt gat cta       912
Ile Val Phe Arg Val Pro Lys Gly Trp Thr Gly Pro Lys Phe Asp Leu
    290                 295                 300

gat ggc aat cca att gaa aat agt ttc cgt gct cac caa att cca att       960
Asp Gly Asn Pro Ile Glu Asn Ser Phe Arg Ala His Gln Ile Pro Ile
305                 310                 315                 320

cct gtt gct caa gat gac atg aat cat aaa gaa atg ctt act gat tgg      1008
Pro Val Ala Gln Asp Asp Met Asn His Lys Glu Met Leu Thr Asp Trp
                325                 330                 335

atg gaa agt tat aag cca gaa gaa tta ttc aat gaa gat ggc tca cca      1056
Met Glu Ser Tyr Lys Pro Glu Glu Leu Phe Asn Glu Asp Gly Ser Pro
            340                 345                 350

aaa gat atc gtt aaa gaa aat acc tta tca ggc gac caa aga atg gct      1104
Lys Asp Ile Val Lys Glu Asn Thr Leu Ser Gly Asp Gln Arg Met Ala
        355                 360                 365

atg aat cca gta act aat ggt ggg att gat cca aaa gtc tta aat atg      1152
Met Asn Pro Val Thr Asn Gly Gly Ile Asp Pro Lys Val Leu Asn Met
    370                 375                 380

cct gac tat cgc gac ttt gca att aaa ttt gat aag cct gga tct gtt      1200
Pro Asp Tyr Arg Asp Phe Ala Ile Lys Phe Asp Lys Pro Gly Ser Val
385                 390                 395                 400

gaa aaa caa gat atg gcc gaa tgg gca aaa tat tta gac aag atg tct      1248
Glu Lys Gln Asp Met Ala Glu Trp Ala Lys Tyr Leu Asp Lys Met Ser
                405                 410                 415

gaa ttg aac cca act aat ttc cgt ggt ttt ggt cct gat gaa act aaa      1296
Glu Leu Asn Pro Thr Asn Phe Arg Gly Phe Gly Pro Asp Glu Thr Lys
            420                 425                 430

tct aat cgt tta ttc caa ctt tta gat aat caa aaa cgt caa tgg atg      1344
Ser Asn Arg Leu Phe Gln Leu Leu Asp Asn Gln Lys Arg Gln Trp Met
        435                 440                 445

gaa agt att cat act cca aac gat gaa aac ttg gct cac gaa ggt cgt      1392
Glu Ser Ile His Thr Pro Asn Asp Glu Asn Leu Ala His Glu Gly Arg
    450                 455                 460

gta att gac tca caa ttg tca gaa cac caa gat gaa ggt tgg ctt gaa      1440
Val Ile Asp Ser Gln Leu Ser Glu His Gln Asp Glu Gly Trp Leu Glu
465                 470                 475                 480

gga tat gta tta act ggt cgt cac gga ttc ttt gct act tat gaa gca      1488
Gly Tyr Val Leu Thr Gly Arg His Gly Phe Phe Ala Thr Tyr Glu Ala
                485                 490                 495

ttt ggt cgt gta gtt gat tca atg ctt acg caa cat atg aaa tgg ttg      1536
Phe Gly Arg Val Val Asp Ser Met Leu Thr Gln His Met Lys Trp Leu
            500                 505                 510
```

-continued

```
aga aaa gct aaa gag caa gct tgg aga cat gat tat cca gcc tta aac      1584
Arg Lys Ala Lys Glu Gln Ala Trp Arg His Asp Tyr Pro Ala Leu Asn
        515                 520                 525

tta gtt gat act tca act gtt ttc cag caa gat cac aat ggt tat act      1632
Leu Val Asp Thr Ser Thr Val Phe Gln Gln Asp His Asn Gly Tyr Thr
    530                 535                 540

cac caa gat cca ggt atg tta act cat ttg tat gaa aag aat cgt cca      1680
His Gln Asp Pro Gly Met Leu Thr His Leu Tyr Glu Lys Asn Arg Pro
545                 550                 555                 560

gat tta att cac gaa tac tta cca gca gat act aat tca ctt ctt gct      1728
Asp Leu Ile His Glu Tyr Leu Pro Ala Asp Thr Asn Ser Leu Leu Ala
                565                 570                 575

gta tct gat aag gca ttt aga gat cgc gaa tgc atc aat gtt tta gta      1776
Val Ser Asp Lys Ala Phe Arg Asp Arg Glu Cys Ile Asn Val Leu Val
            580                 585                 590

act tct aaa caa cct cgt cct cag tgg ttc tca att gaa gaa gct aaa      1824
Thr Ser Lys Gln Pro Arg Pro Gln Trp Phe Ser Ile Glu Glu Ala Lys
        595                 600                 605

aaa ttg gtt gat aag ggt ctt ggt tat gtt gac tgg gca tca act gat      1872
Lys Leu Val Asp Lys Gly Leu Gly Tyr Val Asp Trp Ala Ser Thr Asp
    610                 615                 620

aag ggc gct aag cca gat gtt gtt ttt gct tca act ggt act gaa cca      1920
Lys Gly Ala Lys Pro Asp Val Val Phe Ala Ser Thr Gly Thr Glu Pro
625                 630                 635                 640

aca att gaa tct tta gct gcc att gac tta ctt cat aag aaa ttc cca      1968
Thr Ile Glu Ser Leu Ala Ala Ile Asp Leu Leu His Lys Lys Phe Pro
                645                 650                 655

gac tta aag att cgc tat att aat gta att gat gtt atg aag tta atg      2016
Asp Leu Lys Ile Arg Tyr Ile Asn Val Ile Asp Val Met Lys Leu Met
            660                 665                 670

tcc cca gaa aag aat cca aat gca atc agt aat gaa gaa ttc aac cgt      2064
Ser Pro Glu Lys Asn Pro Asn Ala Ile Ser Asn Glu Glu Phe Asn Arg
        675                 680                 685

ctt ttc cct aaa ggt aca cca gtt atc ttt gca tgg cat gga ttt aag      2112
Leu Phe Pro Lys Gly Thr Pro Val Ile Phe Ala Trp His Gly Phe Lys
    690                 695                 700

cca atg atg gaa tca att tgg ttt gat cgc ggc cgt ggt aaa gat gat      2160
Pro Met Met Glu Ser Ile Trp Phe Asp Arg Gly Arg Gly Lys Asp Asp
705                 710                 715                 720

gtt cat att cat ggc tat gaa gaa aat ggt gac att act act cct ttt      2208
Val His Ile His Gly Tyr Glu Glu Asn Gly Asp Ile Thr Thr Pro Phe
                725                 730                 735

gat atg cgt gtc tta aac cac atg gat cgc tat gac tta gca aaa gat      2256
Asp Met Arg Val Leu Asn His Met Asp Arg Tyr Asp Leu Ala Lys Asp
            740                 745                 750

gta gta gaa agt att cct gag cta aat gaa aag aat gcg gat ttc att      2304
Val Val Glu Ser Ile Pro Glu Leu Asn Glu Lys Asn Ala Asp Phe Ile
        755                 760                 765

gat gag atg gat agc ttg ctt gct aaa cac cat caa tat atc cgt gat      2352
Asp Glu Met Asp Ser Leu Leu Ala Lys His His Gln Tyr Ile Arg Asp
    770                 775                 780

aac ggt aaa gat atg cct gaa gtt act gaa tgg caa tgg aat ggt tta      2400
Asn Gly Lys Asp Met Pro Glu Val Thr Glu Trp Gln Trp Asn Gly Leu
785                 790                 795                 800

aaa taa                                                              2406
Lys
```

<210> SEQ ID NO 69
<211> LENGTH: 801
<212> TYPE: PRT
<213> ORGANISM: Lactobacillus johnsonii -continued

<400> SEQUENCE: 69

```
Met Ala Val Asn Tyr Asp Ser Gln Glu Tyr Leu Lys Ser Val Asp Ala
1               5                   10                  15

Tyr Trp Arg Ala Ala Asn Tyr Leu Ser Val Gly Gln Leu Phe Leu Met
            20                  25                  30

Asn Asn Pro Leu Leu Lys Arg Glu Leu Lys Ala Glu Asp Val Lys Pro
        35                  40                  45

Lys Pro Ile Gly His Trp Gly Thr Ile Val Pro Gln Asn Phe Ile Tyr
    50                  55                  60

Gly His Leu Asn Arg Ala Ile Lys Lys Tyr Asp Leu Asn Met Phe Tyr
65                  70                  75                  80

Ile Glu Gly Ser Gly His Gly Gly Gln Val Met Val Ser Asn Ser Tyr
                85                  90                  95

Leu Asp Gly Ser Tyr Thr Glu Arg Tyr Pro Glu Ile Thr Gln Asp Glu
            100                 105                 110

Lys Gly Met Ala Lys Leu Phe Lys Gln Phe Ser Phe Pro Gly Gly Val
        115                 120                 125

Ala Ser His Ala Ala Pro Glu Thr Pro Gly Ser Ile His Glu Gly Gly
    130                 135                 140

Glu Leu Gly Tyr Ser Leu Ser His Gly Val Gly Ala Ile Leu Asp Asn
145                 150                 155                 160

Pro Asp Val Ile Ala Ala Val Glu Ile Gly Asp Gly Glu Ser Glu Thr
                165                 170                 175

Gly Pro Leu Ala Thr Ser Trp Phe Ser Ser Lys Phe Ile Asn Pro Ile
            180                 185                 190

Lys Asp Gly Ala Val Ile Pro Ile Leu Gln Ile Asn Gly Phe Lys Ile
        195                 200                 205

Ser Asn Pro Thr Ile Val Ser Arg Met Ser Asp Glu Asp Leu Thr Lys
    210                 215                 220

Tyr Phe Glu Gly Met Gly Trp Lys Pro Tyr Phe Val Ser Ala Tyr Lys
225                 230                 235                 240

Asp Gly Glu Phe Asn Gly Tyr Lys Asp His Met Glu Val His Gln Glu
                245                 250                 255

Met Ala Lys Thr Met Asp Glu Val Val Glu Glu Ile Lys Ala Ile Gln
            260                 265                 270

Lys His Ala Arg Glu Asn Asn Asp Asp Ser Leu Val Lys Trp Pro Met
        275                 280                 285

Ile Val Phe Arg Val Pro Lys Gly Trp Thr Gly Pro Lys Phe Asp Leu
    290                 295                 300

Asp Gly Asn Pro Ile Glu Asn Ser Phe Arg Ala His Gln Ile Pro Ile
305                 310                 315                 320

Pro Val Ala Gln Asp Asp Met Asn His Lys Glu Met Leu Thr Asp Trp
                325                 330                 335

Met Glu Ser Tyr Lys Pro Glu Glu Leu Phe Asn Glu Asp Gly Ser Pro
            340                 345                 350

Lys Asp Ile Val Lys Glu Asn Thr Leu Ser Gly Asp Gln Arg Met Ala
        355                 360                 365

Met Asn Pro Val Thr Asn Gly Gly Ile Asp Pro Lys Val Leu Asn Met
    370                 375                 380

Pro Asp Tyr Arg Asp Phe Ala Ile Lys Phe Asp Lys Pro Gly Ser Val
385                 390                 395                 400

Glu Lys Gln Asp Met Ala Glu Trp Ala Lys Tyr Leu Asp Lys Met Ser
                405                 410                 415
```

```
Glu Leu Asn Pro Thr Asn Phe Arg Gly Phe Gly Pro Asp Glu Thr Lys
            420                 425                 430

Ser Asn Arg Leu Phe Gln Leu Leu Asp Asn Gln Lys Arg Gln Trp Met
        435                 440                 445

Glu Ser Ile His Thr Pro Asn Asp Glu Asn Leu Ala His Glu Gly Arg
    450                 455                 460

Val Ile Asp Ser Gln Leu Ser Glu His Gln Asp Glu Gly Trp Leu Glu
465                 470                 475                 480

Gly Tyr Val Leu Thr Gly Arg His Gly Phe Phe Ala Thr Tyr Glu Ala
                485                 490                 495

Phe Gly Arg Val Val Asp Ser Met Leu Thr Gln His Met Lys Trp Leu
            500                 505                 510

Arg Lys Ala Lys Glu Gln Ala Trp Arg His Asp Tyr Pro Ala Leu Asn
        515                 520                 525

Leu Val Asp Thr Ser Thr Val Phe Gln Gln Asp His Asn Gly Tyr Thr
    530                 535                 540

His Gln Asp Pro Gly Met Leu Thr His Leu Tyr Glu Lys Asn Arg Pro
545                 550                 555                 560

Asp Leu Ile His Glu Tyr Leu Pro Ala Asp Thr Asn Ser Leu Leu Ala
                565                 570                 575

Val Ser Asp Lys Ala Phe Arg Asp Arg Glu Cys Ile Asn Val Leu Val
            580                 585                 590

Thr Ser Lys Gln Pro Arg Pro Gln Trp Phe Ser Ile Glu Glu Ala Lys
        595                 600                 605

Lys Leu Val Asp Lys Gly Leu Gly Tyr Val Asp Trp Ala Ser Thr Asp
    610                 615                 620

Lys Gly Ala Lys Pro Asp Val Val Phe Ala Ser Thr Gly Thr Glu Pro
625                 630                 635                 640

Thr Ile Glu Ser Leu Ala Ala Ile Asp Leu Leu His Lys Lys Phe Pro
                645                 650                 655

Asp Leu Lys Ile Arg Tyr Ile Asn Val Ile Asp Val Met Lys Leu Met
            660                 665                 670

Ser Pro Glu Lys Asn Pro Asn Ala Ile Ser Asn Glu Glu Phe Asn Arg
        675                 680                 685

Leu Phe Pro Lys Gly Thr Pro Val Ile Phe Ala Trp His Gly Phe Lys
    690                 695                 700

Pro Met Met Glu Ser Ile Trp Phe Asp Arg Gly Arg Gly Lys Asp Asp
705                 710                 715                 720

Val His Ile His Gly Tyr Glu Glu Asn Gly Asp Ile Thr Thr Pro Phe
                725                 730                 735

Asp Met Arg Val Leu Asn His Met Asp Arg Tyr Asp Leu Ala Lys Asp
            740                 745                 750

Val Val Glu Ser Ile Pro Glu Leu Asn Glu Lys Asn Ala Asp Phe Ile
        755                 760                 765

Asp Glu Met Asp Ser Leu Leu Ala Lys His His Gln Tyr Ile Arg Asp
    770                 775                 780

Asn Gly Lys Asp Met Pro Glu Val Thr Glu Trp Gln Trp Asn Gly Leu
785                 790                 795                 800

Lys
```

<210> SEQ ID NO 70
<211> LENGTH: 2400
<212> TYPE: DNA
<213> ORGANISM: Lactobacillus acidophilus -continued

<220> FEATURE:
<221> NAME/KEY: CDS
<222> LOCATION: (1)..(2400)

<400> SEQUENCE: 70

```
atg aca gtt aat tac gat tcc aaa gat tac tta aag agc gtt gac gca       48
Met Thr Val Asn Tyr Asp Ser Lys Asp Tyr Leu Lys Ser Val Asp Ala
1               5                   10                  15

tat tgg cgt gca gct aat tat ttg tca gtt gga caa tta ttt tta atg       96
Tyr Trp Arg Ala Ala Asn Tyr Leu Ser Val Gly Gln Leu Phe Leu Met
            20                  25                  30

aaa aat ccg ttg tta aag aaa cct tta aca gct gaa gat gta aaa cct      144
Lys Asn Pro Leu Leu Lys Lys Pro Leu Thr Ala Glu Asp Val Lys Pro
        35                  40                  45

aag cca atc ggt cac tgg ggt act att gct cca caa aac ttt att tat      192
Lys Pro Ile Gly His Trp Gly Thr Ile Ala Pro Gln Asn Phe Ile Tyr
    50                  55                  60

gct cac tta aat cgt gcg ctt aaa aaa tat gac ttg gat atg ttc tat      240
Ala His Leu Asn Arg Ala Leu Lys Lys Tyr Asp Leu Asp Met Phe Tyr
65                  70                  75                  80

att gaa ggt tca ggt cac ggt ggc caa gtg atg gtt tca aat tca tat      288
Ile Glu Gly Ser Gly His Gly Gly Gln Val Met Val Ser Asn Ser Tyr
                85                  90                  95

ctt gat ggt tca tat act gaa cgt tat cca gaa att acc caa gat gaa      336
Leu Asp Gly Ser Tyr Thr Glu Arg Tyr Pro Glu Ile Thr Gln Asp Glu
            100                 105                 110

aag ggt atg gct aaa ttg ttt aag cgc ttt agt ttc cca ggt ggt gta      384
Lys Gly Met Ala Lys Leu Phe Lys Arg Phe Ser Phe Pro Gly Gly Val
        115                 120                 125

gct tct cac gct gct cct gaa act cca ggt tct att cat gaa ggt ggg      432
Ala Ser His Ala Ala Pro Glu Thr Pro Gly Ser Ile His Glu Gly Gly
    130                 135                 140

gaa tta gga tac gca ctt tca cat ggg gta ggt gct att tta gac aat      480
Glu Leu Gly Tyr Ala Leu Ser His Gly Val Gly Ala Ile Leu Asp Asn
145                 150                 155                 160

cca gat gta att gct gcc gtt gaa att ggt gat ggt gaa gca gaa act      528
Pro Asp Val Ile Ala Ala Val Glu Ile Gly Asp Gly Glu Ala Glu Thr
                165                 170                 175

ggt cca ctt gca gct agc tgg ttc agt gac aag ttt att aat cca att      576
Gly Pro Leu Ala Ala Ser Trp Phe Ser Asp Lys Phe Ile Asn Pro Ile
            180                 185                 190

aag gat ggt gca gtt tta cca att ctt caa att aat ggt ttc aag att      624
Lys Asp Gly Ala Val Leu Pro Ile Leu Gln Ile Asn Gly Phe Lys Ile
        195                 200                 205

tct aac cca act atc gtt tca aga atg agc gat gaa gaa tta act gaa      672
Ser Asn Pro Thr Ile Val Ser Arg Met Ser Asp Glu Glu Leu Thr Glu
    210                 215                 220

tac ttc cgt ggc atg ggt tgg gat ccg cac ttt gtt tca gta ttt aag      720
Tyr Phe Arg Gly Met Gly Trp Asp Pro His Phe Val Ser Val Phe Lys
225                 230                 235                 240

ggt ggc cgc ttt gac ggt gaa aag gat cca atg caa gtc cac gaa gaa      768
Gly Gly Arg Phe Asp Gly Glu Lys Asp Pro Met Gln Val His Glu Glu
                245                 250                 255

atg gct aaa acc atg gac gaa gta att gaa gaa att aag gct att caa      816
Met Ala Lys Thr Met Asp Glu Val Ile Glu Glu Ile Lys Ala Ile Gln
            260                 265                 270

aag cat gct cgt gaa aat aat gat gct act ttg cca cat tgg cca ttg      864
Lys His Ala Arg Glu Asn Asn Asp Ala Thr Leu Pro His Trp Pro Leu
        275                 280                 285

att atc ttc caa tgt cca aag ggc tgg acc ggt cca aag aag gat ctt      912
Ile Ile Phe Gln Cys Pro Lys Gly Trp Thr Gly Pro Lys Lys Asp Leu
```

```
    290                 295                 300

gac ggc aat cca att gaa aac tca ttt aga gca cac caa att cca att      960
Asp Gly Asn Pro Ile Glu Asn Ser Phe Arg Ala His Gln Ile Pro Ile
305                 310                 315                 320

cct gtc tca caa tac gat atg aaa cat gtt gat atg ttg act gat tgg     1008
Pro Val Ser Gln Tyr Asp Met Lys His Val Asp Met Leu Thr Asp Trp
                325                 330                 335

ctt gaa agt tat aag cca aac gaa tta ttc aac gaa gat ggt tca cca     1056
Leu Glu Ser Tyr Lys Pro Asn Glu Leu Phe Asn Glu Asp Gly Ser Pro
            340                 345                 350

aag gaa att gtt act gaa aac act gct aag ggt gat caa cgt atg gca     1104
Lys Glu Ile Val Thr Glu Asn Thr Ala Lys Gly Asp Gln Arg Met Ala
        355                 360                 365

atg aat ccg atc act aat ggt ggt aag gat cct aaa cga ttg aac cta     1152
Met Asn Pro Ile Thr Asn Gly Gly Lys Asp Pro Lys Arg Leu Asn Leu
    370                 375                 380

cca gat tat cgc aac ttt gca ctt aag ttt gac aag cca ggt tca gtt     1200
Pro Asp Tyr Arg Asn Phe Ala Leu Lys Phe Asp Lys Pro Gly Ser Val
385                 390                 395                 400

gaa gca caa gac atg gtt gaa tgg gct aaa tat tta aac gaa gtt gct     1248
Glu Ala Gln Asp Met Val Glu Trp Ala Lys Tyr Leu Asn Glu Val Ala
                405                 410                 415

aaa ctt aac cca act act ttc cgt ggc ttt ggt cct gat gaa tct aaa     1296
Lys Leu Asn Pro Thr Thr Phe Arg Gly Phe Gly Pro Asp Glu Ser Lys
            420                 425                 430

tca aac cgt tta ttt aaa ctt tta gat gat caa aag cgt caa tgg gaa     1344
Ser Asn Arg Leu Phe Lys Leu Leu Asp Asp Gln Lys Arg Gln Trp Glu
        435                 440                 445

cct gaa gtt cat gaa cca aat gat gaa aac ttg gca cca agt ggc cgc     1392
Pro Glu Val His Glu Pro Asn Asp Glu Asn Leu Ala Pro Ser Gly Arg
    450                 455                 460

gtt atc gat tca caa tta tca gaa cac caa gac gaa ggc ttc ctt gaa     1440
Val Ile Asp Ser Gln Leu Ser Glu His Gln Asp Glu Gly Phe Leu Glu
465                 470                 475                 480

ggc tac gtt tta act ggt cgt cac ggc ttc ttt gca acc tac gaa gca     1488
Gly Tyr Val Leu Thr Gly Arg His Gly Phe Phe Ala Thr Tyr Glu Ala
                485                 490                 495

ttt ggt cgt gta gta gat tcg atg ctt act caa cat atg aag tgg ctt     1536
Phe Gly Arg Val Val Asp Ser Met Leu Thr Gln His Met Lys Trp Leu
            500                 505                 510

aga aaa gct aaa gaa caa tat tgg cgt cat gat tat cca tca ctt aac     1584
Arg Lys Ala Lys Glu Gln Tyr Trp Arg His Asp Tyr Pro Ser Leu Asn
        515                 520                 525

ttt gtt gct act tca aca gta ttc caa caa gat cac aat ggt tac act     1632
Phe Val Ala Thr Ser Thr Val Phe Gln Gln Asp His Asn Gly Tyr Thr
    530                 535                 540

cac caa gat cca ggc att tta act cac tta tat gaa aag aat cgt cca     1680
His Gln Asp Pro Gly Ile Leu Thr His Leu Tyr Glu Lys Asn Arg Pro
545                 550                 555                 560

gat tta gtt cat gaa tac ttg cca tca gat act aat act tta ctt gct     1728
Asp Leu Val His Glu Tyr Leu Pro Ser Asp Thr Asn Thr Leu Leu Ala
                565                 570                 575

gta ggt aac aag gca ttt act gat cgt gaa tgt att aat gtt tta gta     1776
Val Gly Asn Lys Ala Phe Thr Asp Arg Glu Cys Ile Asn Val Leu Val
            580                 585                 590

act tca aag caa cct cgt cca caa tgg ttc tca att gag gaa gca caa     1824
Thr Ser Lys Gln Pro Arg Pro Gln Trp Phe Ser Ile Glu Glu Ala Gln
        595                 600                 605

aag tta gtt gat aaa ggt tta agt tac att gat tgg gct tca act gat     1872
Lys Leu Val Asp Lys Gly Leu Ser Tyr Ile Asp Trp Ala Ser Thr Asp
```

```
    610                 615                 620

aaa ggt gta aaa cca gat att gtc ttt gct tca aca gaa act gaa cca      1920
Lys Gly Val Lys Pro Asp Ile Val Phe Ala Ser Thr Glu Thr Glu Pro
625                 630                 635                 640

aca att gaa act ttg gca gca att gat att ttg cat gac aag ttc cca      1968
Thr Ile Glu Thr Leu Ala Ala Ile Asp Ile Leu His Asp Lys Phe Pro
            645                 650                 655

gat ctt aag att cgc tac att aac gta att gat gtg atg aaa tta atg      2016
Asp Leu Lys Ile Arg Tyr Ile Asn Val Ile Asp Val Met Lys Leu Met
            660                 665                 670

tca cca aag gac aat aag aat ggt att tct gat gaa gaa ttt gat cgc      2064
Ser Pro Lys Asp Asn Lys Asn Gly Ile Ser Asp Glu Glu Phe Asp Arg
        675                 680                 685

tta ttc cca aag gac gtt cct gta atc ttt gca tgg cac ggc tac aag      2112
Leu Phe Pro Lys Asp Val Pro Val Ile Phe Ala Trp His Gly Tyr Lys
    690                 695                 700

agt atg atg gaa tca att tgg ttt gca cgt aac cgt cat aat gta cat      2160
Ser Met Met Glu Ser Ile Trp Phe Ala Arg Asn Arg His Asn Val His
705                 710                 715                 720

att cac tgc tac gaa gaa aac ggt gat att act acc cca ttt gat atg      2208
Ile His Cys Tyr Glu Glu Asn Gly Asp Ile Thr Thr Pro Phe Asp Met
            725                 730                 735

cgt gtt ttg aac cac ctt gac aga ttt gat ctt gcc aaa gat gct gtt      2256
Arg Val Leu Asn His Leu Asp Arg Phe Asp Leu Ala Lys Asp Ala Val
            740                 745                 750

gaa agt gtt gat aaa ttg aag ggc aag aac gct gac ttt atc agt cat      2304
Glu Ser Val Asp Lys Leu Lys Gly Lys Asn Ala Asp Phe Ile Ser His
        755                 760                 765

atg gat gac ttg ctt gaa aag cac cac caa tac att cgt gat aat ggt      2352
Met Asp Asp Leu Leu Glu Lys His His Gln Tyr Ile Arg Asp Asn Gly
    770                 775                 780

aaa gat atg cca gaa gtt act gaa tgg aag tgg aag ggc ttg aag taa      2400
Lys Asp Met Pro Glu Val Thr Glu Trp Lys Trp Lys Gly Leu Lys
785                 790                 795


<210> SEQ ID NO 71
<211> LENGTH: 799
<212> TYPE: PRT
<213> ORGANISM: Lactobacillus acidophilus

<400> SEQUENCE: 71

Met Thr Val Asn Tyr Asp Ser Lys Asp Tyr Leu Lys Ser Val Asp Ala
1               5                   10                  15

Tyr Trp Arg Ala Ala Asn Tyr Leu Ser Val Gly Gln Leu Phe Leu Met
            20                  25                  30

Lys Asn Pro Leu Leu Lys Lys Pro Leu Thr Ala Glu Asp Val Lys Pro
        35                  40                  45

Lys Pro Ile Gly His Trp Gly Thr Ile Ala Pro Gln Asn Phe Ile Tyr
    50                  55                  60

Ala His Leu Asn Arg Ala Leu Lys Lys Tyr Asp Leu Asp Met Phe Tyr
65                  70                  75                  80

Ile Glu Gly Ser Gly His Gly Gly Gln Val Met Val Ser Asn Ser Tyr
                85                  90                  95

Leu Asp Gly Ser Tyr Thr Glu Arg Tyr Pro Glu Ile Thr Gln Asp Glu
            100                 105                 110

Lys Gly Met Ala Lys Leu Phe Lys Arg Phe Ser Phe Pro Gly Gly Val
        115                 120                 125

Ala Ser His Ala Ala Pro Glu Thr Pro Gly Ser Ile His Glu Gly Gly
    130                 135                 140
```

```
Glu Leu Gly Tyr Ala Leu Ser His Gly Val Gly Ala Ile Leu Asp Asn
145                 150                 155                 160

Pro Asp Val Ile Ala Ala Val Glu Ile Gly Asp Gly Glu Ala Glu Thr
                165                 170                 175

Gly Pro Leu Ala Ala Ser Trp Phe Ser Asp Lys Phe Ile Asn Pro Ile
            180                 185                 190

Lys Asp Gly Ala Val Leu Pro Ile Leu Gln Ile Asn Gly Phe Lys Ile
        195                 200                 205

Ser Asn Pro Thr Ile Val Ser Arg Met Ser Asp Glu Glu Leu Thr Glu
    210                 215                 220

Tyr Phe Arg Gly Met Gly Trp Asp Pro His Phe Val Ser Val Phe Lys
225                 230                 235                 240

Gly Gly Arg Phe Asp Gly Glu Lys Asp Pro Met Gln Val His Glu Glu
                245                 250                 255

Met Ala Lys Thr Met Asp Glu Val Ile Glu Glu Ile Lys Ala Ile Gln
            260                 265                 270

Lys His Ala Arg Glu Asn Asn Asp Ala Thr Leu Pro His Trp Pro Leu
        275                 280                 285

Ile Ile Phe Gln Cys Pro Lys Gly Trp Thr Gly Pro Lys Lys Asp Leu
    290                 295                 300

Asp Gly Asn Pro Ile Glu Asn Ser Phe Arg Ala His Gln Ile Pro Ile
305                 310                 315                 320

Pro Val Ser Gln Tyr Asp Met Lys His Val Asp Met Leu Thr Asp Trp
                325                 330                 335

Leu Glu Ser Tyr Lys Pro Asn Glu Leu Phe Asn Glu Asp Gly Ser Pro
            340                 345                 350

Lys Glu Ile Val Thr Glu Asn Thr Ala Lys Gly Asp Gln Arg Met Ala
        355                 360                 365

Met Asn Pro Ile Thr Asn Gly Gly Lys Asp Pro Lys Arg Leu Asn Leu
    370                 375                 380

Pro Asp Tyr Arg Asn Phe Ala Leu Lys Phe Asp Lys Pro Gly Ser Val
385                 390                 395                 400

Glu Ala Gln Asp Met Val Glu Trp Ala Lys Tyr Leu Asn Glu Val Ala
                405                 410                 415

Lys Leu Asn Pro Thr Thr Phe Arg Gly Phe Gly Pro Asp Glu Ser Lys
            420                 425                 430

Ser Asn Arg Leu Phe Lys Leu Leu Asp Asp Gln Lys Arg Gln Trp Glu
        435                 440                 445

Pro Glu Val His Glu Pro Asn Asp Glu Asn Leu Ala Pro Ser Gly Arg
    450                 455                 460

Val Ile Asp Ser Gln Leu Ser Glu His Gln Asp Glu Gly Phe Leu Glu
465                 470                 475                 480

Gly Tyr Val Leu Thr Gly Arg His Gly Phe Phe Ala Thr Tyr Glu Ala
                485                 490                 495

Phe Gly Arg Val Val Asp Ser Met Leu Thr Gln His Met Lys Trp Leu
            500                 505                 510

Arg Lys Ala Lys Glu Gln Tyr Trp Arg His Asp Tyr Pro Ser Leu Asn
        515                 520                 525

Phe Val Ala Thr Ser Thr Val Phe Gln Gln Asp His Asn Gly Tyr Thr
    530                 535                 540

His Gln Asp Pro Gly Ile Leu Thr His Leu Tyr Glu Lys Asn Arg Pro
545                 550                 555                 560

Asp Leu Val His Glu Tyr Leu Pro Ser Asp Thr Asn Thr Leu Leu Ala
```

```
                565                 570                 575

Val Gly Asn Lys Ala Phe Thr Asp Arg Glu Cys Ile Asn Val Leu Val
            580                 585                 590

Thr Ser Lys Gln Pro Arg Pro Gln Trp Phe Ser Ile Glu Glu Ala Gln
        595                 600                 605

Lys Leu Val Asp Lys Gly Leu Ser Tyr Ile Asp Trp Ala Ser Thr Asp
    610                 615                 620

Lys Gly Val Lys Pro Asp Ile Val Phe Ala Ser Thr Glu Thr Glu Pro
625                 630                 635                 640

Thr Ile Glu Thr Leu Ala Ala Ile Asp Ile Leu His Asp Lys Phe Pro
                645                 650                 655

Asp Leu Lys Ile Arg Tyr Ile Asn Val Ile Asp Val Met Lys Leu Met
            660                 665                 670

Ser Pro Lys Asp Asn Lys Asn Gly Ile Ser Asp Glu Glu Phe Asp Arg
        675                 680                 685

Leu Phe Pro Lys Asp Val Pro Val Ile Phe Ala Trp His Gly Tyr Lys
    690                 695                 700

Ser Met Met Glu Ser Ile Trp Phe Ala Arg Asn Arg His Asn Val His
705                 710                 715                 720

Ile His Cys Tyr Glu Glu Asn Gly Asp Ile Thr Thr Pro Phe Asp Met
                725                 730                 735

Arg Val Leu Asn His Leu Asp Arg Phe Asp Leu Ala Lys Asp Ala Val
            740                 745                 750

Glu Ser Val Asp Lys Leu Lys Gly Lys Asn Ala Asp Phe Ile Ser His
        755                 760                 765

Met Asp Asp Leu Leu Glu Lys His His Gln Tyr Ile Arg Asp Asn Gly
    770                 775                 780

Lys Asp Met Pro Glu Val Thr Glu Trp Lys Trp Lys Gly Leu Lys
785                 790                 795


<210> SEQ ID NO 72
<211> LENGTH: 2478
<212> TYPE: DNA
<213> ORGANISM: Bifidobacterium longum
<220> FEATURE:
<221> NAME/KEY: CDS
<222> LOCATION: (1)..(2478)

<400> SEQUENCE: 72

atg acg agt cct gtt att ggc acc cct tgg aag aag ctc aac gct ccg       48
Met Thr Ser Pro Val Ile Gly Thr Pro Trp Lys Lys Leu Asn Ala Pro
1               5                   10                  15

gtt tcc gag gaa gcc ctc gaa ggc gtt gac aag tac tgg cgc gtt gcc       96
Val Ser Glu Glu Ala Leu Glu Gly Val Asp Lys Tyr Trp Arg Val Ala
            20                  25                  30

aac tac ctt tcc atc ggc cag att tat ctg cgt tcc aac ccg ctg atg      144
Asn Tyr Leu Ser Ile Gly Gln Ile Tyr Leu Arg Ser Asn Pro Leu Met
        35                  40                  45

aag gag ccc ttc acc cgc gaa gat gtg aag cac cgt ctg gtg ggc cac      192
Lys Glu Pro Phe Thr Arg Glu Asp Val Lys His Arg Leu Val Gly His
    50                  55                  60

tgg ggc act acc cct ggc ctg aac ttc ctc atc ggc cac atc aac cgt      240
Trp Gly Thr Thr Pro Gly Leu Asn Phe Leu Ile Gly His Ile Asn Arg
65                  70                  75                  80

ttc att gct gac cac ggc cag aac acc gtg atc atc atg ggc ccg ggc      288
Phe Ile Ala Asp His Gly Gln Asn Thr Val Ile Ile Met Gly Pro Gly
                85                  90                  95

cac ggt ggc ccg gcc ggt acc tcc cag tcc tac ctg gac ggc acc tac      336
```

-continued

```
His Gly Gly Pro Ala Gly Thr Ser Gln Ser Tyr Leu Asp Gly Thr Tyr
            100                 105                 110

acc gag acc ttc ccg aag atc acc aag gac gaa gct ggt ctg cag aag      384
Thr Glu Thr Phe Pro Lys Ile Thr Lys Asp Glu Ala Gly Leu Gln Lys
        115                 120                 125

ttc ttc cgt cag ttc tct tac ccg ggc ggc att ccg tcc cac ttc gct      432
Phe Phe Arg Gln Phe Ser Tyr Pro Gly Gly Ile Pro Ser His Phe Ala
    130                 135                 140

ccg gag acc ccg ggc tcc atc cac gag ggt ggt gag ctg ggt tac gct      480
Pro Glu Thr Pro Gly Ser Ile His Glu Gly Gly Glu Leu Gly Tyr Ala
145                 150                 155                 160

ctg tcc cac gct tac ggc gcc atc atg gac aac ccg agc ctg ttt gtc      528
Leu Ser His Ala Tyr Gly Ala Ile Met Asp Asn Pro Ser Leu Phe Val
                165                 170                 175

ccg gcc atc gtc ggc gac ggc gag gct gag acc ggc ccg ctg gct acc      576
Pro Ala Ile Val Gly Asp Gly Glu Ala Glu Thr Gly Pro Leu Ala Thr
            180                 185                 190

ggc tgg cag tcc aac aag ctc gtg aac ccg cgc acc gac ggt atc gtg      624
Gly Trp Gln Ser Asn Lys Leu Val Asn Pro Arg Thr Asp Gly Ile Val
        195                 200                 205

ctg ccg atc ctg cac ctc aac ggc tac aag atc gcc aac ccg acc atc      672
Leu Pro Ile Leu His Leu Asn Gly Tyr Lys Ile Ala Asn Pro Thr Ile
    210                 215                 220

ctg tcc cgc atc tcc gac gaa gag ctc cac gag ttc ttc cac ggc atg      720
Leu Ser Arg Ile Ser Asp Glu Glu Leu His Glu Phe Phe His Gly Met
225                 230                 235                 240

ggt tac gag ccc tac gag ttc gtc gct ggc ttc gat gat gag gac cac      768
Gly Tyr Glu Pro Tyr Glu Phe Val Ala Gly Phe Asp Asp Glu Asp His
                245                 250                 255

atg tcc atc cac cgt cgc ttc gcc gag ctg tgg gag acc atc tgg gac      816
Met Ser Ile His Arg Arg Phe Ala Glu Leu Trp Glu Thr Ile Trp Asp
            260                 265                 270

gag atc tgc gac atc aag gcc acc gct cag acc gac aac gtg cac cgt      864
Glu Ile Cys Asp Ile Lys Ala Thr Ala Gln Thr Asp Asn Val His Arg
        275                 280                 285

ccg ttc tac ccg atg ctg atc ttc cgc acc ccg aag ggc tgg acc tgc      912
Pro Phe Tyr Pro Met Leu Ile Phe Arg Thr Pro Lys Gly Trp Thr Cys
    290                 295                 300

ccg aag tac atc gac ggc aag aag acc gag ggc tcc tgg cgt tcc cac      960
Pro Lys Tyr Ile Asp Gly Lys Lys Thr Glu Gly Ser Trp Arg Ser His
305                 310                 315                 320

cag gtg ccg ctg gct tcc gcc cgc gac acc gag gcc cac ttc gag gtt     1008
Gln Val Pro Leu Ala Ser Ala Arg Asp Thr Glu Ala His Phe Glu Val
                325                 330                 335

ctc aag aac tgg ctc gag tcc tac aag ccg gaa gag ctg ttc gac gcc     1056
Leu Lys Asn Trp Leu Glu Ser Tyr Lys Pro Glu Glu Leu Phe Asp Ala
            340                 345                 350

aac ggt gct gtc aag gac gac gtc ctt gcc ttc atg ccg aag ggc gag     1104
Asn Gly Ala Val Lys Asp Asp Val Leu Ala Phe Met Pro Lys Gly Glu
        355                 360                 365

ctg cgt atc ggt gcc aac ccg aac gcc aac ggt ggt gtg atc cgc aac     1152
Leu Arg Ile Gly Ala Asn Pro Asn Ala Asn Gly Gly Val Ile Arg Asn
    370                 375                 380

gac ctg aag ctg ccg aac ctc gag gac tac gag gtc aag gaa gtg gct     1200
Asp Leu Lys Leu Pro Asn Leu Glu Asp Tyr Glu Val Lys Glu Val Ala
385                 390                 395                 400

gag tac ggc cac ggc tgg ggc cag ctc gag gcc acc cgt acc ctg ggt     1248
Glu Tyr Gly His Gly Trp Gly Gln Leu Glu Ala Thr Arg Thr Leu Gly
                405                 410                 415

gcc tac act cgc gac atc atc aag aac aac ccg cgc gac ttc cgc atc     1296
```

-continued

```
Ala Tyr Thr Arg Asp Ile Ile Lys Asn Asn Pro Arg Asp Phe Arg Ile
            420                 425                 430

ttc gga ccg gat gag acc gct tcc aac cgt ctg cag gct tcc tac gaa     1344
Phe Gly Pro Asp Glu Thr Ala Ser Asn Arg Leu Gln Ala Ser Tyr Glu
        435                 440                 445

gtc acc aac aag cag tgg gat gcc ggc tac atc tcc gac gag gtc gac     1392
Val Thr Asn Lys Gln Trp Asp Ala Gly Tyr Ile Ser Asp Glu Val Asp
    450                 455                 460

gag cac atg cac gtc tcc ggc cag gtc gtt gag cag ctg tcc gag cac     1440
Glu His Met His Val Ser Gly Gln Val Val Glu Gln Leu Ser Glu His
465                 470                 475                 480

cag atg gaa ggc ttc ctc gag gct tac ctg ctg acc ggt cgt cac ggc     1488
Gln Met Glu Gly Phe Leu Glu Ala Tyr Leu Leu Thr Gly Arg His Gly
                485                 490                 495

atc tgg agc tcc tac gag tcc ttc gtc cac gtg atc gac tcc atg ctg     1536
Ile Trp Ser Ser Tyr Glu Ser Phe Val His Val Ile Asp Ser Met Leu
            500                 505                 510

aac cag cac gcc aag tgg ctt gag gct acc gtc cgc gag att ccg tgg     1584
Asn Gln His Ala Lys Trp Leu Glu Ala Thr Val Arg Glu Ile Pro Trp
        515                 520                 525

cgc aag ccg att gcc tcc atg aac ctg ctg gtc tcc tcc cac gtt tgg     1632
Arg Lys Pro Ile Ala Ser Met Asn Leu Leu Val Ser Ser His Val Trp
    530                 535                 540

cgt cag gac cac aac ggc ttc tcc cac cag gat ccg ggt gtc acc tcc     1680
Arg Gln Asp His Asn Gly Phe Ser His Gln Asp Pro Gly Val Thr Ser
545                 550                 555                 560

gtc ctg ctg aac aag tgc ttc cac aac gac cac gtc atc ggc atc tac     1728
Val Leu Leu Asn Lys Cys Phe His Asn Asp His Val Ile Gly Ile Tyr
                565                 570                 575

ttc gcc acc gat gcg aac atg ctg ctg gcc atc gcc gag aag tgc tac     1776
Phe Ala Thr Asp Ala Asn Met Leu Leu Ala Ile Ala Glu Lys Cys Tyr
            580                 585                 590

aag tcc acc aac aag atc aac gcc atc atc gct ggt aag cag cct gct     1824
Lys Ser Thr Asn Lys Ile Asn Ala Ile Ile Ala Gly Lys Gln Pro Ala
        595                 600                 605

gcc acc tgg ctg acc ctg gac gag gct cgt gcc gag ctc gag aag ggt     1872
Ala Thr Trp Leu Thr Leu Asp Glu Ala Arg Ala Glu Leu Glu Lys Gly
    610                 615                 620

gcc gcc gct tgg gat tgg gct tcc acc gcc aag aac aac gat gag gcc     1920
Ala Ala Ala Trp Asp Trp Ala Ser Thr Ala Lys Asn Asn Asp Glu Ala
625                 630                 635                 640

gag gtc gtg ctt gcc gcc gcc ggc gat gtc ccg act cag gag atc atg     1968
Glu Val Val Leu Ala Ala Ala Gly Asp Val Pro Thr Gln Glu Ile Met
                645                 650                 655

gct gct tcc gac aag ctg aag gaa ctg ggc atc aag ttc aag gtt gtg     2016
Ala Ala Ser Asp Lys Leu Lys Glu Leu Gly Ile Lys Phe Lys Val Val
            660                 665                 670

aac gtt gcc gac ctg ctc tcc ctg cag tcc gcc aag gag aac gac gag     2064
Asn Val Ala Asp Leu Leu Ser Leu Gln Ser Ala Lys Glu Asn Asp Glu
        675                 680                 685

gct ctg acc gac gag gag ttc gcc gac atc ttc acc gcc gac aag ccg     2112
Ala Leu Thr Asp Glu Glu Phe Ala Asp Ile Phe Thr Ala Asp Lys Pro
    690                 695                 700

gtg ctg ttc gcg tac cac tcc tac gct cac gac gtg cgt ggc ctg atc     2160
Val Leu Phe Ala Tyr His Ser Tyr Ala His Asp Val Arg Gly Leu Ile
705                 710                 715                 720

tac gac cgt ccg aac cac gac aac ttc aac gtc cac ggc tac gag gag     2208
Tyr Asp Arg Pro Asn His Asp Asn Phe Asn Val His Gly Tyr Glu Glu
                725                 730                 735

gag ggc tcc acc acc acc ccg tac gac atg gtt cgt gtc aac cgc atc     2256
```

```
Glu Gly Ser Thr Thr Thr Pro Tyr Asp Met Val Arg Val Asn Arg Ile
            740                 745                 750

gac cgc tac gag ctg acc gct gag gct ctg cgc atg atc gac gcc gac      2304
Asp Arg Tyr Glu Leu Thr Ala Glu Ala Leu Arg Met Ile Asp Ala Asp
        755                 760                 765

aag tac gcc gac aag atc gac gag ctc gag aag ttc cgt gat gag gcc      2352
Lys Tyr Ala Asp Lys Ile Asp Glu Leu Glu Lys Phe Arg Asp Glu Ala
    770                 775                 780

ttc cag ttc gcc gtc gac aac ggc tac gat cac ccg gac tac acc gac      2400
Phe Gln Phe Ala Val Asp Asn Gly Tyr Asp His Pro Asp Tyr Thr Asp
785                 790                 795                 800

tgg gtg tac tcc ggc gtg aac acc gac aag aag ggt gcc gtc acc gct      2448
Trp Val Tyr Ser Gly Val Asn Thr Asp Lys Lys Gly Ala Val Thr Ala
                805                 810                 815

acc gcc gct acc gct ggc gac aac gag tga                              2478
Thr Ala Ala Thr Ala Gly Asp Asn Glu
            820                 825


<210> SEQ ID NO 73
<211> LENGTH: 825
<212> TYPE: PRT
<213> ORGANISM: Bifidobacterium longum

<400> SEQUENCE: 73

Met Thr Ser Pro Val Ile Gly Thr Pro Trp Lys Lys Leu Asn Ala Pro
1               5                   10                  15

Val Ser Glu Glu Ala Leu Glu Gly Val Asp Lys Tyr Trp Arg Val Ala
            20                  25                  30

Asn Tyr Leu Ser Ile Gly Gln Ile Tyr Leu Arg Ser Asn Pro Leu Met
        35                  40                  45

Lys Glu Pro Phe Thr Arg Glu Asp Val Lys His Arg Leu Val Gly His
    50                  55                  60

Trp Gly Thr Thr Pro Gly Leu Asn Phe Leu Ile Gly His Ile Asn Arg
65                  70                  75                  80

Phe Ile Ala Asp His Gly Gln Asn Thr Val Ile Ile Met Gly Pro Gly
                85                  90                  95

His Gly Gly Pro Ala Gly Thr Ser Gln Ser Tyr Leu Asp Gly Thr Tyr
            100                 105                 110

Thr Glu Thr Phe Pro Lys Ile Thr Lys Asp Glu Ala Gly Leu Gln Lys
        115                 120                 125

Phe Phe Arg Gln Phe Ser Tyr Pro Gly Gly Ile Pro Ser His Phe Ala
    130                 135                 140

Pro Glu Thr Pro Gly Ser Ile His Glu Gly Gly Glu Leu Gly Tyr Ala
145                 150                 155                 160

Leu Ser His Ala Tyr Gly Ala Ile Met Asp Asn Pro Ser Leu Phe Val
                165                 170                 175

Pro Ala Ile Val Gly Asp Gly Glu Ala Glu Thr Gly Pro Leu Ala Thr
            180                 185                 190

Gly Trp Gln Ser Asn Lys Leu Val Asn Pro Arg Thr Asp Gly Ile Val
        195                 200                 205

Leu Pro Ile Leu His Leu Asn Gly Tyr Lys Ile Ala Asn Pro Thr Ile
    210                 215                 220

Leu Ser Arg Ile Ser Asp Glu Glu Leu His Glu Phe Phe His Gly Met
225                 230                 235                 240

Gly Tyr Glu Pro Tyr Glu Phe Val Ala Gly Phe Asp Asp Glu Asp His
                245                 250                 255

Met Ser Ile His Arg Arg Phe Ala Glu Leu Trp Glu Thr Ile Trp Asp
```

```
            260                 265                 270

Glu Ile Cys Asp Ile Lys Ala Thr Ala Gln Thr Asp Asn Val His Arg
        275                 280                 285

Pro Phe Tyr Pro Met Leu Ile Phe Arg Thr Pro Lys Gly Trp Thr Cys
    290                 295                 300

Pro Lys Tyr Ile Asp Gly Lys Lys Thr Glu Gly Ser Trp Arg Ser His
305                 310                 315                 320

Gln Val Pro Leu Ala Ser Ala Arg Asp Thr Glu Ala His Phe Glu Val
                325                 330                 335

Leu Lys Asn Trp Leu Glu Ser Tyr Lys Pro Glu Glu Leu Phe Asp Ala
            340                 345                 350

Asn Gly Ala Val Lys Asp Asp Val Leu Ala Phe Met Pro Lys Gly Glu
        355                 360                 365

Leu Arg Ile Gly Ala Asn Pro Asn Ala Asn Gly Gly Val Ile Arg Asn
    370                 375                 380

Asp Leu Lys Leu Pro Asn Leu Glu Asp Tyr Glu Val Lys Glu Val Ala
385                 390                 395                 400

Glu Tyr Gly His Gly Trp Gly Gln Leu Glu Ala Thr Arg Thr Leu Gly
                405                 410                 415

Ala Tyr Thr Arg Asp Ile Ile Lys Asn Asn Pro Arg Asp Phe Arg Ile
            420                 425                 430

Phe Gly Pro Asp Glu Thr Ala Ser Asn Arg Leu Gln Ala Ser Tyr Glu
        435                 440                 445

Val Thr Asn Lys Gln Trp Asp Ala Gly Tyr Ile Ser Asp Glu Val Asp
    450                 455                 460

Glu His Met His Val Ser Gly Gln Val Val Glu Gln Leu Ser Glu His
465                 470                 475                 480

Gln Met Glu Gly Phe Leu Glu Ala Tyr Leu Leu Thr Gly Arg His Gly
                485                 490                 495

Ile Trp Ser Ser Tyr Glu Ser Phe Val His Val Ile Asp Ser Met Leu
            500                 505                 510

Asn Gln His Ala Lys Trp Leu Glu Ala Thr Val Arg Glu Ile Pro Trp
        515                 520                 525

Arg Lys Pro Ile Ala Ser Met Asn Leu Leu Val Ser Ser His Val Trp
    530                 535                 540

Arg Gln Asp His Asn Gly Phe Ser His Gln Asp Pro Gly Val Thr Ser
545                 550                 555                 560

Val Leu Leu Asn Lys Cys Phe His Asn Asp His Val Ile Gly Ile Tyr
                565                 570                 575

Phe Ala Thr Asp Ala Asn Met Leu Leu Ala Ile Ala Glu Lys Cys Tyr
            580                 585                 590

Lys Ser Thr Asn Lys Ile Asn Ala Ile Ile Ala Gly Lys Gln Pro Ala
        595                 600                 605

Ala Thr Trp Leu Thr Leu Asp Glu Ala Arg Ala Glu Leu Glu Lys Gly
    610                 615                 620

Ala Ala Ala Trp Asp Trp Ala Ser Thr Ala Lys Asn Asn Asp Glu Ala
625                 630                 635                 640

Glu Val Val Leu Ala Ala Ala Gly Asp Val Pro Thr Gln Glu Ile Met
                645                 650                 655

Ala Ala Ser Asp Lys Leu Lys Glu Leu Gly Ile Lys Phe Lys Val Val
            660                 665                 670

Asn Val Ala Asp Leu Leu Ser Leu Gln Ser Ala Lys Glu Asn Asp Glu
        675                 680                 685
```

```
Ala Leu Thr Asp Glu Glu Phe Ala Asp Ile Phe Thr Ala Asp Lys Pro
    690                 695                 700

Val Leu Phe Ala Tyr His Ser Tyr Ala His Asp Val Arg Gly Leu Ile
705                 710                 715                 720

Tyr Asp Arg Pro Asn His Asp Asn Phe Asn Val His Gly Tyr Glu Glu
                725                 730                 735

Glu Gly Ser Thr Thr Thr Pro Tyr Asp Met Val Arg Val Asn Arg Ile
            740                 745                 750

Asp Arg Tyr Glu Leu Thr Ala Glu Ala Leu Arg Met Ile Asp Ala Asp
        755                 760                 765

Lys Tyr Ala Asp Lys Ile Asp Glu Leu Glu Lys Phe Arg Asp Glu Ala
    770                 775                 780

Phe Gln Phe Ala Val Asp Asn Gly Tyr Asp His Pro Asp Tyr Thr Asp
785                 790                 795                 800

Trp Val Tyr Ser Gly Val Asn Thr Asp Lys Lys Gly Ala Val Thr Ala
                805                 810                 815

Thr Ala Ala Thr Ala Gly Asp Asn Glu
            820                 825


<210> SEQ ID NO 74
<211> LENGTH: 2454
<212> TYPE: DNA
<213> ORGANISM: Chlorobium tepidum
<220> FEATURE:
<221> NAME/KEY: CDS
<222> LOCATION: (1)..(2454)

<400> SEQUENCE: 74

ttg att gta aga tcg gaa aat aga gtt ccg gat gaa ctc cgg act cag       48
Leu Ile Val Arg Ser Glu Asn Arg Val Pro Asp Glu Leu Arg Thr Gln
1               5                   10                  15

cat aca aca act atc aaa tca aca ata ctg atg act gaa atg acg act       96
His Thr Thr Thr Ile Lys Ser Thr Ile Leu Met Thr Glu Met Thr Thr
            20                  25                  30

ccg ctt tcc cct cgc gaa ctc gat ctg atg aac gct tac tgg cga gcg      144
Pro Leu Ser Pro Arg Glu Leu Asp Leu Met Asn Ala Tyr Trp Arg Ala
        35                  40                  45

gcg aac tac ctt tcc gtc ggc cag att tat ctg atg gac aat cca ctc      192
Ala Asn Tyr Leu Ser Val Gly Gln Ile Tyr Leu Met Asp Asn Pro Leu
    50                  55                  60

ctg aaa gag ccg ctc tcc aaa gaa cat atc aag ccc cgc ctg ctc ggc      240
Leu Lys Glu Pro Leu Ser Lys Glu His Ile Lys Pro Arg Leu Leu Gly
65                  70                  75                  80

cac tgg ggc acc act ccc ggt ctc aat ttc ctt tac gtg cac ctg aac      288
His Trp Gly Thr Thr Pro Gly Leu Asn Phe Leu Tyr Val His Leu Asn
                85                  90                  95

cgc atc atc cgc aac cgc gat ctt gac att atc tat atc gcc ggg ccg      336
Arg Ile Ile Arg Asn Arg Asp Leu Asp Ile Ile Tyr Ile Ala Gly Pro
            100                 105                 110

gga cat ggc ggg cct gcg ctg gtg gcg aac gta tgg ctg gag ggt acc      384
Gly His Gly Gly Pro Ala Leu Val Ala Asn Val Trp Leu Glu Gly Thr
        115                 120                 125

tac agt gag tac tat ccc gat gtg tcg ttc gac gag gcg ggc atg aag      432
Tyr Ser Glu Tyr Tyr Pro Asp Val Ser Phe Asp Glu Ala Gly Met Lys
    130                 135                 140

cgg ctg ttc cgg cag ttc tcg ttt ccg ggc ggt att ccg agc cac gtg      480
Arg Leu Phe Arg Gln Phe Ser Phe Pro Gly Gly Ile Pro Ser His Val
145                 150                 155                 160

gct ccc gca acg ccg gga tcg atc cat gag ggc gga gag ctg ggc tat      528
Ala Pro Ala Thr Pro Gly Ser Ile His Glu Gly Gly Glu Leu Gly Tyr
```

-continued

```
                165                 170                 175

gcg ttg tcg cac gct tac ggc gcg gtg ttc gac aat ccc gat ctt gtc      576
Ala Leu Ser His Ala Tyr Gly Ala Val Phe Asp Asn Pro Asp Leu Val
            180                 185                 190

gca gcc tgt gtc atc ggc gat ggc gag gca gag acg ggg cca ctg gcg      624
Ala Ala Cys Val Ile Gly Asp Gly Glu Ala Glu Thr Gly Pro Leu Ala
        195                 200                 205

acg gcg tgg cac agc aac aag ttc ctg aac ccg aag cgc gac ggg gcg      672
Thr Ala Trp His Ser Asn Lys Phe Leu Asn Pro Lys Arg Asp Gly Ala
    210                 215                 220

gtg ctg ccg gtt ctg cac ctg aac ggc tac aag atc gcc aac cca acg      720
Val Leu Pro Val Leu His Leu Asn Gly Tyr Lys Ile Ala Asn Pro Thr
225                 230                 235                 240

gtg ctg gcg cgc att tcg cac gag gag ctg gag cag ctc atg att ggc      768
Val Leu Ala Arg Ile Ser His Glu Glu Leu Glu Gln Leu Met Ile Gly
                245                 250                 255

tac ggc tac aaa ccg tac ttc gtt gag ggg gat gac ccg gcg acg atg      816
Tyr Gly Tyr Lys Pro Tyr Phe Val Glu Gly Asp Asp Pro Ala Thr Met
            260                 265                 270

cac cag atg atg gcg gcg acg atg gac cgc tgc ttc gat gag atc gcc      864
His Gln Met Met Ala Ala Thr Met Asp Arg Cys Phe Asp Glu Ile Ala
        275                 280                 285

gaa atc cag cgc cgg gcg agg gtc gat ggc gtg acc gag cga ccg atg      912
Glu Ile Gln Arg Arg Ala Arg Val Asp Gly Val Thr Glu Arg Pro Met
    290                 295                 300

tgg ccg atg atc gtg ttt cgc tct ccg aaa ggg tgg acg ggg ccg aag      960
Trp Pro Met Ile Val Phe Arg Ser Pro Lys Gly Trp Thr Gly Pro Lys
305                 310                 315                 320

gtg gtt gac ggc aaa ccc gcc gag ggg agc tgg cgt tca cac cag gtg     1008
Val Val Asp Gly Lys Pro Ala Glu Gly Ser Trp Arg Ser His Gln Val
                325                 330                 335

ccg ttc agc acg gtg cga gac aat ccg gag cac atg gcg ctg ctc gaa     1056
Pro Phe Ser Thr Val Arg Asp Asn Pro Glu His Met Ala Leu Leu Glu
            340                 345                 350

acg tgg ctg aaa agc tac cgt gcc gaa gag ctg ttc aca gcg gat ggc     1104
Thr Trp Leu Lys Ser Tyr Arg Ala Glu Glu Leu Phe Thr Ala Asp Gly
        355                 360                 365

gtt ctt ctt cct gag ttg cag gag ctg gct ccg cgt ggc aag aag cgc     1152
Val Leu Leu Pro Glu Leu Gln Glu Leu Ala Pro Arg Gly Lys Lys Arg
    370                 375                 380

atg ggc gat att cca cac gcc aac ggc ggc ctg ttg ctc aag gag ttg     1200
Met Gly Asp Ile Pro His Ala Asn Gly Gly Leu Leu Leu Lys Glu Leu
385                 390                 395                 400

cgg atg ccg gac ttt cgg gaa tat gga atc gat gta ccg aag ccc gga     1248
Arg Met Pro Asp Phe Arg Glu Tyr Gly Ile Asp Val Pro Lys Pro Gly
                405                 410                 415

tcg gtg gag gcc gaa gcg cct aag ccg atg gcc cgc ttt ctg cgc gac     1296
Ser Val Glu Ala Glu Ala Pro Lys Pro Met Ala Arg Phe Leu Arg Asp
            420                 425                 430

atc atg aag atg aac gag aag gcg gcc aac ttc cgc gtt ttc ggg ccg     1344
Ile Met Lys Met Asn Glu Lys Ala Ala Asn Phe Arg Val Phe Gly Pro
        435                 440                 445

gac gag acc gca tca aac cgc ctt ggc gag ctg ttc gaa gag acc gac     1392
Asp Glu Thr Ala Ser Asn Arg Leu Gly Glu Leu Phe Glu Glu Thr Asp
    450                 455                 460

cgc acg tgg atg gcc ggg atg ctg ccg acc gac gat cat ctg tcg cgc     1440
Arg Thr Trp Met Ala Gly Met Leu Pro Thr Asp Asp His Leu Ser Arg
465                 470                 475                 480

gat ggc cgc gtg atg gaa att ctc tcg gag cac acc tgc cag ggg tgg     1488
Asp Gly Arg Val Met Glu Ile Leu Ser Glu His Thr Cys Gln Gly Trp
```

```
                485                 490                 495

ctt gaa gga tac ctt ttg acc gga cgc cac ggc ttc ttc tca tgc tac      1536
Leu Glu Gly Tyr Leu Leu Thr Gly Arg His Gly Phe Phe Ser Cys Tyr
            500                 505                 510

gag gcg ttc atc cac atc atc gac tcg atg ttc aac cag cac gcc aag      1584
Glu Ala Phe Ile His Ile Ile Asp Ser Met Phe Asn Gln His Ala Lys
        515                 520                 525

tgg ctg aag gtg act ggt gcc gaa att ccc tgg cgc cgg ccc atc gct      1632
Trp Leu Lys Val Thr Gly Ala Glu Ile Pro Trp Arg Arg Pro Ile Ala
    530                 535                 540

tcg ctg aac tat ttc ctg act tcg cac gtg tgg cgg cag gat cac aac      1680
Ser Leu Asn Tyr Phe Leu Thr Ser His Val Trp Arg Gln Asp His Asn
545                 550                 555                 560

ggc ttt tcg cat cag gat ccc ggt ttt att gac cat gtg gtc aac aag      1728
Gly Phe Ser His Gln Asp Pro Gly Phe Ile Asp His Val Val Asn Lys
                565                 570                 575

aag tcg agc gtg att cgt gtt tat ctg ccg cca gac gcc aat tcg ctg      1776
Lys Ser Ser Val Ile Arg Val Tyr Leu Pro Pro Asp Ala Asn Ser Leu
            580                 585                 590

ctg tcg gtc aca aac cat tgc ctg cgc tcc cgc aat tac atc aat gtg      1824
Leu Ser Val Thr Asn His Cys Leu Arg Ser Arg Asn Tyr Ile Asn Val
        595                 600                 605

att gtg gcg ggt aaa cag cca gcg tgg cag tgg ctt gac atg gag tcc      1872
Ile Val Ala Gly Lys Gln Pro Ala Trp Gln Trp Leu Asp Met Glu Ser
    610                 615                 620

gcc gtg cgg cac tgt acc agc ggc atc ggc atc tgg gag tgg gcc tcg      1920
Ala Val Arg His Cys Thr Ser Gly Ile Gly Ile Trp Glu Trp Ala Ser
625                 630                 635                 640

aat gac gcg aat gag ggc gag ccg gac gtg gtg atg gct tgt gcg ggc      1968
Asn Asp Ala Asn Glu Gly Glu Pro Asp Val Val Met Ala Cys Ala Gly
                645                 650                 655

gac gtg ccg acg ctt gaa acg ctg gcc gcc gtc aag att ctg cgc aaa      2016
Asp Val Pro Thr Leu Glu Thr Leu Ala Ala Val Lys Ile Leu Arg Lys
            660                 665                 670

ctc gcg ccg gag ttg aag atc agg gtg gtc aac gtg gtc gat ctc atg      2064
Leu Ala Pro Glu Leu Lys Ile Arg Val Val Asn Val Val Asp Leu Met
        675                 680                 685

act ctc cag ccg aaa gag gag cac ccg cac ggc ctt gcc gat cgc gat      2112
Thr Leu Gln Pro Lys Glu Glu His Pro His Gly Leu Ala Asp Arg Asp
    690                 695                 700

ttc gac gac atg ttt act aca gac aag ccg atc atc ttc gcc tat cac      2160
Phe Asp Asp Met Phe Thr Thr Asp Lys Pro Ile Ile Phe Ala Tyr His
705                 710                 715                 720

ggt tac ccg tgg ctg atc cac cgg ctg acc tac cgc cgc acg aac cac      2208
Gly Tyr Pro Trp Leu Ile His Arg Leu Thr Tyr Arg Arg Thr Asn His
                725                 730                 735

cac aac ctg cac gtg cgt ggc tac aag gag gag ggc acc acg acg acg      2256
His Asn Leu His Val Arg Gly Tyr Lys Glu Glu Gly Thr Thr Thr Thr
            740                 745                 750

ccg ttc gac atg gtg gtg atg aac gag ctc gac cgc ttc cac ctg gta      2304
Pro Phe Asp Met Val Val Met Asn Glu Leu Asp Arg Phe His Leu Val
        755                 760                 765

gcc gac gta gcc aac cgc gtg gag agc ctc agg cca caa gct gcc tac      2352
Ala Asp Val Ala Asn Arg Val Glu Ser Leu Arg Pro Gln Ala Ala Tyr
    770                 775                 780

atc aaa caa tac gtc cgc gac cgc ctg atc gag cac aag gag tac atc      2400
Ile Lys Gln Tyr Val Arg Asp Arg Leu Ile Glu His Lys Glu Tyr Ile
785                 790                 795                 800

acg aaa tat ggc gag gat atg ccg gaa gtg agg gat tgg cgc tgg gag      2448
Thr Lys Tyr Gly Glu Asp Met Pro Glu Val Arg Asp Trp Arg Trp Glu
```

805 810 815 gat tga 2454
Asp

<210> SEQ ID NO 75
<211> LENGTH: 817
<212> TYPE: PRT
<213> ORGANISM: Chlorobium tepidum

<400> SEQUENCE: 75

Leu Ile Val Arg Ser Glu Asn Arg Val Pro Asp Glu Leu Arg Thr Gln
1 5 10 15

His Thr Thr Thr Ile Lys Ser Thr Ile Leu Met Thr Glu Met Thr Thr
20 25 30

Pro Leu Ser Pro Arg Glu Leu Asp Leu Met Asn Ala Tyr Trp Arg Ala
35 40 45

Ala Asn Tyr Leu Ser Val Gly Gln Ile Tyr Leu Met Asp Asn Pro Leu
50 55 60

Leu Lys Glu Pro Leu Ser Lys Glu His Ile Lys Pro Arg Leu Leu Gly
65 70 75 80

His Trp Gly Thr Thr Pro Gly Leu Asn Phe Leu Tyr Val His Leu Asn
85 90 95

Arg Ile Ile Arg Asn Arg Asp Leu Asp Ile Ile Tyr Ile Ala Gly Pro
100 105 110

Gly His Gly Gly Pro Ala Leu Val Ala Asn Val Trp Leu Glu Gly Thr
115 120 125

Tyr Ser Glu Tyr Tyr Pro Asp Val Ser Phe Asp Glu Ala Gly Met Lys
130 135 140

Arg Leu Phe Arg Gln Phe Ser Phe Pro Gly Gly Ile Pro Ser His Val
145 150 155 160

Ala Pro Ala Thr Pro Gly Ser Ile His Glu Gly Gly Glu Leu Gly Tyr
165 170 175

Ala Leu Ser His Ala Tyr Gly Ala Val Phe Asp Asn Pro Asp Leu Val
180 185 190

Ala Ala Cys Val Ile Gly Asp Gly Glu Ala Glu Thr Gly Pro Leu Ala
195 200 205

Thr Ala Trp His Ser Asn Lys Phe Leu Asn Pro Lys Arg Asp Gly Ala
210 215 220

Val Leu Pro Val Leu His Leu Asn Gly Tyr Lys Ile Ala Asn Pro Thr
225 230 235 240

Val Leu Ala Arg Ile Ser His Glu Glu Leu Glu Gln Leu Met Ile Gly
245 250 255

Tyr Gly Tyr Lys Pro Tyr Phe Val Glu Gly Asp Asp Pro Ala Thr Met
260 265 270

His Gln Met Met Ala Ala Thr Met Asp Arg Cys Phe Asp Glu Ile Ala
275 280 285

Glu Ile Gln Arg Arg Ala Arg Val Asp Gly Val Thr Glu Arg Pro Met
290 295 300

Trp Pro Met Ile Val Phe Arg Ser Pro Lys Gly Trp Thr Gly Pro Lys
305 310 315 320

Val Val Asp Gly Lys Pro Ala Glu Gly Ser Trp Arg Ser His Gln Val
325 330 335

Pro Phe Ser Thr Val Arg Asp Asn Pro Glu His Met Ala Leu Leu Glu
340 345 350

Thr Trp Leu Lys Ser Tyr Arg Ala Glu Glu Leu Phe Thr Ala Asp Gly

```
        355                 360                 365

Val Leu Leu Pro Glu Leu Gln Glu Leu Ala Pro Arg Gly Lys Lys Arg
    370                 375                 380

Met Gly Asp Ile Pro His Ala Asn Gly Gly Leu Leu Leu Lys Glu Leu
385                 390                 395                 400

Arg Met Pro Asp Phe Arg Glu Tyr Gly Ile Asp Val Pro Lys Pro Gly
                405                 410                 415

Ser Val Glu Ala Glu Ala Pro Lys Pro Met Ala Arg Phe Leu Arg Asp
            420                 425                 430

Ile Met Lys Met Asn Glu Lys Ala Ala Asn Phe Arg Val Phe Gly Pro
        435                 440                 445

Asp Glu Thr Ala Ser Asn Arg Leu Gly Glu Leu Phe Glu Glu Thr Asp
    450                 455                 460

Arg Thr Trp Met Ala Gly Met Leu Pro Thr Asp Asp His Leu Ser Arg
465                 470                 475                 480

Asp Gly Arg Val Met Glu Ile Leu Ser Glu His Thr Cys Gln Gly Trp
                485                 490                 495

Leu Glu Gly Tyr Leu Leu Thr Gly Arg His Gly Phe Phe Ser Cys Tyr
            500                 505                 510

Glu Ala Phe Ile His Ile Ile Asp Ser Met Phe Asn Gln His Ala Lys
        515                 520                 525

Trp Leu Lys Val Thr Gly Ala Glu Ile Pro Trp Arg Arg Pro Ile Ala
    530                 535                 540

Ser Leu Asn Tyr Phe Leu Thr Ser His Val Trp Arg Gln Asp His Asn
545                 550                 555                 560

Gly Phe Ser His Gln Asp Pro Gly Phe Ile Asp His Val Val Asn Lys
                565                 570                 575

Lys Ser Ser Val Ile Arg Val Tyr Leu Pro Pro Asp Ala Asn Ser Leu
            580                 585                 590

Leu Ser Val Thr Asn His Cys Leu Arg Ser Arg Asn Tyr Ile Asn Val
        595                 600                 605

Ile Val Ala Gly Lys Gln Pro Ala Trp Gln Trp Leu Asp Met Glu Ser
    610                 615                 620

Ala Val Arg His Cys Thr Ser Gly Ile Gly Ile Trp Glu Trp Ala Ser
625                 630                 635                 640

Asn Asp Ala Asn Glu Gly Glu Pro Asp Val Val Met Ala Cys Ala Gly
                645                 650                 655

Asp Val Pro Thr Leu Glu Thr Leu Ala Ala Val Lys Ile Leu Arg Lys
            660                 665                 670

Leu Ala Pro Glu Leu Lys Ile Arg Val Val Asn Val Val Asp Leu Met
        675                 680                 685

Thr Leu Gln Pro Lys Glu Glu His Pro His Gly Leu Ala Asp Arg Asp
    690                 695                 700

Phe Asp Asp Met Phe Thr Thr Asp Lys Pro Ile Ile Phe Ala Tyr His
705                 710                 715                 720

Gly Tyr Pro Trp Leu Ile His Arg Leu Thr Tyr Arg Arg Thr Asn His
                725                 730                 735

His Asn Leu His Val Arg Gly Tyr Lys Glu Glu Gly Thr Thr Thr Thr
            740                 745                 750

Pro Phe Asp Met Val Val Met Asn Glu Leu Asp Arg Phe His Leu Val
        755                 760                 765

Ala Asp Val Ala Asn Arg Val Glu Ser Leu Arg Pro Gln Ala Ala Tyr
    770                 775                 780
```

```
Ile Lys Gln Tyr Val Arg Asp Arg Leu Ile Glu His Lys Glu Tyr Ile
785                 790                 795                 800

Thr Lys Tyr Gly Glu Asp Met Pro Glu Val Arg Asp Trp Arg Trp Glu
                805                 810                 815

Asp


<210> SEQ ID NO 76
<211> LENGTH: 2370
<212> TYPE: DNA
<213> ORGANISM: Brucella suis
<220> FEATURE:
<221> NAME/KEY: CDS
<222> LOCATION: (1)..(2370)

<400> SEQUENCE: 76

gtg cca gca aaa ggg cct ctc aca ccg cag cag ctt tca ctc atc aac       48
Val Pro Ala Lys Gly Pro Leu Thr Pro Gln Gln Leu Ser Leu Ile Asn
1               5                   10                  15

cgt tac tgg cgc gcg gcg aat tat ctt tcc gtc ggc cag att tat ctg       96
Arg Tyr Trp Arg Ala Ala Asn Tyr Leu Ser Val Gly Gln Ile Tyr Leu
            20                  25                  30

atg aaa aat ccc ctg ttg cgc gaa ccg ctc cag cct gag cac atc aag      144
Met Lys Asn Pro Leu Leu Arg Glu Pro Leu Gln Pro Glu His Ile Lys
        35                  40                  45

ccg cgg ctt ctc ggc cat tgg ggc acg aca ccc ggc ctc aat ttc atc      192
Pro Arg Leu Leu Gly His Trp Gly Thr Thr Pro Gly Leu Asn Phe Ile
    50                  55                  60

tat gcg cat ctc aac cgc att att cag cag cgc aac gcc aat gtg atc      240
Tyr Ala His Leu Asn Arg Ile Ile Gln Gln Arg Asn Ala Asn Val Ile
65                  70                  75                  80

tat att tgc ggc ccc ggc cat ggc ggg ccg ggc atg gtg gcc aac acc      288
Tyr Ile Cys Gly Pro Gly His Gly Gly Pro Gly Met Val Ala Asn Thr
                85                  90                  95

tat ctg gag ggc acc tat tcc gaa atc tat ccc gca atc agc gaa gat      336
Tyr Leu Glu Gly Thr Tyr Ser Glu Ile Tyr Pro Ala Ile Ser Glu Asp
            100                 105                 110

gaa gcg ggc atg gaa agg ctc ttc cgc cag ttt tcc ttc ccc ggc gga      384
Glu Ala Gly Met Glu Arg Leu Phe Arg Gln Phe Ser Phe Pro Gly Gly
        115                 120                 125

ata cca agc cat gcc gcg ccg gaa aca ccg ggc tct atc cac gaa ggg      432
Ile Pro Ser His Ala Ala Pro Glu Thr Pro Gly Ser Ile His Glu Gly
    130                 135                 140

ggc gaa ctg ggt tat gcg ctc gtc cac gcc tat ggt gcg gcc ttc gac      480
Gly Glu Leu Gly Tyr Ala Leu Val His Ala Tyr Gly Ala Ala Phe Asp
145                 150                 155                 160

aat ccc gat ctg gtg gtg gcc tgc gtc gtg ggc gac gga gaa gcg gaa      528
Asn Pro Asp Leu Val Val Ala Cys Val Val Gly Asp Gly Glu Ala Glu
                165                 170                 175

acc ggc gcg ctt gca act tcg tgg cac tcc aac aaa ttc ctc aat ccg      576
Thr Gly Ala Leu Ala Thr Ser Trp His Ser Asn Lys Phe Leu Asn Pro
            180                 185                 190

gcg cgc gat ggt gcg gtt ctg ccg atc ctg cat ctc aat ggc tac aag      624
Ala Arg Asp Gly Ala Val Leu Pro Ile Leu His Leu Asn Gly Tyr Lys
        195                 200                 205

atc gcc aac ccc acc gtg ctg gcc cgc ctt tcg gat gat gat ctg gac      672
Ile Ala Asn Pro Thr Val Leu Ala Arg Leu Ser Asp Asp Asp Leu Asp
    210                 215                 220

aat ctt ttc cgt ggc tac ggt tat gag cct ttc ttt gtt gaa ggc agc      720
Asn Leu Phe Arg Gly Tyr Gly Tyr Glu Pro Phe Phe Val Glu Gly Ser
225                 230                 235                 240

gag cct gcc gac atg cac cag aag atg gcc gca aca ctg gac acg att      768
```

```
Glu Pro Ala Asp Met His Gln Lys Met Ala Ala Thr Leu Asp Thr Ile
            245                 250                 255

ttc cag cgc att cag gac atc aag aaa aat gcc gat gtg cac tcg ccc      816
Phe Gln Arg Ile Gln Asp Ile Lys Lys Asn Ala Asp Val His Ser Pro
            260                 265                 270

gag cgc ccg cgc tgg ccg atg att att ctc aga agc ccg aag ggc tgg      864
Glu Arg Pro Arg Trp Pro Met Ile Ile Leu Arg Ser Pro Lys Gly Trp
        275                 280                 285

acc ggc cca aaa acc gtg gac ggt ctg gtt gtt gaa aac tat tgg cgc      912
Thr Gly Pro Lys Thr Val Asp Gly Leu Val Val Glu Asn Tyr Trp Arg
    290                 295                 300

gcc cat cag gtg ccg gtt gcc aat tgc cgc gaa aac gat gcc cat cgc      960
Ala His Gln Val Pro Val Ala Asn Cys Arg Glu Asn Asp Ala His Arg
305                 310                 315                 320

aaa atc ctc gaa gac tgg atg aag agt tac gac ccg tcc gat ctg ttc     1008
Lys Ile Leu Glu Asp Trp Met Lys Ser Tyr Asp Pro Ser Asp Leu Phe
            325                 330                 335

gac gaa aaa ggg gcg ctg aag cct gaa ttg cgg gcg ctg gcg cca aag     1056
Asp Glu Lys Gly Ala Leu Lys Pro Glu Leu Arg Ala Leu Ala Pro Lys
            340                 345                 350

ggt gaa gcg cgc ata ggg gcc aat ccg cat gcc aat ggc ggg ctc ttg     1104
Gly Glu Ala Arg Ile Gly Ala Asn Pro His Ala Asn Gly Gly Leu Leu
        355                 360                 365

cgt aaa gag ctt cac atg ccg gat ttc cgc caa tat gcg gtc aat gtc     1152
Arg Lys Glu Leu His Met Pro Asp Phe Arg Gln Tyr Ala Val Asn Val
    370                 375                 380

acc gaa ccg gga gcg ata gaa gcg caa tca acc aaa ata ttg ggc gat     1200
Thr Glu Pro Gly Ala Ile Glu Ala Gln Ser Thr Lys Ile Leu Gly Asp
385                 390                 395                 400

ttt ctg cgc gat gtg atg aaa ctg aac gag acg gaa aag aac ttc cgc     1248
Phe Leu Arg Asp Val Met Lys Leu Asn Glu Thr Glu Lys Asn Phe Arg
            405                 410                 415

atc ttc ggc ccc gac gaa acc gcc tcc aac agg ctc ggc agc gta tta     1296
Ile Phe Gly Pro Asp Glu Thr Ala Ser Asn Arg Leu Gly Ser Val Leu
            420                 425                 430

gag gcg acg aac cgg gtc tgg atg gcc gaa acg ctg gac atg gat gac     1344
Glu Ala Thr Asn Arg Val Trp Met Ala Glu Thr Leu Asp Met Asp Asp
        435                 440                 445

cac ctc gcc gcc gac ggg cgt gta atg gag gtt ctc agc gaa cat ctc     1392
His Leu Ala Ala Asp Gly Arg Val Met Glu Val Leu Ser Glu His Leu
    450                 455                 460

tgc cag ggc tgg ctt gaa ggc tat ctt ctc agt ggc cgg cac ggc ttc     1440
Cys Gln Gly Trp Leu Glu Gly Tyr Leu Leu Ser Gly Arg His Gly Phe
465                 470                 475                 480

ttt tcc tgc tac gaa gcc ttc atc cac att atc gat tcc atg ttc aac     1488
Phe Ser Cys Tyr Glu Ala Phe Ile His Ile Ile Asp Ser Met Phe Asn
            485                 490                 495

caa cat gcc aaa tgg ttg cag gtt gcg cgc gaa ctg gaa tgg cgc aag     1536
Gln His Ala Lys Trp Leu Gln Val Ala Arg Glu Leu Glu Trp Arg Lys
            500                 505                 510

ccc atc tca tcg ctc aat tat ctg ctg acc tcc cat gtc tgg cgg cag     1584
Pro Ile Ser Ser Leu Asn Tyr Leu Leu Thr Ser His Val Trp Arg Gln
        515                 520                 525

gac cat aac ggc ttc tcc cat cag gat ccc ggc ttc gtc gat ctc gtc     1632
Asp His Asn Gly Phe Ser His Gln Asp Pro Gly Phe Val Asp Leu Val
    530                 535                 540

gcc aac aaa agc gcc gat atc gtg cgt gtc tat ttc ccg ccg gat gcc     1680
Ala Asn Lys Ser Ala Asp Ile Val Arg Val Tyr Phe Pro Pro Asp Ala
545                 550                 555                 560

aac acc ctt ttg tgg gtg gga gat cac tgc ctg aaa acc tgg aac cgc     1728
```

```
Asn Thr Leu Leu Trp Val Gly Asp His Cys Leu Lys Thr Trp Asn Arg
                565                 570                 575

gtg aat gtc atc gtg gcg ggc aag cag ccg gaa ccg caa tgg ctg acc      1776
Val Asn Val Ile Val Ala Gly Lys Gln Pro Glu Pro Gln Trp Leu Thr
            580                 585                 590

atg gcg gag gct gag aaa cat tgc gaa gca ggt ctc ggc ata tgg gaa      1824
Met Ala Glu Ala Glu Lys His Cys Glu Ala Gly Leu Gly Ile Trp Glu
        595                 600                 605

tgg gcg ggc acg gaa gac ggg ctg gag ccg gat atc gtc atg gcc tgc      1872
Trp Ala Gly Thr Glu Asp Gly Leu Glu Pro Asp Ile Val Met Ala Cys
    610                 615                 620

gcg ggc gat gtg ccg acc atg gaa acg ctt gcc gcg gtt gat ctt ctg      1920
Ala Gly Asp Val Pro Thr Met Glu Thr Leu Ala Ala Val Asp Leu Leu
625                 630                 635                 640

cgc cag tcc ctg ccg cat ctg cgc att cgc gtg gtg aat gtg gtt gac      1968
Arg Gln Ser Leu Pro His Leu Arg Ile Arg Val Val Asn Val Val Asp
                645                 650                 655

ctc atg gtg ctg caa tcg ccg cat cag cac ccg cat ggc att tcc gat      2016
Leu Met Val Leu Gln Ser Pro His Gln His Pro His Gly Ile Ser Asp
            660                 665                 670

gag gaa ttc gac cgg atg ttc acc acc aac agg ccc gtc atc ttc gcc      2064
Glu Glu Phe Asp Arg Met Phe Thr Thr Asn Arg Pro Val Ile Phe Ala
        675                 680                 685

tat cac ggc tat cct tat ctc atc cat cga ctg gtc tat aag cgc acc      2112
Tyr His Gly Tyr Pro Tyr Leu Ile His Arg Leu Val Tyr Lys Arg Thr
    690                 695                 700

aac cac tcc aat ttc cac gtt cgt ggt ttt atc gag cag gga acg acc      2160
Asn His Ser Asn Phe His Val Arg Gly Phe Ile Glu Gln Gly Thr Thr
705                 710                 715                 720

aca acg cct ttc gac atg acc gtg ctg aac gag ctg gat cgt ttc cac      2208
Thr Thr Pro Phe Asp Met Thr Val Leu Asn Glu Leu Asp Arg Phe His
                725                 730                 735

ctc gcg atg gaa gcc gtc gag cgc ctg ccg ctg ggc gaa agc gtt gcc      2256
Leu Ala Met Glu Ala Val Glu Arg Leu Pro Leu Gly Glu Ser Val Ala
            740                 745                 750

aaa ccc ctg atc gac aat ttc acg gag aaa ctt gcg ctg cat aag gac      2304
Lys Pro Leu Ile Asp Asn Phe Thr Glu Lys Leu Ala Leu His Lys Asp
        755                 760                 765

tat atc cga cag cat ggt gag gac atg ccg gaa atc cgc gac tgg aaa      2352
Tyr Ile Arg Gln His Gly Glu Asp Met Pro Glu Ile Arg Asp Trp Lys
    770                 775                 780

tgg aca tgg ccg cga taa                                              2370
Trp Thr Trp Pro Arg
785


<210> SEQ ID NO 77
<211> LENGTH: 789
<212> TYPE: PRT
<213> ORGANISM: Brucella suis

<400> SEQUENCE: 77

Val Pro Ala Lys Gly Pro Leu Thr Pro Gln Gln Leu Ser Leu Ile Asn
1               5                   10                  15

Arg Tyr Trp Arg Ala Ala Asn Tyr Leu Ser Val Gly Gln Ile Tyr Leu
            20                  25                  30

Met Lys Asn Pro Leu Leu Arg Glu Pro Leu Gln Pro Glu His Ile Lys
        35                  40                  45

Pro Arg Leu Leu Gly His Trp Gly Thr Thr Pro Gly Leu Asn Phe Ile
    50                  55                  60

Tyr Ala His Leu Asn Arg Ile Ile Gln Gln Arg Asn Ala Asn Val Ile
```

-continued

```
65                  70                  75                  80

Tyr Ile Cys Gly Pro Gly His Gly Gly Pro Gly Met Val Ala Asn Thr
                85                  90                  95

Tyr Leu Glu Gly Thr Tyr Ser Glu Ile Tyr Pro Ala Ile Ser Glu Asp
            100                 105                 110

Glu Ala Gly Met Glu Arg Leu Phe Arg Gln Phe Ser Phe Pro Gly Gly
        115                 120                 125

Ile Pro Ser His Ala Ala Pro Glu Thr Pro Gly Ser Ile His Glu Gly
    130                 135                 140

Gly Glu Leu Gly Tyr Ala Leu Val His Ala Tyr Gly Ala Ala Phe Asp
145                 150                 155                 160

Asn Pro Asp Leu Val Val Ala Cys Val Val Gly Asp Gly Glu Ala Glu
                165                 170                 175

Thr Gly Ala Leu Ala Thr Ser Trp His Ser Asn Lys Phe Leu Asn Pro
            180                 185                 190

Ala Arg Asp Gly Ala Val Leu Pro Ile Leu His Leu Asn Gly Tyr Lys
        195                 200                 205

Ile Ala Asn Pro Thr Val Leu Ala Arg Leu Ser Asp Asp Asp Leu Asp
    210                 215                 220

Asn Leu Phe Arg Gly Tyr Gly Tyr Glu Pro Phe Phe Val Glu Gly Ser
225                 230                 235                 240

Glu Pro Ala Asp Met His Gln Lys Met Ala Ala Thr Leu Asp Thr Ile
                245                 250                 255

Phe Gln Arg Ile Gln Asp Ile Lys Lys Asn Ala Asp Val His Ser Pro
            260                 265                 270

Glu Arg Pro Arg Trp Pro Met Ile Ile Leu Arg Ser Pro Lys Gly Trp
        275                 280                 285

Thr Gly Pro Lys Thr Val Asp Gly Leu Val Val Glu Asn Tyr Trp Arg
    290                 295                 300

Ala His Gln Val Pro Val Ala Asn Cys Arg Glu Asn Asp Ala His Arg
305                 310                 315                 320

Lys Ile Leu Glu Asp Trp Met Lys Ser Tyr Asp Pro Ser Asp Leu Phe
                325                 330                 335

Asp Glu Lys Gly Ala Leu Lys Pro Glu Leu Arg Ala Leu Ala Pro Lys
            340                 345                 350

Gly Glu Ala Arg Ile Gly Ala Asn Pro His Ala Asn Gly Gly Leu Leu
        355                 360                 365

Arg Lys Glu Leu His Met Pro Asp Phe Arg Gln Tyr Ala Val Asn Val
    370                 375                 380

Thr Glu Pro Gly Ala Ile Glu Ala Gln Ser Thr Lys Ile Leu Gly Asp
385                 390                 395                 400

Phe Leu Arg Asp Val Met Lys Leu Asn Glu Thr Glu Lys Asn Phe Arg
                405                 410                 415

Ile Phe Gly Pro Asp Glu Thr Ala Ser Asn Arg Leu Gly Ser Val Leu
            420                 425                 430

Glu Ala Thr Asn Arg Val Trp Met Ala Glu Thr Leu Asp Met Asp Asp
        435                 440                 445

His Leu Ala Ala Asp Gly Arg Val Met Glu Val Leu Ser Glu His Leu
    450                 455                 460

Cys Gln Gly Trp Leu Glu Gly Tyr Leu Leu Ser Gly Arg His Gly Phe
465                 470                 475                 480

Phe Ser Cys Tyr Glu Ala Phe Ile His Ile Ile Asp Ser Met Phe Asn
                485                 490                 495
```

```
Gln His Ala Lys Trp Leu Gln Val Ala Arg Glu Leu Glu Trp Arg Lys
            500                 505                 510

Pro Ile Ser Ser Leu Asn Tyr Leu Leu Thr Ser His Val Trp Arg Gln
        515                 520                 525

Asp His Asn Gly Phe Ser His Gln Asp Pro Gly Phe Val Asp Leu Val
    530                 535                 540

Ala Asn Lys Ser Ala Asp Ile Val Arg Val Tyr Phe Pro Pro Asp Ala
545                 550                 555                 560

Asn Thr Leu Leu Trp Val Gly Asp His Cys Leu Lys Thr Trp Asn Arg
                565                 570                 575

Val Asn Val Ile Val Ala Gly Lys Gln Pro Glu Pro Gln Trp Leu Thr
            580                 585                 590

Met Ala Glu Ala Glu Lys His Cys Glu Ala Gly Leu Gly Ile Trp Glu
        595                 600                 605

Trp Ala Gly Thr Glu Asp Gly Leu Glu Pro Asp Ile Val Met Ala Cys
    610                 615                 620

Ala Gly Asp Val Pro Thr Met Glu Thr Leu Ala Ala Val Asp Leu Leu
625                 630                 635                 640

Arg Gln Ser Leu Pro His Leu Arg Ile Arg Val Val Asn Val Val Asp
                645                 650                 655

Leu Met Val Leu Gln Ser Pro His Gln His Pro His Gly Ile Ser Asp
            660                 665                 670

Glu Glu Phe Asp Arg Met Phe Thr Thr Asn Arg Pro Val Ile Phe Ala
        675                 680                 685

Tyr His Gly Tyr Pro Tyr Leu Ile His Arg Leu Val Tyr Lys Arg Thr
    690                 695                 700

Asn His Ser Asn Phe His Val Arg Gly Phe Ile Glu Gln Gly Thr Thr
705                 710                 715                 720

Thr Thr Pro Phe Asp Met Thr Val Leu Asn Glu Leu Asp Arg Phe His
                725                 730                 735

Leu Ala Met Glu Ala Val Glu Arg Leu Pro Leu Gly Glu Ser Val Ala
            740                 745                 750

Lys Pro Leu Ile Asp Asn Phe Thr Glu Lys Leu Ala Leu His Lys Asp
        755                 760                 765

Tyr Ile Arg Gln His Gly Glu Asp Met Pro Glu Ile Arg Asp Trp Lys
    770                 775                 780

Trp Thr Trp Pro Arg
785


<210> SEQ ID NO 78
<211> LENGTH: 2379
<212> TYPE: DNA
<213> ORGANISM: Brucella abortus
<220> FEATURE:
<221> NAME/KEY: CDS
<222> LOCATION: (1)..(2379)

<400> SEQUENCE: 78

atg agc act gtg cca gca aaa ggg cct ctc aca ccg cag cag ctt tca       48
Met Ser Thr Val Pro Ala Lys Gly Pro Leu Thr Pro Gln Gln Leu Ser
1               5                   10                  15

ctc atc aac cgt tac tgg cgc gcg gcg aat tat ctt tcc gtc ggc cag       96
Leu Ile Asn Arg Tyr Trp Arg Ala Ala Asn Tyr Leu Ser Val Gly Gln
            20                  25                  30

att tat ctg atg aaa aat ccc ctg ttg cgc gaa ccg ctc cag cct gag      144
Ile Tyr Leu Met Lys Asn Pro Leu Leu Arg Glu Pro Leu Gln Pro Glu
        35                  40                  45
```

-continued

```
cac atc aag ccg cgg ctt ctc ggc cat tgg ggc acg aca ccc ggc ctc       192
His Ile Lys Pro Arg Leu Leu Gly His Trp Gly Thr Thr Pro Gly Leu
    50                  55                  60

aat ttc atc tat gcg cat ctc aac cgc att att cag cag cgc aac gcc       240
Asn Phe Ile Tyr Ala His Leu Asn Arg Ile Ile Gln Gln Arg Asn Ala
65                  70                  75                  80

aat gtg atc tat att tgc ggc ccc ggc cat ggc ggg ccg ggc atg gtg       288
Asn Val Ile Tyr Ile Cys Gly Pro Gly His Gly Gly Pro Gly Met Val
                85                  90                  95

gcc aac acc tat ctg gag ggc acc tat tcc gaa atc tat ccc gca atc       336
Ala Asn Thr Tyr Leu Glu Gly Thr Tyr Ser Glu Ile Tyr Pro Ala Ile
            100                 105                 110

agc gaa gat gaa gcg ggc atg gaa agg ctc ttc cgc cag ttt tcc ttc       384
Ser Glu Asp Glu Ala Gly Met Glu Arg Leu Phe Arg Gln Phe Ser Phe
        115                 120                 125

ccc ggc gga ata cca agc cat gcc gcg ccg gaa aca ccg ggc tct atc       432
Pro Gly Gly Ile Pro Ser His Ala Ala Pro Glu Thr Pro Gly Ser Ile
    130                 135                 140

cac gaa ggg ggc gaa ctg ggt tat gcg ctc gtc cac gcc tat ggt gcg       480
His Glu Gly Gly Glu Leu Gly Tyr Ala Leu Val His Ala Tyr Gly Ala
145                 150                 155                 160

gcc ttc gac aat ccc gat ctg gtg gtg gcc tgc gtc gtg ggc gac gga       528
Ala Phe Asp Asn Pro Asp Leu Val Val Ala Cys Val Val Gly Asp Gly
                165                 170                 175

gaa gcg gaa acc ggc gcg ctt gca act tcg tgg cac tcc aac aaa ttc       576
Glu Ala Glu Thr Gly Ala Leu Ala Thr Ser Trp His Ser Asn Lys Phe
            180                 185                 190

ctc aat ccg gcg cgc gat ggt gcg gtt ctg ccg atc ctg cat ctc aat       624
Leu Asn Pro Ala Arg Asp Gly Ala Val Leu Pro Ile Leu His Leu Asn
        195                 200                 205

ggc tac aag atc gcc aac ccc acc gtg ctg gcc cgc ctt tcg gat gat       672
Gly Tyr Lys Ile Ala Asn Pro Thr Val Leu Ala Arg Leu Ser Asp Asp
    210                 215                 220

gat ctg gac aat ctt ttc cgt ggc tac ggt tat gag cct ttc ttt gtt       720
Asp Leu Asp Asn Leu Phe Arg Gly Tyr Gly Tyr Glu Pro Phe Phe Val
225                 230                 235                 240

gaa ggc agc gag cct gcc gac atg cac cag aag atg gcc gca aca ctg       768
Glu Gly Ser Glu Pro Ala Asp Met His Gln Lys Met Ala Ala Thr Leu
                245                 250                 255

gac acg att ttc cag cgc att cag gac atc aag aaa aat gcc gat gtg       816
Asp Thr Ile Phe Gln Arg Ile Gln Asp Ile Lys Lys Asn Ala Asp Val
            260                 265                 270

cac tcg ccc gag cgc ccg cgc tgg ccg atg att att ctc aga agc ccg       864
His Ser Pro Glu Arg Pro Arg Trp Pro Met Ile Ile Leu Arg Ser Pro
        275                 280                 285

aag ggc tgg acc ggc cca aaa acc gtg gac ggt ctg gtt gtt gaa aac       912
Lys Gly Trp Thr Gly Pro Lys Thr Val Asp Gly Leu Val Val Glu Asn
    290                 295                 300

tat tgg cgc gcc cat gag gtg ccg gtt gcc aat tgc cgc gaa aac gat       960
Tyr Trp Arg Ala His Glu Val Pro Val Ala Asn Cys Arg Glu Asn Asp
305                 310                 315                 320

gcc cat cgc aaa atc ctc gaa gac tgg atg aag agt tac gac ccg tcc      1008
Ala His Arg Lys Ile Leu Glu Asp Trp Met Lys Ser Tyr Asp Pro Ser
                325                 330                 335

gat ctg ttc gac gaa aaa ggg gcg ctg aag cct gaa ttg cgg gcg ctg      1056
Asp Leu Phe Asp Glu Lys Gly Ala Leu Lys Pro Glu Leu Arg Ala Leu
            340                 345                 350

gcg cca aag ggt gaa gcg cgc ata ggg gcc aat ccg cat gcc aat ggc      1104
Ala Pro Lys Gly Glu Ala Arg Ile Gly Ala Asn Pro His Ala Asn Gly
        355                 360                 365
```

```
ggg ctc ttg cgt aaa gag ctt cac atg ccg gat ttc cgc caa tat gcg      1152
Gly Leu Leu Arg Lys Glu Leu His Met Pro Asp Phe Arg Gln Tyr Ala
    370                 375                 380

gtc aat gtc acc gaa ccg gga gcg ata gaa gcg caa tca acc aaa ata      1200
Val Asn Val Thr Glu Pro Gly Ala Ile Glu Ala Gln Ser Thr Lys Ile
385                 390                 395                 400

ttg ggc gat ttt ctg cgc gat gtg atg aaa ctg aac gag acg gaa aag      1248
Leu Gly Asp Phe Leu Arg Asp Val Met Lys Leu Asn Glu Thr Glu Lys
                405                 410                 415

aac ttc cgc atc ttc ggc ccc gac gaa acc gcc tcc aac agg ctc ggc      1296
Asn Phe Arg Ile Phe Gly Pro Asp Glu Thr Ala Ser Asn Arg Leu Gly
            420                 425                 430

agc gta tta gag gcg acg aac cgg gtc tgg atg gcc gaa acg ctg gac      1344
Ser Val Leu Glu Ala Thr Asn Arg Val Trp Met Ala Glu Thr Leu Asp
        435                 440                 445

atg gat gac cac ctc gcc gcc gac ggg cgt gta atg gag gtt ctc agc      1392
Met Asp Asp His Leu Ala Ala Asp Gly Arg Val Met Glu Val Leu Ser
    450                 455                 460

gaa cat ctc tgc cag ggc tgg ctt gaa ggc tat ctt ctc agt ggc cgg      1440
Glu His Leu Cys Gln Gly Trp Leu Glu Gly Tyr Leu Leu Ser Gly Arg
465                 470                 475                 480

cac ggc ttc ttt tcc tgc tac gaa gcc ttc atc cac att atc gat tcc      1488
His Gly Phe Phe Ser Cys Tyr Glu Ala Phe Ile His Ile Ile Asp Ser
                485                 490                 495

atg ttc aac caa cat gcc aaa tgg ttg cag gtt gcg cgc gaa ctg gaa      1536
Met Phe Asn Gln His Ala Lys Trp Leu Gln Val Ala Arg Glu Leu Glu
            500                 505                 510

tgg cgc aag ccc atc tca tcg ctc aat tat ctg ctg acc tcc cat gtc      1584
Trp Arg Lys Pro Ile Ser Ser Leu Asn Tyr Leu Leu Thr Ser His Val
        515                 520                 525

tgg cgg cag gac cat aac ggc ttc tcc cat cag gat ccc ggc ttc gtc      1632
Trp Arg Gln Asp His Asn Gly Phe Ser His Gln Asp Pro Gly Phe Val
    530                 535                 540

gat ctc gtc gcc aac aaa agc gcc gat atc gcg cgt gtc tat ttc ccg      1680
Asp Leu Val Ala Asn Lys Ser Ala Asp Ile Ala Arg Val Tyr Phe Pro
545                 550                 555                 560

ccg gat gcc aac acc ctt ttg tgg gtg gga gat cac tgc ctg aaa acc      1728
Pro Asp Ala Asn Thr Leu Leu Trp Val Gly Asp His Cys Leu Lys Thr
                565                 570                 575

tgg aac cgc gtg aat gtc atc gtg gcg ggc aag cag ccg gaa ccg caa      1776
Trp Asn Arg Val Asn Val Ile Val Ala Gly Lys Gln Pro Glu Pro Gln
            580                 585                 590

tgg ctg acc atg gcg gag gct gag aaa cat tgc gaa gca ggt ctc ggc      1824
Trp Leu Thr Met Ala Glu Ala Glu Lys His Cys Glu Ala Gly Leu Gly
        595                 600                 605

ata tgg gaa tgg gcg ggt acg gaa gac ggg ctg gag ccg gat atc gtc      1872
Ile Trp Glu Trp Ala Gly Thr Glu Asp Gly Leu Glu Pro Asp Ile Val
    610                 615                 620

atg gcc tgc gcg ggc gat gtg ccg acc atg gaa acg ctt gcc gcg gtt      1920
Met Ala Cys Ala Gly Asp Val Pro Thr Met Glu Thr Leu Ala Ala Val
625                 630                 635                 640

gat ctt ctg cgc cag tcc ctg ccg cat ctg cgc att cgc gtg gtg aat      1968
Asp Leu Leu Arg Gln Ser Leu Pro His Leu Arg Ile Arg Val Val Asn
                645                 650                 655

gtg gtt gac ctc atg gtg ctg caa tcg ccg cat cag cac ccg cat ggc      2016
Val Val Asp Leu Met Val Leu Gln Ser Pro His Gln His Pro His Gly
            660                 665                 670

att tcc gat gag gaa ttc gac cgg atg ttc acc acc aac agg ccc gtc      2064
Ile Ser Asp Glu Glu Phe Asp Arg Met Phe Thr Thr Asn Arg Pro Val
        675                 680                 685
```

```
atc ttc gcc tat cac ggc tat cct tat ctc atc cat cga ctg gtc tat      2112
Ile Phe Ala Tyr His Gly Tyr Pro Tyr Leu Ile His Arg Leu Val Tyr
    690                 695                 700

aag cgc acc aac cac tcc aat ttc cac gtt cgt ggt ttt atc gag cag      2160
Lys Arg Thr Asn His Ser Asn Phe His Val Arg Gly Phe Ile Glu Gln
705                 710                 715                 720

gga acg acc aca acg cct ttc gac atg acc gtg ctg aac gag ctg gat      2208
Gly Thr Thr Thr Thr Pro Phe Asp Met Thr Val Leu Asn Glu Leu Asp
                725                 730                 735

cgt ttc cac ctc gcg atg gaa gcc gtc gag cgc ctg ccg ctg ggc gaa      2256
Arg Phe His Leu Ala Met Glu Ala Val Glu Arg Leu Pro Leu Gly Glu
            740                 745                 750

agc gtt gcc aaa ccc ctg atc gac aat ttc acg gag aaa ctt gcg ctg      2304
Ser Val Ala Lys Pro Leu Ile Asp Asn Phe Thr Glu Lys Leu Ala Leu
        755                 760                 765

cat aag gac tat atc cga cag cat ggt gag gac atg ccg gaa atc cgc      2352
His Lys Asp Tyr Ile Arg Gln His Gly Glu Asp Met Pro Glu Ile Arg
    770                 775                 780

gac tgg aaa tgg aca tgg ccg cga taa                                  2379
Asp Trp Lys Trp Thr Trp Pro Arg
785                 790


<210> SEQ ID NO 79
<211> LENGTH: 792
<212> TYPE: PRT
<213> ORGANISM: Brucella abortus

<400> SEQUENCE: 79

Met Ser Thr Val Pro Ala Lys Gly Pro Leu Thr Pro Gln Gln Leu Ser
1               5                   10                  15

Leu Ile Asn Arg Tyr Trp Arg Ala Ala Asn Tyr Leu Ser Val Gly Gln
            20                  25                  30

Ile Tyr Leu Met Lys Asn Pro Leu Leu Arg Glu Pro Leu Gln Pro Glu
        35                  40                  45

His Ile Lys Pro Arg Leu Leu Gly His Trp Gly Thr Thr Pro Gly Leu
    50                  55                  60

Asn Phe Ile Tyr Ala His Leu Asn Arg Ile Ile Gln Gln Arg Asn Ala
65                  70                  75                  80

Asn Val Ile Tyr Ile Cys Gly Pro Gly His Gly Gly Pro Gly Met Val
                85                  90                  95

Ala Asn Thr Tyr Leu Glu Gly Thr Tyr Ser Glu Ile Tyr Pro Ala Ile
            100                 105                 110

Ser Glu Asp Glu Ala Gly Met Glu Arg Leu Phe Arg Gln Phe Ser Phe
        115                 120                 125

Pro Gly Gly Ile Pro Ser His Ala Ala Pro Glu Thr Pro Gly Ser Ile
    130                 135                 140

His Glu Gly Gly Glu Leu Gly Tyr Ala Leu Val His Ala Tyr Gly Ala
145                 150                 155                 160

Ala Phe Asp Asn Pro Asp Leu Val Val Ala Cys Val Val Gly Asp Gly
                165                 170                 175

Glu Ala Glu Thr Gly Ala Leu Ala Thr Ser Trp His Ser Asn Lys Phe
            180                 185                 190

Leu Asn Pro Ala Arg Asp Gly Ala Val Leu Pro Ile Leu His Leu Asn
        195                 200                 205

Gly Tyr Lys Ile Ala Asn Pro Thr Val Leu Ala Arg Leu Ser Asp Asp
    210                 215                 220

Asp Leu Asp Asn Leu Phe Arg Gly Tyr Gly Tyr Glu Pro Phe Phe Val
225                 230                 235                 240
```

-continued

```
Glu Gly Ser Glu Pro Ala Asp Met His Gln Lys Met Ala Ala Thr Leu
                245                 250                 255

Asp Thr Ile Phe Gln Arg Ile Gln Asp Ile Lys Lys Asn Ala Asp Val
            260                 265                 270

His Ser Pro Glu Arg Pro Arg Trp Pro Met Ile Ile Leu Arg Ser Pro
        275                 280                 285

Lys Gly Trp Thr Gly Pro Lys Thr Val Asp Gly Leu Val Val Glu Asn
    290                 295                 300

Tyr Trp Arg Ala His Glu Val Pro Val Ala Asn Cys Arg Glu Asn Asp
305                 310                 315                 320

Ala His Arg Lys Ile Leu Glu Asp Trp Met Lys Ser Tyr Asp Pro Ser
                325                 330                 335

Asp Leu Phe Asp Glu Lys Gly Ala Leu Lys Pro Glu Leu Arg Ala Leu
            340                 345                 350

Ala Pro Lys Gly Glu Ala Arg Ile Gly Ala Asn Pro His Ala Asn Gly
        355                 360                 365

Gly Leu Leu Arg Lys Glu Leu His Met Pro Asp Phe Arg Gln Tyr Ala
    370                 375                 380

Val Asn Val Thr Glu Pro Gly Ala Ile Glu Ala Gln Ser Thr Lys Ile
385                 390                 395                 400

Leu Gly Asp Phe Leu Arg Asp Val Met Lys Leu Asn Glu Thr Glu Lys
                405                 410                 415

Asn Phe Arg Ile Phe Gly Pro Asp Glu Thr Ala Ser Asn Arg Leu Gly
            420                 425                 430

Ser Val Leu Glu Ala Thr Asn Arg Val Trp Met Ala Glu Thr Leu Asp
        435                 440                 445

Met Asp Asp His Leu Ala Ala Asp Gly Arg Val Met Glu Val Leu Ser
    450                 455                 460

Glu His Leu Cys Gln Gly Trp Leu Glu Gly Tyr Leu Leu Ser Gly Arg
465                 470                 475                 480

His Gly Phe Phe Ser Cys Tyr Glu Ala Phe Ile His Ile Ile Asp Ser
                485                 490                 495

Met Phe Asn Gln His Ala Lys Trp Leu Gln Val Ala Arg Glu Leu Glu
            500                 505                 510

Trp Arg Lys Pro Ile Ser Ser Leu Asn Tyr Leu Leu Thr Ser His Val
        515                 520                 525

Trp Arg Gln Asp His Asn Gly Phe Ser His Gln Asp Pro Gly Phe Val
    530                 535                 540

Asp Leu Val Ala Asn Lys Ser Ala Asp Ile Ala Arg Val Tyr Phe Pro
545                 550                 555                 560

Pro Asp Ala Asn Thr Leu Leu Trp Val Gly Asp His Cys Leu Lys Thr
                565                 570                 575

Trp Asn Arg Val Asn Val Ile Val Ala Gly Lys Gln Pro Glu Pro Gln
            580                 585                 590

Trp Leu Thr Met Ala Glu Ala Glu Lys His Cys Glu Ala Gly Leu Gly
        595                 600                 605

Ile Trp Glu Trp Ala Gly Thr Glu Asp Gly Leu Glu Pro Asp Ile Val
    610                 615                 620

Met Ala Cys Ala Gly Asp Val Pro Thr Met Glu Thr Leu Ala Ala Val
625                 630                 635                 640

Asp Leu Leu Arg Gln Ser Leu Pro His Leu Arg Ile Arg Val Val Asn
                645                 650                 655

Val Val Asp Leu Met Val Leu Gln Ser Pro His Gln His Pro His Gly
```

```
            660                 665                 670

Ile Ser Asp Glu Glu Phe Asp Arg Met Phe Thr Thr Asn Arg Pro Val
        675                 680                 685

Ile Phe Ala Tyr His Gly Tyr Pro Tyr Leu Ile His Arg Leu Val Tyr
    690                 695                 700

Lys Arg Thr Asn His Ser Asn Phe His Val Arg Gly Phe Ile Glu Gln
705                 710                 715                 720

Gly Thr Thr Thr Thr Pro Phe Asp Met Thr Val Leu Asn Glu Leu Asp
                725                 730                 735

Arg Phe His Leu Ala Met Glu Ala Val Glu Arg Leu Pro Leu Gly Glu
            740                 745                 750

Ser Val Ala Lys Pro Leu Ile Asp Asn Phe Thr Glu Lys Leu Ala Leu
        755                 760                 765

His Lys Asp Tyr Ile Arg Gln His Gly Glu Asp Met Pro Glu Ile Arg
    770                 775                 780

Asp Trp Lys Trp Thr Trp Pro Arg
785                 790


<210> SEQ ID NO 80
<211> LENGTH: 2436
<212> TYPE: DNA
<213> ORGANISM: Methylococcus capsulatus
<220> FEATURE:
<221> NAME/KEY: CDS
<222> LOCATION: (1)..(2436)

<400> SEQUENCE: 80

atg gca acc caa ttc ccc ctg tcc tcc gaa ttc gaa cgg ctc acc gtc       48
Met Ala Thr Gln Phe Pro Leu Ser Ser Glu Phe Glu Arg Leu Thr Val
1               5                   10                  15

tac ggg ccg acc cgc gcc act gtc agc gga aca ccg ctg gat gcc gaa       96
Tyr Gly Pro Thr Arg Ala Thr Val Ser Gly Thr Pro Leu Asp Ala Glu
            20                  25                  30

gaa gtc cgc aaa atc cat gcg ttc tgg cga gcc tgc aat tac ctg gcg      144
Glu Val Arg Lys Ile His Ala Phe Trp Arg Ala Cys Asn Tyr Leu Ala
        35                  40                  45

ctg ggc atg atc tac ctg cgg ggg aat ccg ctg ctg cgt gaa ccg ctc      192
Leu Gly Met Ile Tyr Leu Arg Gly Asn Pro Leu Leu Arg Glu Pro Leu
    50                  55                  60

aaa ccc gag cac atc aag cac cgt ctg ctc ggc cat tgg ggc tcc agc      240
Lys Pro Glu His Ile Lys His Arg Leu Leu Gly His Trp Gly Ser Ser
65                  70                  75                  80

ccc aac ctt gcg ttc gtc tac acc cat ctg aac cgg gcc atc cgg aaa      288
Pro Asn Leu Ala Phe Val Tyr Thr His Leu Asn Arg Ala Ile Arg Lys
                85                  90                  95

cac gac ctc gac atg atc ttc atg gcc ggc ccc ggc cac ggc gcc ccc      336
His Asp Leu Asp Met Ile Phe Met Ala Gly Pro Gly His Gly Ala Pro
            100                 105                 110

ggc gtg ctg ggc ccg ctc tac ctg gaa ggc agc tac tcc gaa atc tac      384
Gly Val Leu Gly Pro Leu Tyr Leu Glu Gly Ser Tyr Ser Glu Ile Tyr
        115                 120                 125

ccc gac aag gac ctg agc gaa gaa ggc ctg ctg aac ttc ttc aag cag      432
Pro Asp Lys Asp Leu Ser Glu Glu Gly Leu Leu Asn Phe Phe Lys Gln
    130                 135                 140

ttc tcc ttc ccc ggc gga atc ggc agc cat tgc acc ccc gag aca ccg      480
Phe Ser Phe Pro Gly Gly Ile Gly Ser His Cys Thr Pro Glu Thr Pro
145                 150                 155                 160

ggc tcg atc cac gag ggc ggc gag ctg ggc tac gtg ctg tcg cac gcc      528
Gly Ser Ile His Glu Gly Gly Glu Leu Gly Tyr Val Leu Ser His Ala
                165                 170                 175
```

```
tgc ggc gca gcc ttc gac aac ccg gac ctg atc gtg gcc gcc gtg gtc      576
Cys Gly Ala Ala Phe Asp Asn Pro Asp Leu Ile Val Ala Ala Val Val
            180                 185                 190

ggc gac ggc gag gcg gaa acc ggc ccc ctg gcc act tcc tgg cac atc      624
Gly Asp Gly Glu Ala Glu Thr Gly Pro Leu Ala Thr Ser Trp His Ile
        195                 200                 205

aac aaa ttt ctc aac ccg atc cgc gac ggc gcg gtg ctg ccg atc ctc      672
Asn Lys Phe Leu Asn Pro Ile Arg Asp Gly Ala Val Leu Pro Ile Leu
    210                 215                 220

aac ctc aac ggc tac aag atc aac aac ccc acc ctg ctg gcg cgc atc      720
Asn Leu Asn Gly Tyr Lys Ile Asn Asn Pro Thr Leu Leu Ala Arg Ile
225                 230                 235                 240

agc cac gaa gaa ttg gaa aat ctg ctc agg ggt tac ggc tac acg cct      768
Ser His Glu Glu Leu Glu Asn Leu Leu Arg Gly Tyr Gly Tyr Thr Pro
                245                 250                 255

tat ttc gtg gag ggc tcg gaa ccg gaa agc atg cac cag gcg atg gcc      816
Tyr Phe Val Glu Gly Ser Glu Pro Glu Ser Met His Gln Ala Met Ala
            260                 265                 270

gcg acg gtg gac cgc agc atc gaa gac atc cgc gcc gcc cag acc gag      864
Ala Thr Val Asp Arg Ser Ile Glu Asp Ile Arg Ala Ala Gln Thr Glu
        275                 280                 285

gcc cgc gcc agc ggc atc gcc cga cgg ccg cgc tgg ccg atg atc gtg      912
Ala Arg Ala Ser Gly Ile Ala Arg Arg Pro Arg Trp Pro Met Ile Val
    290                 295                 300

ctg cgc tcg ccc aag ggc tgg acc gcg cca cgc cag atc gac ggc cac      960
Leu Arg Ser Pro Lys Gly Trp Thr Ala Pro Arg Gln Ile Asp Gly His
305                 310                 315                 320

aac gtc gag ggc ttc tgg cgc gct cat cag gtg ccg gta gcc gac gtc     1008
Asn Val Glu Gly Phe Trp Arg Ala His Gln Val Pro Val Ala Asp Val
                325                 330                 335

gcg aaa aat ccc gaa cac ctg aag ctg ctg gaa ggc tgg atg cgc agc     1056
Ala Lys Asn Pro Glu His Leu Lys Leu Leu Glu Gly Trp Met Arg Ser
            340                 345                 350

tac aag ccg gaa gaa ctg ttc gac gcc gaa ggc tgc ccc gtc gcc gaa     1104
Tyr Lys Pro Glu Glu Leu Phe Asp Ala Glu Gly Cys Pro Val Ala Glu
        355                 360                 365

atc cgg gaa atg gcg ccg gcc ggt ctc cgc cgc atg ggt ctc aac ccc     1152
Ile Arg Glu Met Ala Pro Ala Gly Leu Arg Arg Met Gly Leu Asn Pro
    370                 375                 380

cac gcc aac ggc ggc cat ctg aaa aag gcc ctg cgc atc cct aat ttc     1200
His Ala Asn Gly Gly His Leu Lys Lys Ala Leu Arg Ile Pro Asn Phe
385                 390                 395                 400

cgc aac tac ggc atc gaa gtc gcc aaa ccg ggc cag atc gaa gcg ccg     1248
Arg Asn Tyr Gly Ile Glu Val Ala Lys Pro Gly Gln Ile Glu Ala Pro
                405                 410                 415

aac acc cag ccg ctg ggc gtg ttc ctg cgc gac gtg atg aag gag aac     1296
Asn Thr Gln Pro Leu Gly Val Phe Leu Arg Asp Val Met Lys Glu Asn
            420                 425                 430

gcg cac aac ttc cgg ctg ttc ggc cct gac gag aat acc tcc aac aag     1344
Ala His Asn Phe Arg Leu Phe Gly Pro Asp Glu Asn Thr Ser Asn Lys
        435                 440                 445

ctg gac gcc gtc tac gcc gct gcc aag aaa ttc tgg atc gcc gag tat     1392
Leu Asp Ala Val Tyr Ala Ala Ala Lys Lys Phe Trp Ile Ala Glu Tyr
    450                 455                 460

ttc ccc gaa gac cag gat ggc ggc gaa ctg gcc ccc gac ggc cgg gtc     1440
Phe Pro Glu Asp Gln Asp Gly Gly Glu Leu Ala Pro Asp Gly Arg Val
465                 470                 475                 480

atg gaa atg ctc agc gag cat acc ctg gaa ggc atg ctg gaa ggc tac     1488
Met Glu Met Leu Ser Glu His Thr Leu Glu Gly Met Leu Glu Gly Tyr
                485                 490                 495
```

```
ctt ctg acc ggg cgc cac ggc ttc ctc tcg acc tac gaa gcc ttc gtc      1536
Leu Leu Thr Gly Arg His Gly Phe Leu Ser Thr Tyr Glu Ala Phe Val
            500                 505                 510

cac gtc atc gat tcg atg ttc aac cag cac gcc aag tgg ctg tcc atc      1584
His Val Ile Asp Ser Met Phe Asn Gln His Ala Lys Trp Leu Ser Ile
        515                 520                 525

tgc aac cag ctg tcc tgg cgc cag gac gtg gcc tcg ctc aac ctg ctc      1632
Cys Asn Gln Leu Ser Trp Arg Gln Asp Val Ala Ser Leu Asn Leu Leu
    530                 535                 540

atc act tcg acg gtc tgg cga cag gac cac aac ggc ttc acc cac cag      1680
Ile Thr Ser Thr Val Trp Arg Gln Asp His Asn Gly Phe Thr His Gln
545                 550                 555                 560

gac ccc ggt ttc ctg gac gtc gtc gtg aac aag agc gcc gac gtc acc      1728
Asp Pro Gly Phe Leu Asp Val Val Val Asn Lys Ser Ala Asp Val Thr
                565                 570                 575

cgc atc tac ctg ccg ccc gac gtc aac agc ctg ctg tcg gtc gcc gac      1776
Arg Ile Tyr Leu Pro Pro Asp Val Asn Ser Leu Leu Ser Val Ala Asp
            580                 585                 590

cac tgc ctg cgc agc cag aac tac atc aac gtg atc gtg tcg gac aaa      1824
His Cys Leu Arg Ser Gln Asn Tyr Ile Asn Val Ile Val Ser Asp Lys
        595                 600                 605

cag ttg cat ctg cag ttc atg gac atg gac gcc gcg atc gcc cat tgc      1872
Gln Leu His Leu Gln Phe Met Asp Met Asp Ala Ala Ile Ala His Cys
    610                 615                 620

acg gag ggc ttg ggc atc tgg gaa tgg gcc agc aac gac gag ggc cag      1920
Thr Glu Gly Leu Gly Ile Trp Glu Trp Ala Ser Asn Asp Glu Gly Gln
625                 630                 635                 640

gag ccc gac gtg gtc atg gcc tgc gcc ggc gac atc ccg acc ctg gaa      1968
Glu Pro Asp Val Val Met Ala Cys Ala Gly Asp Ile Pro Thr Leu Glu
                645                 650                 655

gcc ctg gcc gcc acc gcc ctg ctg cgc gag gag ttc ccg gaa ctg aag      2016
Ala Leu Ala Ala Thr Ala Leu Leu Arg Glu Glu Phe Pro Glu Leu Lys
            660                 665                 670

atc cgc ttc atc aac gtg gtg gat ctg ttc aag ctg cag ccc gag tcc      2064
Ile Arg Phe Ile Asn Val Val Asp Leu Phe Lys Leu Gln Pro Glu Ser
        675                 680                 685

gag cat ccg cac ggt ctc agc gac aag gat ttc gac agc ctg ttc acc      2112
Glu His Pro His Gly Leu Ser Asp Lys Asp Phe Asp Ser Leu Phe Thr
    690                 695                 700

agg gac aag ccg gtc atc ttc aac ttc cac ggc tat ccc tgg ctg atc      2160
Arg Asp Lys Pro Val Ile Phe Asn Phe His Gly Tyr Pro Trp Leu Ile
705                 710                 715                 720

cac cgc ctc gcc tac cgg cgc acc aac cac gcc aac atg cac gtg cgc      2208
His Arg Leu Ala Tyr Arg Arg Thr Asn His Ala Asn Met His Val Arg
                725                 730                 735

ggc tac aag gag aaa ggc aac atc aac acc ccg ctg gaa ctg gcg atc      2256
Gly Tyr Lys Glu Lys Gly Asn Ile Asn Thr Pro Leu Glu Leu Ala Ile
            740                 745                 750

aac aac cag atc gac cgc ttc agc ctg gcc atc gac gtc atc gac cgg      2304
Asn Asn Gln Ile Asp Arg Phe Ser Leu Ala Ile Asp Val Ile Asp Arg
        755                 760                 765

att ccg gag atc gcg gtc tcc ggc gcc cac gcc aag gcc cgg ttc cgc      2352
Ile Pro Glu Ile Ala Val Ser Gly Ala His Ala Lys Ala Arg Phe Arg
    770                 775                 780

aaa cag cag atc gcc tgc cgc cag tat gcc tac gag cac ggc gtc gac      2400
Lys Gln Gln Ile Ala Cys Arg Gln Tyr Ala Tyr Glu His Gly Val Asp
785                 790                 795                 800

atg ccg gag gtc gcg ggc tgg cgc tgg ccg ggc tga                      2436
Met Pro Glu Val Ala Gly Trp Arg Trp Pro Gly
                805                 810
```

<210> SEQ ID NO 81
<211> LENGTH: 811
<212> TYPE: PRT
<213> ORGANISM: Methylococcus capsulatus

<400> SEQUENCE: 81

Met Ala Thr Gln Phe Pro Leu Ser Ser Glu Phe Glu Arg Leu Thr Val
1 5 10 15

Tyr Gly Pro Thr Arg Ala Thr Val Ser Gly Thr Pro Leu Asp Ala Glu
20 25 30

Glu Val Arg Lys Ile His Ala Phe Trp Arg Ala Cys Asn Tyr Leu Ala
35 40 45

Leu Gly Met Ile Tyr Leu Arg Gly Asn Pro Leu Leu Arg Glu Pro Leu
50 55 60

Lys Pro Glu His Ile Lys His Arg Leu Leu Gly His Trp Gly Ser Ser
65 70 75 80

Pro Asn Leu Ala Phe Val Tyr Thr His Leu Asn Arg Ala Ile Arg Lys
85 90 95

His Asp Leu Asp Met Ile Phe Met Ala Gly Pro Gly His Gly Ala Pro
100 105 110

Gly Val Leu Gly Pro Leu Tyr Leu Glu Gly Ser Tyr Ser Glu Ile Tyr
115 120 125

Pro Asp Lys Asp Leu Ser Glu Glu Gly Leu Leu Asn Phe Phe Lys Gln
130 135 140

Phe Ser Phe Pro Gly Gly Ile Gly Ser His Cys Thr Pro Glu Thr Pro
145 150 155 160

Gly Ser Ile His Glu Gly Gly Glu Leu Gly Tyr Val Leu Ser His Ala
165 170 175

Cys Gly Ala Ala Phe Asp Asn Pro Asp Leu Ile Val Ala Ala Val Val
180 185 190

Gly Asp Gly Glu Ala Glu Thr Gly Pro Leu Ala Thr Ser Trp His Ile
195 200 205

Asn Lys Phe Leu Asn Pro Ile Arg Asp Gly Ala Val Leu Pro Ile Leu
210 215 220

Asn Leu Asn Gly Tyr Lys Ile Asn Asn Pro Thr Leu Leu Ala Arg Ile
225 230 235 240

Ser His Glu Glu Leu Glu Asn Leu Leu Arg Gly Tyr Gly Tyr Thr Pro
245 250 255

Tyr Phe Val Glu Gly Ser Glu Pro Glu Ser Met His Gln Ala Met Ala
260 265 270

Ala Thr Val Asp Arg Ser Ile Glu Asp Ile Arg Ala Ala Gln Thr Glu
275 280 285

Ala Arg Ala Ser Gly Ile Ala Arg Arg Pro Arg Trp Pro Met Ile Val
290 295 300

Leu Arg Ser Pro Lys Gly Trp Thr Ala Pro Arg Gln Ile Asp Gly His
305 310 315 320

Asn Val Glu Gly Phe Trp Arg Ala His Gln Val Pro Val Ala Asp Val
325 330 335

Ala Lys Asn Pro Glu His Leu Lys Leu Leu Glu Gly Trp Met Arg Ser
340 345 350

Tyr Lys Pro Glu Glu Leu Phe Asp Ala Glu Gly Cys Pro Val Ala Glu
355 360 365

-continued

```
Ile Arg Glu Met Ala Pro Ala Gly Leu Arg Arg Met Gly Leu Asn Pro
    370                 375                 380

His Ala Asn Gly Gly His Leu Lys Lys Ala Leu Arg Ile Pro Asn Phe
385                 390                 395                 400

Arg Asn Tyr Gly Ile Glu Val Ala Lys Pro Gly Gln Ile Glu Ala Pro
                405                 410                 415

Asn Thr Gln Pro Leu Gly Val Phe Leu Arg Asp Val Met Lys Glu Asn
            420                 425                 430

Ala His Asn Phe Arg Leu Phe Gly Pro Asp Glu Asn Thr Ser Asn Lys
        435                 440                 445

Leu Asp Ala Val Tyr Ala Ala Ala Lys Lys Phe Trp Ile Ala Glu Tyr
    450                 455                 460

Phe Pro Glu Asp Gln Asp Gly Gly Glu Leu Ala Pro Asp Gly Arg Val
465                 470                 475                 480

Met Glu Met Leu Ser Glu His Thr Leu Glu Gly Met Leu Glu Gly Tyr
                485                 490                 495

Leu Leu Thr Gly Arg His Gly Phe Leu Ser Thr Tyr Glu Ala Phe Val
            500                 505                 510

His Val Ile Asp Ser Met Phe Asn Gln His Ala Lys Trp Leu Ser Ile
        515                 520                 525

Cys Asn Gln Leu Ser Trp Arg Gln Asp Val Ala Ser Leu Asn Leu Leu
    530                 535                 540

Ile Thr Ser Thr Val Trp Arg Gln Asp His Asn Gly Phe Thr His Gln
545                 550                 555                 560

Asp Pro Gly Phe Leu Asp Val Val Val Asn Lys Ser Ala Asp Val Thr
                565                 570                 575

Arg Ile Tyr Leu Pro Pro Asp Val Asn Ser Leu Leu Ser Val Ala Asp
            580                 585                 590

His Cys Leu Arg Ser Gln Asn Tyr Ile Asn Val Ile Val Ser Asp Lys
        595                 600                 605

Gln Leu His Leu Gln Phe Met Asp Met Asp Ala Ala Ile Ala His Cys
    610                 615                 620

Thr Glu Gly Leu Gly Ile Trp Glu Trp Ala Ser Asn Asp Glu Gly Gln
625                 630                 635                 640

Glu Pro Asp Val Val Met Ala Cys Ala Gly Asp Ile Pro Thr Leu Glu
                645                 650                 655

Ala Leu Ala Ala Thr Ala Leu Leu Arg Glu Glu Phe Pro Glu Leu Lys
            660                 665                 670

Ile Arg Phe Ile Asn Val Val Asp Leu Phe Lys Leu Gln Pro Glu Ser
        675                 680                 685

Glu His Pro His Gly Leu Ser Asp Lys Asp Phe Asp Ser Leu Phe Thr
    690                 695                 700

Arg Asp Lys Pro Val Ile Phe Asn Phe His Gly Tyr Pro Trp Leu Ile
705                 710                 715                 720

His Arg Leu Ala Tyr Arg Arg Thr Asn His Ala Asn Met His Val Arg
                725                 730                 735

Gly Tyr Lys Glu Lys Gly Asn Ile Asn Thr Pro Leu Glu Leu Ala Ile
            740                 745                 750

Asn Asn Gln Ile Asp Arg Phe Ser Leu Ala Ile Asp Val Ile Asp Arg
        755                 760                 765

Ile Pro Glu Ile Ala Val Ser Gly Ala His Ala Lys Ala Arg Phe Arg
    770                 775                 780

Lys Gln Gln Ile Ala Cys Arg Gln Tyr Ala Tyr Glu His Gly Val Asp
```

-continued

```
785                 790                 795                 800

Met Pro Glu Val Ala Gly Trp Arg Trp Pro Gly
                805                 810
```